US007741309B2

(12) United States Patent
Hansen et al.

(10) Patent No.: US 7,741,309 B2
(45) Date of Patent: Jun. 22, 2010

(54) OLIGOMERIC COMPOUNDS FOR THE MODULATION OF SURVIVIN EXPRESSION

(75) Inventors: Jens Bo Rode Hansen, Hellerup (DK); Charlotte Albaek Thrue, Copenhagen (DK); Majken Westergaard, Birkerod (DK); Kamille Dumong Petersen, Lyngby (DK); Margit Wissenbach, Fredensborg (DK)

(73) Assignees: Enzon Pharmaceuticals; Santaris Pharma A/S (DK)

( * ) Notice: Subject to any disclaimer, the term of this patent is extended or adjusted under 35 U.S.C. 154(b) by 0 days.

(21) Appl. No.: 12/493,625

(22) Filed: Jun. 29, 2009

(65) Prior Publication Data

US 2009/0318362 A1 Dec. 24, 2009

Related U.S. Application Data

(62) Division of application No. 10/776,934, filed on Feb. 10, 2004.

(60) Provisional application No. 60/523,591, filed on Nov. 19, 2003, provisional application No. 60/446,372, filed on Feb. 10, 2003.

(51) Int. Cl.
*A61K 48/00* (2006.01)
(52) U.S. Cl. .................. 514/44; 536/24.5; 536/24.31; 536/24.1
(58) Field of Classification Search .............. None
See application file for complete search history.

(56) References Cited

U.S. PATENT DOCUMENTS

| 5,108,921 A | 4/1992 | Low et al. |
| 5,227,400 A | 7/1993 | Holton et al. |
| 5,248,796 A | 9/1993 | Chen et al. |
| 5,250,683 A | 10/1993 | Holton et al. |
| 5,254,580 A | 10/1993 | Chen et al. |
| 5,272,171 A | 12/1993 | Ueda et al. |
| 5,278,324 A | 1/1994 | Kingston et al. |
| 5,874,416 A | 2/1999 | Sheikhnejad |
| 6,077,709 A | 6/2000 | Bennett et al. |
| 6,117,848 A | 9/2000 | Monia et al. |
| 6,310,044 B1 | 10/2001 | Draper et al. |
| 6,509,162 B1 | 1/2003 | Altieri |
| 6,593,091 B2 | 7/2003 | Keys et al. |
| 2002/0137708 A1 | 9/2002 | Bennett et al. |
| 2003/0032794 A1 | 2/2003 | Koch et al. |
| 2004/0241717 A1 | 12/2004 | Hansen et al. |
| 2004/0248840 A1 | 12/2004 | Hansen et al. |
| 2005/0014712 A1 | 1/2005 | Hansen et al. |
| 2006/0160095 A1 | 7/2006 | Hayes et al. |

FOREIGN PATENT DOCUMENTS

| EP | 0 253 739 B1 | 10/1989 |
| WO | WO 92/09589 A1 | 6/1992 |
| WO | WO 92/22651 | 12/1992 |
| WO | WO 93/18210 A1 | 9/1993 |
| WO | WO 94/08003 | 4/1994 |
| WO | WO 94/28720 | 12/1994 |
| WO | WO 98/22589 | 5/1998 |
| WO | WO 98/49349 | 11/1998 |
| WO | WO 98/50540 | 11/1998 |
| WO | WO 99/02732 | 1/1999 |
| WO | WO 99/14226 A2 | 3/1999 |
| WO | WO 99/22772 | 5/1999 |
| WO | WO 00/18781 | 4/2000 |
| WO | WO 00/56746 A2 | 9/2000 |
| WO | WO 00/56748 A1 | 9/2000 |
| WO | WO 00/66604 A2 | 11/2000 |
| WO | WO 01/25248 A2 | 4/2001 |
| WO | WO 01/46455 | 6/2001 |
| WO | WO 01/48190 A2 | 7/2001 |
| WO | WO 01/57059 | 8/2001 |
| WO | WO 01/64741 | 9/2001 |
| WO | WO 02/28875 A2 | 4/2002 |
| WO | WO 02/094250 A2 | 11/2002 |
| WO | WO 03/006475 A2 | 1/2003 |
| WO | WO 03/027244 | 4/2003 |
| WO | WO 03/091384 A3 | 11/2003 |
| WO | WO 03/095467 A1 | 11/2003 |
| WO | WO 2004/069991 A2 | 8/2004 |

OTHER PUBLICATIONS

Mita et al. Survivin: Key regulator of mitosis and apoptosis and novel target for cancer therapeutics. Clin Cancer Res 2008;14(6):5000-5005.*
Adida et al., "Anti-apoptosis gene, surviving, and prognosis of neuroblastoma," *Lancet*, vol. 351, pp. 882-883 (1998).
Adida et al., "Expression and prognostic significance of survivin in de novo acute myeloid leukaemia," *Br. J. Haematol.*, vol. 111, pp. 196-203 (2000).
Adida et al., "Prognostic significance of survivin expression in diffuse large B-cell lymphomas," *Blood*, vol. 96, No. 5, pp. 1921-1925 (2000).
Altieri, "Survivin, versatile modulation of cell division and apoptosis in cancer," *Oncogene*, vol. 22, pp. 8551-8589 (2003).

(Continued)

*Primary Examiner*—Kimberly Chong
(74) *Attorney, Agent, or Firm*—Dechert LLP

(57) ABSTRACT

Oligonucleotides directed against the survivin gene are provided for modulating the expression of survivin. The compositions comprise oligonucleotides, particularly antisense oligonucleotides, targeted to nucleic acids encoding the survivin. Methods of using these compounds for modulation of survivin expression and for the treatment of diseases associated with either overexpression of survivin, expression of mutated survivin or both are provided. Examples of diseases are cancer such as lung, breast, colon, prostate, pancreas, lung, liver, thyroid, kidney, brain, testes, stomach, intestine, bowel, spinal cord, sinuses, bladder, urinary tract or ovaries cancers. The oligonucleotides may be composed of deoxyribonucleosides or a nucleic acid analogue such as for example locked nucleic acid or a combination thereof.

12 Claims, 12 Drawing Sheets

OTHER PUBLICATIONS

Altmann et al., "Novel Chemistry," *Applied Antisense Oligonucleotide Technology*, Chapter 4, Stein, Krieg, Wiley-Liss, pp. 73-107 (1998).

Ambrosini et al., "A novel anti-apoptosis gene, *survivin*, expressed in cancer and lymphoma," *Nat. Med.*, vol. 3, No. 8, pp. 917-921 (1997).

Ambrosini et al., "Induction of Apoptosis and Inhibition of Cell Proliferation by *survivin* Gene Targeting," *J. Biol. Chem.*, vol. 273, No. 18, pp. 11177-11182 (1998).

Ansell et al., "Inhibition of survivin expression suppresses the growth of aggressive non-Hodgkin's lymphoma," *Leukemia*, vol. 18, pp. 616-623 (2004).

Asanuma et al., "A Role for Survivin in Radioresistance of Pancreatic Cancer Cells," *Jpn. J. Cancer Res.*, vol. 93, pp. 1057-1062 (2002).

Ashkenazi et al., "Death Receptors: Signaling and Modulation," *Science*, vol. 281, pp. 1305-1308 (1998).

Beaucage et al., "Advances in the Synthesis of Oligonucleotides by the Phosphoramidite Approach," *Tetrahedron*, vol. 48, No. 12, pp. 2223-2311 (1992).

Beaucage et al., "The Synthesis of Modified Oligonucleotides by the Phosphoramidite Approach and Their Applications," *Tetrahedron*, vol. 49, No. 28, pp. 6123-6194 (1993).

Beltrami et al., "Acute Ablation of Survivin Uncovers p53-Dependent Mitotic Checkpoint Functions and Control of Mitochondrial Apoptosis," *J. Biol. Chem*, vol. 279, pp. 2077-2084 (2003).

Bennett et al., "ras Oncogenes," *Antisense Therapeutics*, pp. 16-27 (1996).

Blanc-Brude et al., "Therapeutic Targeting of the Survivin Pathway in Cancer: Initiation of Mitochondrial Apoptosis and Suppression of Tumor-associated Angiogenesis," *Clin. Cancer Res.*, vol. 9, pp. 2683-2692 (2003).

Brown et al., "In Oligonucleotides and Analogues. A Practical Approach," Oxford: IRL 13-14 (1991).

Cao et al., "XIAP and Survivin as Therapeutic Targets for Radiation Sensitization in Preclinical Models of Lung Cancer," *Oncogene*, vol. 23, pp. 1-6 (2004).

Carvalho et al., "Survivin is required for stable checkpoint activation in taxol-treated HeLa cells," *J. Cell. Sci.*, vol. 116, No. 14, pp. 2987-2998 (2003).

Chakravarti et al. "Quantitatively Determined Survivin Expression Levels Are of Prognostic Value in Human Gliomas," *J. Clin. Oncol.* vol. 20, No. 4, pp. 1063-1068 (2002).

Chen et al., "Down-regulation of Survivin by Antisense Oligonucleotides Increases Apoptosis, Inhibits Cytokinesis and Anchorage-Independent Growth," *Neoplasia*, vol. 2, No. 3, pp. 235-241 (2000).

Chen et al., "Survivin Enhances Aurora-B Kinase Activity and Localizes Aurora-B in Human Cells," *J. Biol. Chem.*, vol. 278, pp. 486-490 (2003).

Chin et al., "Essential role for oncogenic Ras in tumour maintenance," *Nature*, vol. 400, pp. 468-472 (1999).

Chin et al., "On the Preparation and Utilization of Isolated and Purified Oligonucleotides," *Public Collection of the Kathrine R. Everett law Library of the University of North Carolina*, Mar. 9, 2002 (on CD).

Cohen, "Caspases: the executioners of apoptosis," *Biochem J.*, vol. 326, pp. 1-16 (1997).

Conway et al., "Deficiency of Survivin in Transgenic Mice Exacerbates Fas-Induced Apoptosis Via Mitochondrial Pathways," *Gastroenterology*, vol. 123, pp. 619-631 (2002).

Cowsert, "In vitro and in vivo activity of antisense inhibitors of *ras*: potential for clinical development," *Anti-Cancer Drug Design*, vol. 12, pp. 359-371 (1997).

Crooke, R.M., "In Vitro Cellular Uptake, Distribution and Metabolism of Oligonucleotides," *Antisense Res. and Application* 131:103-140 1997).

Cunningham et al., "A phase I Trial of H-*ras* Antisense Oligonucleotide ISIS 2503 Administered as a Continuous Intravenous Infusion in Patients with Advanced Carcinoma," *Amer. Cancer Soc.*, vol. 92, pp. 1265-1271 (2001).

Dass, C.R., "Vehicles for oligonucleotide delivery to tumours," *J Pharm Pharmacol.*, vol. 54, pp. 3-27 (2002).

Dean et al., "Inhibition of Protein Knase C-α Expression in Human A549 Cells by Antisense Oligonucleotides Inhibits Induction of Intercellular Adhesion Molecule 1 (ICAM-1) mRNA by Phorbol Esters," *J. Biol. Chem.*, vol. 269, No. 23, pp. 16416-16424 (1994).

Evan et al., "Proliferation, cell cycle and apoptosis in cancer," *Nature*, vol. 411, pp. 342-348 (2001).

Freier et al., "The ups and downs of nucleic acid duplex stability: structure-stability studies on chemically-modified DANN:RNA duplexes," *Nucl. Acid Res.*, vol. 25, pp. 4429-4443 (1997).

Garcia et al., "Hodgkin and Reed-Sternberg cells harbor alterations in the major tumor suppressor pathways and cell-cycle checkpoints: analyses using tissue microarrays," *Blood*, vol. 101, pp. 681-689 (2003).

Graham, M.J. et al., "In Vivo Distribution and Metabolism of a Phosphorothioate Oligonucleotide within Rat Liver after Intravenous Administration," , vol. 286, pp. 447-458 (1998).

Gray et al., "Antisense DNA Inhibition of Tumor Growth Induced by c-Ha-*ras* Oncogene in Nude Mice," *Cancer Research*, vol. 53, pp. 577-580 (1993).

Green et al., "Mitochondria and Apoptosis," *Science*, vol. 281, pp. 1309-1312 (1998).

Grossman et al., "Expression and Targeting of the Apoptosis Inhibitor, Survivin, in Human Melanoma," *J. Invest. Dematol.*, vol. 113, No. 6, pp. 1076-1081 (1999).

Grossman et al., "Inhibition of melanoma tumor growth in vivo by survivin targeting," *Proc. Natl. Sci.*, vol. 98, pp. 635-640 (2001).

Grossman et al., "Transgenic expression of surviving in keratinocytes counteracts UVB-induced apoptosis and cooperates with loss of p53," *J. Clin. Invest.*, vol. 108, No. 7, pp. 991-999 (2001).

Hanahan et al., "The Hallmarks of Cancer," *Cell*, vol. 100, pp. 57-70 (2000).

Heid et al. "Real time quantitative PCR," *Genome Research*, vol. 6, pp. 986-994 (1996).

Hengartner, "The biochemistry of apoptosis," *Nature*, vol. 407, pp. 770-776 (2000).

Holmes et al., "Phase II Trial of Taxol, an Active Drug in the Treatment of Metastatic Breast Cancer," *J. Natl. Cancer Inst.*, 83(24)1797-1805 (1991).

Holton et al., "First Total Synthesis of Taxol. 1. Functionalization of the B Ring," *J. Am. Chem. Soc.*, vol. 116, No. 4, pp. 1597-1598 (1994).

Ikeguchi et al., "Inducible Nitric Oxide Synthase and Survivin Messenger RNA Expression in Hepatocellular Carcinoma," Clin. Cancer Res. 8, 3131-3136.

Ikeguchi et al., "*survivin* messenger RNA expression is a good prognostic biomarker for oesophageal carcinoma," *Br. J. Cancer*, vol. 87, pp. 883-887 (2002).

Islam et al., "High expression of *Survivin*, mapped to 17q25, is significantly associated with poor prognostic factors and promotes cell survival in human neuroblastoma," *Oncogene*, vol. 19, pp. 617-623 (2000).

Jiang et al., "Participation of Survivin in Mitotic and Apoptotic Activities of Normal and Tumor-Derived Cells," *J. Cell. Biochem.*, vol. 83, pp. 342-354 (2001).

Kamihira et al., "Aberrant expression of caspase cascade regulatory genes in adult T-cell leukaemia : survivin is an important determinant for prognosis," *Br. J. Haematol.* vol. 114, pp. 63-69.

Kato et al., "Expression of Survivin in Esophageal Cancer : Correlation with the Prognosis and Response to Chemotherapy," *Int. J. Cancer*, vol. 95, pp. 92-95 (2001).

Kawasaki et al., "Inhibition of Apoptosis by Survivin Predicts Shorter Survival Rates in colorectal Cancer," *Cancer Res.*, vol. 58, pp. 5071-5074 (1998).

Kim et al., "Expression of Survivin in CIN and Invasive Squamous Cell Carcinoma of Uterine Cervix," *Anticancer Res.* vol. 22, pp. 805-808 (2002).

Koch et al., "Survivin: a novel neuroendocrine marker for pheochromocytoma," *Eur. J. Endocrino.* vol. 146, pp. 381-388 (2002).

Kohn et al., "Dose-Intense Taxol: High Response Rate in Patients With Platinum-Resistant Recurrent Ovarian Cancer," *J. Natl. Cancer Inst.*, 86(1)18-24 (1994).

Kurreck et al., "Design of antisense Oligonucleotides stabilized by locked nucleic acids," *Nucleic Acids Research*, vol. 30, No. 9, pp. 1911-1918 (2002).

Kuttler et al., Relationship between expression of genes involved in cell cycle control and apoptosis in diffuse large B cell lymphoma: a preferential survivin-cyclin B link, *Leukemia*, vol. 16, pp. 726-735 (2002).

Leamon et al., "Delivery of Macromolecules into Living Cells: A Method that Exploits Folate Receptor Endocytosis," *Proc. Nat. Acad. Sci.*, vol. 88, pp. 5572-5576 (1991).

Lens et al., "Survivin is required for a sustained spindle checkpoint arrest in response to lack of tension," *EMBO J.*, vol. 22, pp. 2934-2947 (2003).

Li et al., "Pleiotropic cell-division defects and apoptosis induced by interference with surviving function," *Nature Cell Biology*, vol. 1, pp. 461-466 (1999).

Li et al., "Control of apoptosis and mitotic spindle checkpoint by survivin," *Nature*, vol. 396, pp. 580-584 (1998).

Ling et al., "Induction of survivin expression by taxol (paclitaxel) is an early event which is indepedent of taxol-mediated G2/M arrest," *J. Biol. Chem.* (2004).

Lu et al., Expression of A Novel Antiapoptosis Gene, Survivin, Correlated with Tumor Cell Apoptosis and p53 Accumulation in Gastric Carcinomas, *Cancer Res.*, vol. 58, pp. 1808-1812 (1998).

Lu et al., "Survivin as a Therapeutic Target for Radiation Sensitization in Lung Cancer," *Cancer Research*, vol. 64, pp. 2840-2845 (2004).

Mahotka et al., "Survivin-Δ-Ex3 and Survivin-2B: Tow Novel Splice Variants of the Apoptosis Inhibitor Survivin with Different Antiapoptotic Properties," *Cancer Res.*, vol. 59, pp. 6097-6102 (1999).

Marusawa et al., "HBXIP functions as a cofactor of surviving in apoptosis suppression," *EMBO Journal*, vol. 22, No. 11, pp. 2729-2740 (2003).

McGuire et al., "Taxol: A Unique Antineoplastic Agent with Significant Activity in Advanced Ovarian Epithelial Neoplasms." *Ann. Intern. Med.* vol. 111, pp. 273-279 (1989).

Mesri et al., "Cancer gene therapy using a survivin mutant adenovirus," *J. Clin. Invest.*, vol. 108, pp. 981-990 (2001).

Mesri et al., "Suppression of Vascular Endothelial Growth Factor-Mediated Endothelial Cell Protection by Survivin Targeting," *Am. J. Pathol.*, vol. 158, pp. 1757-1765 (2001).

Monzo et al., A Novel Anti-Apoptosis Gene: Re-expression of Survivin Messenger RNA as a Prognosis Marker in Non-Small-Cell Lung Cancers, *J. Clin. Oncol*, vol. 17, pp. 2100-2104 (1999).

Mori et al., "Expression of the Antiapoptosis Gene Survivin in Human Leukemia," *Int. J. Haemato.* vol. 75, pp. 161-165 (2001).

Morita et al., "2'-O,4'-C-Ethylene-Bridged Nucleic Acids (ENA): Highly Nuclease-Resistant and Thermodynamically Stable Oligonucleotides for Antisense Drug," *Bioorganic & Medicinal Chemistry Letters*, vol. 12, pp. 73-76 (2002).

Nasu et al., "Survivin mRNA Expression in Patients with Breast Cancer," *Anticancer Res.* vol. 22, pp. 1839-1844 (2002).

Nicholson, "From bench to clinic with apoptosis-based therapeutic agents," *Nature*, vol. 407, pp. 810-816 (2000).

Nicolaou et al., "Total Synthesis of Taxol," *Nature* vol. 367, pp. 630-634 (1994).

O'Connor et al., "Control of Apoptosis during Angiogenesis by Survivin Expression in Endothelial Cells," *Am. J. Pathol.*, vol. 156, pp. 393-398 (2000).

Office Action from U.S. Appl. No. 11/272,124, dated May 16, 2008.

Olie et al., "A Novel Antisense Oligonucleotide Targeting Survivin Expression Induces Apoptosis and Sensitizes Lung Cancer Cells to Chemotherapy," *Cancer Res.*, vol. 60, pp. 2805-2809 (2000).

Pedersen et al., "Preparation of LNA Phosphoramidites", *Synthesis*, No. 6, pp. 802-808 (2002).

Pennati et al., "Radiosensitization of Human Melanoma Cells by Ribozyme-Mediated Inhibition of Survivin Expression," *J. Invest. Dermatol.*, vol. 120, pp. 648-654 (2003).

Pennati et al., "Ribozyme-mediated inhibition of surviving expression increases spontaneous and drug-induced apoptosis and decreases the tumorigenic potential of human prostate cancer cells," *Oncogene*, vol. 23, pp. 386-394 (2004).

Rait et al., "Inhibitory effects of the combination of HER-2 antisense oligonucleotide and chemotherapeutic agents used for the treatment of human breast cancer," *Cancer Gene Therapy*, vol. 8, No. 10, pp. 728-739 (2001).

Rodel et al., "High Survivin Expression in Associated with Reduced Apoptosis in Rectal Cancer and May Predict Disease-Free Survival after Preoperative Radiochemotherapy and Surgical Resection," *Strahlenther. Onkol.*, vol. 8, pp. 426-434 (2002).

Rodel et al., "Spontaneous and Radiation-Induced Apoptosis in Colorectal Carcinoma Cells with Different Intrinsic Radiosensitivities: Survivin as a Radioresistance Factor," *Int. J. Rdiat. Oncol. Biol. Phys.*, vol. 55, No. 5, pp. 1341-1347 (2003).

Rosenbohm et al., "Synthesis of 2'-amino-LNA: a new strategy," *Org. Biomol. Chem.*, vol. 1, pp. 655-663 (2003).

Saitoh et al., "Analysis of *Bcl-2*, *Bax* and *Survivin* genes in uterine cancer," *Int. J. Oncol.* vol. 15, pp. 137-141 (1999).

Sarela et al., "Expression of survivin, a novel inhibitor of apoptosis and cell cycle regulatory protein, in pancreatic adenocarcinoma," *Br. J. Cancer*, vol. 86, pp. 886-892 (2002).

Satoh et al., "Expression of Survivin Is Correlated with Cancer Cell Apoptosis and Is Involved in the Development of Human Pancreatic Duct Cell Turmors," *Cancer*, vol. 92, pp. 271-278 (2001).

Schwab et al., "Antisense oligonucleotides adsorbed to polyalkylcyanoacrylate nanoparticles specifically inhibit mutated Ha-*ras*-mediated cell proliferation and tumorigenicity in nude mice," *Proc. Natl. Acad. Sci. USA*, vol. 91, pp. 10460-10464 (1994).

Schwartz, et al., "Phase I Study of the Cyclin-Dependent Kinase Inhibitor Flavopiridol in combination with Paclitaxel in Patients With Advanced Solid Tumors," *J. Clin. Oncol.*, vol. 20, No. 8, pp. 2157-2170 (2002).

Shankar et al., "Survivin inhibition induces human neural tumor cell death through caspase-independent and —dependent pathways," *Journal of Neurochemistry*, vol. 79, pp. 426-436 (2001).

Shin et al., "An Anti-apoptotic Protein Human Survivin is a Direct Inhibitor of Caspase-3," *BioChem.*, vol. 40, pp. 1117-1123 (2001).

Singh et al., "Synthesis of Novel Bicycle[2.2.1] Rib nucleosides: 2'-Amino- and 2'-Thio-LNA Monomer Nucleosides," *J. Org. Chem.*, vol. 63, No. 18, pp. 6078-6079 (1998).

Smith et al., "Urine Detection of Survivin and Diagnosis of Bladder Cancer," *JAMA*, vol. 285, pp. 324-328 (2001).

Sorensen et al., "α-L-rib-Configured Locked Nucleic Acid (α-L-LNA): Synthesis and Properties," *Am. Chem. Soc.*, pp. 2164-2176 (2002).

Swana et al., "Tumor Content of the Antiapoptosis Molecule Survivin and Recurrence of Bladder Cancer," *New Engl. J. Med.* vol. 341, pp. 452-453 (1999).

Takai et al., "Expression of survivin is associated with malignant potential in epithelial ovarian carcinoma," *Int. J. Mol. Med.* vol. 10, pp. 211-216 (2002).

Takai et al., Survivin expression correlates with clinical stage, histological grade, invasive behavior and survival rate in endometrial carcinoma, *Cancer Lett.*, vol. 184, pp. 105-116 (2002).

Tamm et al., "IAP-Family Protein Survivin Inhibits Caspase Activity and Apoptosis Induced by Fas (CD95), Bax, Caspases, and Anticancer Drugs," *Cancer Res.*, vol. 58, pp. 5315-5320 (1998).

Tanaka et al., "Expression of *survivin* AND Its Relationship to Loss of Apoptosis in Breast Carcinomas," *Clin. Cancer Res.* vol. 6, pp. 127-134 (2000).

Tran et al., "A role for survivin in chemoresistance of endothelial cells mediated by VEGF," *Proc. Natl. Acad. Sci.*, vol. 99, No. 7, pp. 4349-4354 (2002).

Tran et al., "Marked induction of the IAP Family antiapoptotic Proteins Survivin and XIAP by VEGF in Vascular Endothelial Cells," *Biochem. Biophys. Res. Commun.*, vol. 264, pp. 781-788 (1999).

Tsuburaya et al., "An Anti-apoptosis Gene, Survivin and Telomerase Expression in Gastric Cancer," *Hepatogastroenterology*, vol. 49, pp. 1150-1152 (2002).

Uhlmann et al., "Recent advances in the medicinal chemistry of antisense oligonucleotides," *Curr. Opinion in Drug Discovery & Development*, vol. 3, No. 2, pp. 203-213 (2000).

Uren et al., "Survivin and the inner centromere protein INCENP show similar cell-cycle localization and gene knockout phenotype," *Curr. Biol.*, vol. 10, No. 21, pp. 1319-1328 (2000).

Wagner et al., "Transferrin-Polycation Conjugates as Carriers for DNA Uptake into Cells," *Proc. Nat. Acad. Sci.*, 87:3410-3414 (1990).

Wang et al., "Survivin Antisense RNA Enhances Taxol Induced Apoptosis in Leukemia Cell Line HL-60," *Zhonghua Xue Ye Xue Za Zhi*, vol. 24, No. 7, pp. 351-354 (2003).

Watts et al, "Antisense Effects of ISIS 114926 on the Novel IAP Family Member, Survivin in CCL4-induced Mouse Liver Regeneration Model," *Molecular Biology*, vol. 42, No. 17, p. 459, #2468 (2001).

Wurl et al., "Co-expression of surviving and TERT and risk of tumour-related death in patients with soft-tissue sarcoma," *Lancet*, vol. 359, pp. 943-945 (2002).

Xia et al., "Induction of Apoptosis in Mesothelioma Cells by Antisurvivin Oligonucleotides," *Molecular Cancer Therapeutics*, vol. 1, pp. 687-694 (2002).

Yoshida et al., "Expression of surviving and matrix metalloproteinases in adenocarcinoma and squamous cell carcinoma of the uterine cervix," *Oncol. Rep.* vol. 10, 45-49 (2003).

Yoshida et al., "Survivin, bcl-2 and matrix metalloproteinase-2 enhance progression of clear cell- and serous-type ovarian carcinomas," *Int. J. Oncol.*, vol. 19, pp. 537-542 (2001).

Zaffaroni et al., "Expression of the anti-apoptotic gene survivin correlates with taxol resistance in human ovarian cancer," *Cell. Mol. Life Sci.*, vol. 59, pp. 1406-1412 (2002).

Zangemeister-Wittke, "Antisense to Apoptosis Inhibitors Facilitates Chemotherapy and TRAIL-Induced Death Signaling," *Ann. N.Y. Acad. Sci.* vol. 1002, pp. 90-94 (2003).

Zhao et al, "The ubiqutin-proteasome pathway regulates survivin degradation in a cell cycle-dependent manner," *J Cell Sci.* vol. 113, pp. 4363-4371 (2000).

Zhao, et al., "The ubiquitin-proteasome pathway regulates survivin degradation in a cell cycle-dependent manner," *Jr. Cell Sci.*, vol. 113, pp. 4363-4371 (2000).

Zhou et al., "DNA Damage Induces a Novel p53-Survivin Signaling Pathway Regulating Cell Cycle and Apoptosis in Acute Lymphoblastic Leukemia Cells," *J. Pharmacol. Exp. Ther.*, vol. 303, pp. 124-131 (2002).

Zhu et al., "Upregulation of surviving by HIV-1 Vpr," *Apoptosis*, vol. 8, pp. 71-79 (2003).

\* cited by examiner

Figure 3
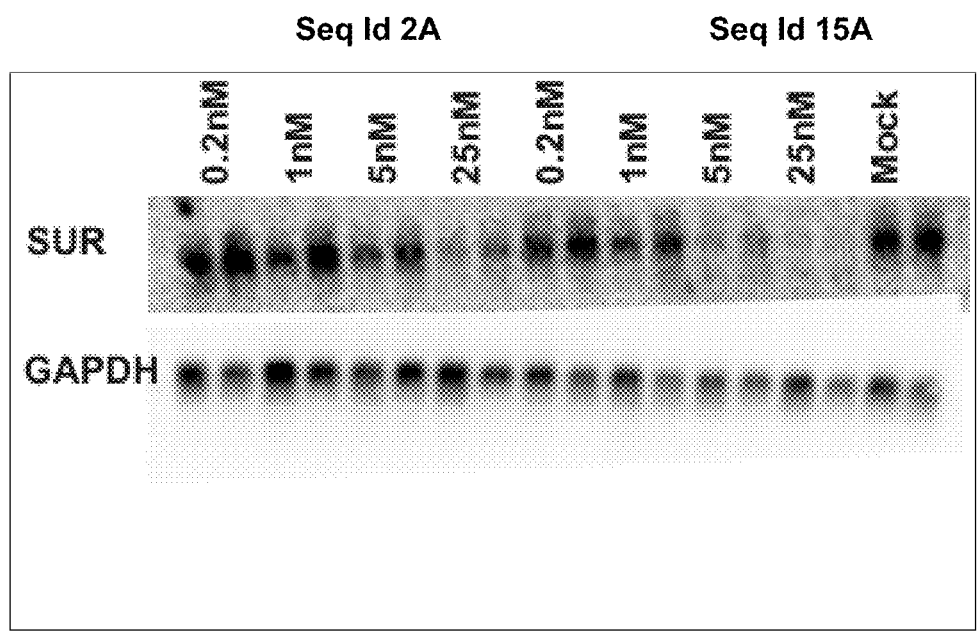
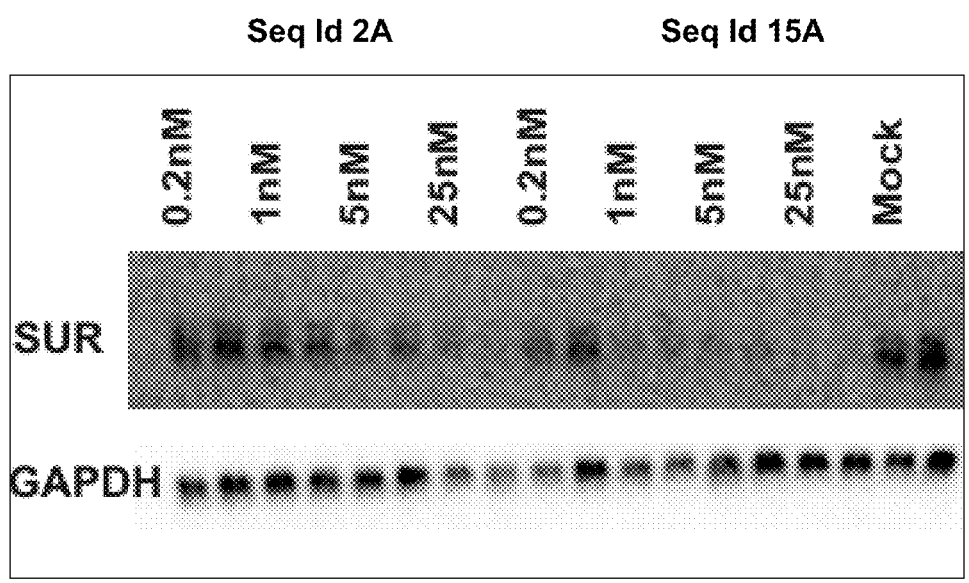

Figure 5

Seq ID NO: 1

```
human Survivin
Genbank accession no. NM_001168

1    CCGCCAGATT TGAATCGCGG GACCCGTTGG CAGAGGTGGC GGCGGCGGCA
  51    TGGGTGCCCC GACGTTGCCC CCTGCCTGGC AGCCCTTTCT CAAGGACCAC
 101    CGCATCTCTA CATTCAAGAA CTGGCCCTTC TTGGAGGGCT GCGCCTGCAC
 151    CCCGGAGCGG ATGGCCGAGG CTGGCTTCAT CCACTGCCCC ACTGAGAACG
 201    AGCCAGACTT GGCCCAGTGT TTCTTCTGCT TCAAGGAGCT GGAAGGCTGG
 251    GAGCCAGATG ACGACCCCAT AGAGGAACAT AAAAAGCATT CGTCCGGTTG
 301    CGCTTTCCTT TCTGTCAAGA AGCAGTTTGA AGAATTAACC CTTGGTGAAT
 351    TTTTGAAACT GGACAGAGAA AGAGCCAAGA ACAAAATTGC AAAGGAAACC
 401    AACAATAAGA AGAAAGAATT TGAGGAAACT GCGAAGAAAG TGCGCCGTGC
 451    CATCGAGCAG CTGGCTGCCA TGGATTGAGG CCTCTGGCCG GAGCTGCCTG
 501    GTCCCAGAGT GGCTGCACCA CTTCCAGGGT TTATTCCCTG GTGCCACCAG
 551    CCTTCCTGTG GGCCCCTTAG CAATGTCTTA GGAAGGAGA TCAACATTTT
 601    CAAATTAGAT GTTTCAACTG TGCTCCTGTT TTGTCTTGAA AGTGGCACCA
 651    GAGGTGCTTC TGCCTGTGCA GCGGGTGCTG CTGGTAACAG TGGCTGCTTC
 701    TCTCTCTCTC TCTCTTTTTT GGGGGCTCAT TTTTGCTGTT TTGATTCCCG
 751    GGCTTACCAG GTGAGAAGTG AGGGAGGAAG AAGGCAGTGT CCCTTTTGCT
 801    AGAGCTGACA GCTTTGTTCG CGTGGGCAGA GCCTTCCACA GTGAATGTGT
 851    CTGGACCTCA TGTTGTTGAG CTGTCACAG TCCTGAGTGT GGACTTGGCA
 901    GGTGCCTGTT GAATCTGAGC TGCAGGTTCC TTATCTGTCA CACCTGTGCC
 951    TCCTCAGAGG ACAGTTTTTT TGTTGTTGTG TTTTTTTGTT TTTTTTTTT
1001    GGTAGATGCA TGACTTGTGT GTGATGAGAG AATGGAGACA GAGTCCCTGG
1051    CTCCTCTACT GTTTAACAAC ATGGCTTTCT TATTTTGTTT GAATTGTTAA
1101    TTCACAGAAT AGCACAAACT ACAATTAAAA CTAAGCACAA AGCCATTCTA
1151    AGTCATTGGG GAAACGGGGT GAACTTCAGG TGGATGAGGA GACAGAATAG
1201    AGTGATAGGA AGCGTCTGGC AGATACTCCT TTTGCCACTG CTGTGTGATT
1251    AGACAGGCCC AGTGAGCCGC GGGGCACATG CTGGCCGCTC CTCCCTCAGA
1301    AAAAGGCAGT GGCCTAAATC CTTTTTAAAT GACTTGGCTC GATGCTGTGG
1351    GGGACTGGCT GGGCTGCTGC AGGCCGTGTG TCTGTCAGCC CAACCTTCAC
1401    ATCTGTCACG TTCTCCACAC GGGGGAGAGA CGCAGTCCGC CCAGGTCCCC
1451    GCTTTCTTTG GAGGCAGCAG CTCCCGCAGG GCTGAAGTCT GGCGTAAGAT
1501    GATGGATTTG ATTCGCCCTC CTCCCTGTCA TAGAGCTGCA GGGTGGATTG
1551    TTACAGCTTC GCTGGAAACC TCTGGAGGTC ATCTCGGCTG TTCCTGAGAA
1601    ATAAAAAGCC TGTCATTTC
```

Figure 8
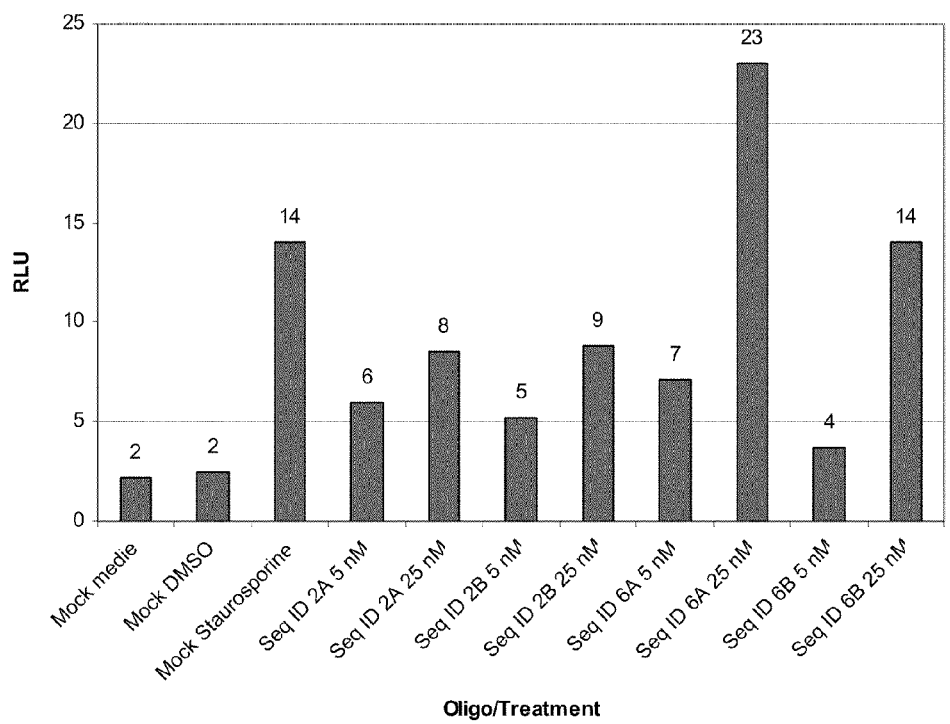
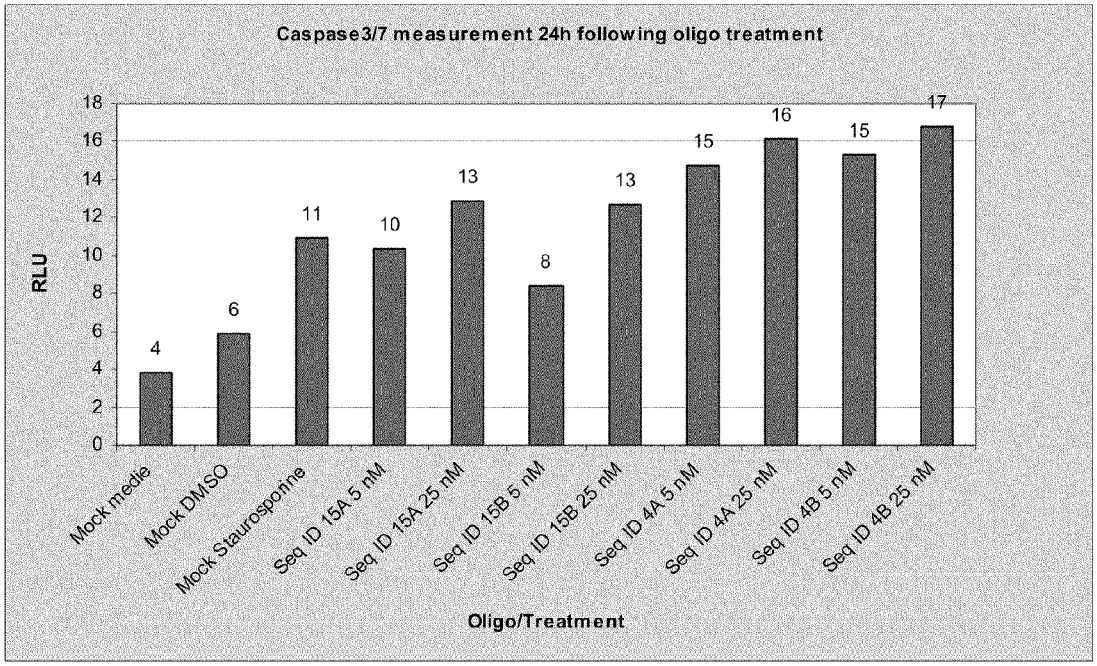

Figure 9
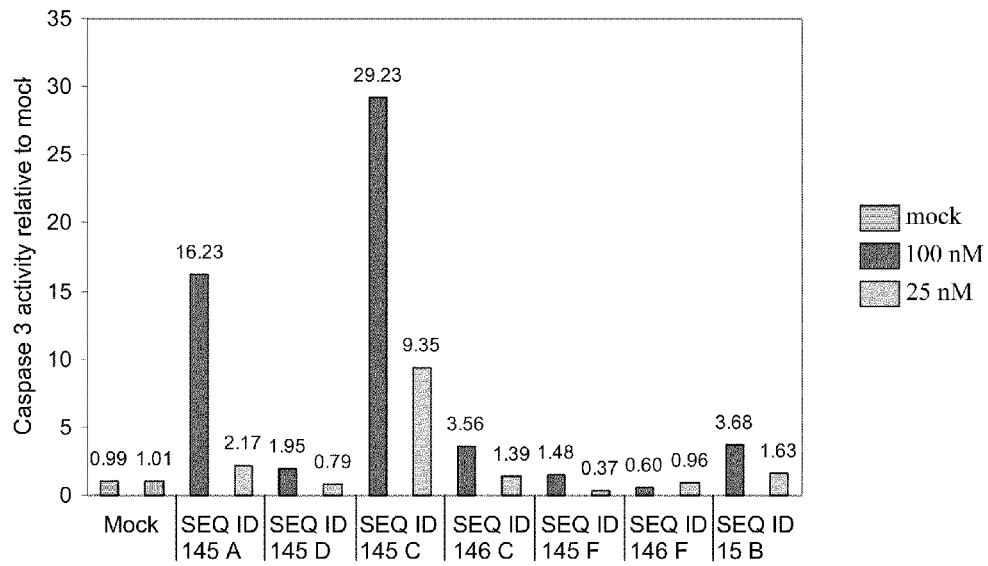
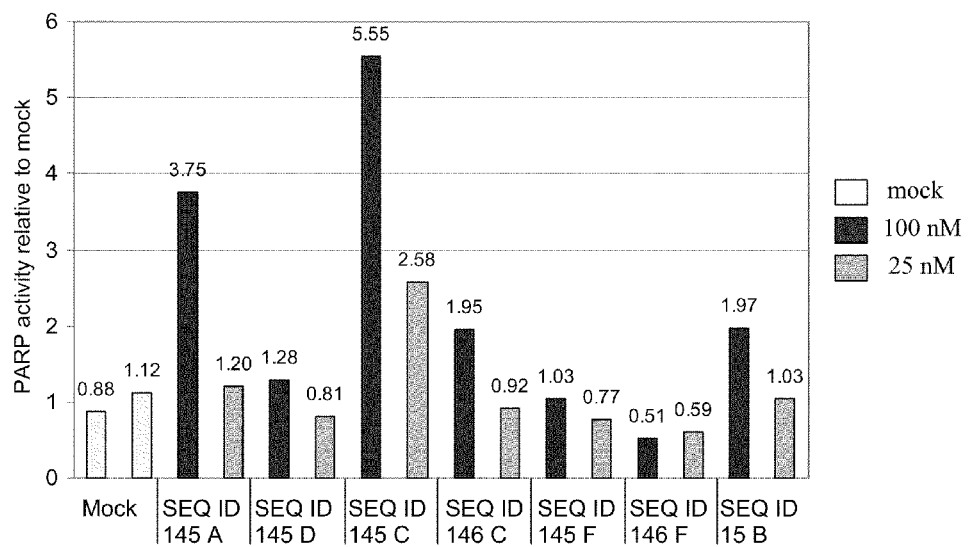

OLIGOMERIC COMPOUNDS FOR THE MODULATION OF SURVIVIN EXPRESSION

CROSS-REFERENCE TO RELATED APPLICATIONS

This application is a divisional application of U.S. patent application Ser. No. 10/776,934 filed on Feb. 10, 2004, which claims the benefit under 35 U.S.C. §119(e) to U.S. Provisional Patent Application Ser. No. 60/446,372 filed on Feb. 10, 2003 and U.S. Provisional Patent Application Ser. No. 60/523,591 filed on Nov. 19, 2003, the entire teachings of which are hereby incorporated by reference.

FIELD OF THE INVENTION

The present invention provides compositions and methods for modulating the expression of survivin. In particular, this invention relates to oligomeric compounds and preferred such compounds are oligonucleotides, which are specifically hybridisable with nucleic acids encoding survivin. The oligonucleotide compounds have been shown to modulate the expression of survivin and pharmaceutical preparations thereof and their use as treatment of cancer diseases are disclosed.

BACKGROUND OF THE INVENTION

Cancer, a leading cause of death worldwide, comprises a group of diseases, which are caused by genetic disorders resulting from genomic instability. It has been postulated that all cancer cells harbour defects in several regulatory pathways, which govern normal cell proliferation and homeostasis. Theses defects result in acquirement of various cancer cell specific hallmark capabilities (Hanahan and Weinberg, 2000, Cell 100, 57-70). One of these hallmarks of cancer is evasion of apoptosis or programmed cell death, an evolutionary conserved program of cellular suicide (Hengartner, 2000, Nature 407, 770-776.). Apoptosis is essential in fetal development by removal of cells not needed any longer, and maintenance of homeostasis of adult tissues by balancing cell production and cell elimination. Additionally, cells exhibiting aberrant features like mutations or genomic damages induced by infectious agents or drugs are removed in this way. In malignant cells this cellular surveillance is missing due to inhibition of apoptosis, which results in extended cell viability increasing the risk of cellular transformation, accelerated disease progression and resistance to therapy (Evan and Vousden, 2001, Nature 411, 342-348. Therefore, manipulation of apoptosis has emerged as a new therapeutic strategy for treatment of cancer (Nicholson D W, 2000, Nature 407, 810-816).

Two signaling pathways leading to induction of apoptosis are known, the intrinsic or mitochondrial pathway, induced by environmental stress and chemotherapeutics, and the extrinsic or death receptor pathway, induced by effector cells of the immune system (Ashkenazi and Dixit, 1998 Science 281, 1305-1308; Green and Reed, 1998, Science 281, 1309-1312). Both pathways culminate with the activation of caspases, a family of intracellular cystein proteases, which within minutes dismantle the cell's structures leading to rapid cell death (Cohen, 1997, Biochem J 326, 1-16). Both, apoptosis promoting as well as inhibiting proteins are known. The Bcl-2 protein family comprises both, pro- and anti-apoptotic proteins. Among the inhibitors of apoptosis, the evolutionary highly conserved inhibitor of apoptosis protein (IAP) family comprises eight proteins in humans. One of them, survivin, has only recently been identified (Ambrosini et al., 1997, Nat. Med. 3, 917-921). Survivin inhibits apoptosis downstream of Bcl-2 by directly or indirectly inhibiting the effector caspase −3 and −7 intracellular proteases responsible or apoptosis (Shin et al., 2001, Biochemistry 40, 1117-1123) Recent evidence suggests that survivin directly controls the activation of the upstream acting caspase 9. A survivin Thr$^{34}$-Ala dominant negative mutant fails to induce apoptosis in mouse embryonic fibroblasts deficient in apoptosome components Apaf-1 or caspase 9 (Blanc-Brude et al., 2003, Clin. Cancer Res. 9, 2683-2692) The hepatitis B X-interacting protein (HBXIP) operates as a cofactor for phosphorylated survivin allowing it to bind and suppress activation of pro-caspase 9 (Marusawa et al., 2003, EMBO J. 22, 2729-2740). Other modes of action are discussed, too (Beltrami et al., 2004, J. Biol. Chem. 279, 2077-2084).

Survivin has attracted great intention as novel therapeutic target, because it is selectively expressed in cancer cells and it is required for their viability. Survivin is normally expressed during embryogenesis. Apart from the thyme, CD34+ bone-marrow-derived stem cells, placenta and the basal colonic epithelium, survivin is not detecTable in normal adult tissues, but is basically overexpressed in all transformed cells independent of their mitotic status. Expression is generally regulated in a cell-cycle dependent manner peaking at mitosis (Li et al. 1998, Nature 396, 580-584). Upregulation in G2/M phase compared to interphase can be more than 40-fold. Also, increased protein stability due to phosphorylation of Thr 34 by CDC2-cyclin-B1 may account for elevated survivin levels at mitosis. In the interphase, the protein level declines due to ubiquitin dependent proteolysis (Zhao et al., 2000, J Cell Sci. 113, 4363-71) to basal levels. It has been suggested that overexpression of survivin in cancer cells counteracts a default induction of apoptosis, overcomes the G2/M checkpoint and thus enforces progression of cells through mitosis (Li et al., 1998, Nature 396, 580-584).

In cell culture systems, inhibition of cell death by overexpression of survivin is well established (Ambrosini et al. 1997, Nat. Med. 3, 917-921; Tamm et al. 1998, Cancer Res. 58, 5315-5320; Mahotka et al., 1999, Cancer Res. 59, 6097-6102).

In vivo, survivin's role as inhibitor of apoptosis has been demonstrated in transgenic mice expressing survivin in the skin, which inhibited UVB induced apoptosis of the keratinocytes (Grossman at al., 2001, J. Clin. Invest. 108, 991-999). Apart from its role in cellular apoptosis, survivin plays a critical role in various aspects of mitosis. For example, knocking out survivin in homozygous survivin knock-out mice leads to 100% lethality (Uren et al. 2000, Curr. Biol. 10, 1319-1328; Conway et al., 2002, Gastroenterolgy 123, 619-631). Survivin has been found to be associated with various components of the mitotic apparatus, such as centrosomes, mictrotubules and the remnants of the spindle apparatus—the midbodies. Microtubule association is essential for survivin's anti-apoptotic action.

Survivin's dual role as apoptosis inhibitor and essential factor in cell division was demonstrated by targeted downregulation of survivin by transfecting HeLa cells with EPR-1 cDNA, which is complementary to survivin. Downregualtion of survivin by EPR-1 antisense resulted in increased apoptosis and inhibition of cell proliferation (Ambrosini et al., 1998, J. Biol. Chem. 273, 11177-11182). Other hallmarks of survivin ablation are mitotic arrest, polyploidy, defect centrosome replication, microtubule nucleation and mitotic spindle assembly/stability and inhibition of cell division. Most of these effects are exacerbated in a p53$^{-/-}$ mutant background (Beltrami et al., 2004, J. Biol. Chem. 279, 2077-2084; Carvalho et al, 2003, J. Cell. Sci. 116, 2987-2998; Lens et al., 2003, EMBO J. 22, 2934-2947). The pivotal role of survivin in mitosis is underscored by its association with the mitotic apparatus, including microtubules of the metaphase and anaphase spindle, and kinetochores of metaphase chromosomes (Beltrami et al., 2004, J. Biol. Chem. 279, 2077-2084). Survivin colocalizes with other chromosomal passenger proteins such as INCENP and Aurora B (Carvalho et al, 2003, J. Cell. Sci. 116, 2987-2998; Lens et al., 2003, EMBO J. 22, 2934-2947). Kinase activity of Aurora B is dependent upon interaction with surviving (Chen et al., 2003, J. Biol. Chem. 278, 486-490). It has been suggested that Aurora B kinase activity is essential to cytokinesis providing a mechanistic link between survivin and cell division (Chen et al., 2003, J. Biol. Chem. 278, 486-490). Two reports demonstrate that survivin is required for sustained the checkpoint arrest in response to lack of tension on kinetochores of sister chromatides. Survivin appears to be essential for the maintenance of checkpoint protein BubR1 at the kinetochores and mitotic arrest under protracted conditions of lack of tension at the kinetochores. Taxol, a microtubule stabilizing agent, allows attachment of microtubules to kinetochores, but prevents generation of tension. Normally taxol treated cells arrest in mitosis due to checkpoint activation mediated by kinetochore associated BubR1. Taxol treated Survivin depleted cells however manage to complete mitosis after a delay during which BubR1 is lost from the kinetochore. Nocodazol also prevents tension forming at the kinetochores but by preventing microtubule attachment. However depletion of Survivin has no effect on checkpoint activation and mitotic arrest induced by Nocodazol. Survivin is apparently not involved in monitoring kinetochore occupancy by microtubuli but instead required for checkpoint monitoring spindle tension excerted on the kinetochore. (Carvalho et al, 2003, J. Cell. Sci. 116, 2987-2998; Lens et al., 2003, EMBO J. 22, 2934-2947). Moreover it has been suggested that survivin serves as a crucial p53 dependent mitotic checkpoint protein required for genomic integrity and cytoprotection (Beltrami et al., 2004, J. Biol. Chem. 279, 2077-2084). Survivin may therefore be an important link between cell death and the regulation of cell division. Due to its dual role as inhibitor of apoptosis and promoter of mitosis survivin is an important factor in onset and progression of cancer as well as resistance to chemotherapeutic agents.

Its clinical role in cancer has been emphasized by detection of high levels of survivin in almost all tumour types. Elevated expression of survivin in tumours is associated with poor prognosis, increased cancer recurrence and resistance to therapy (Kawasaki et al., 1998, Cancer Res. 58, 5071-5074; Adida et al., 1998, Lancet 351, 882-883). Interestingly, lung and breast tumours express the highest levels of survivin. These tumours are generally associated with unfavourable prognosis due to early metastasizing and development of resistance to a number of mechanistically unrelated chemotherapeutic agents. Downregulation of survivin has been shown to sensitize tumor cells to DNA damaging agents such as etoposide (Li et al., 1999, Nature Cell Biology 1, 461-466; Olie et al., 2000, Cancer Res. 60, 2805-2809; Jiang et al., 2001, J. Cell. Biochem. 83, 342-354), cisplatin (Pennati et al., 2004, Oncogene 23, 386-394), doxorubicin (Zhou et al., 2002, J. Pharmacol. Exp. Ther. 303, 124-131) and radiotherapy (Pennati et al., 2003, J. Invest. Dermatol. 120, 648-654; Asanuma et al., 2002, Jpn. J. Cancer Res. 93, 1057-1062). Survivin depleted cells are particularly senetive to texol is also true for taxol (Zaffaroni et al., 2002, Cell. Mol. Life Sci. 59, 1406-1412; Ling et al., 2004, J. Biol. Chem. Epub ahead of print). Resistance to taxol and radiotherapy has been shown to correlate with the expression level of survivin (Zaffaroni et al., 2002, Cell. Mol. Life Sci. 59, 1406-1412; Rodel et al., 2003, Int. J. Radiat. Oncol. Biol. Phys. 55, 1341-1347) and sublethal concentrations of taxol has been shown to upregulate survivin expression significantly in MCF-7 breast cancer cells (Ling et al., 2004, J. Biol. Chem. Epub ahead of print). Survivin appears to be required for the function of the spindle checkpoint in response to taxol treatment (Carvalho et al, 2003, J. Cell. Sci. 116, 2987-2998; Lens et al., 2003, EMBO J. 22, 2934-2947). In the absence of survivin cells are therefore deprived of one of their natural resistance mechanisms that allows repair of the adverse effects of taxol on mitosis.

Interestingly, survivin also plays a critical role in angiogenesis. Survivin was found upregulated in angiogenically stimulated endothelium in vitro and in vivo (O'Connor et al., 2000, Am. J. Pathol. 156, 393-398; Tran et al., 1999, Biochem. Biophys. Res. Commun. 264, 781-788). Antisense targeting of survivin caused endothelial apoptosis and rapid involution of capillary-like vessels in vitro (Mesri et al., 2001a, Am. J. Pathol. 158, 1757-1765). Injection into human breast cancer xenografts of an adenovirus expressing a dominant negative version of survivin inhibited growth of established tumors. This was associated with apoptosis of both tumor cells and endothelial cells and a significant reduction in tumor derived blood vessels (Blanc-Brude et al., 2003, Clin. Cancer Res. 9, 2683-2692). Chemotherapy and radiotherapy targets both tumor cells and the proliferating endothelial cells of the tumor vasculature. Vascular endothelial growth factor (VEGF) has been shown to significantly reduce the proapoptotic potency of chemotherapy on vascular endothelial cells. This cytoprotection to drug toxicity has been linked to a VEGF mediated upregulation of survivin expression. Suppression of survivin activity abrogates the cytoprotective effect of VEGF to drugs that interfere with microtubule dynamics (Taxol) and damage DNA as well as protection against tumor necrosis factor α (Tran et al., 2002, Proc. Natl. Acad. Sci. USA 99, 4349-4354; Mesri et al., 2001a, Am. J. Pathol. 158, 1757-1765). In addition expression of a dominant negative survivin (T34A) protein in endothelial cells (HUVECC and DMVEC) resulted in massive induction of apoptosis (Blanc-Brude et al., 2003, Clin. Cancer Res. 9, 2683-2692).

Targeting survivin is increasingly being mentioned as having a dual anticancer activity by inducing tumor cell apoptosis and suppression of tumor associated angiogenesis (Altieri D C, 2003, Oncogene 22, 8581-8591).

Several therapeutic approaches using survivin as target have been initiated. The most promising ones comprise vaccination strategies, use of mutant survivin as dominant-negative antagonists, and application of survivin specific antisense oligonucleotides. Application of a replication deficient adenovirus expressing a dominant negative survivin mutant protein (Thr34-Ala) caused inhibited tumour growth in three distinct breast cancer xenograft models in mice. This adenovirus has shown in vivo efficacy in a breast cancer xenograft models and induced expression of survivin (T34A) in melanoma cells inhibited tumor growth in a melanoma xenograft model (Blanc-Brude et al., 2003, Clin. Cancer Res. 9, 2683-2692; Grossman et al., 2001 Proc. Natl. Sci. USA 98; 635-640). In cell cultures apoptosis was increased by binding of mutant survivin to CDC2-cyclin-B1 and thus preventing phosphorylation of wildtype survivin (Mesri et al., 2001b, J. Clin. Invest 108, 981-990). Some CDC2 antagonists like purvalanol A and flavopiridol, preventing survivin phospholylation, are currently being tested in clinical trials in combination with taxol (Schwartz et al., 2002, J. Clin. Oncol. 20, 2157-2170).

Several approaches using antisense oligonucleotides have shown that anti-survivin antisense oligonucleotides downregulate survivin in cell cultures, induce apoptosis and sensitize lung cancer cells and HeLa cells to the chemotherapeutic agent etoposide (Li et al., 1999, Nature Cell Biology 1, 461-466; Olie et al., 2000, Cancer Res. 60, 2805-2809; Jiang et al., 2001, J. Cell. Biochem. 83, 342-354). Inhibition of several cell lines with antisense oligo ISIS 28599, a mixed backbone 2'-O-MOE wingmer, resulted in multinucleated cells and induction of apoptosis (Chen at al., 2000, Neoplasia 2, 235-241). In a mouse liver regeneration model survivin mRNA was reduced 90% by the antisense oligonucleotide ISIS 114926 (Proceedings of the American Association for Cancer Research, vol. 42, 2001, abstract #2468). Intratumoral injection of antisense oligonucleotide ISIS 23722 reduced had limited effect on the growth rate of aggressive non-Hodgkin's lymphoma xengraft tumors in mice (Ansell et al., 2004, Leukemia—Epub ahead of print).

There are currently no therapeutic agents, which effectively inhibit the synthesis of survivin. Therefore, there is a longfelt need for agents inhibiting tumor cell growth by reducing survivin expression. In WO9822589 methods of modulating apoptosis with agents, that modulates the amount or activity of survivin and methods for reducing the severity of a pathological state mediated by survivin with such agents are disclosed. Such an agent is a construct encoding the EPR-1 coding strand, which is complementary to survivin but no specific antisense oligos are disclosed. WO0164741 discloses a "tet-off" promoter system regulating a survivin antisense mRNA transcript. However, this application does not disclose any antisense oligonucleotides.

Most of the oligonucleotides currently in clinical trials are based on the phosphorothioate chemistry from 1988, which was the first useful antisense chemistry to be developed. However, as it has become clear in recent years this chemistry has serious shortcomings that limit its clinical use. These include low affinity for their target mRNA, which negatively affects potency and puts restrictions on how small active oligonucleotides can be thus complicating manufacture and increasing treatment costs. Also, their low affinity translate into poor accessibility to the target mRNA thus complicating identification of active compounds. Finally, phosphorothioate oligonucleotides suffer from a range of side effects that narrow their therapeutic window.

To deal with these and other problems, much effort has been invested in creating novel analogues with improved properties. As depicted in the scheme 1 below, these include wholly artificial analogues such as PNA and Morpholino and more conventional DNA analogues such as boranosphosphates, N3'-P5' phosphoroamidates and several 2' modified analogues, such as 2'-F, 2'-O-Me, 2'-O-methoxyethyl (MOE) and 2'-O-(3-aminopropyl) (AP). More recently hexitol nucleic acid (HNA), 2'-F-arabino nucleic acid (2'-F-ANA) and D-cyclohexenyl nucleoside (CeNA) have been introduced.

Many of these analogues exhibit improved binding to complementary nucleic acids, improvements in bio-stability or they retain the ability to recruit a cellular enzyme, RNAseH, which is involved in the mode-of-action of many antisense compounds. None of them, however, combine all of these advantages and in many cases improvements in one of the properties compromise one or more of the other properties. Also, in many cases new complications have been noted which seriously limits the commercial value of some of the analogues. These include low solubility, complex oligomerisation chemistries, very low cellular up-take, incompatibility with other chemistries, etc.

Antisense oligonucleotides for modulation of survivin expression for treatment of diseases are disclosed in WO0018781 and WO0157059. These oligonucleotides are all between 18-20 bp in length and designed with the phosphorothioate or the MOE chemistry.

WO014655 discloses one single antisense oligonucleotide targeting Survivin and it is a fully modified phosphorthioate with some MOE nucleosides. The MOE chemistry has several limitations. It has only modest affinity, which only manifests when several MOE's are inserted en block into the oligo. MOE belongs to the family of 2'-modifications and it is well known, for this group of compound, that the antisense activity is directly correlated with RNA binding affinity in vitro. A MOE 20 bp gapmer (5MOE/PO-10PS-5MOE/PO) targeting c-raf has been reported to have an $IC_{50}$ of about 20 nm in T24 cells and an MOE gapmer targeting PKC-a has been reported to have an $IC_{50}$ of 25 nm in A549 cells. In comparison, phosphorthioate compounds used in antisense experiments typically exhibit $IC_{50}$ in the 150 nm range. (Stein, Kreig, Applied Antisense Oligonucleotide Technology, Wiley-Liss, 1988, p 87-90)

WO03027244, filed subsequent to the present invention, discloses a 20-mer phosphorthioate antisense oligonucleotides targeting survivin which show down regulation at very high concentrations (for example compound 903 showed 51% protein reduction at 200 nM).

It is a principal object of the present invention to provide novel oligomeric compounds, against the survivin mRNA. The compounds of the invention have been found to exhibit an decreased $IC_{50}$ (thus increased activity), thereby facilitating an effective treatment of a variety of cancer diseases in which the expression of survivin is implied as a causative or related agent. As explained in the following, this objective is best achieved through the utilisation of a super high affinity chemistry termed LNA (Locked Nucleic Acid).

The present invention is directed to oligomeric compounds, particularly LNA antisense oligonucleotides, which are targeted to a nucleic acid encoding survivin and which modulate the expression of the survivin. This modulation was particularly a very potent down regulation survivin mRNA as well as elicitation of apoptotic response. The LNA-containing oligomeric compounds can be as low as an 8-mer and certainly highly active as a 16-mers, which is considerably shorter than the reported antisense compounds targeting survivin. These 16-mer oligomeric compounds have an $IC_{50}$ in the sub-nanomolar range. The invention enables a considerable shortening of the usual length of an antisense oligomers (from 20-25 mers to, e.g., 8-16 mers) without compromising the affinity required for pharmacological activity. As the intrinsic specificity of an oligo is inversely correlated to its length, such a shortening will significantly increase the specificity of the antisense compound towards its RNA target. Furthermore, it is anticipated that shorter oligomeric compounds have a higher biostability and cell permeability than longer oligomeric compounds. For at least these reasons, the present invention is a considerable contribution to the art.

SUMMARY OF THE INVENTION

Survivin is essential to cell proliferation and involved in multiple phases of mitosis. It is involved in several checkpoints linking mitosis with cell division and apoptosis. Survivin is a member of the inhibitor pf apoptosis (IAP) gene family that suppresses programmed cell death (apoptosis) (see FIG. 6). Increased survivin expression is observed in most common human neoplasms, including colorectal cancer, bladder cancer, lung carcinoma, breast cancer, malignant gloma and haematological cancers. Expression of survivin correlates with advanced grade and invasiveness in several cancers. Survivin is undetectable or present at very low levels in normal differentiated tissues, making survivin a preferred target in several human cancers.

A central aspect of the invention to provide a compound consisting of from 8-50 nucleosides, wherein said compound comprises a subsequence of at least 8 nucleosides, said subsequence being located within a sequence selected those listed in Table 1 and 2.

One embodiment of the invention is, since the sequence of the humane genome is available and the annotation of its genes rapidly progressing, to identify the shortest possible, unique sequences in the target mRNA. LNA containing oligomeric compounds of the invention have also been compared to a number of 18-mers containing LNA and/or phosphorthioates which are iso-sequential to the antisense oligomer the ISIS 23722. A comparison to the ISIS 23722 (being a 18-mer 4 MOE 10 phosphorthioate followed by 4 MOE) has also been performed.

Pharmaceutical and other compositions comprising the oligomeric compounds of the invention are also provided. Further provided are methods of modulating the expression of survivin in cells or tissues comprising contacting said cells or tissues with one or more of the oligomeric compounds or compositions of the invention. Also disclosed are methods of treating an animal or a human, suspected of having or being prone to a disease or condition, associated with expression of survivin by administering a therapeutically or prophylactically effective amount of one or more of the oligomeric compounds or compositions of the invention. Further, methods of using oligomeric compounds for the inhibition of expression of survivin and for treatment of diseases associated with survivin activity are provided. Examples of such diseases are different types of cancer, such as for instance lung, breast, colon, prostate, pancreas, lung, liver, thyroid, kidney, brain, testes, stomach, intestine, bowel, spinal cord, sinuses, bladder, urinary tract or ovaries.

BRIEF DESCRIPTION OF THE FIGURES

FIG. 3 Survivin mRNA downregulation by LNA antisense oligomeric compound. Northern Blot of total RNA from SW480 (upper panel) and A549 (lower panel) that have been treated with 0.2, 1, 5, 25 nM compound 2A and 15A, respectively. Cells were transfected with oligonucleotide and cultured for 24 h.

FIG. 5 SEQ ID No 1 GenBank accession number NM_001168 human survivin mRNA sequence.

FIG. 8 Induction of apoptosis by LNA containing antisense oligo nucleotides. 15PC3 cells transfected with the oligos and concentrations indicated in 96 well. 24 h following transfection Caspase 3/7-Glo reagens were added as described and the induction of luminescence (luciferase activity) were recorded in a Luminoskan Ascent instrument from Thermo Labsystems. The luciferase activity is measured as Relative Light Units per seconds (RLU/s).

FIG. 9. shows that the LNA containing compounds (145A and 145C) improves induction of apoptosis compared to the iso-sequential MOE compound ISIS27322 (here 145F) and the iso-sequential phosphorthioate compound (145D). Mismatch controls of a LNA compound (146C) and the MOE compound (146F) as well as the LNA compound 15B was also included in the study. The targeted downregulation of Survivin mRNA using LNA antisense oligomeric compound results in increased apoptosis in 15PC3 cells. Activation of apoptosis is measured by cytometric bead array. Fold induction is presented relative to mock treated cells.

DESCRIPTION OF THE INVENTION

Figure 1:
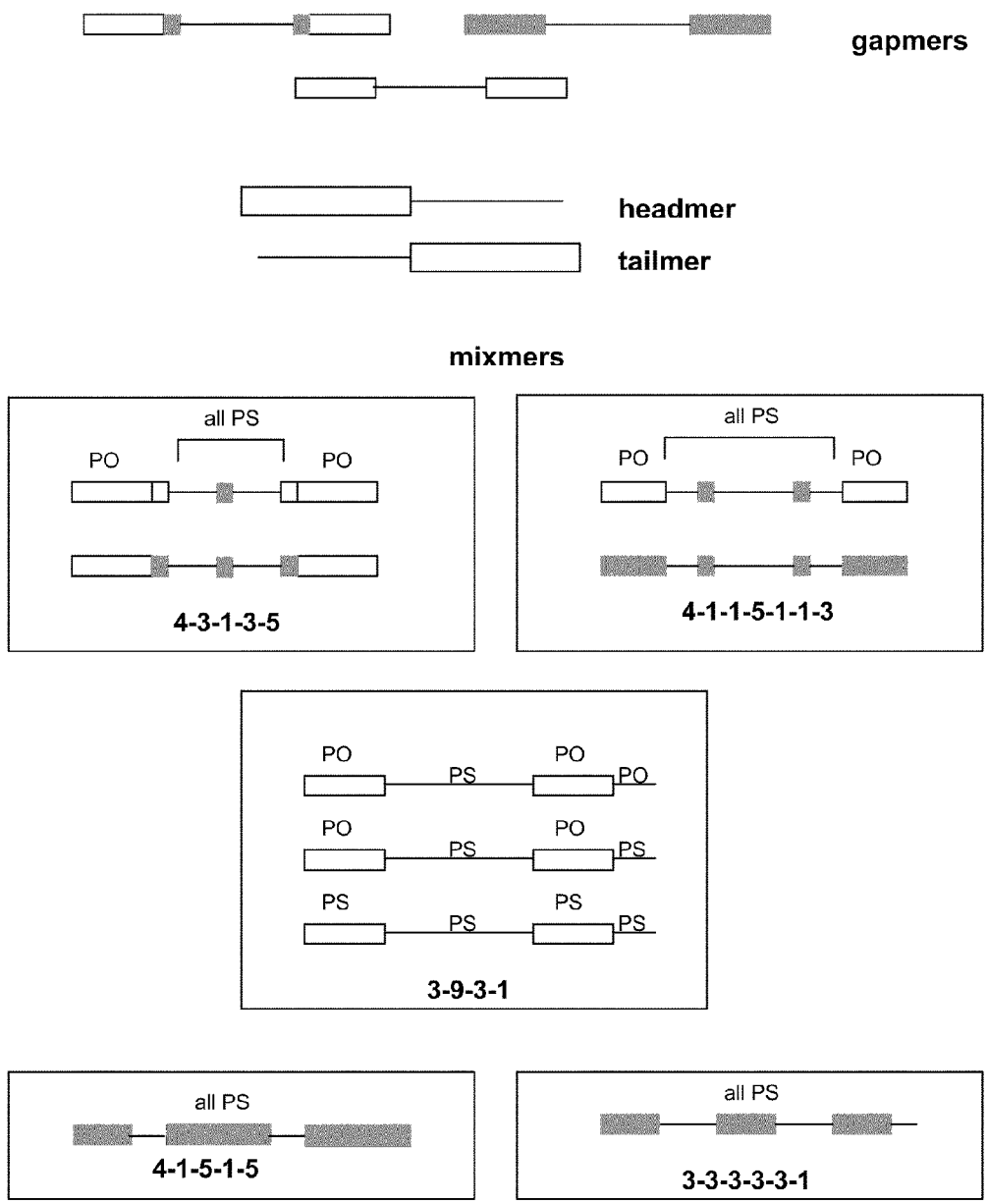
FIG. 1. Illustration of the different designs of the invention: Gapmers, Head- and Tailmers and Mixmers of different composition. For the mixmer, the numbers designate the alternate contiguous stretch of DNA, β-D-oxy-LNA or α-L-LNA. In the drawing, the line is DNA, the gray shadow corresponds to α-L-LNA residues and the rectangle is β-D-oxy-LNA.

The present invention employs oligomeric compounds, particularly antisense oligonucleotides, for use in modulating the function of nucleic acid molecules encoding survivin. The modulation is ultimately a change in the amount of survivin produced. In one embodiment this is accomplished by providing antisense compounds, which specifically hybridise with nucleic acids encoding survivin. The modulation is preferably an inhibition of the expression of survivin, which leads to a decrease in the number of functional proteins produced.

Antisense and other oligomeric compounds of the invention, which modulate expression of the target, are identified through experimentation or though rational design based on sequence information on the target and know-how on how best to design an oligomeric compound against a desired target. The sequences of these compounds are preferred embodiments of the invention. Likewise, the sequence motifs in the target to which these preferred oligomeric compounds are complementary (referred to as "hot spots") are preferred sites for targeting.

The invention is directed to a compound consisting of 8-50 nucleotides and/or nucleotide analogues, wherein said compound comprises a subsequence of at least 8 nucleotides or nucleotide analogues, said subsequence being located within a sequence selected from the group consisting of SEQ ID NOS: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143 and 144. The nucleotide analogues are typically analogues of the nucleotides of the sequence SEQ ID NOS: 2-144. Thus, the subsequence of the compound of the invention is typically located within a sequence selected from the group consisting of SEQ ID NOS: 2-144 or comprise analogues of the nucleotides within the sequence of SEQ ID NOS 2-144. A preferred nucleotide analogue of the invention is LNA.

The total of 8-50 nucleotides and/or nucleotide analogues is intended to mean 8-50 nucleotides or 8-50 nucleotide analogues or a combination thereof not exceeding a combined total of 50 nucleoside units.

In the present context, the term "nucleoside" is used in its normal meaning, i.e. it contains a 2-deoxyribose unit or a ribose unit which is bonded through its number one carbon atom to one of the nitrogenous bases adenine (A), cytosine (C), thymine (T), uracil (U) or guanine (G).

In a similar way, the term "nucleotide" means a 2-deoxyribose unit or RNA unit which is bonded through its number one carbon atom to one of the nitrogenous bases adenine (A), cytosine (C), thymine (T) or guanine (G), uracil (U) and which is bonded through its number five carbon atom to an internucleoside phosphate group, or to a terminal group.

When used herein, the term "nucleotide analogue" refers to a non-natural occurring nucleotide wherein either the ribose unit is different from 2-deoxyribose or RNA and/or the nitrogenous base is different from A, C, T and G and/or the internucleoside phosphate linkage group is different. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213.

The terms "corresponding nucleoside analogue" and "corresponding nucleoside" are intended to indicate that the nucleobase in the nucleoside analogue and the nucleoside is identical. For example, when the 2-deoxyribose unit of the nucleotide is linked to an adenine, the "corresponding nucleoside analogue" contains a pentose unit (different from 2-deoxyribose) linked to an adenine.

The term "nucleic acid" is defined as a molecule formed by covalent linkage of two or more nucleotides. The terms "nucleic acid" and "polynucleotide" are used interchangeable herein The term "nucleic acid analogue" refers to a non-natural nucleic acid binding compound.

Nucleotide analogues and nucleic acid analogues are described in e.g. Freier & Altmann (Nucl. Acid Res., 1997, 25, 4429-4443) and Uhlmann (Curr. Opinion in Drug & Development (2000, 3(2): 293-213). Scheme 1 illustrates selected examples of nucleotide analogues suitable for making nucleic acids.

The term "LNA" refers to a nucleotide containing one bicyclic nucleoside analogue, also referred to as a LNA monomer, or an oligonucleotide containing one or more bicyclic nucleoside analogues. LNA monomers are described in WO 9914226 and subsequent applications, WO0056746, WO0056748, WO0066604, WO00125248, WO0228875, WO2002094250 and PCT/DK02/00488. One particular example of a thymidine LNA monomer is the (1S,3R,4R,7S)-7-hydroxy-1-hydroxymethyl-5-methyl-3-(thymin-1-yl)-2,5-dioxa-bicyclo[2:2:1]heptane.

The term "oligonucleotide" refers, in the context of the present invention, to an oligomer (also called oligo) or nucleic acid polymer (e.g. ribonucleic acid (RNA) or deoxyribonucleic acid (DNA)) or nucleic acid analogue of those known in the art, preferably Locked Nucleic Acid (LNA), or a mixture thereof. This term includes oligonucleotides composed of naturally occurring nucleobases, sugars and internucleoside (backbone) linkages as well as oligonucleotides having non-naturally-occurring portions which function similarly or with specific improved functions. A fully or partly modified or substituted oligonucleotides are often preferred over native forms because of several desirable properties of such oligonucleotides such as for instance, the ability to penetrate a cell membrane, good resistance to extra- and intracellular nucleases, high affinity and specificity for the nucleic acid target. The LNA analogue is particularly preferred exhibiting the above-mentioned properties.

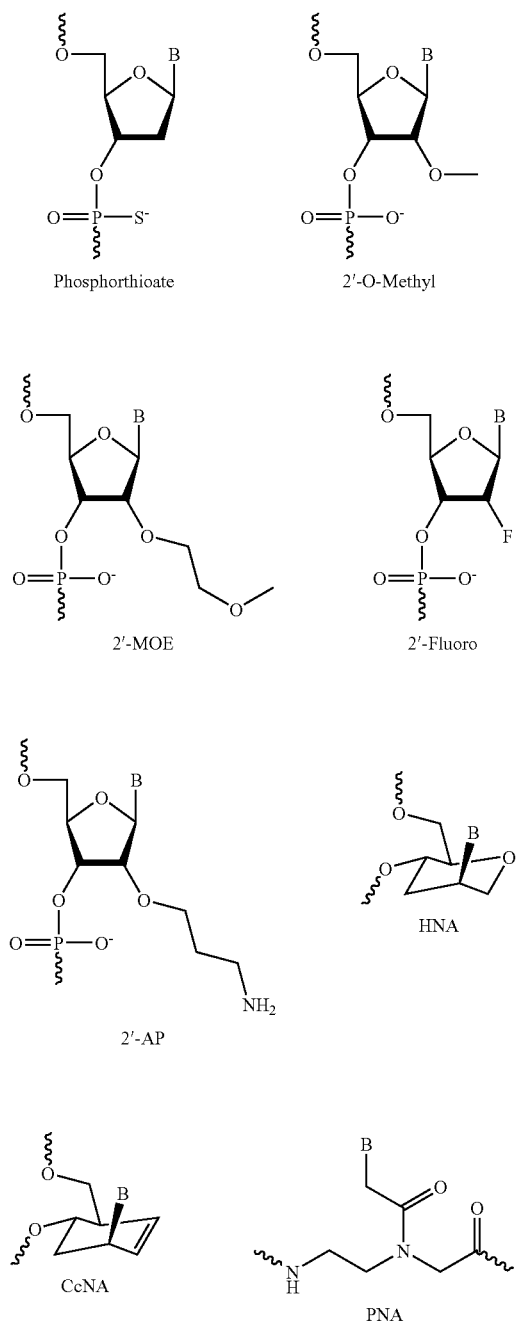

Scheme 1

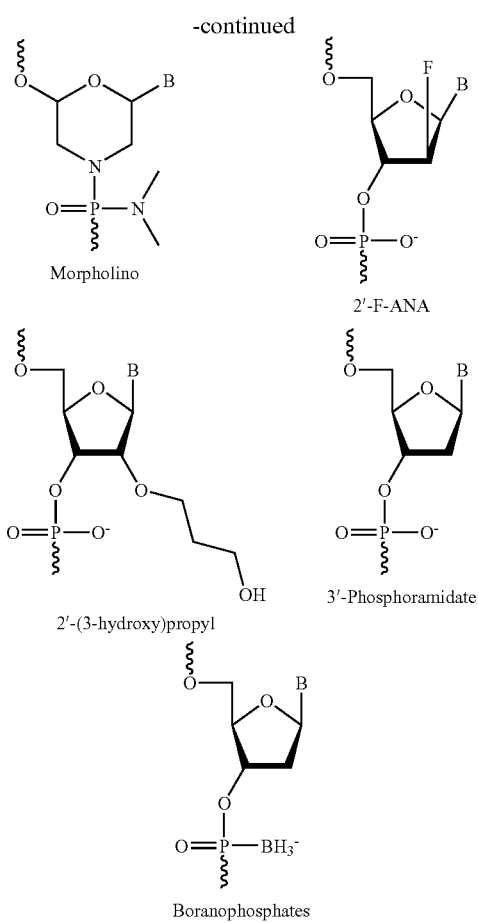

-continued

Morpholino

2'-F-ANA

2'-(3-hydroxy)propyl

3'-Phosphoramidate

Boranophosphates

By the term "unit" is understood a monomer.

The term "at least one" comprises the integers larger than or equal to 1, such as 1, 2, 3, 4, 5, 6, 7, 8, 9, 10, 11, 12, 13, 14, 15, 16, 17 and so forth.

The term "thio-LNA" comprises a locked nucleotide in which at least one of X or Y in Scheme 2 is selected from S or —CH$_2$—S—. Thio-LNA can be in both beta-D and alpha-L-configuration.

The term "amino-LNA" comprises a locked nucleotide in which at least one of X or Y in Scheme 2 —N(H)—, N(R)—, CH$_2$—N(H)—, —CH$_2$—N(R)— where R is selected form hydrogen and C$_{1-4}$-alkyl. Amino-LNA can be in both beta-D and alpha-L-configuration.

The term "oxy-LNA" comprises a locked nucleotide in which at least one of X or Y in Scheme 2 represents —O— or —CH$_2$—O—. Oxy-LNA can be in both beta-D and alpha-L-configuration.

The term "ena-LNA" comprises a locked nucleotide in which Y in Scheme 2 is —CH$_2$—O—.

By the term "alpha-L-LNA" comprises a locked nucleotide represented as shown in Scheme 3 (structure to the right).

By the term "LNA derivatives" comprises all locked nucleotide in Scheme 2 except beta-D-methylene LNA e.g. thio-LNA, amino-LNA, alpha-L-oxy-LNA and ena-LNA.

The term "linkage group" is intended to mean a group capable of covalently coupling together two nucleosides, two nucleoside analogues, a nucleoside and a nucleoside analogue, etc. Specific and preferred examples include phosphate groups and phosphorothioate groups.

In the present context the term "conjugate" is intended to indicate a heterogenous molecule formed by the covalent attachment of a compound as described herein (i.e. a compound comprising a sequence of nucleosides or nucleoside analogues) to one or more non-nucleotide or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethelene glycol.

The term "carcinoma" is intended to indicate a malignant tumor of epithelial origin. Epithelial tissue covers or lines the body surfaces inside and outside the body. Examples of epithelial tissue are the skin and the mucosa and serosa that line the body cavities and internal organs, such as intestines, urinary bladder, uterus, etc. Epithelial tissue may also extend into deeper tissue layers to from glands, such as mucus-secreting glands.

The term "sarcoma" is intended to indicate a malignant tumor growing from connective tissue, such as cartilage, fat, muscles, tendons and bones.

The term "glioma", when used herein, is intended to cover a malignant tumor originating from glial cells The term "a" as used about a nucleoside, a nucleoside analogue, a SEQ ID NO, etc. is intended to mean one or more. In particular, the expression "a component (such as a nucleoside, a nucleoside analogue, a SEQ ID NO or the like) selected from the group consisting of . . . " is intended to mean that one or more of the cited components may be selected. Thus, expressions like "a component selected from the group consisting of A, B and C" is intended to include all combinations of A, B and C, i.e. A, B, C, A+B, A+C, B+C and A+B+C.

In the present context, the term "C$_{1-4}$-alkyl" is intended to mean a linear or branched saturated hydrocarbon chain wherein the chain has from one to four carbon atoms, such as methyl, ethyl, n-propyl, isopropyl, n-butyl, isobutyl, sec-butyl and tert-butyl.

As used herein, the terms "target nucleic acid" encompass DNA encoding the survivin, RNA (including pre-mRNA and mRNA) transcribed from such DNA, and also cDNA derived from such RNA.

As used herein, the term "gene" means the gene including exons, introns, non-coding 5' and 3' regions and regulatory elements and all currently known variants thereof and any further variants, which may be elucidated.

As used herein, the terms "oligomeric compound" refers to an oligonucleotide which can induce a desired therapeutic effect in humans through for example binding by hydrogen bonding to either a target gene "Chimeraplast" and "TFO", to the RNA transcript(s) of the target gene "antisense inhibitors", "siRNA", "ribozymes" and oligozymes" or to the protein(s) encoding by the target gene "aptamer", spiegelmer" or "decoy".

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

As used herein, "hybridisation" means hydrogen bonding, which may be Watson-Crick, Holstein, reversed Holstein hydrogen bonding, etc. between complementary nucleoside or nucleotide bases. Watson and Crick showed approximately fifty years ago that deoxyribo nucleic acid (DNA) is composed of two strands which are held together in a helical configuration by hydrogen bonds formed between opposing complementary nucleobases in the two strands. The four nucleobases, commonly found in DNA are guanine (G), adenine (A), thymine (T) and cytosine (C) of which the G nucleobase pairs with C, and the A nucleobase pairs with T. In RNA the nucleobase thymine is replaced by the nucleobase uracil (U), which similarly to the T nucleobase pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

In the context of the present invention "complementary" refers to the capacity for precise pairing between two nucleotides or nucleoside sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA and the oligonucleotide are considered complementary to each other when a sufficient number of nucleotides in the oligonucleotide can form hydrogen bonds with corresponding nucleotides in the target DNA or RNA to enable the formation of a sTable complex. To be stable in vitro or in vivo the sequence of an antisense compound need not be 100% complementary to its target nucleic acid. The terms "complementary" and "specifically hybridisable" thus imply that the antisense compound binds sufficiently strongly and specifically to the target molecule to provide the desired interference with the normal function of the target whilst leaving the function of non-target mRNAs unaffected.

Figure 2:
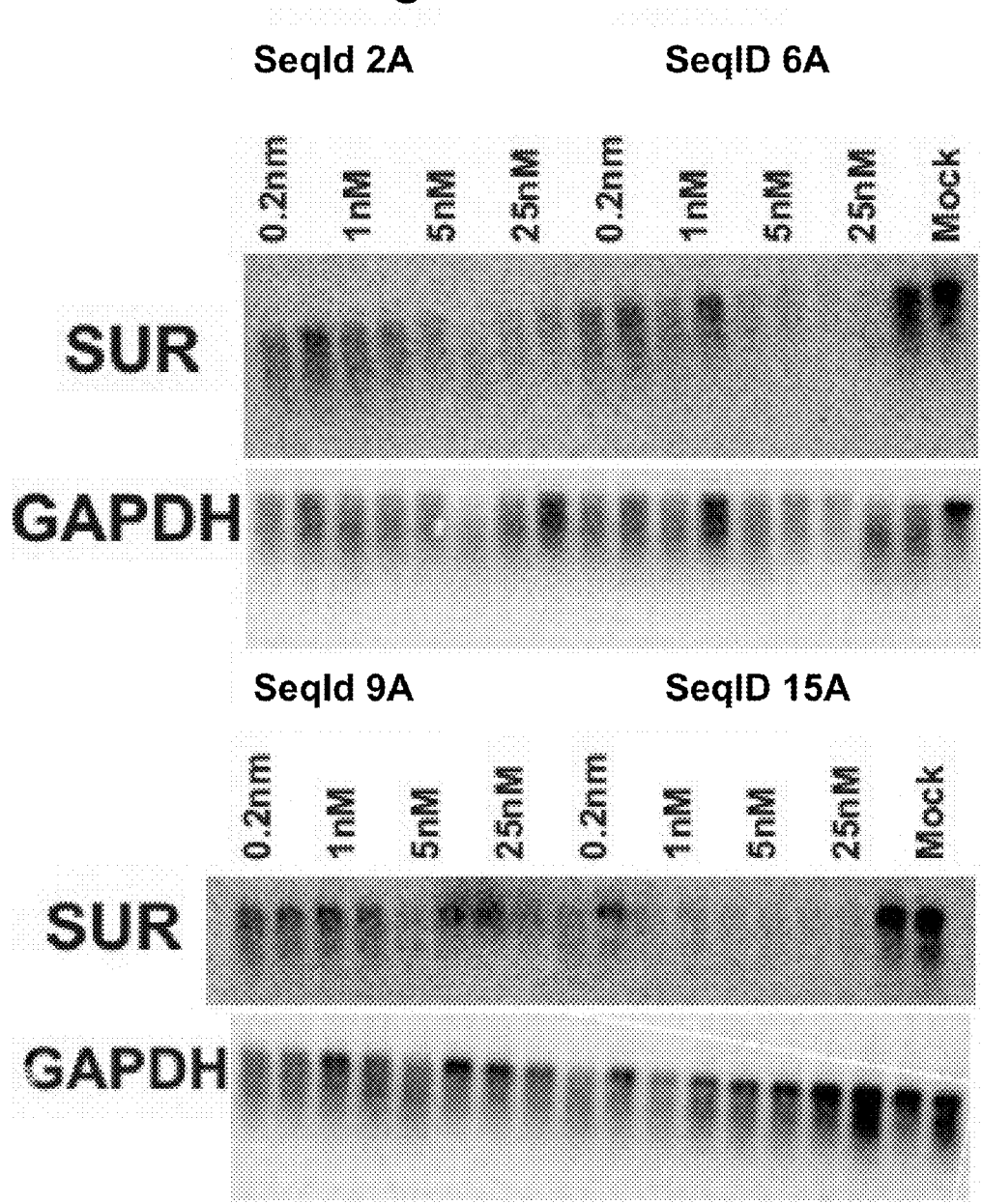
FIG. 2 Survivin mRNA downregulation by LNA antisense oligomeric compound. Northern blot of total RNA from 15PC3 that have been treated with 0.2, 1, 5, 25 nM compound 2A, 6A, 9A, 15A respectively. All compounds were effective inhibitors at low concentrations.

The oligomeric compounds according to the invention are potent modulators of target. For example, in vitro inhibition of target is shown in Table 1 measured by Real time PCR. FIG. 2 shows in vitro potency of oligomeric compounds according to the invention measured by Northern Blot. Very low $IC_{50}$ values of oligomeric compounds are shown in Table 3. All the above-mentioned experimental observations show that the compounds according to the invention can constitute the active compound in a pharmaceutical composition.

The subsequence of the compound of the invention is typically located within a sequence selected from the group consisting of SEQ ID NOS: 2, 3, 4, 5, 6, 7, 8, 9, 10, 11, 12, 13, 14, 15, 117, 118, 119, 120, 121, 122, 123, 124, 125, 126, 127, 128, 129, 130, 131, 132 and 133. The analogues of the nucleotides are suitably of nucleotides within the these sequences.

Typically, the compound of the invention comprises from 8-40 nucleotides, more typically 8-35 nucleotides, even more typically 8-30 nucleotides, suitably 8-25 nucleotides, more suitably 8-20 nucleotides, most suitably 12-20 nucleotides, such as 12, 13, 14, 15, 16, 17, 18, 19 or 20 nucleotides. In a highly attractive embodiment of the invention, the compound of the invention comprises 14-18 nucleotides, such as 14, 15, 16, 17 or 18 nucleotides, preferably 15-17 nucleotides, such as 15, 16 or 17 nucleotides, more typically 15 nucleotides, or 16 nucleotides, or 17 nucleotides.

In a suitable embodiment of the invention, the subsequence within the sequence of SEQ ID NOS: 2-144 is typically at least 8 nucleotides or nucleotide analogues, such as at least 9 nucleotides from within the sequence or nucleotide analogues of the nucleotides within said sequences. More typically, the subsequence is of at least 12 nucleotides or nucleotide analogues from within said sequences, such as at least 14 nucleotides or nucleotide analogues, such as 10, 11, 12, 13 14 15 or 16 nucleotides or nucleotide analogues.

The nucleotides are typically linked to each other by means of a linkage group selected from the group consisting of a phosphate group, a phosphorothioate group and a boranophosphate group. Suitably, some or all of the nucleotides are linked to each other by means of a phosphate group. Suitably, all nucleotides are linked to each other by means of a phosphate group.

Similarly, the nucleotides of the invention are typically linked to each other by means of a linkage group selected from the group consisting of a phosphate group, a phosphorothioate group and a boranophosphate group.

Preferred oligomeric compounds according to the invention are SEQ ID NO 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144 and their sequences are presented in Table 1.

In another embodiment of the invention, said nucleotides are linked to each other by means of a phosphorothioate group, such as all nucleotides being linked to each other by means of a phosphorothioate group. An interesting embodiment of the invention is directed to compounds of SEQ NO 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, and 144 wherein each linkage group within each compound is a phosphorothioate group. Such modifications is denoted by the subscript S. Alternatively stated, one aspect of the invention is directed to compounds of SEQ NO 147, 151, 155, 159, 163, 167, 171, 175, 179, 183, 187, 191, 195, 199, 204, 208, 212, 216, 220, 224, 228, 232, 236, 240, 244, 248, 252, 256, 260, 264, 268, 272, 276, 280, 284, 288, 292, 296, 300, 304, 308, 312, 316, 320, 324, 328, 332, 336, 340, 344, 348, 352, 356, 360, 364, 368, 372, 376, 380, 384, 388, 392, 396, 400, 404, 408, 412, 416, 420, 424, 428, 432, 436, 440, 444, 448, 452, 456, 460, 464, 468, 472, 476, 480, 484, 488, 492, 496, 500, 504, 508, 512, 516, 520, 524, 528, 532, 536, 540, 544, 548, 552, 556, 560, 564, 568, 572, 576, 580, 584, 588, 592, 596, 600, 604, 608, 612, 616, 620, 624, 628, 632, 636, 640, 644, 648, 652, 656, 660, 664, 668, 672, 676, 680, 684, 688, 692, 696, 700, 704, 708, 712 and 716.

A preferred subset of embodiments of the invention are compounds comprising sequences of the formula SEQ ID NOS 147, 155, 163, 175, 199, 612, 620, 632, 652, 656 and 664.

A further aspect of the invention is directed to compounds of SEQ NOS 148, 152, 156, 160, 164, 168, 172, 176, 180, 184, 188, 192, 196, 200, 205, 209, 213, 217, 221, 225, 229, 233, 237, 241, 245, 249, 253, 257, 261, 265, 269, 273, 277, 281, 285, 289, 293, 297, 301, 305, 309, 313, 317, 321, 325, 329, 333, 337, 341, 345, 349, 353, 357, 361, 365, 369, 373, 377, 381, 385, 389, 393, 397, 401, 405, 409, 413, 417, 421, 425, 429, 433, 437, 441, 445, 449, 453, 457, 461, 465, 469, 473, 477, 481, 485, 489, 493, 497, 501, 505, 509, 513, 517, 521, 525, 529, 533, 537, 541, 545, 549, 553, 557, 561, 565, 569, 573, 577, 581, 585, 589, 593, 597, 601, 605, 609, 613, 617, 621, 625, 629, 633, 637, 641, 645, 649, 653, 657, 661, 665, 669, 673, 677, 681, 685, 689, 693, 697, 701, 705, 709, 713 and 717.

A preferred subset of embodiments of the invention are compounds comprising sequences of the SEQ ID NOS 613, 617, 621, 625, 629, 633, 653, 657, 661 and 665.

A further aspect of the invention is directed to compounds of SEQ NOS 149, 153, 157, 161, 165, 169, 173, 177, 181, 185, 189, 193, 197, 201, 206, 210, 214, 218, 222, 226, 230, 234, 238, 242, 246, 250, 254, 258, 262, 266, 270, 274, 278, 282, 286, 290, 294, 298, 302, 306, 310, 314, 318, 322, 326, 330, 334, 338, 342, 346, 350, 354, 358, 362, 366, 370, 374, 378, 382, 386, 390, 394, 398, 402, 406, 410, 414, 418, 422, 426, 430, 434, 438, 442, 446, 450, 454, 458, 462, 466, 470, 474, 478, 482, 486, 490, 494, 498, 502, 506, 510, 514, 518, 522, 526, 530, 534, 538, 542, 546, 550, 554, 558, 562, 566, 570, 574, 578, 582, 586, 590, 594, 598, 602, 606, 610, 614, 618, 622, 626, 630, 634, 638, 642, 646, 650, 654, 658, 662, 666, 670, 674, 678, 682, 686, 690, 694, 698, 702, 706, 710, 714 and 718.

A further aspect of the invention is directed to compounds of SEQ NOS 150, 154, 158, 162, 166, 170, 174, 178, 182, 186, 190, 194, 198, 202, 207, 211, 215, 219, 223, 227, 231, 235, 239, 243, 247, 251, 255, 259, 263, 267, 271, 275, 279, 283, 287, 291, 295, 299, 303, 307, 311, 315, 319, 323, 327, 331, 335, 339, 343, 347, 351, 355, 359, 363, 367, 371, 375, 379, 383, 387, 391, 395, 399, 403, 407, 411, 415, 419, 423, 427, 431, 435, 439, 443, 447, 451, 455, 459, 463, 467, 471, 475, 479, 483, 487, 491, 495, 499, 503, 507, 511, 515, 519, 523, 527, 531, 535, 539, 543, 547, 551, 555, 559, 563, 567, 571, 575, 579, 583, 587, 591, 595, 599, 603, 607, 611, 615, 619, 623, 627, 631, 635, 639, 643, 647, 651, 655, 659, 663, 667, 671, 675, 679, 683, 687, 691, 695, 699, 703, 707, 711, 715 and 719.

A further aspect of the invention is directed to compounds of (SEQ ID NO: 203).

In an interesting embodiment, the compound of the invention comprises sequence 15E.

In a preferred embodiment, the compound of the invention comprises from 8-50 nucleotides, wherein said compound comprises a subsequence of at least 8 nucleotides, said subsequence being located within a sequence selected from the group consisting of SEQ ID NOS: 2-144, wherein at least one nucleotide is replaced by a corresponding nucleotide analogue. Typically, the compound of the invention comprises 1-50 nucleotide analogues, such as 2-45 nucleotide analogues, 3-40 nucleotide analogues, suitably 4-35 nucleotide analogues, 5-30 nucleotide analogues, 6-25 nucleotide analogues, typically 6-20 nucleotide analogues, more typically 6-14 nucleotide analogues, such as 6-12 nucleotide analogues, such as 6, 7, 8, 9, 10, 11 or 12 nucleotide analogues.

The inventors have found that compounds of the invention comprising from 6-16 nucleotide analogues with a different ribose unit suffice to have improved affinity over nucleotides. Thus, an interesting aspect of the invention relates to a compound of the invention comprising 6-10, such as 6, 7, 8, 9 or 10 nucleotide analogues with a different ribose unit, preferably 7, 8 or 9 nucleotide analogues with a different ribose unit, most typically 8 nucleotide analogues with a different ribose unit. Preferably, the nucleotide analogues with a different ribose unit is LNA The present inventors have further found that nucleotide analogues with a different ribose units and furthermore with a modified internucleoside linkade have a further improved effect for purposes of antisense modifications. Thus, the 6-16 nucleotide analogues may have a modified ribose unit, a different linkage group, or both.

Suitably, all nucleotides are replaced by a corresponding nucleotide analogues.

A preferred nucleotide analogue of the invention is LNA.

A further preferred nucleotide analogue of the invention is wherein the internucleoside phosphate linkage is a phosphorothioate.

A still further preferred nucleotide analogue is wherein the nucleotide is LNA with an internucleoside phosphorothioate linkage.

In an interesting embodiment, the compound of the invention comprises from 8-50 nucleotides, wherein said compound comprises a subsequence of at least 8 nucleotides, said subsequence being located within a sequence selected from the group consisting of SEQ ID NOS: 2-144, wherein at least one nucleotide is replaced by a corresponding nucleotide analogue and wherein the 3' end comprises nucleotide, rather than a nucleotide analogue.

In a particularly interesting embodiment, the compound comprises at least one of nucleotide analogues, wherein said nucleotide analogue is a locked nucleic acid (LNA) of the formula

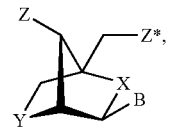

wherein Z and Z* are independently absent, selected among an internucleoside linkage, a terminal group or a protecting group; wherein X and Y are independently selected from the group consisting of O, S, NR, $CH_2$, CH, (if part of a double bond), $CH_2$—O, $CH_2$—S, $CH_2$—NR, $CH_2$—$CH_2$, $CH_2$—CH (if part of a double bond) and CH=CH, where R is hydrogen or $C_{1-4}$-alkyl. The bonds represent connection to the linkage group. Typically, X is O and Y are independently selected from the group consisting of O, S and NR, where R is hydrogen or $C_{1-4}$-alkyl. More typically, X is O and Y is selected from the group consisting of O, S and NH. Most typically, X is O and Y is O. In embodiments wherein at least one of the LNA nucleotides is at the 3'-end, at said position Z is a terminal group and Z* is an internucleoside linkage. In embodiments wherein at least one of the LNA nucleotides is at the 5'-end, at said position Z is absent and Z* is a terminal group. Within the nucleotide sequence, Z is absent and Z* is an internucleoside linkage In a suitable embodiment of the invention comprising LNA as the nucleotide analogues, said LNA is in the β-D or alpha-L also form, preferably in the β-D form.

In embodiments of the invention comprising at least one LNA as the nucleotide analogues, such as 1-50 LNA nucleotide analogues, such as 2-45 LNA nucleotide analogues, 3-40 LNA nucleotide analogues, suitably 4-35 LNA nucleotide analogues, 5-30 LNA nucleotide analogues, 6-25 LNA nucleotide analogues, typically 6-20 LNA nucleotide analogues, more typically 6-14 LNA nucleotide analogues, such as 6-12 LNA nucleotide analogues, such as 6, 7, 8, 9, 10, 11 or 12 LNA nucleotide analogues said nucleotides and/or nucleotide analogues are linked to each other by means of a linkage group selected from the group consisting of a phosphate group, a phosphorothioate group and a boranophosphate group. In a suitable embodiment of the invention comprising LNA nucleotide analogues, said nucleotides and/or nucleotide analogues are linked to each other by means of a phosphate group. In a preferred embodiment of the invention comprising LNA nucleotide analogues said nucleotides and/or nucleotide analogues are linked to each other by means of a phosphorothioate group.

In a combination of interesting embodiment, in embodiments of the invention comprising LNA nucleotide analogues said nucleotide and/or nucleotide analogues are linked to each other by means of a phosphorothioate group, wherein X is O and Y is O, and said LNA is in the β-D form.

In embodiments of the compound of the invention comprising from 8-50 nucleotides, wherein said compound comprises a subsequence of at least 8 nucleotides, said subsequence being located within a sequence selected from the group consisting of SEQ ID NOS: 2-144 and said nucleotides comprising LNA nucleotide analogues, the subsequence typically may comprise a stretch of 2-6 LNAs, as defined herein, followed by a stretch of 4-12 nucleotides, which is followed by a stretch of 2-6 LNAs, as defined herein.

Subsequences comprising a stretch of LNAs, followed by a stretch of nucleotides, followed by a stretch of LNAs are known as gapmers.

Suitably, said subsequence comprises a stretch of 4 LNAs, as defined herein, followed by a stretch of 8 nucleotides, which is followed by a stretch of 4 LNAs as defined herein.

In embodiments of the compound of the invention comprising from 8-50 nucleotides, wherein said compound comprises a subsequence of at least 8 nucleotides, said subsequence being located within a sequence selected from the group consisting of SEQ ID NOS: 2-144 and said 8-50 nucleotides comprising LNA nucleotide analogues, said subsequence may comprises a stretch of 2-6 LNAs as defined herein, followed by a stretch of 4-12 nucleotides, which is followed by a stretch of 2-5 LNAs as defined herein, which is followed by 1-4 nucleotides, such as 1 or 2 nucleotides, more typically a single nucleoside. The 1-4 nucleotides, 1 or 2 nucleotides or single nucleotide is typically located at the 3' end of the subsequence and more typically at the 3' end of the oligomer.

In embodiments of the compound of the invention comprising from 8-50 nucleotides, wherein said compound comprises a subsequence of at least 8 nucleotides, said subsequence being located within a sequence selected from the group consisting of SEQ ID NOS: 2-144 and said nucleotides comprising LNA nucleotide analogues, said subsequence may typically comprise a stretch of 4 LNAs as defined herein, followed by a stretch of 8 nucleotides, which is followed by a stretch of 3 LNAs as defined herein, which is followed by a single natural nucleotide. The single nucleotide is typically located at the 3' end of the subsequence and more typically at the 3' end of the oligomer.

In embodiments of the compound of the invention comprising from 8-50 nucleotides, wherein said compound comprises a subsequence of at least 8 nucleotides, said subsequence being located within a sequence selected from the group consisting of SEQ ID NOS: 2-144 and said nucleotides comprising LNA nucleotide analogues, said subsequence comprising a stretch of LNAs, followed by a stretch of nucleotides, which is followed by a stretch of LNAs as defined herein as gapmers, said nucleotides and/or LNAs are linked to each other by means of a linkage group selected from the group consisting of a phosphate group, a phosphorothioate group and a boranophosphate group.

Suitably, said nucleotides and/or said LNAs are linked together by means of phosphate groups. Typically, said nucleotides and/or said LNAs are linked together by means of phosphorothioate groups.

In embodiments of the compound of the invention comprising a total of from 8-50 nucleotides and/or nucleotide analogues, wherein said compound comprises a subsequence of at least 8 nucleotides, said subsequence being located within a sequence selected from the group consisting of SEQ ID NOS: 2-144 and wherein said subsequence may consist of a stretch of 4 LNAs, as defined herein, a stretch of 8 nucleotides, and a stretch of 4 LNAs, as defined herein, so as to make a total of 16 nucleotides and nucleotide analogues in said subsequence, said nucleotides and said LNAs are linked together by means of phosphorothioate groups.

In a suitable embodiment, the subsequence is SEQ ID NO: 147. In a suitable embodiment, the subsequence is SEQ ID NO: 151. In a suitable embodiment, the subsequence is SEQ ID NO:155. In a suitable embodiment, the subsequence is SEQ ID NO: 159. In a suitable embodiment, the subsequence is SEQ ID NO: 163. In a suitable embodiment, the subsequence is SEQ ID NO: 167. In a suitable embodiment, the subsequence is SEQ ID NO: 171. In a suitable embodiment, the subsequence is SEQ ID NO: 175. In a suitable embodiment, the subsequence is SEQ ID NO: 179. In a suitable embodiment, the subsequence is SEQ ID NO: 183. In a suitable embodiment, the subsequence is SEQ ID NO: 187. In a suitable embodiment, the subsequence is SEQ ID NO: 191. In a suitable embodiment, the subsequence is SEQ ID NO: 195. In a suitable embodiment, the subsequence is SEQ ID NO: 199. In a suitable embodiment, the subsequence is SEQ ID NO: 608. In a suitable embodiment, the subsequence is SEQ ID NO: 612. In a suitable embodiment, the subsequence is SEQ ID NO: 616. In a suitable embodiment, the subsequence is SEQ ID NO: 620. In a suitable embodiment, the subsequence is SEQ ID NO: 624. In a suitable embodiment, the subsequence is SEQ ID NO: 628. In a suitable embodiment, the subsequence is SEQ ID NO: 632. In a suitable embodiment, the subsequence is SEQ ID NO: 636. In a suitable embodiment, the subsequence is SEQ ID NO: 640. In a suitable embodiment, the subsequence is SEQ ID NO: 644. In a suitable embodiment, the subsequence is SEQ ID NO: 648. In a suitable embodiment, the subsequence is SEQ ID NO: 652. In a suitable embodiment, the subsequence is SEQ ID NO: 656. In a suitable embodiment, the subsequence is SEQ ID NO: 660. In a suitable embodiment, the subsequence is SEQ ID NO: 664. In a suitable embodiment, the subsequence is SEQ ID NO: 668. In a suitable embodiment, the subsequence is SEQ ID NO: 672. In the immediately aforementioned individual suitable embodiments wherein the subsequence is one selected from SEQ ID NOS: 148, 152, 156, 160, 164, 168, 172, 176, 180, 184, 188, 192, 196, 200, 205, 209, 213, 217, 221, 225, 229, 233, 237, 241, 245, 249, 253, 257, 261, 265, 269, 273, 277, 281, 285, 289, 293, 297, 301, 305, 309, 313, 317, 321, 325, 329, 333, 337, 341, 345, 349, 353, 357, 361, 365, 369, 373, 377, 381, 385, 389, 393, 397, 401, 405, 409, 413, 417, 421, 425, 429, 433, 437, 441, 445, 449, 453, 457, 461, 465, 469, 473, 477, 481, 485, 489, 493, 497, 501, 505, 509, 513, 517, 521, 525, 529, 533, 537, 541, 545, 549, 553, 557, 561, 565, 569, 573, 577, 581, 585, 589, 593, 597, 601, 605, 609, 613, 617, 621, 625, 629, 633, 637, 641, 645, 649, 653, 657, 661, 665, 669, 673, 677, 681, 685, 689, 693, 697, 701, 705, 709, 713 and 717, the 3' end LNA of the subsequence may suitably be replaced by the corresponding nucleotide.

In a further suitable embodiment, the compound of the invention is a sequence selected from the group consisting of SEQ ID NOS: 2-144 and wherein said sequence consisting of a stretch of 4 LNAs, as defined herein, a stretch of 8 nucleotides, and a stretch of 4 LNAs, as defined herein, so as to make a total of 16 nucleotides and nucleotide analogues in said compound, said nucleotides and said LNAs being linked together by means of phosphorothioate groups.

In a suitable embodiment, the compound consists of SEQ ID NO:147. In a suitable embodiment, the compound consists of SEQ ID NO: 151. In a suitable embodiment, the compound consists of SEQ ID NO: 155. In a suitable embodiment, the compound consists of SEQ ID NO: 159. In a suitable embodiment, the compound consists of SEQ ID NO: 163. In a suitable embodiment, the compound consists of SEQ ID NO: 167. In a suitable embodiment, the compound consists of SEQ ID NO: 171. In a suitable embodiment, the compound consists of SEQ ID NO: 175. In a suitable embodiment, the compound consists of SEQ ID NO: 179. In a suitable embodiment, the compound consists of SEQ ID NO: 183. In a suitable embodiment, the compound consists of SEQ ID NO: 187. In a suitable embodiment, the compound consists of SEQ ID NO: 191. In a suitable embodiment, the compound consists of SEQ ID NO: 195. In a suitable embodiment, the compound consists of SEQ ID NO: 199. In a suitable embodiment, the compound consists of SEQ ID NO: 608. In a suitable embodiment, the compound consists of SEQ ID NO: 612. In a suitable embodiment, the compound consists of SEQ ID NO: 616. In a suitable embodiment, the compound consists of SEQ ID NO: 620. In a suitable embodiment, the compound consists of SEQ ID NO: 624. In a suitable embodiment, the compound consists of SEQ ID NO: 628. In a suitable embodiment, the compound consists of SEQ ID NO: 632. In a suitable embodiment, the compound consists of SEQ ID NO: 636. In a suitable embodiment, the compound consists of SEQ ID NO: 640. In a suitable embodiment, the compound consists of SEQ ID NO: 644. In a suitable embodiment, the compound consists of SEQ ID NO: 648. In a suitable embodiment, the compound consists of SEQ ID NO: 652. In a suitable embodiment, the compound consists of SEQ ID NO: 656. In a suitable embodiment, the compound consists of SEQ ID NO: 660. In a suitable embodiment, the compound consists of SEQ ID NO: 664. In a suitable embodiment, the compound consists of SEQ ID NO: 668. In a suitable embodiment, the compound consists of SEQ ID NO: 672. In the immediately aforementioned individual suitable embodiments wherein the compound is one selected from SEQ ID NOS: 147, 151, 155, 159, 163, 167, 171, 175, 179, 183, 187, 191, 195, 199, 204, 208, 212, 216, 220, 224, 228, 232, 236, 240, 244, 248, 252, 256, 260, 264, 268, 272, 276, 280, 284, 288, 292, 296, 300, 304, 308, 312, 316, 320, 324, 328, 332, 336, 340, 344, 348, 352, 356, 360, 364, 368, 372, 376, 380, 384, 388, 392, 396, 400, 404, 408, 412, 416, 420, 424, 428, 432, 436, 440, 444, 448, 452, 456, 460, 464, 468, 472, 476, 480, 484, 488, 492, 496, 500, 504, 508, 512, 516, 520, 524, 528, 532, 536, 540, 544, 548, 552, 556, 560, 564, 568, 572, 576, 580, 584, 588, 592, 596, 600, 604, 608, 612, 616, 620, 624, 628, 632, 636, 640, 644, 648, 652, 656, 660, 664, 668, 672, 676, 680, 684, 688, 692, 696, 700, 704, 708, 712 and 716, the 3' end LNA of the compound may suitably be replaced by the corresponding nucleotide.

A further aspect of the invention relates to a conjugate comprising the compound as defined herein at least one non-nucleotide or non-polynucleotide moiety covalently attached to said compound.

In a related aspect of the invention, the compound of the invention is linked to ligands so as to form a conjugates said ligands intended to increase the cellular uptake of the conjugate relative to the antisense oligonucleotides. This conjugation can take place at the terminal positions 5'/3'-OH but the ligands may also take place at the sugars and/or the bases. In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/lingands are cholesterol moieties, duplex intercalators such as acridine, poly-L-lysine, "end-capping" with one or more nuclease-resistant linkage groups such as phosphoromonothioate, and the like.

The preparation of transferrin complexes as carriers of oligonucleotide uptake into cells is described by Wagner et al., *Proc. Natl. Acad. Sci. USA* 87, 3410-3414 (1990). Cellular delivery of folate-macromolecule conjugates via folate receptor endocytosis, including delivery of an antisense oligonucleotide, is described by Low et al., U.S. Pat. No. 5,108, 921. Also see, Leamon et al., *Proc. Natl. Acad. Sci.* 88, 5572 (1991).

The compounds or conjugates of the invention may also be conjugated or further conjugated to active drug substances, for example, aspirin, ibuprofen, a sulfa drug, an antidiabetic, an antibacterial agent, a chemotherapeutic agent or an antibiotic.

A particularly interesting aspect of the invention is directed to a pharmaceutical composition comprising a compound as defined herein or a conjugate as defined herein, and a pharmaceutically acceptable diluent, carrier or adjuvant.

It should be understood that the present invention also particularly relevant for a pharmaceutical composition, which comprises a least one antisense oligonucleotide construct of the invention as an active ingredient. It should be understood that the pharmaceutical composition according to the invention optionally comprises a pharmaceutical carrier, and that the pharmaceutical composition optionally comprises further antisense compounds, chemotherapeutic agents, anti-inflammatory compounds, antiviral compounds and/or immuno-modulating compounds.

As stated, the pharmaceutical composition of the invention may further comprise at least one chemotherapeutic agent. The chemotherapeutic compound is typically selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab);

hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine).

The oligomeric compound or conjugate comprised in this invention can be employed in a variety of pharmaceutically acceptable salts. As used herein, the term refers to salts that retain the desired biological activity of the herein identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combinations of (a) and (b); e.g., a zinc tannate salt or the like.

In one embodiment of the invention the oligomeric compound of conjugate may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthioethyl (t-butyl-SATE). These protection groups are nuclease resistant and are selectively removed intracellulary.

The invention also includes the formulation of one or more oligonucleotide compound or conjugate as disclosed herein. Pharmaceutically acceptable binding agents and adjuvants may comprise part of the formulated drug. Capsules, Tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion.

An oligonucleotide of the invention may be mixed with any material that do not impair the desired action, or with material that supplement the desired action. These could include other drugs including other nucleotide compounds.

For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

Preferably, an oligomeric compound is included in a unit formulation such as in a pharmaceutically accepTable carrier or diluent in an amount sufficient to deliver to a patient a therapeutically effective amount without causing serious side effects in the treated patient.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the active oligo is administered IV, IP, orally, topically or as a bolus injection or administered directly in to the target organ.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, Tablets or miniTablets. Compositions and formulations for parenteral, intrathecal or intraventricular administration may include sterile aqueous solutions which may also contain buffers, diluents and other suiTable additives such as, but not limited to, penetration enhancers, carrier compounds and other pharmaceutically accepTable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, Tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

LNA containing oligomeric compound are useful for a number of therapeutic applications as indicated above. In general, therapeutic methods of the invention include administration of a therapeutically effective amount of an LNA-modified oligonucleotide to a mammal, particularly a human.

In a certain embodiment, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention.

Anti-inflammatory drugs, including but not limited to non-steroidal anti-inflammatory drugs and corticosteroids, antiviral drugs, and immuno-modulating drugs may also be combined in compositions of the invention. Two or more combined compounds may be used together or sequentially.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

Dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient.

Optimum dosages may vary depending on the relative potency of individual oligonucleotides. Generally it can be estimated based on EC50s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

As stated, in an interesting embodiment of the invention, the oligomeric compounds contain at least one unit of chemistry termed LNA (Locked Nucleic Acid).

LNA monomer typically refers to a bicyclic nucleotide analogue wherein the nucleoside moiety is an analogue as described in the International Patent Application WO 99/14226 and subsequent applications, WO0056746, WO0056748, WO0066604, WO000125248, WO0228875, WO2002094250 and PCT/DK02/00488 all incorporated herein by reference. Preferred LNA nucleotide structures for forming a compound of the invention are exemplified in Scheme 2

Scheme 2

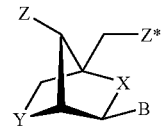

wherein X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected form hydrogen and C$_{1-4}$-alky; wherein Z and Z* are independently absent, selected among an internucleoside linkage, a terminal group or a protecting group. In embodiments wherein at least one of the LNA nucleotides is at the 3'-end, at said position Z is a terminal group and Z* is an internucleoside linkage. In embodiments wherein at least one of the LNA nucleotides is at the 5'-end, at said position Z is absent and Z* is a terminal group. Within the nucleotide sequence, Z is absent and Z* is an internucleoside linkage. The asymmetric groups may be found in either orientation. In Scheme 2, the 4 chiral centers are shown in a fixed configuration. However, the configurations in Scheme 2 are not necessarily fixed. Also comprised in this invention are compounds of the general Scheme 2 in which the chiral centers are found in different configurations, such as those represented in Scheme 3 or 4. Thus, the intention in the illustration of Scheme 2 is not to limit the configuration of the chiral centre. Each chiral center in Scheme 2 can exist in either R or S configuration. The definition of R (rectus) and S (sinister) are described in the IUPAC 1974 Recommendations, Section E, Fundamental Stereochemistry: The rules can be found in Pure Appl. Chem. 45, 13-30, (1976) and in "Nomenclature of organic Chemistry" pergamon, New York, 1979.

Z and Z* serve for forming an internucleoside linkage, are a terminal group or a protecting group, depending on the position of the LNA within the compound, namely within the subsequence or at the 3' end of the subsequence or compound.

The internucleoside linkage may be —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R$^H$)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected form hydrogen and C$_{1-4}$-alkyl, The terminal groups are selected independently among from hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl) amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, monothiophosphate, diphosphate, dithiophosphate, triphosphate, trithiophosphate, DNA intercalators, photochemically active groups, thermochemically active groups, chelating groups, reporter groups, ligands, carboxy, sulphono, hydroxymethyl, Prot-O—CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH, and —NH(R$^H$), respectively, Act is an activation group for —OH, —SH, and —NH (R$^H$), respectively, and R$^H$ is selected from hydrogen and C$_{1-6}$-alkyl;

The protection groups of hydroxy substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetrahydro-pyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-Cl$_2$Bzl). Alternatively when Z or Z* is hydroxyl they may be protected by attachment to a solid support optionally through a linker.

When Z or Z* is amino groups illustrative examples of the amino protection protections are fluorenylmethoxycarbonylamino (Fmoc), tert-butyloxycarbonylamino (BOC), trifluoroacetylamino, allyloxycarbonylamino (alloc, AOC), Z benzyloxycarbonylamino (Cbz), substituted benzyloxycarbonylaminos such as 2-chloro benzyloxycarbonylamino (2-ClZ), monomethoxytritylamino (MMT), dimethoxytritylamino (DMT), phthaloylamino, and 9-(9-phenyl)xanthenylamino (pixyl).

In the embodiment above, Act designates an activation group for —OH, —SH, and —NH(R$^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designate optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designate isopropyl. Thus, an especially relevant phosphoramidite is N,N-diisopropyl-O-(2-cyanoethyl)phosphoramidite.

B constitutes a natural or non-natural nucleobase and selected among adenine, cytosine, 5-methylcytosine, isocytosine, pseudoisocytosine, guanine, thymine, uracil, 5-bromouracil, 5-propynyluracil, 5-propyny-6-fluoroluracil, 5-methylthiazoleuracil, 6-aminopurine, 2-aminopurine, inosine, 2,6-diaminopurine, 7-propyne-7-deazaadenine, 7-propyne-7-deazaguanine, 2-chloro-6-aminopurine.

Particularly preferred bicyclic structures are shown in Scheme 3 below:

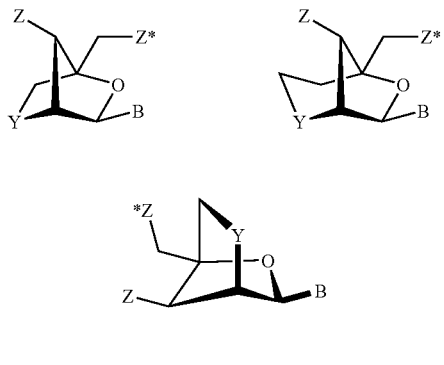

Where Y is —O—, —S—, —NH—, or N(R$^H$),

Z and Z* are independently absent, selected among an internucleoside linkage, a terminal group or a protecting group. In embodiments wherein at least one of the LNA nucleotides is at the 3'-end, at said position Z is a terminal group and Z* is an internucleoside linkage. In embodiments wherein at least one of the LNA nucleotides is at the 5'-end, at said position Z is absent and Z* is a terminal group. Within the nucleotide sequence, Z is absent and Z* is an internucleoside linkage.

The internucleotide linkage may be —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected form hydrogen and C$_{1-4}$-alkyl.

The terminal groups are selected independently among from hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl) amino, optionally substituted C$_{1-6}$-alkoxy, optionally substituted C$_{1-6}$-alkyl, optionally substituted monophosphate, monothiophosphate, diphosphate, dithiophosphate triphosphate, trithiophosphate, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl.

The protection groups of hydroxy substituents comprises substituted trityl, such as 4,4'-dimethoxytrityloxy (DMT), 4-monomethoxytrityloxy (MMT), optionally substituted 9-(9-phenyl)xanthenyloxy (pixyl), optionally substituted methoxytetrahydropyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl Alternatively when Z or Z* is hydroxyl they may be protected by attachment to a solid support optionally through a linker.

Specifically preferred LNA units are shown in scheme 4.

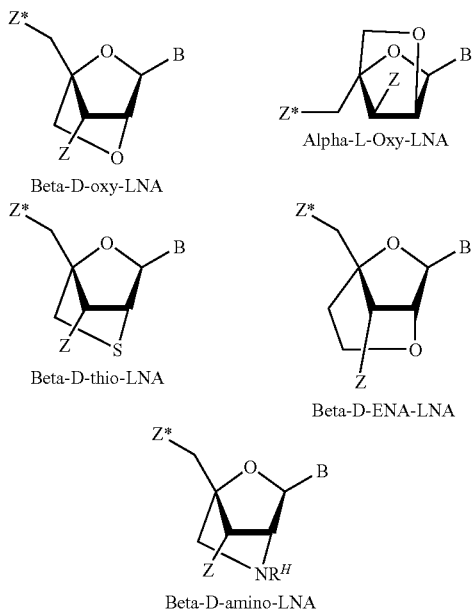

Scheme 4

Beta-D-oxy-LNA

Alpha-L-Oxy-LNA

Beta-D-thio-LNA

Beta-D-ENA-LNA

Beta-D-amino-LNA

When Z or Z* is amino groups, illustrative examples of the amino protection protections are fluorenylmethoxycarbonylamino (Fmoc), tert-butyloxycarbonylamino (BOC), trifluoroacetylamino, allyloxycarbonylamino (alloc, AOC), monomethoxytritylamino (MMT), dimethoxytritylamino (DMT), phthaloylamino.

In the embodiments above, Act designates an activation group for —OH, —SH, and —NH($R^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, and each of $R^y$ designate optionally substituted alkyl groups, $R^x$ preferably designates 2-cyanoethyl and the two $R^y$ are preferably identical and designate isopropyl. Thus, an especially relevant phosphoramidite is N,N-diisopropyl-O-(2-cyanoethyl)-phosphoramidite.

B, in the context of Schemes 3 and 4, constitutes a natural or non-natural nucleobase and selected among adenine, cytosine, 5-methylcytosine, isocytosine, pseudoisocytosine, guanine, thymine, uracil, 5-bromouracil, 5-propynyluracil, 6-aminopurine, 2-aminopurine, inosine, diaminopurine, 2-chloro-6-aminopurine.

A person skilled in the art will appreciate that oligomeric compounds containing LNA can be used to combat survivin linked diseases by many different principles, which thus falls within the spirit of the present invention.

For instance, LNA oligomeric compounds may be designed as antisense inhibitors, which are single stranded nucleic acids that prevent the production of a disease causing protein, by intervention at the mRNA level. Also, they may be designed as Ribozymes or Oligozymes which are antisense oligonucleotides which in addition to the target binding domain(s) comprise a catalytic activity that degrades the target mRNA (ribozymes) or comprise an external guide sequence (EGS) that recruit an endogenous enzyme (RNase P) which degrades the target mRNA (oligozymes)

Equally well, the LNA oligomeric compounds may be designed as siRNA's which are small double stranded RNA molecules that are used by cells to silence specific endogenous or exogenous genes by an as yet poorly understood "antisense-like" mechanism.

LNA oligomeric compounds may also be designed as Aptamers (and a variation thereof, termed Spiegelmers) which are nucleic acids that through intra-molecular hydrogen bonding adopt three-dimensional structures that enable them to bind to and block their biological targets with high affinity and specificity. Also, LNA oligomeric compounds may be designed as Decoys, which are small double-stranded nucleic acids that prevent cellular transcription factors from transactivating their target genes by selectively blocking their DNA binding site.

Furthermore, LNA oligomeric compounds may be designed as Chimeraplasts, which are small single stranded nucleic acids that are able to specifically pair with and alter a target gene sequence. LNA containing oligomeric compounds exploiting this principle therefore may be particularly useful for treating survivin linked diseases that are caused by a mutation in the survivin gene.

Dictated in part by the therapeutic principle by which the oligonucleotide is intended to operate, the LNA oligomeric compounds in accordance with this invention preferably comprise from about 8 to about 60 nucleobases i.e. from about 8 to about 60 linked nucleotides. Particularly preferred compounds are antisense oligonucleotides comprising from about 12 to about 30 nucleobases and most preferably are antisense compounds comprising about 12-20 nucleobases. The compounds shown in Table 1 and 2 are all 16-mers.

Referring to the above principles by which an LNA oligomeric compound can elicit its therapeutic action the target of the present invention may be the survivin gene, the mRNA or the protein. In the most preferred embodiment the LNA oligomeric compounds is designed as an antisense inhibitor directed against the survivin pre-mRNA or survivin mRNA. The oligonucleotides may hybridize to any site along the survivin pre-mRNA or mRNA such as sites in the 5' untranslated leader, exons, introns and 3' untranslated tail.

In a preferred embodiment, the oligonucleotide hybridizes to a portion of the human survivin pre-mRNA or mRNA that comprises the translation-initiation site. More preferably, the survivin oligonucleotide comprises a CAT sequence, which is complementary to the AUG initiation sequence of the survivin pre-mRNA or RNA. In another embodiment, the survivin oligonucleotide hybridizes to a portion of the splice donor site of the human survivin pre-mRNA. In yet another embodiment, survivin oligonucleotide hybridizes to a portion of the splice acceptor site of the human survivin pre-mRNA. In another embodiment, the survivin oligonucleotide hybridizes to portions of the human survivin pre-mRNA or mRNA involved in polyadenylation, transport or degradation.

The skilled person will appreciate that preferred oligonucleotides are those that hybridize to a portion of the survivin pre-mRNA or mRNA whose sequence does not commonly occur in transcripts from unrelated genes so as to maintain treatment specificity.

The oligomeric compound of the invention are designed to be sufficiently complementary to the target to provide the desired clinical response e.g. the oligomeric compound must bind with sufficient strength and specificity to its target to give the desired effect. In one embodiment, said compound modulating survivin is designed so as to also modulate other specific nucleic acids which do not encode survivin.

It is preferred that the oligomeric compound according to the invention is designed so that intra- and intermolecular oligonucleotide hybridisation is avoided.

In many cases the identification of an LNA oligomeric compound effective in modulating survivin activity in vivo or clinically is based on sequence information on the target gene. However, one of ordinary skill in the art will appreciate that such oligomeric compounds can also be identified by empirical testing. As such survivin oligomeric compounds having, for example, less sequence homology, greater or fewer modified nucleotides, or longer or shorter lengths, compared to those of the preferred embodiments, but which nevertheless demonstrate responses in clinical treatments, are also within the scope of the invention.

In one embodiment of the invention the oligomeric compounds are suitable antisense drugs. The design of a potent and safe antisense drug requires the fine-tuning of diverse parameters such as affinity/specificity, stability in biological fluids, cellular uptake, mode of action, pharmacokinetic properties and toxicity.

Affinity & specificity: LNA with an oxymethylene 2'-O, 4'-C linkage (β-D-oxy-LNA), exhibits unprecedented binding properties towards DNA and RNA target sequences. Likewise LNA derivatives, such as amino-, thio- and α-L-oxy-LNA display unprecedented affinities towards complementary RNA and DNA and in the case of thio-LNA the affinity towards RNA is even better than with the β-D-oxy-LNA.

In addition to these remarkable hybridization properties, LNA monomers can be mixed and act cooperatively with DNA and RNA monomers, and with other nucleic acid analogues, such as 2'-O-alkyl modified RNA monomers. As such, the oligonucleotides of the present invention can be composed entirely of β-D-oxy-LNA monomers or it may be composed of β-D-oxy-LNA in any combination with DNA, RNA or contemporary nucleic acid analogues which includes LNA derivatives such as for instance amino-, thio- and α-L-oxy-LNA. The unprecedented binding affinity of LNA towards DNA or RNA target sequences and its ability to mix freely with DNA, RNA and a range of contemporary nucleic acid analogues has a range of important consequences according to the invention for the development of effective and safe antisense compounds.

Firstly, in one embodiment of the invention it enables a considerable shortening of the usual length of an antisense oligo (from 20-25 mers to, e.g., 12-16 mers) without compromising the affinity required for pharmacological activity. As the intrinsic specificity of an oligo is inversely correlated to its length, such a shortening will significantly increase the specificity of the antisense compound towards its RNA target. One embodiment of the invention is to, due to the sequence of the humane genome is available and the annotation of its genes rapidly progressing, identify the shortest possible, unique sequences in the target mRNA.

In another embodiment, the use of LNA to reduce the size of oligos significantly eases the process and prize of manufacture thus providing the basis for antisense therapy to become a commercially competitive treatment offer for a diversity of diseases.

In another embodiment, the unprecedented affinity of LNA can be used to substantially enhance the ability of an antisense oligo to hybridize to its target mRNA in-vivo thus significantly reducing the time and effort required for identifying an active compound as compared to the situation with other chemistries.

In another embodiment, the unprecedented affinity of LNA is used to enhance the potency of antisense oligonucleotides thus enabling the development of compounds with more favorable therapeutic windows than those currently in clinical trials.

When designed as an antisense inhibitor, the oligonucleotides of the invention bind to the target nucleic acid and modulate the expression of its cognate protein. Preferably, such modulation produces an inhibition of expression of at least 10% or 20% compared to the normal expression level, more preferably at least a 30%, 40%, 50%, 60%, 70%, 80%, or 90% inhibition compared to the normal expression level.

Typically, the LNA oligonucleotides of the invention will contain other residues than β-D-oxy-LNA such as native DNA monomers, RNA monomers, N3'-P5' phosphoroamidates, 2'-F, 2'-O-Me, 2'-O-methoxyethyl (MOE), 2'-O-(3-aminopropyl) (AP), hexitol nucleic acid (HNA), 2'-F-arabino nucleic acid (2'-F-ANA) and D-cyclohexenyl nucleoside (CeNA). Also, the β-D-oxy-LNA-modified oligonucleotide may also contain other LNA units in addition to or in place of an oxy-LNA group. In particular, preferred additional LNA units include thio-LNA or amino-LNA monomers in either the D-β or L-α configurations or combinations thereof or ena-LNA. In general, an LNA-modified oligonucleotide will contain at least about 5, 10, 15 or 20 percent LNA units, based on total nucleotides of the oligonucleotide, more typically at least about 20, 25, 30, 40, 50, 60, 70, 80 or 90 percent LNA units, based on total bases of the oligonucleotide.

Stability in biological fluids: One embodiment of the invention includes the incorporation of LNA monomers into a standard DNA or RNA oligonucleotide to increase the stability of the resulting oligomeric compound in biological fluids e.g. through the increase of resistance towards nucleases (endonucleases and exonucleases). The extent of stability will depend on the number of LNA monomers used, their position in the oligonucleotide and the type of LNA monomer used. Compared to DNA and phosphorothioates the following order of ability to stabilize an oligonucleotide against nucleolytic degradation can be established: DNA<<phosphorothioates~oxy-LNA<α-L-LNA<amino-LNA<thio-LNA.

Given the fact that LNA is compatible with standard DNA synthesis and mixes freely with many contemporary nucleic acid analogues nuclease resistance of LNA-oligomeric compounds can be further enhanced according to the invention by either incorporating other analogues that display increased nuclease stability or by exploiting nuclease-resistant internucleoside linkages e.g. phosphoromonothioate, phosphorodithioate, and methylphosphonate linkages, etc.

Mode of action: Antisense compounds according to the invention may elicit their therapeutic action via a variety of mechanisms and may be able to combine several of these in the same compound. In one scenario, binding of the oligonucleotide to its target (pre-mRNA or mRNA) acts to prevent binding of other factors (proteins, other nucleic acids, etc.) needed for the proper function of the target i.e. operate by steric hindrance. For instance, the antisense oligonucleotide may bind to sequence motifs in either the pre-mRNA or mRNA that are important for recognition and binding of transacting factors involved in splicing, poly-adenylation, cellular transport, post-transcriptional modifications of nucleosides in the RNA, capping of the 5'-end, translation, etc. In the case of pre-mRNA splicing, the outcome of the interaction between the oligonucleotide and its target may be either suppression of expression of an undesired protein, generation of alternative spliced mRNA encoding a desired protein or both.

In another embodiment, binding of the oligonucleotide to its target disables the translation process by creating a physical block to the ribosomal machinery, i.e. translational arrest.

In yet another embodiment, binding of the oligonucleotide to its target interferes with the RNAs ability to adopt secondary and higher order structures that are important for its proper function, i.e. structural interference. For instance, the oligonucleotide may interfere with the formation of stem-loop structures that play crucial roles in different functions, such as providing additional stability to the RNA or adopting essential recognition motifs for different proteins.

In still another embodiment, binding of the oligonucleotide inactivates the target toward further cellular metabolic processes by recruiting cellular enzymes that degrades the mRNA. For instance, the oligonucleotide may comprise a segment of nucleosides that have the ability to recruit ribonuclease H (RNaseH) that degrades the RNA part of a DNA/RNA duplex. Likewise, the oligonucleotide may comprise a segment which recruits double stranded RNAses, such as for instance RNAseIII or it may comprise an external guide sequence (EGS) that recruit an endogenous enzyme (RNase P) which degrades the target mRNA Also, the oligonucleotide may comprise a sequence motif which exhibit RNAse catalytic activity or moieties may be attached to the oligonucleotides which when brought into proximity with the target by the hybridization event disables the target from further metabolic activities.

It has been shown that β-D-oxy-LNA does not support RNaseH activity. However, this can be changed according to the invention by creating chimeric oligonucleotides composed of β-D-oxy-LNA and DNA, called gapmers. A gapmer is based on a central stretch of 4-12 nt DNA or modified monomers recognizable and cleavable by the RNaseH (the gap) typically flanked by 1 to 6 residues of β-D-oxy-LNA (the flanks). The flanks can also be constructed with LNA derivatives. There are other chimeric constructs according to the invention that are able to act via an RNaseH mediated mechanism. A headmer is defined by a contiguous stretch of β-D-oxy-LNA or LNA derivatives at the 5'-end followed by a contiguous stretch of DNA or modified monomers recognizable and cleavable by the RNaseH towards the 3'-end, and a tailmer is defined by a contiguous stretch of DNA or modified monomers recognizable and cleavable by the RNaseH at the 5'-end followed by a contiguous stretch of β-D-oxy-LNA or LNA derivatives towards the 3'-end. Other chimeras according to the invention, called mixmers consisting of an alternate composition of DNA or modified monomers recognizable and cleavable by RNaseH and β-D-oxy-LNA and/or LNA derivatives might also be able to mediate RNaseH binding and cleavage. Since α-L-LNA recruits RNaseH activity to a certain extent, smaller gaps of DNA or modified monomers recognizable and cleavable by the RNaseH for the gapmer construct might be required, and more flexibility in the mixmer construction might be introduced. FIG. 1 shows an outline of different designs according to the invention.

The clinical effectiveness of antisense oligonucleotides depends to a significant extent on their pharmacokinetics e.g. absorption, distribution, cellular uptake, metabolism and excretion. In turn these parameters are guided significantly by the underlying chemistry and the size and three-dimensional structure of the oligonucleotide.

As mentioned earlier LNA according to the invention is not a single, but several related chemistries, which although molecularly different all exhibit stunning affinity towards complementary DNA and RNA, Thus, the LNA family of chemistries are uniquely suited of development oligos according to the invention with tailored pharmacokinetic properties exploiting either the high affinity of LNA to modulate the size of the active compounds or exploiting different LNA chemistries to modulate the exact molecular composition of the active compounds. In the latter case, the use of for instance amino-LNA rather than oxy-LNA will change the overall charge of the oligo and affect uptake and distribution behavior. Likewise the use of thio-LNA instead of oxy-LNA will increase the lipophilicity of the oligonucleotide and thus influence its ability to pass through lipophilic barriers such as for instance the cell membrane.

Modulating the pharmacokinetic properties of an LNA oligonucleotide according to the invention may further be achieved through attachment of a variety of different moieties. For instance, the ability of oligonucleotides to pass the cell membrane may be enhanced by attaching for instance lipid moieties such as a cholesterol moiety, a thioether, an aliphatic chain, a phospholipid or a polyamine to the oligonucleotide. Likewise, uptake of LNA oligonucleotides into cells may be enhanced by conjugating moieties to the oligonucleotide that interacts with molecules in the membrane, which mediates transport into the cytoplasm.

The pharmacodynamic properties can according to the invention be enhanced with groups that improve oligomer uptake, enhance biostability such as enhance oligomer resistance to degradation, and/or increase the specificity and affinity of oligonucleotides hybridisation characteristics with target sequence e.g. a mRNA sequence.

There are basically two types of toxicity associated with antisense oligos: sequence-dependant toxicity, involving the base sequence, and sequence-independent, class-related toxicity. With the exception of the issues related to immunostimulation by native CpG sequence motifs, the toxicities that have been the most prominent in the development of antisense oligonucleotides are independent of the sequence, e.g. related to the chemistry of the oligonucleotide and dose, mode, frequency and duration of administration. The phosphorothioates class of oligonucleotides have been particularly well characterized and found to elicit a number of adverse effects such as complement activation, prolonged PTT (partial thromboplastin time), thrombocytopenia, hepatotoxicity (elevation of liver enzymes), cardiotoxicity, splenomegaly and hyperplasia of reticuloendothelial cells.

As mentioned earlier, the LNA family of chemistries provide unprecedented affinity, very high bio-stability and the ability to modulate the exact molecular composition of the oligonucleotide. In one embodiment of the invention, LNA containing compounds enables the development of oligonucleotides which combine high potency with little—if any—phosphorothioate linkages and which are therefore likely to display better efficacy and safety than contemporary antisense compounds.

Oligo- and polynucleotides of the invention may be produced using the polymerisation techniques of nucleic acid chemistry well known to a person of ordinary skill in the art of organic chemistry. Generally, standard oligomerisation cycles of the phosphoramidite approach (S. L. Beaucage and R. P. Iyer, *Tetrahedron,* 1993, 49, 6123; S. L. Beaucage and R. P. Iyer, *Tetrahedron,* 1992, 48, 2223) is used, but e.g. H-phosphonate chemistry, phosphortriester chemistry can also be used.

For some monomers of the invention longer coupling time, and/or repeated couplings with fresh reagents, and/or use of more concentrated coupling reagents were used. The phosphoramidites employed coupled with satisfactory >95% stepwise coupling yields. Thiolation of the phosphate is performed by exchanging the normal, e.g. iodine/pyridine/$H_2O$, oxidation used for synthesis of phosphordiester oligomers with an oxidation using Beaucage's reagent (commercially available) other sulfurisation reagents are also comprised. The phosphorthioate LNA oligomers were efficiently synthesised with stepwise coupling yields >=98%.

The β-D-amino-LNA, β-D-thio-LNA oligonucleotides, α-L-LNA and β-D-methylamino-LNA oligonucleotides were also efficiently synthesised with step-wise coupling yields ≧98% using the phosphoramidite procedures.

Purification of LNA oligomeric compounds was done using disposable reversed phase purification cartridges and/or reversed phase HPLC and/or precipitation from ethanol or butanol. Capillary gel electrophoresis, reversed phase HPLC, MALDI-MS, and ESI-MS was used to verify the purity of the synthesized oligonucleotides. Furthermore, solid support materials having immobilised thereto an optionally nucleobase protected and optionally 5'-OH protected LNA are especially interesting as material for the synthesis of LNA containing oligomeric compounds where an LNA monomer is included in at the 3' end. In this instance, the solid support material is preferable CPG, e.g. a readily (commercially) available CPG material or polystyrene onto which a 3'-functionalised, optionally nucleobase protected and optionally 5'-OH protected LNA is linked using the conditions stated by the supplier for that particular material.

As it must be clear by now, an interesting aspect of the invention is directed to a compound of the invention or a conjugate of the invention for use as a medicament. As it must also be unambiguous by now, the use of a compound of the invention or as conjugate of the invention for the manufacture of a medicament for the treatment of cancer is a particularly interesting aspect of the invention.

The pharmaceutical composition according to the invention can be used for the treatment of many different diseases. For example survivin has been found to be overexpressed in human tumours of lung (Monzo et al., 1999, J. Clin. Oncol 17, 2100-2104), breast (Tanaka et al., 2000, Clin. Cancer Res. 6, 127-134; Nasu et al., 2002, Anticancer Res. 22, 1839-1844), colon/rectum (Kawasaki et al., 1998, Cancer Res. 58, 5071-5074; Rbdel et al., 2002, Strahlenther. Onkol. 8, 426-434), stomach (Lu et al., 1998, Cancer Res. 58, 1808-1812; Tsuburaya et al., 2002, Hepatogastroenterology 49, 1150-1152), oesophagus (Kato et al., 2001, Int. J. Cancer 95, 92-95; Ikeguchi and Kaibara, 2002, Br. J. Cancer 87, 883-887), pancreas (Satoh et al., 2001, Cancer 92, 271-278; Sarela et al., 2002, Br. J. Cancer 86, 886-892), liver (Ikeguchi et al., 2002, Clin. Cancer Res. 8, 3131-3136), uterus (Saitoh et al., 1999, Int. J. Oncol. 15, 137-141; Takai et al., 2002, Cancer Lett. 184, 105-116), ovaries (Yoshoda et al., 2001, Int. J. Oncol. 19, 537-542; Takai et al., 2002, Int. J. Mol. Med. 10, 211-216), Hodgkin's disease (Garcia et al., 2003, Blood 101, 681-689), non-Hodgkin's lymphoma (Adida et al., 2000, Blood 96, 1921-1925; Kuttler et al., 2002, Leukemia 16, 726-735), leukemias (Adida et al., 2000, Br. J. Haematol. 111, 196-203; Kamihira et al., 2001, Br. J. Haematol. 114, 63-69; Mori et al., 2001, Int. J. Haematol. 75, 161-165), neuroblastoma (Islam et al., 2000, Oncogene 19, 617-623; Adida et al., 1998, Lancet 351, 882-883), phaeochromocytoma (Koch et al., 2002, Eur. J. Endocrinol. 146, 381-388), soft tissue sarcomas (Würl et al., 2002, Lancet 359, 943-945), gliomas (Chakravarti et al. 2002, J. Clin. Oncol. 20, 1063-1068), melanoma (Grossman et al., 1999, J. Invest. Dermatol. 113, 1076-1081), bladder (Swana et al., 1999, New Engl. J. Med. 341, 452-453; Smith et al., 2001, JAMA 285, 324-328), cervix (Kim et al., 2002, Anticancer Res. 22, 805-808; Yoshida et al., 2003, Oncol. Rep. 10, 45-49), prostate (Ambrosini et al., 1997, Nat. Med. 3, 917-921). Like cancer cells proliferating vascular endothelial cells are sensitive to downregulation of survivin expression. The pharmaceutical composition according to the invention can therefore be used in the treatments of diseases characterized by abnormal disease causing angiogenesis. Examples of such diseases are cancers in general and artherosclerosis, psoriasis, diabetic retinopathy, rheumatoid arthritis, asthma, warts, allergic dermatitis and Karposis sarcoma. Furthermore, survivin may be actively involved in regulating cell viability during HIV-1 infection (Zhu et al., 2003, Apoptosis 8, 71-79). Survivin is essential to the correct execution of mitosis and completion of cell division. Downregulation of survivin should therefore be relevant in the treatment of any disease characterized by uncontrolled or abnormal cell growth.

Generally stated, one aspect of the invention is directed to a method of treating a mammal suffering from or susceptible to a disease caused by abnormal angiogenesis, comprising administering to the mammal an therapeutically effective amount of an oligonucleotide targeted to survivin that comprises one or more LNA units.

An interesting aspect of the invention is directed to the use of a compound as defined herein or as conjugate as defined herein for the preparation of a medicament for the treatment of artherosclerosis, psoriasis, diabetic retinopathy, rheumatoid arthritis, asthma, warts and allergic dermatitis.

The methods of the invention is preferably employed for treatment or prophylaxis against diseases caused by cancer, particularly for treatment of cancer as may occur in tissue such as lung, breast, colon, prostate, pancreas, liver, brain, testes, stomach, intestine, bowel, spinal cord, sinuses, urinary tract or ovaries cancer.

Furthermore, the invention described herein encompasses a method of preventing or treating cancer comprising a therapeutically effective amount of a survivin modulating oligomeric compound, including but not limited to high doses of the oligomer, to a human in need of such therapy. The invention further encompasses the use of a short period of administration of a survivin modulating oligomeric compound. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

In the use of a compound of the invention or as conjugate of the invention for the manufacture of a medicament for the treatment of cancer, said cancer may suitably be in the form of a solid tumor. Furthermore, said cancer is also suitably a carcinoma. The carcinoma is typically in the from selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors. More typically, said carcinoma is selected from the group consisting of malignant melanoma, non-small cell lung cancer, breast carcinoma, colon carcinoma and renal cell carcinoma. The malignant melanoma is typically selected from the group consisting of superficial spreading melanoma, nodular melanoma, lentigo maligna melanoma, acral melagnoma, amelanotic melanoma and desmoplastic melanoma.

Alternatively, the cancer may suitably be a sarcoma. The sarcoma is typically in the form selected from the group consisting of osteosarcoma, Ewing's sarcoma, chondrosarcoma, malignant fibrous histiocytoma, fibrosarcoma and Kaposi's sarcoma.

Alternatively, the cancer may suitably be a glioma.

It should be understood that the invention also relates to a pharmaceutical composition, which comprises a least one antisense oligonucleotide construct of the invention as an active ingredient. It should be understood that the pharmaceutical composition according to the invention optionally comprises a pharmaceutical carrier, and that the pharmaceutical composition optionally comprises further antisense compounds, chemotherapeutic compounds, anti-inflammatory compounds, antiviral compounds and/or immuno-modulating compounds.

The oligomeric compound comprised in this invention can be employed in a variety of pharmaceutically acceptable salts. As used herein, the term refers to salts that retain the desired biological activity of the herein identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combinations of (a) and (b); e.g., a zinc tannate salt or the like.

In one embodiment of the invention the oligomeric compound may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthioethyl (t-butyl-SATE). These protection groups are nuclease resistant and are selectively removed intracellularly.

In one embodiment of the invention the oligomeric compound is linked to ligands/conjugates. It is way to increase the cellular uptake of antisense oligonucleotides. This conjugation can take place at the terminal positions 5'/3'-OH but the ligands may also take place at the sugars and/or the bases. Other examples of conjugates/lingands are cholesterol moieties, duplex intercalators such as acridine, poly-L-lysine, "end-capping" with one or more nuclease-resistant linkage groups.

The invention also includes the formulation of one or more oligonucleotide compound as disclosed herein. Pharmaceutically acceptable binding agents and adjuvants may comprise part of the formulated drug. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion. An oligonucleotide of the invention may be mixed with any material that do not impair the desired action, or with material that supplement the desired action. These could include other drugs including other nucleotide compounds. For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline. Preferably, an oligomeric compound is included in a unit formulation such as in a pharmaceutically acceptable carrier or diluent in an amount sufficient to deliver to a patient a therapeutically effective amount without causing serious side effects in the treated patient.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the active oligo is administered IV, IP, orally, topically or as a bolus injection or administered directly in to the target organ. Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. Oligomeric compounds of the invention may also be conjugated to active drug substances, for example, aspirin, ibuprofen, a sulfa drug, an antidiabetic, an antibacterial or an antibiotic.

LNA containing oligomeric compound are useful for a number of therapeutic applications as indicated above. In general, therapeutic methods of the invention include administration of a therapeutically effective amount of an LNA-modified oligonucleotide to a mammal, particularly a human. In a certain embodiment, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention. Anti-inflammatory drugs, including but not limited to nonsteroidal anti-inflammatory drugs and corticosteroids, antiviral drugs, and immuno-modulating drugs may also be combined in compositions of the invention. Two or more combined compounds may be used together or sequentially.

Accordingly, a further aspect of the invention is directed to the use of a compound as defined herein or as conjugate as defined herein for the manufacture of a medicament for the treatment of cancer, wherein said medicament further comprises a chemotherapeutic agent selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, the further chemotherapeutic agent is selected from taxanes such as Taxol, Paclitaxel or Docetaxel.

Similarly, the invention is further directed to the use of a compound as defined herein or as conjugate as defined herein for the manufacture of a medicament for the treatment of cancer, wherein said treatment further comprises the administration of a further chemotherapeutic agent selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, said treatment further comprises the administration of a further chemotherapeutic agent selected from taxanes, such as Taxol, Paclitaxel or Docetaxel.

Alternatively stated, the invention is furthermore directed to a method for treating cancer, said method comprising administering a compound as defined herein, or a conjugate as defined herein or a pharmaceutical composition as defined herein to a patient in need thereof and further comprising the administration of a further chemotherapeutic agent. Said further administration may be such that the further chemotherapeutic agent is conjugated to the compound of the invention, is present in the pharmaceutical composition, or is administered in a separate formulation.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

In a preferred embodiment the present invention provides pharmaceutical compositions containing (a) one or more antisense compounds and (b) one or more other chemotherapeutic agents which stabilize microtubules or dampen microtubule dynamic—and thereby prevent tension forming at the kinetochores of sister chromatids. Such chemotherapeutic agents includes taxanes, in particular Taxol, Paclitaxel and Docetaxel. When used with the compounds of the invention, such chemotherapeutic agents should be used sequentially initiating with oligonucleotide treatment for a period of time which sensitises the target cells to subsequent co-treatment with the chemotherapeutic agent by reducing the level of survivin protein in tumor cells and proliferating endothelial cells of the tumor vasculature.

In another preferred embodiment the present invention provides pharmaceutical compositions containing (a) one or more antisense compounds and (b) radiation therapy. When used with the compounds of the invention, radiation therapy should be used sequentially initiating with oligonucleotide treatment for a period of time which sensitises the target cells to subsequent additional radiotherapy by reducing the level of survivin protein in tumor cells and proliferating endothelial cells of the tumor vasculature.

Dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides.

Generally it can be estimated based on EC50s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

The LNA containing oligomeric compounds of the present invention can also be utilized for as research reagents for diagnostics, therapeutics and prophylaxis. In research, the antisense oligonucleotides may be used to specifically inhibit the synthesis of survivin genes in cells and experimental animals thereby facilitating functional analysis of the target or an appraisal of its usefulness as a target for therapeutic intervention. In diagnostics the antisense oligonucleotides may be used to detect and quantitate survivin expression in cell and tissues by Northern blotting, in-situ hybridisation or similar techniques. For therapeutics, an animal or a human, suspected of having a disease or disorder, which can be treated by modulating the expression of survivin is treated by administering antisense compounds in accordance with this invention. Further provided are methods of treating an animal particular mouse and rat and treating a human, suspected of having or being prone to a disease or condition, associated with expression of survivin by administering a therapeutically or prophylactically effective amount of one or more of the antisense compounds or compositions of the invention.

A further aspect of the invention is directed to a method of preventing or limiting apoptosis comprising the administration of a compound as herein, a conjugate as defined herein or a pharmaceutical composition as defined herein. The prevention of apoptosis may be in vitro or in vivo. The prevention may be done on a cellular assay or within a tissue sample or within the living mammal.

A related aspect of the invention is directed method of preventing cellular proliferation comprising the administration of a compound as defined herein, a conjugate as defined herein or a pharmaceutical composition as defined herein. The prevention of proliferation may be in vitro or in vivo. The prevention may be done on a cellular assay or within a tissue sample or within the living mammal.

The invention is further illustrated in a non-limiting manner by the following examples.

EXAMPLES

Example 1

Monomer Synthesis

The LNA monomer building blocks and derivatives thereof were prepared following published procedures and references cited therein, see:

WO 03/095467 A1

D. S. Pedersen, C. Rosenbohm, T. Koch (2002) Preparation of LNA Phosphoramidites, Synthesis 6, 802-808.

M. D. Sørensen, L. Kværnø, T. Bryld, A. E. Håkansson, B. Verbeure, G. Gaubert, P. Herdewijn, J. Wengel (2002) α-L-ribo-configured Locked Nucleic Acid (α-l-LNA): Synthesis and Properties, J. Am. Chem. Soc., 124, 2164-2176.

S. K. Singh, R. Kumar, J. Wengel (1998) Synthesis of Novel Bicyclo[2.2.1] Ribonucleosides: 2'-Amino- and 2'-Thio-LNA Monomeric Nucleosides, J. Org. Chem. 1998, 63, 6078-6079.

C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663.

Synthesis of the 2'-thio-LNA ribothymidine phosphoramidite. Reagents and conditions: i) Pd/C, $H_2$, acetone, MeOH; ii) BzCl, pyridine, DMF; iii) 0.25 M $H_2SO_4$ (aq), DMF, 80° C. (79% from 4; 3 steps); iv) $Tf_2O$, DMAP, $CH_2Cl_2$, 0° C.; v) $Na_2S$, DMF (72% from 7; 2 steps); vi) NaOBz, DMF, 100° C. (81%); vii) $NH_3$, MeOH (76%); viii) DMT-Cl, pyridine (88%); ix) $P(OCH_2CH_2CN)(N(^iPr)_2)_2$, 4,5-dicyanoimidazole, $CH_2Cl_2$ (99%). DMT=4,4'-dimethoxytrityl, $PN_2$=2-cyanoethoxy(diisopropylamino)phosphinoyl.

Figure 4:
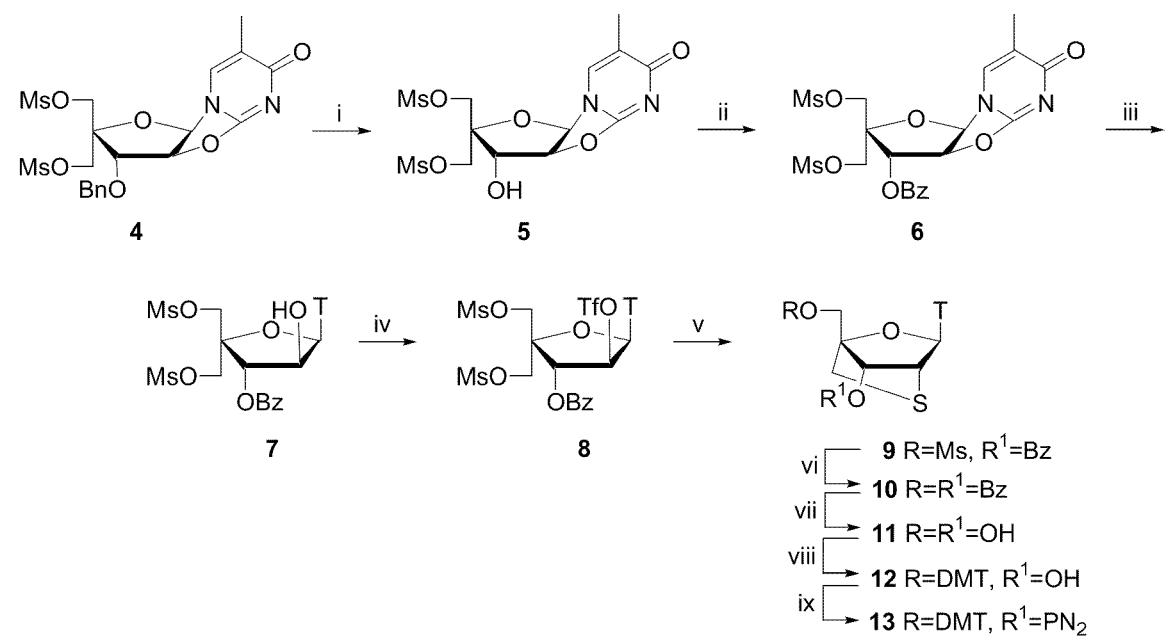
FIG. 4 General scheme of the synthesis of thio-LNA.
Figure 6:
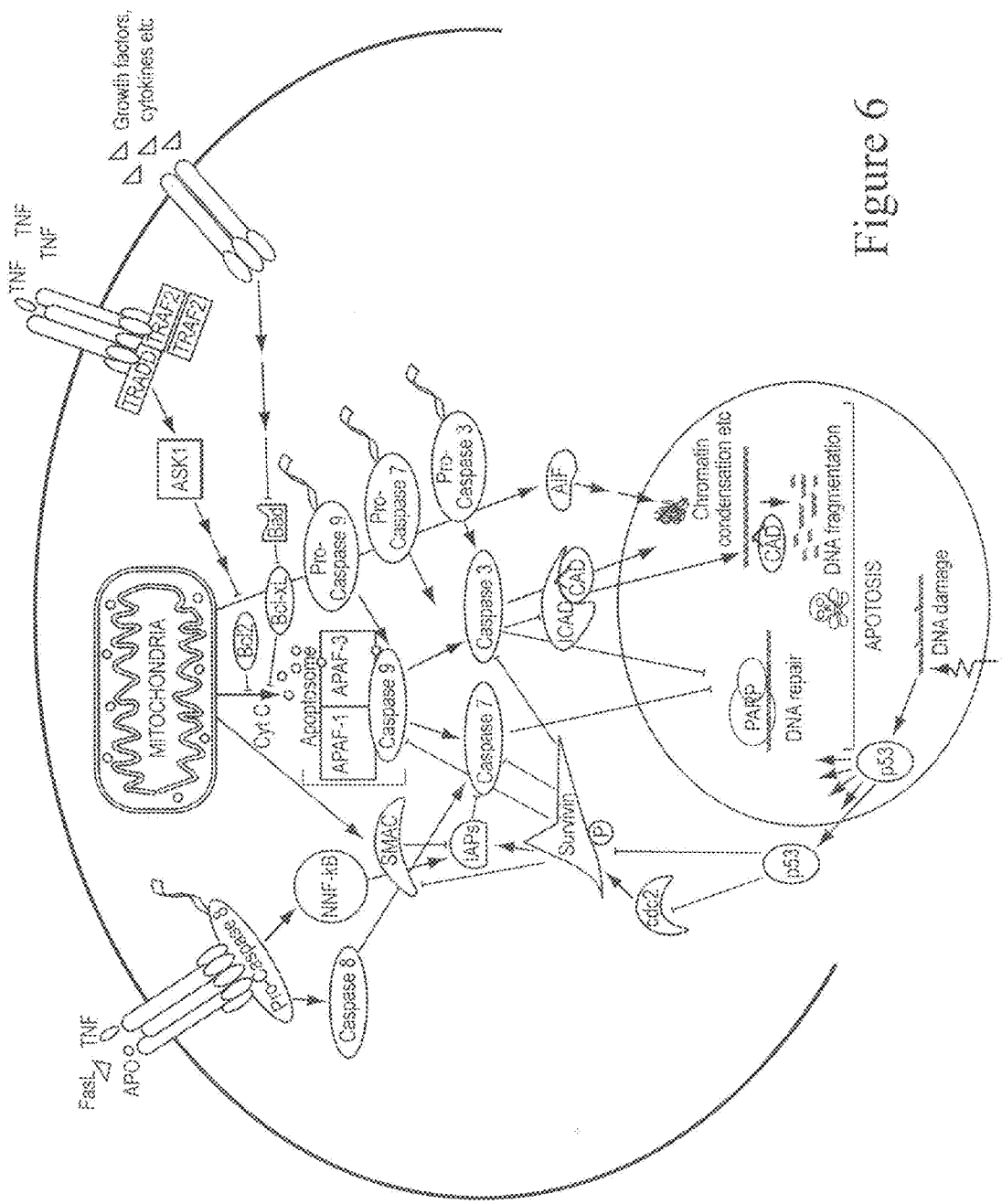
FIG. 6 Schematic way of Survivin in the apoptotic pathway.

1-(3-O-Benzoyl-5-O-methanesulfonyl-4-C-methanesulfonyloxymethyl-β-D-threo-pentofuranosyl)thymine (7, FIG. 4)

Anhydro-nucleoside 4 (C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663) (30.0 g, 58.1 mmol) was heated to 70° C. in a mixture of methanol (1000 cm$^3$) and acetone (1000 cm$^3$) until a clear solution was obtained and the solution was allowed to reach room temperature. The reaction flask was flushed with argon and Pd/C (10 wt. % Pd on carbon, 6.2 g, 5.8 mmol) was added. The mixture was stirred vigorously under an atmosphere of hydrogen gas (balloon). After 23 h the slurry was filtered through a pad of celite. The catalyst was recovered from the celite and refluxed in DMF (1000 cm$^3$) for 1 h. The hot DMF slurry was filtered through a pad of celite and the organic layers combined and evaporated in vacuo to give nucleoside 5 as a yellow powder. Residual solvents were removed on a high vacuum pump overnight.

The crude nucleoside 5 (23 g) was heated to 70° C. in DMF (300 cm$^3$) to give a clear yellow solution that was allowed to cool to room temperature. Benzoyl chloride (81.7 g, 581 mmol, 67.4 cm$^3$) was added followed by pyridine (70 cm$^3$). After 18 h the reaction was quenched with methanol (200 cm$^3$) and excess methanol was removed in vacuo. To the dark brown solution of nucleoside 6 aqueous H$_2$SO$_4$ (0.25 M, 400 cm$^3$) was added. The solution was heated to 80° C. on an oil bath (At approx 50° C. precipitation occurs. The solution becomes clear again at 80° C.). After 22 h at 80° C. the solution was allowed to cool to room temperature. The reaction mixture was transferred to a separatory funnel with ethyl acetate (1000 cm$^3$). The organic layer was washed with sat. aq NaHCO$_3$ (2×1000 cm$^3$). The combined aqueous layers were extracted with ethyl acetate (1000+500 cm$^3$). The organic layers were combined and washed with sat. aq NaHCO$_3$ (1000 cm$^3$), dried (Na$_2$SO$_4$), filtered and evaporated in vacuo to give a yellow liquid. Residual solvents were removed on a high vacuum pump overnight to give a yellow syrup. The product was purified by Dry Column Vacuum Chromatography (id 10 cm; 100 cm$^3$ fractions; 50-100% EtOAc in n-heptane (v/v)—10% increments; 2-24% MeOH in EtOAc (v/v)—2% increments). Fractions containing the product were combined and evaporated in vacuo giving nucleoside 7 (25.1 g, 79%) as a white foam.

R$_f$=0.54 (5% MeOH in EtOAc, v/v);

ESI-MS m/z found 549.0 ([MH]$^+$, calcd 549.1);

$^1$H NMR (DMSO-d$_6$) δ 11.39 (br s, 1H, NH), 8.10-8.08 (m, 2H, Ph), 7.74-7.70 (m, 1H, Ph), 7.60-7.56 (m, 2H, Ph), 7.51 (d, J=1.1 Hz, 1H, H6), 6.35 (d, J=4.9 Hz, 1H, H1'), 6.32 (d, J=5.3 Hz, 1H, 2'-OH), 5.61 (d, J=4.0 Hz, 1H, H3'), 4.69 (d, J=10.8 Hz, 1H), 4.59 (m, 1H, H2'), 4.55 (d, J=10.8 Hz, 1H), 4.52 (d, J=10.8 Hz, 1H), 4.46 (d, J=10.6 Hz, 1H) (H$_5$' and H1"), 3.28 (s, 3H, Ms), 3.23 (s, 3H, Ms), 1.81 (s, 3H, CH$_3$);

$^{13}$C NMR (DMSO-d$_6$) δ 164.5, 163.6 (C4, PhC(O)), 150.3 (C2), 137.7 (C6), 133.8, 129.6, 128.7, 128.6 (Ph), 108.1 (C5), 84.8 (C1'), 81.1 (C4'), 78.0 (C3'), 73.2 (C2'), 68.0, 67.1 (C5', C1"), 36.7, 36.6 (2×Ms), 11.9 (CH$_3$);

Elemental anal. calcd for C$_{20}$H$_{24}$N$_2$O$_{12}$S$_2$.0.33H$_2$O (%): C, 44.34; H, 4.65; N, 4.85. Found: C, 44.32; H, 4.58; N, 4.77.

(1R,3R,4R,7R)-7-Benzoyloxy-1-methansulfonyloxymethyl-3-(thymin-1-yl)-2-oxa-5-thiabicyclo[2:2:1]heptane (9)

1-(3-O-Benzoyl-5-O-methanesulfonyl-4-C-methanesulfonyloxymethyl-β-D-threo-pentofuranosyl)thymine (7) (10.00 g, 18.23 mmol) was dissolved in dichloromethane (500 cm$^3$) and cooled to 0° C. Pyridine (15 cm$^3$) and DMAP (8.91 g, 72.9 mmol) was added followed by dropwise addition of trifluoromethanesulfonic anhydride (10.30 g, 36.5 mmol, 6.0 cm$^3$). After 1 h the reaction was quenched with sat. aq NaHCO$_3$ (500 cm$^3$) and transferred to a separatory funnel. The organic layer was washed with 1.0 M aq HCl (500 cm$^3$), sat. aq NaHCO$_3$ (500 cm$^3$) and brine (500 cm$^3$). The organic layer was evaporated in vacuo with toluene (100 cm$^3$) to give 1-(3-O-benzoyl-5-O-methanesulfonyl-4-C-methanesulfonyloxymethyl-2-O-trifluoromethanesulfonyl-β-D-threo-pentofuranosyl)thymine (8) as a yellow powder.

The crude nucleoside 8 was dissolved in DMF (250 cm$^3$) and Na$_2$S (1.57 g, 20.1 mmol) was added to give a dark green slurry. After 3 h the reaction was quenched with half sat. aq NaHCO$_3$ (500 cm$^3$) and extracted with dichloromethane (500+2×250 cm$^3$). The combined organic layers were washed with brine (500 cm$^3$), dried (Na$_2$SO$_4$), filtered and concentrated in vacuo to give a yellow liquid. Residual solvent was removed overnight on a high vacuum pump to give a yellow gum that was purified by Dry Column Vacuum Chromatography (id 6 cm: 50 cm$^3$ fractions; 50-100% EtOAc in n-heptane (v/v)—10% increments; 2-20% MeOH in EtOAc (v/v)—2% increments) to give nucleoside 9 (6.15 g, 72%) as a yellow foam.

R$_f$=0.27 (20% n-heptane in EtOAc, v/v);

ESI-MS m/z found 469.0 ([MH]$^+$, calcd 469.1);

$^1$H NMR (CDCl$_3$) δ 58.70 (br s, 1H, NH), 8.01-7.99 (m, 2H, Ph), 7.67 (d, J=1.1 Hz, 1H, H6), 7.65-7.61 (m, 1H, Ph), 7.50-7.46 (m, 2H, Ph), 5.98 (s, 1H, H1'), 5.34 (d, J=2.4 Hz, 1H, H3'), 4.66 (d, J=11.7 Hz, 1H, H5'a), 4.53 (d, J=11.5 Hz, 1H, H5'b), 4.12 (m (overlapping with residual EtOAc), 1H, H2'), 3.15-3.13 (m, 4H, H1"a and Ms), 3.06 (d, J=10.6 Hz, 1H, H1"b), 1.98 (d, J=1.1 Hz, 3H, CH$_3$);

$^{13}$C NMR (CDCl$_3$) δ 165.2, 163.5 (C4, PhC(O)), 149.9 (C2), 134.1, 133.9, 129.8, 128.7, 128.3 (C6, Ph), 110.7 (C5), 91.1 (C1'), 86.8 (C4'), 72.6 (C3'), 65.8 (C5'), 50.5 (C2'), 37.9 (Ms), 35.1 (C1"), 12.5 (CH$_3$);

Elemental anal. calcd for C$_{19}$H$_{20}$N$_2$O$_8$S$_2$.0.33 EtOAc (%): C, 49.21; H, 4.72; N, 5.47. Found: C, 49.25; H, 4.64; N, 5.48.

(1R,3R,4R,7R)-7-Benzoyloxy-1-benzoyloxymethyl-3-(thymin-1-yl)-2-oxa-5-thiabicyclo[2:2:1]heptane (10)

Nucleoside 9 (1.92 g, 4.1 mmol) was dissolved in DMF (110 cm$^3$). Sodium benzoate (1.2 g, 8.2 mmol) was added and the mixture was heated to 100° C. for 24 h. The reaction mixture was transferred to a separatory funnel with half sat. brine (200 cm$^3$) and extracted with ethyl acetate (3×100 cm$^3$). The combined organic layers were dried (Na$_2$SO$_4$), filtered and evaporated in vacuo to give a brown liquid. The product was put on a high vacuum pump to remove residual solvent. The resulting brown gum was purified by Dry Column Vacuum Chromatography (id 4 cm; 50 cm$^3$ fractions; 0-100% EtOAc in n-heptane (v/v)—10% increments; 2-10% MeOH in EtOAc (v/v)—2% increments) to give nucleoside 10 (1.64 g, 81%) as a slightly yellow foam.

R$_f$=0.57 (20% n-heptane in EtOAc, v/v);

ESI-MS m/z found 495.1 ([MH]$^+$, calcd 495.1);

¹H NMR (CDCl₃) δ 9.02 (br s, 1H, NH), 8.07-7.99 (m, 4H, Ph), 7.62-7.58 (m, 2H, Ph), 7.47-7.42 (m, 5H, Ph and H6), 5.95 (s, 1H, H1'), 5.46 (d, J=2.2 Hz, 1H, H3'), 4.93 (d, J=12.8 Hz, 1H, H5'a), 4.60 (d, J=12.8 Hz, 1H, H5'b), 4.17 (d, J=2.2 Hz, 1H, H2'), 3.27 (d, J=10.6 Hz, 1H, H1"a), 3.16 (d, J=10.6 Hz, 1H, H1"b), 1.55 (d, J=1.1 Hz, 3H, CH₃);

¹³C NMR (CDCl₃) δ 165.8, 165.1, 163.7 (C4, 2×Ph$\underline{C}$(O)), 150.0 (C2), 133.9, 133.7, 133.6, 129.8, 129.6, 129.0, 128.8, 128.6, 128.5 (C6, 2×Ph), 110.3 (C5), 91.3 (C1'), 87.5 (C4'), 72.9 (C3'), 61.3 (C5'), 50.6 (C2'), 35.6 (C1"), 12.3 (CH₃);

Elemental anal. calcd for $C_{25}H_{22}N_2O_7S$ (%): C, 60.72; H, 4.48; N, 5.66. Found: C, 60.34; H, 4.49; N, 5.35.

(1R,3R,4R,7R)-7-Hydroxy-1-hydroxymethyl-3-(thymin-1-yl)-2-oxa-5-thiabicyclo[2:2:1]heptane (11)

Nucleoside 10 (1.50 g, 3.0 mmol) was dissolved in methanol saturated with ammonia (50 cm³). The reaction flask was sealed and stirred at ambient temperature for 20 h. The reaction mixture was concentrated in vacuo to give a yellow gum that was purified by Dry Column Vacuum Chromatography (id 4 cm; 50 cm³ fractions; 0-16% MeOH in EtOAc (v/v)—1% increments) giving nucleoside 11 (0.65 g, 76%) as clear needles.

$R_f$=0.31 (10% MeOH in EtOAc, v/v);

ESI-MS m/z found 287.1 ([MH]⁺, calcd 287.1);

¹H NMR (DMSO-d₆) δ 11.32 (br s, 1H, NH), 7.96 (d, J=1.1 Hz, 1H, H6), 5.95 (s, 1H, H6), 5.70 (d, J=4.2 Hz, 1H, 3'-OH), 5.62 (s, 1H, H1'), 4.49 (t, J=5.3 Hz, 1H, 5'-OH), 4.20 (dd, J=4.1 and 2.1 Hz, 1H, H3'), 3.77-3.67 (m, 2H, H5'), 3.42 (d, J=2.0 Hz, 1H, H2'), 2.83 (d, J=10.1 Hz, 1H, H1"a), 2.64 (d, J=10.1 Hz, 1H, H1"b), 1.75 (d, J=1.1 Hz, 3H, CH₃);

¹³C NMR (DMSO-d₆) δ 163.8 (C4), 150.0 (C2), 135.3 (C6), 107.5 (C5), 90.2, 89.6 (C1' and C4'), 69.4 (C3'), 58.0 (C5'), 52.1 (C2'), 34.6 (C1"), 12.4 (CH₃);

Elemental anal. calcd for $C_{11}H_{14}N_2O_5S$ (%): C, 46.15; H, 4.93; N, 9.78. Found: C, 46.35; H, 4.91; N, 9.54.

(1R,3R,4R,7R)-1-(4,4'-Dimethoxytrityloxymethyl)-7-hydroxy-5-methyl-3-(thymin-1-yl)-2-oxa-5-thiabicyclo[2:2:1]heptane (12)

Nucleoside 11 (0.60 g, 2.1 mmol) was dissolved in pyridine (10 cm³). 4,4'-Dimethoxytrityl chloride (0.88 g, 2.6 mmol) was added and the reaction was stirred at ambient temperature for 3 h. The reaction mixture was transferred to a separatory funnel with water (100 cm³) and extracted with ethyl acetate (100+2×50 cm³). The combined organic layers were washed with sat. aq NaHCO₃ (100 cm³), brine (100 cm³) and evaporated to dryness in vacuo to give a viscous yellow liquid. The product was redissolved in toluene (50 cm³) and concentrated in vacuo to give a yellow foam. The foam was dried on a high vacuum pump overnight and purified by Dry Column Vacuum Chromatography (id 4 cm; 50 cm³ fractions; 10-100% EtOAc in n-heptane (v/v)–10% increments) giving nucleoside 12 (1.08 g, 88%) as a white foam.

$R_f$=0.24 (20% n-heptane in EtOAc, v/v);

ESI-MS m/z found 587.1 ([M-H]⁺, calcd 587.2);

¹H NMR (CDCl₃) δ 8.96 (br s, 1H, NH), 7.74 (d, J=1.1 Hz, 1H, H6), 7.46-7.44 (m, 2H, Ph), 7.35-7.22 (m, 9H, Ph), 7.19-7.15 (m, 2H, Ph), 6.86-6.80 (m, 2H, Ph), 5.82 (s, 1H, H1'), 4.55 (dd, J=9.3 and 2.1 Hz, 1H, H3'), 3.79 (s, 6H, OCH₃), 3.71 (d, J=2.0 Hz, 1H, H2'), 3.50 (s, 2H, H5'), 2.81 (d, J=10.8 Hz, 1H, H1"a), 2.77 (d, J=10.8 Hz, 1H, H1"b), 2.69 (d, J=9.2 Hz, 1H, 3'-OH), 1.42 (s, 3H, CH₃);

¹³C NMR (CDCl₃) δ 158.7 (C4), 150.1 (C2), 144.1, 135.2, 135.1, 130.1, 129.1, 128.1, 128.0, 127.1, 127.0, 113.3 (C6, 3×Ph), 110.0 (C5), 90.2 ($\underline{C}$(Ph)₃), 89.6 (C1'), 87.0 (C4'), 71.7 (C3'), 60.9 (C5'), 55.2 (C2'), 34.7 (C1"), 12.2 (CH₃);

Elemental anal. calcd for $C_{32}H_{32}N_2O_7S \cdot 0.5H_2O$ (%): C, 64.31; H, 5.57; N, 4.69. Found: C, 64.22; H, 5.67; N, 4.47.

(1R,3R,4R,7R)-7-(2-Cyanoethoxy(diisopropylamino)phosphinoxy)-1-(4,4'-dimethoxytrityloxymethyl)-3-(thymin-1-yl)-2-oxa-5-thiabicyclo[2.2.1]heptane (13)

According to the published method (D. S. Pedersen, C. Rosenbohm, T. Koch (2002) Preparation of LNA Phosphoramidites, Synthesis, 6, 802-808) nucleoside 12 (0.78 g, 1.33 mmol) was dissolved in dichloromethane (5 cm³) and a 1.0 M solution of 4,5-dicyanoimidazole in acetonitrile (0.93 cm³, 0.93 mmol) was added followed by dropwise addition of 2-cyanoethyl-N,N,N',N'-tetraisopropylphosphorodiamidite (0.44 cm³, 1.33 mmol). After 2 h the reaction was transferred to a separatory funnel with dichloromethane (40 cm³) and washed with sat. aq NaHCO₃ (2×25 cm³) and brine (25 cm³). The organic layer was dried (Na₂SO₄), filtered and evaporated in vacuo to give nucleoside 13 (1.04 g, 99%) as a white foam. $R_f$=0.29 and 0.37—two diastereoisomers (20% n-heptane in EtOAc, v/v); ESI-MS m/z found 789.3 ([MH]⁺, calcd 789.3); ³¹P NMR (DMSO-d₆) δ 150.39, 150.26.

Example 2

Oligonucleotide Synthesis

Oligonucleotides were synthesized using the phosphoramidite approach on an Expedite 8900/MOSS synthesizer (Multiple Oligonucleotide Synthesis System) at 1 or at 15 μmol. At the end of the synthesis (DMT-on) the oligonucleotides were cleaved from the solid support using aqueous ammonia for 1 h at room temperature, and further deprotected for 3 h at 650° C. The oligonucleotides were purified by reverse phase HPLC (RP-HPLC). After the removal of the DMT-group, the oligonucleotides were characterized by IE-HPLC or RP-HPLC. The identity of the oligonucleotides is confirmed by ESI-MS. See below for more details.

Preparation of the LNA Succinyl Hemiester

5'-O-Dmt-3'-hydroxy-LNA monomer (500 mg), succinic anhydride (1.2 eq.) and DMAP (1.2 eq.) were dissolved in DCM (35 mL). The reaction was stirred at room temperature overnight. After extractions with NaH₂PO₄ 0.1 M pH 5.5 (2×) and brine (1×), the organic layer was further dried with anhydrous Na₂SO₄ filtered and evaporated. The hemiester derivative was obtained in 95% yield and was used without any further purification.

Preparation of the LNA-Support

The above prepared hemiester derivative (90 μmol) was dissolved in a minimum amount of DMF, DIEA and pyBOP (90 μmol) were added and mixed together for 1 min. This pre-activated mixture was combined with LCAA-CPG (500 Å, 80-120 mesh size, 300 mg) in a manual synthesizer and stirred. After 1.5 h at room temperature, the support was filtered off and washed with DMF, DCM and MeOH. After drying the loading was determined to be 57 μmol/g (see Tom Brown, Dorcas J. S. Brown, "Modern machine-aided methods of oligodeoxyribonucleotide synthesis", in: F. Eckstein, editor. Oligonucleotides and Analogues A Practical Approach. Oxford: IRL Press, 1991: 13-14).

Elongation of the Oligonucleotide

The coupling of phosphoramidites (A(bz), G(ibu), 5-methyl-C(bz)) or T-β-cyanoethyl-phosphoramidite) is performed by using a solution of 0.1 M of the 5'-O-DMT-protected amidite in acetonitrile and DCI (4,5-dicyanoimidazole) in acetonitrile (0.25 M) as activator. The thiolation is carried out by using xanthane chloride (0.01 M in acetonitrile:pyridine 10%). The rest of the reagents are the ones typically used for oligonucleotide synthesis.

Purification by RP-HPLC:
  Column: XTerra, RP18, 5 μm, 7.8×50 mm column.
  Eluent: Eluent A: 0.1M NH$_4$OAc, pH: 10.
  Eluent B: Acetonitrile
  Flow: 5 ml/min.
  Gradient:

| Time (min.) | Eluent A | Eluent B |
|---|---|---|
| 0.05 min. | 95% | 5% |
| 5 min. | 95% | 5% |
| 12 min. | 65% | 35% |
| 16 min. | 0% | 100% |
| 19 min. | 0% | 100% |
| 21 min | 100% | 0% |

Analysis by IE-HPLC:
  Column: Dionex, DNAPac PA-100, 2×250 mm column.
  Eluent: Eluent A: 20 mM Tris-HCl, pH 7.6; 1 mM EDTA; 10 mM NaClO$_4$.
  Eluent B: 20 mM Tris-HCl, pH 7.6; 1 mM EDTA; 1M NaClO$_4$.
  Flow: 0.25 ml/min.
  Gradient:

| Time (min.) | Eluent A | Eluent B |
|---|---|---|
| 1 min. | 95% | 5% |
| 10 min. | 65% | 35% |
| 11 min. | 0% | 100% |
| 15 min. | 0% | 100% |
| 16 min | 95% | 5% |
| 21 min. | 95% | 5% |

Abbreviations

DMT: Dimethoxytrityl

DCI: 4,5-Dicyanoimidazole

DMAP: 4-Dimethylaminopyridine

DCM: Dichloromethane

DMF: Dimethylformamide

THF: Tetrahydrofurane

DIEA: N,N-diisopropylethylamine

PyBOP: Benzotriazole-1-yl-oxy-tris-pyrrolidino-phosphonium-hexafluorophosphate

Bz: Benzoyl

Ibu: Isobutyryl

Example 3

Test of Design of the Oligomeric Compound

It was of our interest to evaluate the antisense activity of oligonucleotides with different designs, in order to prove the importance of choosing the best design for an oligonucleotide targeting survivin. For this purpose, we set up an in vitro assay that would allow us to screen many different oligonucleotide designs by measuring the activity of the firefly (*Photinus pyralis*) luciferase after down-regulation by antisense oligonucleotides. FIG. 1 contains an illustration of most the designs mentioned in the text. In a first screen, designs containing β-D-oxy-LNA, which were all targeting the same motif within the mRNA were evaluated. Designs consisting of gapmers with a different gap-size, a different load of phosphorothioate internucleoside linkages, and a different load of LNA were tested. Headmers and tailmers with a different load of β-D-oxy-LNA, a different load of phosphorothioate internucleoside linkages and a different load of DNA were prepared. Mixmers of various compositions, which means that bear an alternate number of units of β-D-oxy-LNA, α-L-LNA and DNA, were also analysed in the in vitro assay. Moreover, LNA derivatives were also included in different designs, and their antisense activity was assessed. The importance of a good design is reflected by the data that can be obtained in a luciferase assay. The luciferase expression levels are measured in %, and give an indication of the antisense activity of the different designs containing β-D-oxy-LNA and LNA derivatives. We can easily see that some designs are potent antisense oligonucleotides, while others give moderate to low down-regulation levels. Therefore, a close correlation between good antisense activity and optimal design of an oligonucleotide is very evident. We appreciated good levels of down-regulation with various designs. Gapmers with gaps of 7-10 nt DNA and thiolation all over the backbone or with thiolation exclusively in the gap and PO in the flanks showed good results. These designs contain β-D-oxy-LNA or LNA derivatives. Headmers of 6 nt and 8 nt β-D-oxy-LNA also presented good levels of down-regulation, when the phosphorothioate internucleoside linkages are all over the backbone or only in the DNA-segment. Different mixmers gave good antisense activity in the luciferase assay. The alternate number of units of each α-L-oxy-LNA, β-D-oxy-LNA or DNA composition defines the mixmers, see FIG. 1. A mixmer 3-9-3-1, which has a deoxynucleoside residue at the 3'-end showed significant levels of down-regulation. In a mixmer 4-1-1-5-1-1-3, we placed two α-L-oxy-LNA residues interrupting the gap, being the flanks β-D-oxy-LNA. Furthermore, we interrupted the gap with two α-L-oxy-LNA residues, and substituted both flanks with α-L-oxy-LNA. Both designs presented significant levels of down-regulation. The presence of α-L-oxy-LNA might introduce a flexible transition between the North-locked flanks (oxy-LNA) and the α-L-oxy-LNA residue by spiking in deoxynucleotide residues. It is also interesting to study design 4-3-1-3-5 where a α-L-oxy-LNA residue interrupts the DNA stretch. In addition to the α-L-oxy-LNA in the gap, we also substituted two oxy-LNA residues at the edges of the flanks with two α-L-oxy-LNA residues. The presence of just one β-D-oxy-LNA residue (design 4-3-1-3-5) interrupting the stretch of DNAs in the gap results in a dramatic loss of down-regulation. Just by using α-L-oxy-LNA instead, the design shows significant down-regulation at 50 nM oligonucleotide concentration. The placement of α-L- oxy-LNA in the junctions and one α-L-oxy-LNA in the middle of the gap also showed down-regulation.

α-L-oxy-LNA reveals to be a potent tool enabling the construction of different mixmers, which are able to present high levels of antisense activity. Other mixmers such as 4-1-5-1-5 and 3-3-3-3-3-1 can also be prepared. We can easily see that some designs are potent antisense oligonucleotides, while others give moderate to low down-regulation levels. Therefore, again a close correlation between good antisense activity and optimal design of an oligonucleotide is very evident. Other preferred designs are (1-3-8-3-1) where DNA residues are located in the flanks with 3 β-D-oxy-LNA monomers at each side of the gap. A further preferred design is (4-9-3-1) with D-oxy-LNA flanks and a 9 gap with a DNA at the 3'-end.

Assay

X1/5 Hela cell line (ECACC Ref. No: 95051229), which was stably transfected with a "tet-off" luciferase system, was used. In the absence of tetracycline the luciferase gene is expressed constitutively. The expression can be measured as light in a luminometer, when the luciferase substrate, luciferin is added. The X1/5 Hela cell line was grown in Minimum Essential Medium Eagle (Sigma M2279) supplemented with 1× Non Essential Amino Acid (Sigma M7145), 1× Glutamax I (Invitrogen 35050-038), 10% FBS calf serum, 25 μg/ml Gentamicin (Sigma G1397), 500 μg/ml G418 (Invitrogen 10131-027) and 300 μg/ml Hygromycin B (Invitrogen 10687-010). The X1/5 Hela cells were seeded at a density of 8000 cells per well in a white 96 well plate (Nunc 136101) the day before the transfection. Before the transfection, the cells were washed one time with OptiMEM (Invitrogen) followed by addition of 40 μl OptiMEM with 2 μg/ml of Lipofectamine2000 (Invitrogen). The cells were incubated for 7 minutes before addition of the oligonucleotides. 10 μl of oligonucleotide solutions were added and the cells were incubated for 4 h at 37° C. and 5% $CO_2$. After the 4 h incubation, the cells were washed once in OptiMEM and growth medium was added (100 μl). The luciferase expression was measure the next day. Luciferase expression was measured with the Steady-Glo luciferase assay system from Promega. 100 μl of the Steady-Glo reagent was added to each well and the plate was shaken for 30 s at 700 rpm. The plate was read in Luminoskan Ascent instrument from ThermoLabsystems after 8 min of incubation to complete total lysis of the cells. The luciferase expression is measured as Relative Light Units per seconds (RLU/s). The data was processed in the Ascent software (v2.6) and graphs were drawn in SigmaPlot2001.

Example 4

In Vitro Model: Cell Culture

The effect of antisense compounds on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin A549: The human non-small cell lung cancer cell line A549 was purchased from ATCC, Manassas and was cultured in DMEM (Sigma)+10% FBS+Glutamax I+gentamicin MCF7: The human breast cancer cell line MCF7 was purchased from ATCC and was cultured in Eagle MEM (Sigma)+10% FBS+Glutamax I+gentamicin SW480: The human colon cancer cell line SW480 was purchased from ATCC and was cultured in L-15 Leibovitz (Sigma)+10% FBS+Glutamax I+gentamicin SW620: The human colon cancer cell line SW620 was purchased from ATCC and was cultured in L-15 Leibovitz (Sigma)+10% FBS+Glutamax I+gentamicin HT29: The human prostate cancer cell line HT29 was purchased from ATCC and was cultured in McCoy's 5a MM (Sigma)+10% FBS+Glutamax I+gentamicin NCI H23: The human non-small-cell lung cancer cell line was purchased from ATCC and was cultured in RPMI 1640 with Glutamax I (Gibco)+10% FBS+HEPES+gentamicin HCT-116: The human colon cancer cell line HCT-116 was purchased from ATCC and was cultured in McCoy's 5a MM+10% FBS+Glutamax I+gentamicin MDA-MB-231: The human breast cancer cell line MDA-MB-231 was purchased from ATCC and was cultured in L-15 Leibovitz+10% FBS+Glutamax I+gentamicin MDA-MB-435s: The human breast cancer cell line MDA-MB-435s was purchased from ATCC and was cultured in L-15 Leibovitz+10% FBS+Glutamax I+gentamicin DMS273: The human small-cell lung cancer cell line DMS273 was purchased from ATCC and was cultured in +10% FBS+Glutamax+gentamicin PC3: The human prostate cancer cell line PC3 was purchased from ATCC and was cultured in F12 Coon's with glutamine (Gibco)+10% FBS+gentamicin U373: The human glioblastoma astrocytoma cancer cell line U373 was purchased from ECACC and was cultured in EMEM+10% FBS+glutamax+NEAA+sodiumpyrovate+gentamicin.

HeLa Sur-GFP: Wheately, S. P. et al, *Curr. Biol.* 11 446-490, 2001

HUVEC-C human umbilical vein endothelial cells were purchased from ATCC and propagated according to the manufacturers instructions.

HMVEC-d (DMVEC's—dermal human microvascular endothelial cells) were purchased from Clonetics and cultured as described by manufacturer.

HMVEC human microvascular endothelial cells were purchased from Clonetics and cultured as stated by manufacturer Human embryonic lung fibroblasts were purchased from ATCC and cultured as described by manufacturer HMEC-1 Human mammary epithelial cells were purchased from Clonetics and maintained as recommended by the manufacturer.

Example 5

In Vitro Model: Treatment with Antisense Oligonucleotide

The cells were treated with oligonucleotide using the cationic liposome formulation LipofectAMINE 2000 (Gibco) as transfection vehicle.

Cells were seeded in 12-well cell culture plates (NUNC) and treated when 80-90% confluent. Oligo concentrations used ranged from 125 nM to 0.2 nM final concentration. Formulation of oligo-lipid complexes were carried out essentially as described in Dean et al. (Journal of Biological Chemistry 1994, 269, 16416-16424) using serum-free OptiMEM (Gibco) and a final lipid concentration of 10 µg/ml LipofectAMINE 2000 in 500 µl total volume.

Cells were incubated at 37° C. for 4 hours and treatment was stopped by removal of oligo-containing culture medium. Cells were washed and serum-containing media was added. After oligo treatment cells were allowed to recover for 18 hours before they were harvested for RNA or protein analysis.

Example 6

In Vitro Model: Extraction of RNA and cDNA Synthesis

Total RNA Isolation

Total RNA was isolated either using RNeasy mini kit (Qiagen cat. no. 74104) or using the Trizol reagent (Life technologies cat. no. 15596). For RNA isolation from cell lines, RNeasy is the preferred method and for tissue samples Trizol is the preferred method.

Total RNA was isolated from cell lines using the Qiagen RNA OPF Robot-BIO Robot 3000 according to the protocol provided by the manufacturer.

Tissue samples were homogenised using an Ultra Turrax T8 homogeniser (IKA Analysen technik) and total RNA was isolated using the Trizol reagent protocol provided by the manufacturer.

First Strand Synthesis

First strand synthesis was performed using OmniScript Reverse Transcriptase kit (cat# 205113, Qiagen) according to the manufacturers instructions.

For each sample 0.5 µg total RNA was adjusted to 12 µl each with RNase free $H_2O$ and mixed with 2 µl poly $(dT)_{12-18}$ (SEQ ID NO: 741)(2.5 µg/ml) (Life Technologies, GibcoBRL, Roskilde, DK), 2 µl dNTP mix (5 mM each dNTP), 2 µl 10× Buffer RT, 1 µl RNAguard™Rnase INHIBITOR (33.3 U/ml), (cat# 27-0816-01, Amersham Pharmacia Biotech, Hørsholm, DK) and 1 µl OmniScript Reverse Transcriptase (4 U/µl) followed by incubation at 37° C. for 60 minutes and heat inactivation of the enzyme at 93° C. for 5 minutes.

Example 7

In Vitro Model: Analysis of Oligonucleotide Inhibition of Survivin Expression by Real-Time PCR Antisense modulation of Survivin expression can be assayed in a variety of ways known in the art. For example, Survivin mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially iQ Multi-Color Real Time PCR Detection System available from BioRAD.

Real-Time Quantitative PCR Analysis of Survivin mRNA Levels

Quantitation of mRNA levels was determined by real-time quantitative PCR using the iQ Multi-Color Real Time PCR Detection System (BioRAD) according to the manufacturers instructions.

Real-time Quantitative PCR is a technique well known in the art and is taught in for example Heid et al. Real time quantitative PCR, Genome Research (1996), 6: 986-994.

Platinum Quantitative PCR SuperMix UDG 2×PCR master mix was obtained from Invitrogen cat# 11730. Primers and TaqMan® probes were obtained from MWG-Biotech AG, Ebersberg, Germany Probes and primers to human Survivin were designed to hybridise to a human Survivin sequence, using published sequence information (GenBank accession number NM 001168, incorporated herein as SEQ ID NO:1).

For human Survivin the PCR primers were:

Assay 1 forward primer: 5' caggtccccgctttctttg 3' (SEQ ID NO: 727) (final concentration in the assay; 0.6 µM)

reverse primer: 5' ggaggagggcgaatcaaa 3' (SEQ ID NO: 728) (final concentration in the assay; 0.6 µM) and the PCR probe was: 5' FAM-ccatcatcttacgccagacttcagcc-TAMRA 3' (SEQ ID NO: 729) (final concentration in the assay; 0.1 µM) Assay 2 forward primer: 5' aaggaccaccgcatctctaca 3' (SEQ ID NO: 730) (final concentration in the assay; 0.9 µM)

reverse primer: 5' ccaagtctggctcgttctcagt 3' (SEQ ID NO: 731) (final concentration in the assay; 0.6 µM) and the PCR probe was: 5' FAM-cgaggctggcttcatccactgcc-TAMRA 3'(SEQ ID NO: 732) (final concentration in the assay; 0.1 µM)

Glyceraldehyde-3-phosphate dehydrogenase (GAPDH) mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. no. 4310884E) according to the manufacturers instructions.

For quantification of mouse GAPDH mRNA the following primers and probes were designed: Sense primer 5'aaggctgtgggcaaggtcatc 3' (SEQ ID NO: 733)(0.3 µM final concentration), antisense primer 5' gtcagatccacgacggacacatt (SEQ ID NO: 734) (0.6 µM final concentration), TaqMan probe 5' FAM-gaagctcactggcatggcatggccttccgtgttc-TAMRA 3' (SEQ ID NO: 735) (0.2 µM final concentration).

Real Time PCR

The cDNA from the first strand synthesis performed as described in example 6 was diluted 2-20 times, and analyzed by real time quantitative PCR. The primers and probe were mixed with 2× Platinum Quantitative PCR SuperMix UDG (cat. # 11730, Invitrogen) and added to 3.3 µl cDNA to a final volume of 25 µl. Each sample was analysed in triplicates. Assaying 2 fold dilutions of a cDNA that had been prepared on material purified from a cell line expressing the RNA of interest generated standard curves for the assays. Sterile $H_2O$ was used instead of cDNA for the no template control. PCR program: 50° C. for 2 minutes, 95° C. for 10 minutes followed by 40 cycles of 95° C., 15 seconds, 60° C., 1 minutes. Relative quantities of target mRNA sequence were determined from the calculated Threshold cycle using the iCycler iQ Real-time Detection System software.

Figure 7:
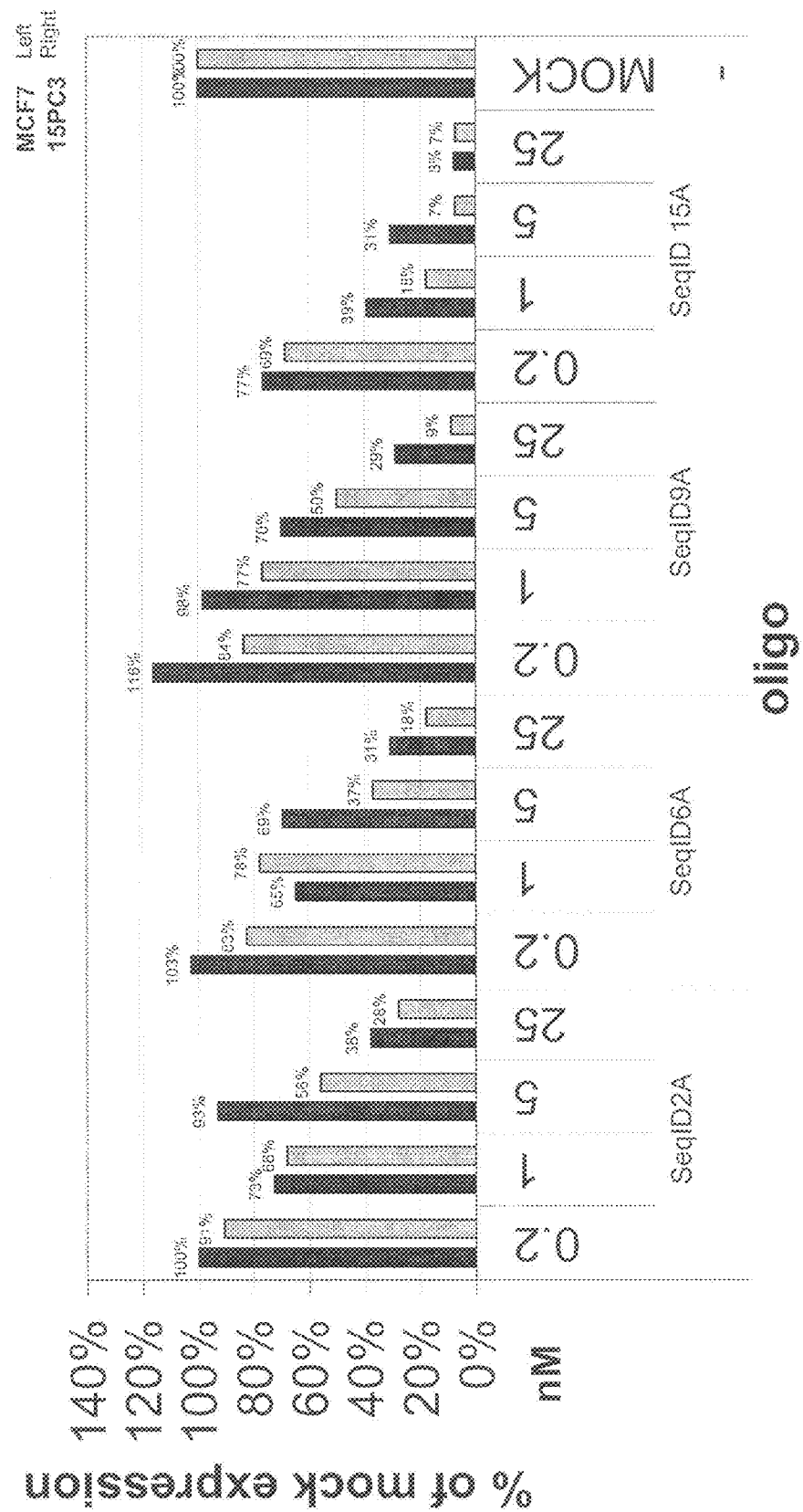
FIG. 7 Survivin mRNA downregulation by LNA antisense oligonucleotides. Cells were transfected with oligo nucleotide and cultures for 24 h. Total RNA was extracted and expression of Survivin mRNA were detected by either Real-time PCR in 15PC3 and MCF-7. Survivin expression is presented normalised to GAPDH transcript steady state.

See FIG. 7 and Table 1, 2, 3, 4 and 5.

Example 8

In Vitro Analysis: Northern Blot Analysis of Survivin mRNA Levels

Northern blot analysis was carried out by procedures well known in the art essentially as described in Current Protocols in Molecular Biology, John Wiley & Sons.

The hybridisation probe was obtained by PCR-amplification of a 373 by fragment from 1 µl cDNA obtained by reverse transcription PCR. The reaction was carried out using primers 5' agcacaaagccattctaagtcattg 3' (SEQ ID NO: 736) (forward) and 5' tccatcatcttacgccagacttc 3'(SEQ ID NO: 737) (reverse) at 0.5 µM final concentration each, 200 nM each dNTP, 1.5 mM MgCl$_2$ and Platinum Taq DNA polymerase (Invitrogen cat. no. 10966-018).

The DNA was amplified for 40 cycles on a Perkin Elmer 9700 thermocycler using the following program: 94° C. for 2 min. then 40 cycles of 94° C. for 30 sec. and 72° C. for 30 sec. with a decrease of 0.5° C. per cycle followed by 72° C. for 7 min.

The amplified PCR product was purified using S-400 MicroSpin columns (Amersham Pharmacia Biotech cat. no. 27-5140-01) according to the manufacturers instructions and quantified by spectrophotometry.

The hybridisation probe was labelled using Redivue™ [α-$^{32}$P]dATP 3000 Ci/mmol (Amersham Pharmacia Biotech cat. # AA 0005) and Prime-It RmT labeling kit (Stratagene cat. no. 300392) according to the manufacturers instructions and the radioactively labeled probe was purified using S-300 MicroSpin columns (Amersham Pharmacia Biotech cat. no. 27-5130-01).

Before use, the probe was denatured at 96° C. and immediately put on ice.

Samples of 2 µg of total RNA purified as described in example 6 were denatured and size separated on a 2.2 M formaldehyde/MOPS agarose gel. RNA was transferred to positively charged nylon membrane by downward capillary transfer using the TurboBlotter (Schleicher & Schuell) and the RNA was immobilised to the membrane by UV crosslinking using a Stratagene crosslinker. The membrane was pre-hybridised in ExpressHyb Hybridization Solution (Clontech cat. No. 8015-1) at 60° C. and the probe was subsequently added for hybridisation. Hybridisation was carried out at 60° C. and the blot was washed with low stringency wash buffer (2×SSC, 0.1% SDS) at room temperature and with high stringency wash buffer (0.1×SSC, 0.1% SDS) at 50° C.

The blot was exposed to Kodak storage phosphor screens and scanned in a BioRAD FX molecular imager. Survivin mRNA levels were quantified by Quantity One software (Bio-RAD)

Equality of RNA sample loading was assessed by stripping the blot in 0.5% SDS in H$_2$O at 85° C. and reprobing with a labelled GAPDH (glyceraldehyde-3-phosphate dehydrogenase) probe obtained essentially as described above using the primers 5' aacggatttggtcgtatt 3' (SEQ ID NO: 739) (forward) and 5' taagcagttggtggtgca 3' (SEQ ID NO: 740) (reverse). See FIGS. 2 and 3. Intensity was monitored with phosphoimager Biorad, FX-scanner (see below). The tested oligomeric compounds are presented in Example 10.

Percentage down regulation of mRNA estimated from Survivin Northern blotting (data is normalised to GAPDH).

| Seq ID | Compound | | | |
|---|---|---|---|---|
| | 0.2 nM | 1 nM | 5 nM | 25 nM |
| 2A | 31% | 34% | 55% | 77% |
| 6A | 22% | 48% | 71% | 91% |
| 9A | 21% | 44% | 67% | 64% |
| 15A | 45% | 79% | 93% | 95% |

Example 9

In Vitro Analysis: Western Blot Analysis of Survivin Protein Levels

Protein levels of Survivin can be quantitated in a variety of ways well known in the art, such as immunoprecipitation, Western blot analysis (immunoblotting), ELISA, RIA (Radio Immuno Assay) or fluorescence-activated cell sorting (FACS). Antibodies directed to Survivin can be identified and obtained from a variety of sources, such as Upstate Biotechnologies (Lake Placid, USA), Novus Biologicals (Littleton, Colo.), Santa Cruz Biotechnology (Santa Cruz, Calif.) or can be prepared via conventional antibody generation methods.

Western Blotting:

The in vitro effect of survivin oligoes on Survivin protein levels in transfected cells was determined by Western Blotting.

Cells were transfected as described in example 5. Approximately 24 hours after transfection, cells were harvested, lysed in 2.5% SDS, 5 mM DTT and 6 M urea supplemented with protease inhibitor cocktail tablets (Roche). Total protein concentrations were measured using a Bradford reagent. 150 µg total proteins was loaded onto a 12% Bis-Tris gel, run with MOPS buffer and blotted onto a PVDF membrane according to manufacture's recommendations (Invitrogen). After overnight incubation in blocking buffer (Invitrogen) the membrane was incubated two hours with rabbit anti-Survivin antibodies (AF886 from R&D or Novus 500-201 from Abcam) followed by one hour incubation in secondary antibodies. A chromogenic immunodetection kit (Invitrogen) was used to visualize Survivin. Alternatively, the membrane was incubated with HRP conjugated rabbit immunoglobulins (DAKO) followed by incubation with ECL$^+$ Plus reagent (Amersham) and visualized using VersaDoc chemiluminescens detection system. (see FIG. 13 The tested oligomeric compounds are presented in Example 10.)

Example 10

In Vitro Analysis: Antisense Inhibition of Human Survivin Expression by Oligomeric Compound In accordance with the present invention, a series of oligonucleotides were designed to target different regions of the human Survivin RNA, using published sequences (GenBank accession number NM_001168, incorporated herein as SEQ ID NO: 1). The oligonucleotides 16 nucleotides in length are shown in Table 1 and 2. "Target site" indicates the first nucleotide number on the particular target sequence to which the oligonucleotide binds. The preferred compounds are the LNA containing compounds. Table 3 shows low IC50 of four compounds.

TABLE 1

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 172 | 2 | GCAGTGGATGAAGCCA | 147 | G$_s$C$_s$A$_s$G$_s$t$_s$g$_s$g$_s$a$_s$t$_s$g$_s$a$_s$a$_s$G$_s$C$_s$A | 85 | 44 |
|  |  |  | 148 | G$_s$C$_s$A$_s$G$_s$t$_s$g$_s$g$_s$a$_s$t$_s$g$_s$a$_s$a$_s$G$_s$C$_s$a | 91 |  |
|  |  |  | 149 | G$_O$C$_O$A$_O$G$_O$t$_s$g$_s$g$_s$a$_s$t$_s$g$_s$a$_s$a$_s$G$_O$C$_O$C$_O$A |  |  |
|  |  |  | 150 | g$_s$c$_s$a$_s$g$_s$tg$_s$g$_s$g$_s$a$_s$t$_s$g$_s$a$_s$a$_s$g$_s$c$_s$c$_s$a |  |  |
| 198 | 3 | GCCAAGTCTGGCTCGT | 151 | G$_s$C$_s$C$_s$A$_s$a$_s$g$_s$t$_s$c$_s$t$_s$g$_s$g$_s$c$_s$T$_s$C$_s$G$_s$T | 49 |  |
|  |  |  | 152 | G$_s$C$_s$C$_s$A$_s$a$_s$g$_s$t$_s$c$_s$t$_s$g$_s$g$_s$c$_s$T$_s$C$_s$G$_s$t |  |  |
|  |  |  | 153 | G$_O$C$_O$C$_O$A$_O$a$_s$g$_s$t$_s$c$_s$t$_s$g$_s$g$_s$c$_s$T$_O$C$_O$G$_O$T |  |  |
|  |  |  | 154 | g$_s$c$_s$c$_s$a$_s$a$_s$g$_s$t$_s$c$_s$t$_s$g$_s$g$_s$c$_s$t$_s$c$_s$g$_s$t |  |  |
| 206 | 4 | AACACTGGGCCAAGTC | 155 | A$_s$A$_s$C$_s$A$_s$c$_s$t$_s$g$_s$g$_s$g$_s$c$_s$c$_s$a$_s$A$_s$G$_s$T$_s$C | 74 |  |
|  |  |  | 156 | A$_s$A$_s$C$_s$A$_s$c$_s$t$_s$g$_s$g$_s$g$_s$c$_s$c$_s$a$_s$A$_s$G$_s$T$_s$c | 91 |  |
|  |  |  | 157 | A$_O$A$_O$C$_O$A$_O$c$_s$t$_s$g$_s$g$_s$g$_s$c$_s$c$_s$a$_s$A$_O$G$_O$T$_O$C |  |  |
|  |  |  | 158 | a$_s$a$_s$c$_s$a$_s$c$_s$t$_s$g$_s$g$_s$g$_s$c$_s$c$_s$a$_s$a$_s$g$_s$t$_s$c |  |  |
| 214 | 5 | GCAGAAGAAACAGTGG | 159 | G$_s$C$_s$A$_s$G$_s$a$_s$a$_s$g$_s$a$_s$a$_s$a$_s$c$_s$a$_s$C$_s$T$_s$G$_s$G | 67 |  |
|  |  |  | 160 | G$_s$C$_s$A$_s$G$_s$a$_s$a$_s$g$_s$a$_s$a$_s$a$_s$c$_s$a$_s$C$_s$T$_s$G$_s$g |  |  |
|  |  |  | 161 | G$_O$C$_O$A$_O$G$_O$a$_s$a$_s$g$_s$a$_s$a$_s$a$_s$c$_s$a$_s$C$_O$T$_O$G$_O$G |  |  |
|  |  |  | 162 | g$_s$c$_s$a$_s$g$_s$a$_s$a$_s$g$_s$a$_s$a$_s$a$_s$c$_s$a$_s$c$_s$t$_s$g$_s$g |  |  |
| 216 | 6 | AAGCAGAAGAAACACT | 163 | A$_s$A$_s$G$_s$C$_s$a$_s$g$_s$a$_s$a$_s$g$_s$a$_s$a$_s$a$_s$C$_s$A$_s$C$_s$T | 88 | 63 |
|  |  |  | 164 | A$_s$A$_s$G$_s$C$_s$a$_s$g$_s$a$_s$a$_s$g$_s$a$_s$a$_s$a$_s$C$_s$A$_s$C$_s$t | 79 |  |
|  |  |  | 165 | A$_O$A$_O$G$_O$C$_O$a$_s$g$_s$a$_s$a$_s$g$_s$a$_s$a$_s$a$_s$C$_O$A$_O$C$_O$T |  |  |
|  |  |  | 166 | a$_s$a$_s$g$_s$c$_s$a$_s$g$_s$a$_s$a$_s$g$_s$a$_s$a$_s$a$_s$c$_s$a$_s$c$_s$t$_s$ |  |  |
| 238 | 7 | CTCCCAGCCTTCCAGC | 167 | C$_s$T$_s$C$_s$C$_s$c$_s$a$_s$g$_s$c$_s$c$_s$t$_s$t$_s$c$_s$C$_s$A$_s$G$_s$C | 26 |  |
|  |  |  | 168 | C$_s$T$_s$C$_s$C$_s$c$_s$a$_s$g$_s$c$_s$c$_s$t$_s$t$_s$c$_s$C$_s$A$_s$G$_s$c |  |  |
|  |  |  | 169 | C$_O$T$_O$C$_O$C$_O$c$_s$a$_s$g$_s$c$_s$c$_s$t$_s$t$_s$c$_s$C$_O$A$_O$G$_O$C |  |  |
|  |  |  | 170 | c$_s$t$_s$c$_s$c$_s$c$_s$a$_s$g$_s$c$_s$c$_s$t$_s$t$_s$c$_s$c$_s$a$_s$g$_s$c |  |  |
| 403 | 8 | TTCTTTCTTCTTATTG | 171 | T$_s$T$_s$C$_s$T$_s$t$_s$t$_s$c$_s$t$_s$t$_s$c$_s$t$_s$t$_s$A$_s$T$_s$T$_s$G | 62 |  |
|  |  |  | 172 | T$_s$T$_s$C$_s$T$_s$t$_s$t$_s$c$_s$t$_s$t$_s$c$_s$t$_s$t$_s$A$_s$T$_s$T$_s$g |  |  |
|  |  |  | 173 | T$_O$T$_O$C$_O$T$_O$t$_s$t$_s$c$_s$t$_s$t$_s$c$_s$t$_s$t$_s$A$_O$T$_O$T$_O$G |  |  |
|  |  |  | 174 | t$_s$t$_s$c$_s$t$_s$t$_s$t$_s$c$_s$t$_s$t$_s$c$_s$t$_s$t$_s$a$_s$t$_s$t$_s$g |  |  |
| 491 | 9 | TGGGACCAGGCAGCTC | 175 | T$_s$G$_s$G$_s$G$_s$a$_s$c$_s$c$_s$a$_s$g$_s$g$_s$c$_s$a$_s$G$_s$C$_s$T$_s$C | 78 | 50 |
|  |  |  | 176 | T$_s$G$_s$G$_s$G$_s$a$_s$c$_s$c$_s$a$_s$g$_s$g$_s$c$_s$a$_s$G$_s$C$_s$T$_s$c |  |  |
|  |  |  | 177 | T$_O$G$_O$G$_O$G$_O$a$_s$c$_s$c$_s$a$_s$g$_s$g$_s$c$_s$a$_s$G$_O$C$_O$T$_O$C |  |  |
|  |  |  | 178 | t$_s$t$_s$c$_s$t$_s$t$_s$t$_s$c$_s$t$_s$t$_s$c$_s$t$_s$t$_s$a$_s$t$_s$t$_s$g |  |  |
| 505 | 10 | TGGTGCAGCCACTCTG | 179 | T$_s$G$_s$G$_s$T$_s$g$_s$c$_s$a$_s$g$_s$c$_s$c$_s$a$_s$c$_s$T$_s$C$_s$T$_s$g | 56 |  |
|  |  |  | 180 | T$_s$G$_s$G$_s$T$_s$g$_s$c$_s$a$_s$g$_s$c$_s$c$_s$a$_s$c$_s$T$_O$C$_O$T$_O$G |  |  |
|  |  |  | 181 | T$_O$G$_O$G$_O$T$_O$g$_s$c$_s$a$_s$g$_s$c$_s$c$_s$a$_s$c$_s$ T$_O$C$_O$T$_O$G |  |  |
|  |  |  | 182 | t$_s$g$_s$g$_s$t$_s$g$_s$c$_s$a$_s$g$_s$c$_s$c$_s$a$_s$c$_s$t$_s$c$_s$t$_s$g |  |  |
| 521 | 11 | GAATAAACCCTGGAAG | 183 | G$_s$A$_s$A$_s$T$_s$a$_s$a$_s$a$_s$c$_s$c$_s$c$_s$t$_s$g$_s$G$_s$A$_s$A$_s$G | 58 |  |
|  |  |  | 184 | G$_s$A$_s$A$_s$T$_s$a$_s$a$_s$a$_s$c$_s$c$_s$c$_s$t$_s$g$_s$G$_s$A$_s$A$_s$g |  |  |
|  |  |  | 185 | G$_O$A$_O$A$_O$T$_O$a$_s$a$_s$a$_s$c$_s$c$_s$c$_s$t$_s$g$_s$G$_O$A$_O$A$_O$G |  |  |
|  |  |  | 186 | g$_s$a$_s$a$_s$t$_s$a$_s$a$_s$a$_s$c$_s$c$_s$c$_s$t$_s$g$_s$g$_s$a$_s$a$_s$g |  |  |
| 531 | 12 | TGGCACCAGGGAATAA | 187 | T$_s$G$_s$G$_s$C$_s$a$_s$c$_s$c$_s$a$_s$g$_s$g$_s$g$_s$a$_s$A$_s$T$_s$A$_s$A | 44 |  |
|  |  |  | 188 | T$_s$G$_s$G$_s$C$_s$a$_s$c$_s$c$_s$a$_s$g$_s$g$_s$g$_s$a$_s$A$_s$T$_s$A$_s$a |  |  |
|  |  |  | 189 | T$_O$G$_O$G$_O$C$_O$a$_s$c$_s$c$_s$a$_s$g$_s$g$_s$g$_s$a$_s$A$_O$T$_O$A$_O$A |  |  |
|  |  |  | 190 | t$_s$g$_s$g$_s$c$_s$a$_s$c$_s$c$_s$a$_s$g$_s$g$_s$g$_s$a$_s$a$_s$t$_s$a$_s$a |  |  |
| 566 | 13 | CTAAGACATTGCTAAG | 191 | C$_s$T$_s$A$_s$A$_s$g$_s$a$_s$c$_s$a$_s$t$_s$t$_s$g$_s$c$_s$T$_s$A$_s$A$_s$G | 78 |  |
|  |  |  | 192 | C$_s$T$_s$A$_s$A$_s$g$_s$a$_s$c$_s$a$_s$t$_s$t$_s$g$_s$c$_s$T$_s$A$_s$A$_s$g |  |  |
|  |  |  | 193 | C$_O$T$_O$A$_O$A$_O$g$_s$a$_s$c$_s$a$_s$t$_s$t$_s$g$_s$c$_s$T$_O$A$_O$A$_O$G |  |  |
|  |  |  | 194 | c$_s$t$_s$a$_s$a$_s$g$_s$a$_s$c$_s$a$_s$t$_s$t$_s$g$_s$c$_s$t$_s$a$_s$a$_s$g |  |  |
| 579 | 14 | TTGATCTCCTTTCCTA | 195 | T$_s$T$_s$G$_s$A$_s$t$_s$c$_s$t$_s$c$_s$c$_s$t$_s$t$_s$t$_s$C$_s$C$_s$T$_s$A | 73 |  |
|  |  |  | 196 | T$_s$T$_s$G$_s$A$_s$t$_s$c$_s$t$_s$c$_s$c$_s$t$_s$t$_s$t$_s$C$_s$C$_s$T$_s$a |  |  |
|  |  |  | 197 | T$_O$T$_O$G$_O$A$_O$t$_s$c$_s$t$_s$c$_s$c$_s$t$_s$t$_s$t$_s$C$_O$C$_O$T$_O$A |  |  |
|  |  |  | 198 | t$_s$t$_s$g$_s$a$_s$t$_s$c$_s$t$_s$c$_s$c$_s$t$_s$t$_s$t$_s$c$_s$c$_s$t$_s$a$_s$ |  |  |

TABLE 1-continued

Oligomeric compounds of the invention
Oligomeric compounds were evaluated for their potential to knockdown Survivin
mRNA in 15PC3 cells. The data are presented as percentage downregulation relative
to mock transfected cells. Transcript steady state was monitored by Real-time PCR
and normalised to the GAPDH transcript steady state. Note that all LNA C are 5'-
Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 608 | 15 | GCACAGTTGAAACATC | 199 | G$_s$C$_s$A$_s$C$_s$a$_s$g$_s$t$_s$t$_s$g$_s$a$_s$a$_s$a$_s$C$_s$A$_s$T$_s$C | 96 | 93 |
| | | | 200 | G$_s$C$_s$A$_s$C$_s$a$_s$g$_s$t$_s$t$_s$g$_s$a$_s$a$_s$a$_s$C$_s$A$_s$T$_s$c | 89 | 79 |
| | | | 201 | G$_O$C$_O$A$_O$C$_O$a$_s$g$_s$t$_s$t$_s$g$_s$a$_s$a$_s$a$_s$C$_O$A$_O$T$_O$C | | |
| | | | 202 | g$_s$c$_s$a$_s$c$_s$a$_s$g$_s$t$_s$t$_s$g$_s$a$_s$a$_s$a$_s$c$_s$a$_s$t$_s$c | | |
| | | | 203 | G$_s$C$_s$A$_s$c$_s$a$_s$g$_s$t$_s$t$_s$g$_s$a$_s$a$_s$a$_s$C$_s$A$_s$T$_s$c | 83 | 78 |
| 1 | 16 | GATTCAAATCTGGCGG | 204 | G$_s$A$_s$T$_s$T$_s$c$_s$a$_s$a$_s$a$_s$t$_s$c$_s$t$_s$g$_s$G$_s$C$_s$G$_s$G | | |
| | | | 205 | G$_s$A$_s$T$_s$T$_s$c$_s$a$_s$a$_s$a$_s$t$_s$c$_s$t$_s$g$_s$G$_s$C$_s$G$_s$g | | |
| | | | 206 | G$_O$A$_O$T$_O$T$_O$c$_s$a$_s$a$_s$a$_s$t$_s$c$_s$t$_s$g$_s$G$_O$C$_O$G$_O$G | | |
| | | | 207 | g$_s$a$_s$t$_s$t$_s$c$_s$a$_s$a$_s$a$_s$t$_s$c$_s$t$_s$g$_s$g$_s$c$_s$g$_s$g | | |
| 17 | 17 | TGCCAACGGGTCCCGC | 208 | T$_s$G$_s$C$_s$C$_s$a$_s$a$_s$c$_s$g$_s$g$_s$g$_s$t$_s$c$_s$C$_s$C$_s$G$_s$C | | |
| | | | 209 | T$_s$G$_s$C$_s$C$_s$a$_s$a$_s$c$_s$g$_s$g$_s$g$_s$t$_s$c$_s$C$_s$C$_s$G$_s$c | | |
| | | | 210 | T$_O$G$_O$C$_O$C$_O$a$_s$a$_s$c$_s$g$_s$g$_s$g$_s$t$_s$c$_s$C$_O$C$_O$G$_O$C | | |
| | | | 211 | t$_s$g$_s$c$_s$c$_s$a$_s$a$_s$c$_s$g$_s$g$_s$g$_s$t$_s$c$_s$c$_s$c$_s$g$_s$c | | |
| 33 | 18 | CCGCCGCCGCCACCTC | 212 | C$_s$C$_s$G$_s$C$_s$c$_s$g$_s$c$_s$c$_s$g$_s$c$_s$c$_s$a$_s$C$_s$C$_s$T$_s$C | | |
| | | | 213 | C$_s$C$_s$G$_s$C$_s$c$_s$g$_s$c$_s$c$_s$g$_s$c$_s$c$_s$a$_s$C$_s$C$_s$T$_s$c | | |
| | | | 214 | C$_O$C$_O$G$_O$C$_O$c$_s$g$_s$c$_s$c$_s$g$_s$c$_s$c$_s$a$_s$C$_O$C$_O$T$_O$C | | |
| | | | 215 | c$_s$c$_s$g$_s$c$_s$c$_s$g$_s$c$_s$c$_s$g$_s$c$_s$c$_s$a$_s$c$_s$c$_s$t$_s$c | | |
| 49 | 19 | CGTCGGGGCACCCATG | 216 | C$_s$G$_s$T$_s$C$_s$g$_s$g$_s$g$_s$g$_s$c$_s$a$_s$c$_s$c$_s$C$_s$A$_s$T$_s$G | | |
| | | | 217 | C$_s$G$_s$T$_s$C$_s$g$_s$g$_s$g$_s$g$_s$c$_s$a$_s$c$_s$c$_s$C$_s$A$_s$T$_s$g | | |
| | | | 218 | C$_O$G$_O$T$_O$C$_O$g$_s$g$_s$g$_s$g$_s$c$_s$a$_s$c$_s$c$_s$C$_O$A$_O$T$_O$G | | |
| | | | 219 | c$_s$g$_s$t$_s$c$_s$g$_s$g$_s$g$_s$g$_s$c$_s$a$_s$c$_s$c$_s$c$_s$a$_s$t$_s$g | | |
| 65 | 20 | GCCAGGCAGGGGGCAA | 220 | G$_s$C$_s$C$_s$A$_s$g$_s$g$_s$c$_s$a$_s$g$_s$g$_s$g$_s$g$_s$G$_s$C$_s$A$_s$A | | |
| | | | 221 | G$_s$C$_s$C$_s$A$_s$g$_s$g$_s$c$_s$a$_s$g$_s$g$_s$g$_s$g$_s$G$_s$C$_s$A$_s$a | | |
| | | | 222 | G$_O$C$_O$C$_O$A$_O$g$_s$g$_s$c$_s$a$_s$g$_s$g$_s$g$_s$g$_s$G$_O$C$_O$A$_O$A | | |
| | | | 223 | g$_s$c$_s$c$_s$a$_s$g$_s$g$_s$c$_s$a$_s$g$_s$g$_s$g$_s$g$_s$g$_s$c$_s$a$_s$a | | |
| 81 | 21 | TCCTTGAGAAAGGGCT | 224 | T$_s$C$_s$C$_s$T$_s$t$_s$g$_s$a$_s$g$_s$a$_s$a$_s$a$_s$g$_s$G$_s$G$_s$C$_s$T | | |
| | | | 225 | T$_s$C$_s$C$_s$T$_s$t$_s$g$_s$a$_s$g$_s$a$_s$a$_s$a$_s$g$_s$G$_s$G$_s$C$_s$t | | |
| | | | 226 | T$_O$C$_O$C$_O$T$_O$t$_s$g$_s$a$_s$g$_s$a$_s$a$_s$a$_s$g$_s$G$_O$G$_O$C$_O$T | | |
| | | | 227 | t$_s$c$_s$c$_s$t$_s$t$_s$g$_s$a$_s$g$_s$a$_s$a$_s$a$_s$g$_s$g$_s$g$_s$c$_s$t | | |
| 97 | 22 | TGTAGAGATGCGGTGG | 228 | T$_s$G$_s$T$_s$A$_s$g$_s$a$_s$g$_s$a$_s$t$_s$g$_s$c$_s$g$_s$G$_s$T$_s$G$_s$G | | |
| | | | 229 | T$_s$G$_s$T$_s$A$_s$g$_s$a$_s$g$_s$a$_s$t$_s$g$_s$c$_s$g$_s$G$_s$T$_s$G$_s$g | | |
| | | | 230 | T$_O$G$_O$T$_O$A$_O$g$_s$a$_s$g$_s$a$_s$t$_s$g$_s$c$_s$g$_s$G$_O$T$_O$G$_O$G | | |
| | | | 231 | t$_s$g$_s$t$_s$a$_s$g$_s$a$_s$g$_s$a$_s$t$_s$g$_s$c$_s$g$_s$g$_s$t$_s$g$_s$g | | |
| 113 | 23 | AGGGCCAGTTCTTGAA | 232 | A$_s$G$_s$G$_s$G$_s$c$_s$c$_s$a$_s$g$_s$t$_s$t$_s$c$_s$t$_s$T$_s$G$_s$A$_s$A | | |
| | | | 233 | A$_s$G$_s$G$_s$G$_s$c$_s$c$_s$a$_s$g$_s$t$_s$t$_s$c$_s$t$_s$T$_s$G$_s$A$_s$a | | |
| | | | 234 | A$_O$G$_O$G$_O$G$_O$c$_s$c$_s$a$_s$g$_s$t$_s$t$_s$c$_s$t$_s$T$_O$G$_O$A$_O$a | | |
| | | | 235 | a$_s$g$_s$g$_s$g$_s$c$_s$c$_s$a$_s$g$_s$t$_s$t$_s$c$_s$t$_s$t$_s$g$_s$a$_s$a | | |
| 129 | 24 | GCGCAGCCCTCCAAGA | 236 | G$_s$C$_s$G$_s$C$_s$a$_s$g$_s$c$_s$c$_s$c$_s$t$_s$c$_s$c$_s$A$_s$A$_s$G$_s$A | | |
| | | | 237 | G$_s$C$_s$G$_s$C$_s$a$_s$g$_s$c$_s$c$_s$c$_s$t$_s$c$_s$c$_s$A$_s$A$_s$G$_s$a | | |
| | | | 238 | G$_O$C$_O$G$_O$C$_O$a$_s$g$_s$c$_s$c$_s$c$_s$t$_s$c$_s$c$_s$A$_O$A$_O$G$_O$A | | |
| | | | 239 | g$_s$c$_s$g$_s$c$_s$a$_s$g$_s$c$_s$c$_s$c$_s$t$_s$c$_s$c$_s$a$_s$a$_s$g$_s$a | | |
| 145 | 25 | CCGCTCCGGGGTGCAG | 240 | C$_s$C$_s$G$_s$C$_s$t$_s$c$_s$c$_s$g$_s$g$_s$g$_s$g$_s$t$_s$G$_s$C$_s$A$_s$G | | |
| | | | 241 | C$_s$C$_s$G$_s$C$_s$t$_s$c$_s$c$_s$g$_s$g$_s$g$_s$g$_s$t$_s$G$_s$C$_s$A$_s$g | | |
| | | | 242 | C$_O$C$_O$G$_O$C$_O$t$_s$c$_s$c$_s$g$_s$g$_s$g$_s$g$_s$t$_s$G$_O$C$_O$A$_O$G | | |
| | | | 243 | c$_s$c$_s$g$_s$c$_s$t$_s$c$_s$c$_s$g$_s$g$_s$g$_s$g$_s$t$_s$g$_s$c$_s$a$_s$g | | |
| 161 | 26 | AGCCAGCCTCGGCCAT | 244 | A$_s$G$_s$C$_s$C$_s$a$_s$g$_s$c$_s$c$_s$t$_s$c$_s$g$_s$g$_s$C$_s$C$_s$A$_s$T | | |
| | | | 245 | A$_s$G$_s$C$_s$C$_s$a$_s$g$_s$c$_s$c$_s$t$_s$c$_s$g$_s$g$_s$C$_s$C$_s$A$_s$t | | |
| | | | 246 | A$_O$G$_O$C$_O$C$_O$a$_s$g$_s$c$_s$c$_s$t$_s$c$_s$g$_s$g$_s$C$_O$C$_O$A$_O$T | | |
| | | | 247 | a$_s$g$_s$c$_s$c$_s$a$_s$g$_s$c$_s$c$_s$t$_s$c$_s$g$_s$g$_s$c$_s$c$_s$a$_s$t | | |
| 177 | 27 | GTGGGCAGTGGATGA | 248 | G$_s$T$_s$G$_s$G$_s$g$_s$g$_s$c$_s$a$_s$g$_s$t$_s$g$_s$g$_s$A$_s$T$_s$G$_s$A | | |
| | | | 249 | G$_s$T$_s$G$_s$G$_s$g$_s$g$_s$c$_s$a$_s$g$_s$t$_s$g$_s$g$_s$A$_s$T$_s$G$_s$a | | |
| | | | 250 | G$_O$T$_O$G$_O$G$_O$g$_s$g$_s$c$_s$a$_s$g$_s$t$_s$g$_s$g$_s$A$_O$T$_O$G$_O$A | | |
| | | | 251 | g$_s$t$_s$g$_s$g$_s$g$_s$g$_s$c$_s$a$_s$g$_s$t$_s$g$_s$g$_s$a$_s$t$_s$g$_s$a | | |

TABLE 1-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 193 | 28 | GTCTGGCTCGTTCTCA | 252 | G$_s$T$_s$C$_s$T$_s$g$_s$g$_s$c$_s$t$_s$c$_s$g$_s$t$_s$t$_s$C$_s$T$_s$C$_s$A | | |
| | | | 253 | G$_s$T$_s$C$_s$T$_s$g$_s$g$_s$c$_s$t$_s$c$_s$g$_s$t$_s$t$_s$C$_s$T$_s$C$_s$a | | |
| | | | 254 | G$_O$T$_O$C$_O$T$_O$g$_s$g$_s$c$_s$t$_s$c$_s$g$_s$t$_s$t$_s$C$_O$T$_O$C$_O$A | | |
| | | | 255 | g$_s$t$_s$c$_s$t$_s$g$_s$g$_s$c$_s$t$_s$c$_s$g$_s$t$_s$t$_s$c$_s$t$_s$c$_s$a | | |
| 209 | 29 | AGAAACACTGGGCCAA | 256 | A$_s$G$_s$A$_s$A$_s$a$_s$c$_s$a$_s$c$_s$t$_s$g$_s$g$_s$g$_s$C$_s$C$_s$A$_s$A | | |
| | | | 257 | A$_s$G$_s$A$_s$A$_s$a$_s$c$_s$a$_s$c$_s$t$_s$g$_s$g$_s$g$_s$C$_s$C$_s$A$_s$a | | |
| | | | 258 | A$_O$G$_O$A$_O$A$_O$a$_s$c$_s$a$_s$c$_s$t$_s$g$_s$g$_s$g$_s$C$_O$C$_O$A$_O$A | | |
| | | | 259 | a$_s$g$_s$a$_s$a$_s$a$_s$c$_s$a$_s$c$_s$t$_s$g$_s$g$_s$g$_s$c$_s$c$_s$a$_s$a | | |
| 225 | 30 | AGCTCCTTGAAGCAGA | 260 | A$_s$G$_s$C$_s$T$_s$c$_s$c$_s$t$_s$t$_s$g$_s$a$_s$a$_s$g$_s$C$_s$A$_s$G$_s$A | | |
| | | | 261 | A$_s$G$_s$C$_s$T$_s$c$_s$c$_s$t$_s$t$_s$g$_s$a$_s$a$_s$g$_s$C$_s$A$_s$G$_s$a | | |
| | | | 262 | A$_O$G$_O$C$_O$T$_O$c$_s$c$_s$t$_s$t$_s$g$_s$a$_s$a$_s$g$_s$C$_O$A$_O$G$_O$A | | |
| | | | 263 | a$_s$g$_s$c$_s$t$_s$c$_s$c$_s$t$_s$t$_s$g$_s$a$_s$a$_s$g$_s$c$_s$a$_s$g$_s$a | | |
| 241 | 31 | TGGCTCCCAGCCTTCC | 264 | T$_s$G$_s$G$_s$C$_s$t$_s$c$_s$c$_s$c$_s$a$_s$g$_s$c$_s$c$_s$T$_s$T$_s$C$_s$C | | |
| | | | 265 | T$_s$G$_s$G$_s$C$_s$t$_s$c$_s$c$_s$c$_s$a$_s$g$_s$c$_s$c$_s$T$_s$T$_s$C$_s$c | | |
| | | | 266 | T$_O$G$_O$G$_O$C$_O$t$_s$c$_s$c$_s$c$_s$a$_s$g$_s$c$_s$c$_s$T$_O$T$_O$C$_O$C | | |
| | | | 267 | t$_s$g$_s$g$_s$c$_s$t$_s$c$_s$c$_s$c$_s$a$_s$g$_s$c$_s$c$_s$t$_s$t$_s$c$_s$c | | |
| 257 | 32 | CTATGGGGTCGTCATC | 268 | C$_s$T$_s$A$_s$T$_s$g$_s$g$_s$g$_s$g$_s$t$_s$c$_s$g$_s$t$_s$C$_s$A$_s$T$_s$C | | |
| | | | 269 | C$_s$T$_s$A$_s$T$_s$g$_s$g$_s$g$_s$g$_s$t$_s$c$_s$g$_s$t$_s$C$_s$A$_s$T$_s$c | | |
| | | | 270 | C$_O$T$_O$A$_O$T$_O$g$_s$g$_s$g$_s$g$_s$t$_s$c$_s$g$_s$t$_s$C$_O$A$_O$T$_O$C | | |
| | | | 271 | c$_s$t$_s$a$_s$t$_s$g$_s$g$_s$g$_s$g$_s$t$_s$c$_s$g$_s$t$_s$c$_s$a$_s$t$_s$c | | |
| 273 | 33 | TGCTTTTTATGTTCCT | 272 | T$_s$G$_s$C$_s$T$_s$t$_s$t$_s$t$_s$t$_s$a$_s$t$_s$g$_s$t$_s$T$_s$C$_s$C$_s$T | | |
| | | | 273 | T$_s$G$_s$C$_s$T$_s$t$_s$t$_s$t$_s$t$_s$a$_s$t$_s$g$_s$t$_s$T$_s$C$_s$C$_s$t | | |
| | | | 274 | T$_O$G$_O$C$_O$T$_O$t$_s$t$_s$t$_s$t$_s$a$_s$t$_s$g$_s$t$_s$T$_O$C$_O$C$_O$T | | |
| | | | 275 | t$_s$g$_s$c$_s$t$_s$t$_s$t$_s$t$_s$t$_s$a$_s$t$_s$g$_s$t$_s$t$_s$c$_s$c$_s$t | | |
| 289 | 34 | AGCGCAACCGGACGAA | 276 | A$_s$G$_s$C$_s$G$_s$c$_s$a$_s$a$_s$c$_s$c$_s$g$_s$g$_s$a$_s$C$_s$G$_s$A$_s$A | | |
| | | | 277 | A$_s$G$_s$C$_s$G$_s$c$_s$a$_s$a$_s$c$_s$c$_s$g$_s$g$_s$a$_s$C$_s$G$_s$A$_s$a | | |
| | | | 278 | A$_O$G$_O$C$_O$G$_O$c$_s$a$_s$a$_s$c$_s$c$_s$g$_s$g$_s$a$_s$C$_O$G$_O$A$_O$A | | |
| | | | 279 | a$_s$g$_s$c$_s$g$_s$c$_s$a$_s$a$_s$c$_s$c$_s$g$_s$g$_s$a$_s$c$_s$g$_s$a$_s$a | | |
| 305 | 35 | TCTTGACAGAAAGGAA | 280 | T$_s$C$_s$T$_s$T$_s$g$_s$a$_s$c$_s$a$_s$g$_s$a$_s$a$_s$a$_s$G$_s$G$_s$A$_s$A | | |
| | | | 281 | T$_s$C$_s$T$_s$T$_s$g$_s$a$_s$c$_s$a$_s$g$_s$a$_s$a$_s$a$_s$G$_s$G$_s$A$_s$a | | |
| | | | 282 | T$_O$C$_O$T$_O$T$_O$g$_s$a$_s$c$_s$a$_s$g$_s$a$_s$a$_s$a$_s$G$_O$G$_O$A$_O$A | | |
| | | | 283 | t$_s$c$_s$t$_s$t$_s$g$_s$a$_s$c$_s$a$_s$g$_s$a$_s$a$_s$a$_s$g$_s$g$_s$a$_s$a | | |
| 321 | 36 | AATTCTTCAAACTGCT | 284 | A$_s$A$_s$T$_s$T$_s$c$_s$t$_s$t$_s$c$_s$a$_s$a$_s$a$_s$c$_s$T$_s$G$_s$C$_s$T | | |
| | | | 285 | A$_s$A$_s$T$_s$T$_s$c$_s$t$_s$t$_s$c$_s$a$_s$a$_s$a$_s$c$_s$T$_s$G$_s$C$_s$t | | |
| | | | 286 | A$_O$A$_O$T$_O$T$_O$c$_s$t$_s$t$_s$c$_s$a$_s$a$_s$a$_s$c$_s$T$_O$G$_O$C$_O$T | | |
| | | | 287 | a$_s$a$_s$t$_s$t$_s$c$_s$t$_s$t$_s$c$_s$a$_s$a$_s$a$_s$c$_s$t$_s$g$_s$c$_s$t | | |
| 337 | 37 | AAATTCACCAAGGGTT | 288 | A$_s$A$_s$A$_s$T$_s$t$_s$c$_s$a$_s$c$_s$c$_s$a$_s$a$_s$g$_s$G$_s$G$_s$T$_s$T | | |
| | | | 289 | A$_s$A$_s$A$_s$T$_s$t$_s$c$_s$a$_s$c$_s$c$_s$a$_s$a$_s$g$_s$G$_s$G$_s$T$_s$t | | |
| | | | 290 | A$_O$A$_O$A$_O$T$_O$t$_s$c$_s$a$_s$c$_s$c$_s$a$_s$a$_s$g$_s$G$_O$G$_O$T$_O$T | | |
| | | | 291 | a$_s$a$_s$a$_s$t$_s$t$_s$c$_s$a$_s$c$_s$c$_s$a$_s$a$_s$g$_s$g$_s$g$_s$t$_s$t | | |
| 353 | 38 | CTCTGTCCAGTTTCAA | 292 | C$_s$T$_s$C$_s$T$_s$g$_s$t$_s$c$_s$c$_s$a$_s$g$_s$t$_s$t$_s$T$_s$C$_s$A$_s$A | | |
| | | | 293 | C$_s$T$_s$C$_s$T$_s$g$_s$t$_s$c$_s$c$_s$a$_s$g$_s$t$_s$t$_s$T$_s$C$_s$A$_s$a | | |
| | | | 294 | C$_O$T$_O$C$_O$T$_O$g$_s$t$_s$c$_s$c$_s$a$_s$g$_s$t$_s$t$_s$T$_O$C$_O$A$_O$A | | |
| | | | 295 | c$_s$t$_s$c$_s$t$_s$g$_s$t$_s$c$_s$c$_s$a$_s$g$_s$t$_s$t$_s$t$_s$c$_s$a$_s$a | | |
| 369 | 39 | TTGTTCTTGGCTCTTT | 296 | T$_s$T$_s$G$_s$T$_s$t$_s$c$_s$t$_s$t$_s$g$_s$g$_s$c$_s$t$_s$C$_s$T$_s$T$_s$T | | |
| | | | 297 | T$_s$T$_s$G$_s$T$_s$t$_s$c$_s$t$_s$t$_s$g$_s$g$_s$c$_s$t$_s$C$_s$T$_s$T$_s$t | | |
| | | | 298 | T$_O$T$_O$G$_O$T$_O$t$_s$c$_s$t$_s$t$_s$g$_s$g$_s$c$_s$t$_s$C$_O$T$_O$T$_O$T | | |
| | | | 299 | t$_s$t$_s$g$_s$t$_s$t$_s$c$_s$t$_s$t$_s$g$_s$g$_s$c$_s$t$_s$c$_s$t$_s$t$_s$t | | |
| 385 | 40 | GGTTTCCTTTGCAATT | 300 | G$_s$G$_s$T$_s$T$_s$t$_s$c$_s$c$_s$t$_s$t$_s$t$_s$g$_s$c$_s$A$_s$A$_s$T$_s$T | | |
| | | | 301 | G$_s$G$_s$T$_s$T$_s$t$_s$c$_s$c$_s$t$_s$t$_s$t$_s$g$_s$c$_s$A$_s$A$_s$T$_s$t | | |
| | | | 302 | G$_O$G$_O$T$_O$T$_O$t$_s$c$_s$c$_s$t$_s$t$_s$t$_s$g$_s$c$_s$A$_O$A$_O$T$_O$T | | |
| | | | 303 | g$_s$g$_s$t$_s$t$_s$t$_s$c$_s$c$_s$t$_s$t$_s$t$_s$g$_s$c$_s$a$_s$a$_s$t$_s$t | | |

TABLE 1-continued

Oligomeric compounds of the invention
Oligomeric compounds were evaluated for their potential to knockdown Survivin
mRNA in 15PC3 cells. The data are presented as percentage downregulation relative
to mock transfected cells. Transcript steady state was monitored by Real-time PCR
and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 401 | 41 | CTTTGTTCTTATTGTT | 304 | $C_sT_sT_sT_sc_st_st_sc_st_st_sa_st_sT_sG_sT_sT$ | | |
| | | | 305 | $C_sT_sT_sT_sc_st_st_sc_st_st_sa_st_sT_sG_sT_st$ | | |
| | | | 306 | $C_OT_OT_OT_Oc_st_st_sc_st_st_sa_st_sT_OG_OT_OT$ | | |
| | | | 307 | $c_st_st_st_sc_st_st_sc_st_st_sa_st_sg_st_st$ | | |
| 417 | 42 | GCAGTTTCCTCAAAIT | 308 | $G_sC_sA_sG_st_st_st_sc_sc_st_sc_sa_sA_sA_sT_sT$ | | |
| | | | 309 | $G_sC_sA_sG_st_st_st_sc_sc_st_sc_sa_sA_sA_sT_st$ | | |
| | | | 310 | $G_OC_OA_OG_Ot_st_st_sc_sc_st_sc_sa_sA_OA_OT_OT$ | | |
| | | | 311 | $g_sc_sa_sg_st_st_st_sc_sc_st_sc_sa_sa_sa_st_st$ | | |
| 433 | 43 | ACGGCGCACTTTCTTC | 312 | $A_sC_sG_sG_sc_sg_sc_sa_sc_st_st_st_sC_sT_sT_sC$ | | |
| | | | 313 | $A_sC_sG_sG_sc_sg_sc_sa_sc_st_st_st_sC_sT_sT_st$ | | |
| | | | 314 | $A_OC_OG_OG_Oc_sg_sc_sa_sc_st_st_st_sC_OT_OT_OC$ | | |
| | | | 315 | $a_sc_sg_sg_sc_sg_sc_sa_sc_st_st_st_sc_st_st_sc$ | | |
| 449 | 44 | CCAGCTGCTCGATGGC | 316 | $C_sC_sA_sG_sc_st_sg_sc_st_sc_sg_sa_sT_sG_sG_sC$ | | |
| | | | 317 | $C_sC_sA_sG_sc_st_sg_sc_st_sc_sg_sa_sT_sG_sG_st$ | | |
| | | | 318 | $C_OC_OA_OG_Oc_st_sg_sc_st_sc_sg_sa_sT_OG_OG_OC$ | | |
| | | | 319 | $c_sc_sa_sg_sc_st_sg_sc_st_sc_sg_sa_st_sg_sg_sc$ | | |
| 465 | 45 | CCTCAATCCATGGCAG | 320 | $C_sC_sT_sC_sa_sa_st_sc_sc_sa_st_sg_sG_sC_sA_sG$ | | |
| | | | 321 | $C_sC_sT_sC_sa_sa_st_sc_sc_sa_st_sg_sG_sC_sA_sg$ | | |
| | | | 322 | $C_OC_OT_OC_Oa_sa_st_sc_sc_sa_st_sg_sG_OC_OA_Og$ | | |
| | | | 323 | $c_sc_st_sc_sa_sa_st_sc_sc_sa_st_sg_sg_sc_sa_sg$ | | |
| 481 | 46 | CAGCTCCGGCCAGAGG | 324 | $C_sA_sG_sC_st_sc_sc_sg_sg_sc_sc_sa_sG_sA_sG_sG$ | | |
| | | | 325 | $C_sA_sG_sC_st_sc_sc_sg_sg_sc_sc_sa_sG_sA_sG_sg$ | | |
| | | | 326 | $C_OA_OG_OC_Oc_sc_sc_sg_sg_sc_sc_sa_sG_OA_OG_OG$ | | |
| | | | 327 | $c_sa_sg_sc_st_sc_sc_sg_sg_sc_sc_sa_sg_sa_sg_sg$ | | |
| 497 | 47 | CCACTCTGGGACCAGG | 328 | $C_sC_sA_sC_st_sc_st_sg_sg_sg_sa_sc_sC_sA_sG_sG$ | | |
| | | | 329 | $C_sC_sA_sC_st_sc_st_sg_sg_sg_sa_sc_sC_sA_sG_sg$ | | |
| | | | 330 | $C_OC_OA_OC_Ot_sc_st_sg_sg_sg_sa_sc_sC_OA_OG_OG$ | | |
| | | | 331 | $c_sc_sa_sc_st_sc_st_sg_sg_sg_sa_sc_sc_sa_sg_sg$ | | |
| 513 | 48 | CCTGGAAGTGGTGCAG | 332 | $C_sC_sT_sG_sg_sa_sa_sg_st_sg_sg_st_sG_sC_sA_sG$ | | |
| | | | 333 | $C_sC_sT_sG_sg_sa_sa_sg_st_sg_sg_st_sG_sC_sA_sg$ | | |
| | | | 334 | $C_OC_OT_OG_Og_sa_sa_sg_st_sg_sg_st_sG_OC_OA_OG$ | | |
| | | | 335 | $c_sc_st_sg_sg_sa_sa_sg_st_sg_sg_st_sg_sc_sa_sg$ | | |
| 529 | 49 | GCACCAGGGAATAAAC | 336 | $G_sC_sA_sC_sc_sa_sg_sg_sg_sa_sa_st_sA_sA_sA_sC$ | | |
| | | | 337 | $G_sC_sA_sC_sc_sa_sg_sg_sg_sa_sa_st_sA_sA_sA_sc$ | | |
| | | | 338 | $G_OC_OA_OC_Oc_sa_sg_sg_sg_sa_sa_st_sA_OA_OA_OC_O$ | | |
| | | | 339 | $g_sc_sa_sc_sc_sa_sg_sg_sg_sa_sa_st_sa_sa_sa_sc$ | | |
| 545 | 50 | CACAGGAAGGCTGGTG | 340 | $C_sA_sC_sA_sg_sg_sa_sa_sg_sg_sc_st_sG_sG_sT_sG$ | | |
| | | | 341 | $C_sA_sC_sA_sg_sg_sa_sa_sg_sg_sc_st_sG_sG_sT_sg$ | | |
| | | | 342 | $C_OA_OC_OA_Og_sg_sa_sa_sg_sg_sc_st_sG_OG_OT_OG$ | | |
| | | | 343 | $c_sa_sc_sa_sg_sg_sa_sa_sg_sg_sc_st_sg_sg_st_sg$ | | |
| 561 | 51 | ACATTGCTAAGGGGCC | 344 | $A_sC_sA_sT_st_sg_sc_st_sa_sa_sg_sg_sG_sG_sC_sC$ | | |
| | | | 345 | $A_sC_sA_sT_st_sg_sc_st_sa_sa_sg_sg_sG_sG_sC_sC$ | | |
| | | | 346 | $A_OC_OA_OT_Ot_sg_sc_st_sa_sa_sg_sg_sG_OG_OC_OC$ | | |
| | | | 347 | $a_sc_sa_st_st_sg_sc_st_sa_sa_sg_sg_sg_sg_sc_sc$ | | |
| 577 | 52 | GATCTCCTTTCCTAAG | 348 | $G_sA_sT_sC_st_sc_sc_st_st_st_sc_sc_sT_sA_sA_sG$ | | |
| | | | 349 | $G_sA_sT_sC_st_sc_sc_st_st_st_sc_sc_sT_sA_sA_sg$ | | |
| | | | 350 | $G_OA_OT_OC_Ot_sc_sc_st_st_st_sc_sc_sT_OA_OA_OG$ | | |
| | | | 351 | $g_sa_st_sc_st_sc_sc_st_st_st_sc_sc_st_sa_sa_sg$ | | |
| 593 | 53 | CTAATTTGAAAATGTT | 352 | $C_sT_sA_sA_st_st_st_sg_sa_sa_sa_sa_st_sT_sG_sT_sT$ | | |
| | | | 353 | $C_sT_sA_sA_st_st_st_sg_sa_sa_sa_sa_sT_sG_sT_st$ | | |
| | | | 354 | $C_OT_OA_OA_Ot_st_st_sg_sa_sa_sa_sa_sT_OG_OT_OT$ | | |
| | | | 355 | $c_st_sa_sa_st_st_st_sg_sa_sa_sa_sa_st_sg_st_st$ | | |

TABLE 1-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 609 | 54 | AGCACAGTTGAAACAT | 356 | $A_sG_sC_sA_sc_sa_sg_st_st_sg_sa_sa_sA_sC_sA_sT$ | | |
|  |  |  | 357 | $A_sG_sC_sA_sc_sa_sg_st_st_sg_sa_sa_sA_sC_sA_st$ | | |
|  |  |  | 358 | $A_oG_oC_oA_oc_sa_sg_st_st_sg_sa_sa_sA_oC_oA_oT$ | | |
|  |  |  | 359 | $a_sg_sc_sa_sc_sa_sg_st_st_sg_sa_sa_sa_sc_sa_st$ | | |
| 625 | 55 | TTCAAGACAAAACAGG | 360 | $T_sT_sC_sA_sa_sg_sa_sc_sa_sa_sa_sa_sC_sA_sG_sG$ | | |
|  |  |  | 361 | $T_sT_sC_sA_sa_sg_sa_sc_sa_sa_sa_sa_sC_sA_sG_sg$ | | |
|  |  |  | 362 | $T_oT_oC_oA_oa_sg_sa_sc_sa_sa_sa_sa_sC_oA_oG_oG$ | | |
|  |  |  | 363 | $t_st_sc_sa_sa_sg_sa_sc_sa_sa_sa_sa_sc_sa_sg_sg$ | | |
| 641 | 56 | CACCTCTGGTGCCACT | 364 | $C_sA_sC_sC_st_sc_st_sg_sg_st_sg_sc_sC_sA_sC_sT$ | | |
|  |  |  | 365 | $C_sA_sC_sC_st_sc_st_sg_sg_st_sg_sc_sC_sA_sC_st$ | | |
|  |  |  | 366 | $C_oA_oC_oC_ot_sc_st_sg_sg_st_sg_sc_sC_oA_oC_oT$ | | |
|  |  |  | 367 | $c_sa_sc_sc_st_sc_st_sg_sg_st_sg_sc_sc_sa_sc_st$ | | |
| 657 | 57 | GCTGCACAGGCAGAAG | 368 | $G_sC_sT_sG_sc_sa_sc_sa_sg_sg_sc_sa_sG_sA_sA_sG$ | | |
|  |  |  | 369 | $G_sC_sT_sG_sc_sa_sc_sa_sg_sg_sc_sa_sG_sA_sA_sg$ | | |
|  |  |  | 370 | $G_oC_oT_oG_oc_sa_sc_sa_sg_sg_sc_sa_sG_oA_oA_oG$ | | |
|  |  |  | 371 | $g_sc_st_sg_sc_sa_sc_sa_sg_sg_sc_sa_sg_sa_sa_sg$ | | |
| 673 | 58 | GTTACCAGCAGCACCC | 372 | $G_sT_sT_sA_sc_sc_sa_sg_sc_sa_sg_sc_sA_sC_sC_sC$ | | |
|  |  |  | 373 | $G_sT_sT_sA_sc_sc_sa_sg_sc_sa_sg_sc_sA_sC_sC_sc$ | | |
|  |  |  | 374 | $G_oT_oT_oA_oc_sc_sa_sg_sc_sa_sg_sc_sA_oC_oC_oC$ | | |
|  |  |  | 375 | $g_st_st_sa_sc_sc_sa_sg_sc_sa_sg_sc_sa_sc_sc_sc$ | | |
| 689 | 59 | GAGAGAAGCAGCCACT | 376 | $G_sA_sG_sA_sg_sa_sa_sg_sc_sa_sg_sc_sC_sA_sC_sT$ | | |
|  |  |  | 377 | $G_sA_sG_sA_sg_sa_sa_sg_sc_sa_sg_sc_sC_sA_sC_st$ | | |
|  |  |  | 378 | $G_oA_oG_oA_og_sa_sa_sg_sc_sa_sg_sc_sC_oA_oC_oT$ | | |
|  |  |  | 379 | $g_sa_sg_sa_sg_sa_sa_sg_sc_sa_sg_sc_sc_sa_sc_st$ | | |
| 705 | 60 | AAAAAAGAGAGAGAGA | 380 | $A_sA_sA_sA_sa_sa_sg_sa_sg_sa_sg_sa_sG_sA_sG_sA$ | | |
|  |  |  | 381 | $A_sA_sA_sA_sa_sa_sg_sa_sg_sa_sg_sa_sG_sA_sG_sa$ | | |
|  |  |  | 382 | $A_oA_oA_oA_oa_sa_sg_sa_sg_sa_sg_sa_sG_oA_oG_oA$ | | |
|  |  |  | 383 | $a_sa_sa_sa_sa_sa_sg_sa_sg_sa_sg_sa_sg_sa_sg_sa$ | | |
| 721 | 61 | GCAAAATGAGCCCCC | 384 | $G_sC_sA_sA_sa_sa_sa_st_sg_sa_sg_sc_sC_sC_sC_sC$ | | |
|  |  |  | 385 | $G_sC_sA_sA_sa_sa_sa_st_sg_sa_sg_sc_sC_sC_sC_sc$ | | |
|  |  |  | 386 | $G_oC_oA_oA_oa_sa_sa_st_sg_sa_sg_sc_sC_oC_oC_oC$ | | |
|  |  |  | 387 | $g_sc_sa_sa_sa_sa_sa_st_sg_sa_sg_sc_sc_sc_sc_sc$ | | |
| 737 | 62 | CCCGGGAATCAAAACA | 388 | $C_sC_sC_sG_sg_sg_sa_sa_st_sc_sa_sa_sA_sA_sC_sA$ | | |
|  |  |  | 389 | $C_sC_sC_sG_sg_sg_sa_sa_st_sc_sa_sa_sA_sA_sC_sa$ | | |
|  |  |  | 390 | $C_oC_oC_oG_og_sg_sa_sa_st_sc_sa_sa_sA_oA_oC_oA$ | | |
|  |  |  | 391 | $c_sc_sc_sg_sg_sg_sa_sa_st_sc_sa_sa_sa_sa_sc_sa$ | | |
| 753 | 63 | CTTCTCACCTGGTAAG | 392 | $C_sT_sT_sC_st_sc_sa_sc_sc_st_sg_sg_sT_sA_sA_sG$ | | |
|  |  |  | 393 | $C_sT_sT_sC_st_sc_sa_sc_sc_st_sg_sg_sT_sA_sA_sg$ | | |
|  |  |  | 394 | $C_oT_oT_oC_ot_sc_sa_sc_sc_st_sg_sg_sT_oA_oA_oG$ | | |
|  |  |  | 395 | $c_st_st_sc_st_sc_sa_sc_sc_st_sg_sg_st_sa_sa_sg$ | | |
| 769 | 64 | CCTTCTTCCTCCCTCA | 396 | $C_sC_sT_sT_sc_st_st_sc_sc_st_sc_sc_sC_sT_sC_sA$ | | |
|  |  |  | 397 | $C_sC_sT_sT_sc_st_st_sc_sc_st_sc_sc_sC_sT_sC_sa$ | | |
|  |  |  | 398 | $C_oC_oT_oT_oc_st_st_sc_sc_st_sc_sc_sC_oT_oC_oA$ | | |
|  |  |  | 399 | $c_sc_st_st_sc_st_st_sc_sc_st_sc_sc_sc_st_sc_sa$ | | |
| 785 | 65 | AGCAAAGGGACAGTG | 400 | $A_sG_sC_sA_sa_sa_sa_sg_sg_sg_sa_sc_sA_sC_sT_sG$ | | |
|  |  |  | 401 | $A_sG_sC_sA_sa_sa_sa_sg_sg_sg_sa_sc_sA_sC_sT_sg$ | | |
|  |  |  | 402 | $A_oG_oC_oA_oa_sa_sa_sg_sg_sg_sa_sc_sA_oC_oT_oG$ | | |
|  |  |  | 403 | $a_sg_sc_sa_sa_sa_sa_sg_sg_sg_sa_sc_sa_sc_st_sg$ | | |
| 801 | 66 | CAAAGCTGTCAGCTCT | 404 | $C_sA_sA_sA_sg_sc_st_sg_st_sc_sa_sg_sC_sT_sC_sT$ | | |
|  |  |  | 405 | $C_sA_sA_sA_sg_sc_st_sg_st_sc_sa_sg_sC_sT_sC_st$ | | |
|  |  |  | 406 | $C_oA_oA_oA_og_sc_st_sg_st_sc_sa_sg_sC_oT_oC_oT$ | | |
|  |  |  | 407 | $c_sa_sa_sa_sg_sc_st_sg_st_sc_sa_sg_sc_st_sc_st$ | | |

TABLE 1-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 817 | 67 | GCTCTGCCCACGCGAA | 408 | G$_s$C$_s$T$_s$C$_s$t$_s$g$_s$c$_s$c$_s$c$_s$a$_s$c$_s$ g$_s$C$_s$G$_s$A$_s$A | | |
| | | | 409 | G$_s$C$_s$T$_s$C$_s$t$_s$g$_s$c$_s$c$_s$c$_s$a$_s$c$_s$ g$_s$C$_s$G$_s$A$_s$a | | |
| | | | 410 | G$_o$C$_o$T$_o$C$_o$t$_s$g$_s$c$_s$c$_s$c$_s$a$_s$c$_s$ g$_o$C$_o$G$_o$A$_o$A | | |
| | | | 411 | g$_s$c$_s$t$_s$c$_s$t$_s$g$_s$c$_s$c$_s$c$_s$a$_s$c$_s$g$_s$c$_s$g$_s$a$_s$a | | |
| 833 | 68 | ACATTCACTGTGGAAG | 412 | A$_s$C$_s$A$_s$T$_s$t$_s$c$_s$a$_s$c$_s$t$_s$g$_s$t$_s$g$_s$ G$_s$A$_s$A$_s$G | | |
| | | | 413 | A$_s$C$_s$A$_s$T$_s$t$_s$c$_s$a$_s$c$_s$t$_s$g$_s$t$_s$g$_s$ G$_s$A$_s$A$_s$g | | |
| | | | 414 | A$_o$C$_o$A$_o$T$_o$t$_s$c$_s$a$_s$c$_s$t$_s$g$_s$t$_s$g$_s$ G$_o$A$_o$A$_o$G | | |
| | | | 415 | a$_s$ac$_s$a$_s$t$_s$t$_s$c$_s$a$_s$c$_s$t$_s$g$_s$t$_s$g$_s$g$_s$a$_s$a$_s$g | | |
| 849 | 69 | AACATGAGGTCCAGAC | 416 | A$_s$A$_s$C$_s$A$_s$t$_s$g$_s$a$_s$g$_s$g$_s$t$_s$c$_s$c$_s$ A$_s$G$_s$A$_s$C | | |
| | | | 417 | A$_s$A$_s$C$_s$A$_s$t$_s$g$_s$a$_s$g$_s$g$_s$t$_s$c$_s$c$_s$ A$_s$G$_s$A$_s$c | | |
| | | | 418 | A$_o$A$_o$C$_o$A$_o$t$_s$g$_s$a$_s$g$_s$g$_s$t$_s$c$_s$c$_s$ A$_o$G$_o$A$_o$C | | |
| | | | 419 | a$_s$a$_s$c$_s$a$_s$t$_s$g$_s$a$_s$g$_s$g$_s$t$_s$c$_s$c$_s$a$_s$g$_s$a$_s$c | | |
| 865 | 70 | CTGTGACAGCCTCAAC | 420 | C$_s$T$_s$G$_s$T$_s$g$_s$a$_s$c$_s$a$_s$g$_s$c$_s$c$_s$t$_s$ C$_s$A$_s$A$_s$C | | |
| | | | 421 | C$_s$T$_s$G$_s$T$_s$g$_s$a$_s$c$_s$a$_s$g$_s$c$_s$c$_s$t$_s$ C$_s$A$_s$A$_s$c | | |
| | | | 422 | C$_o$T$_o$G$_o$T$_o$g$_s$a$_s$c$_s$a$_s$g$_s$c$_s$c$_s$t$_s$ C$_o$A$_o$A$_o$C | | |
| | | | 423 | c$_s$t$_s$g$_s$t$_s$g$_s$a$_s$c$_s$a$_s$g$_s$c$_s$c$_s$t$_s$c$_s$a$_s$a$_s$c | | |
| 881 | 71 | AAGTCCACACTCAGGA | 424 | A$_s$A$_s$G$_s$T$_s$c$_s$c$_s$a$_s$c$_s$a$_s$c$_s$t$_s$c$_s$ A$_s$G$_s$G$_s$A | | |
| | | | 425 | A$_s$A$_s$G$_s$T$_s$c$_s$c$_s$a$_s$c$_s$a$_s$c$_s$t$_s$c$_s$ A$_s$G$_s$G$_s$a | | |
| | | | 426 | A$_o$A$_o$G$_o$T$_o$c$_s$c$_s$a$_s$c$_s$a$_s$c$_s$t$_s$c$_s$ A$_o$G$_o$G$_o$A | | |
| | | | 427 | a$_s$a$_s$g$_s$t$_s$c$_s$c$_s$a$_s$c$_s$a$_s$c$_s$t$_s$c$_s$a$_s$g$_s$g$_s$a | | |
| 897 | 72 | TCAACAGGCACCTGCC | 428 | T$_s$C$_s$A$_s$A$_s$c$_s$a$_s$g$_s$g$_s$c$_s$a$_s$c$_s$c$_s$ T$_s$G$_s$C$_s$C | | |
| | | | 429 | T$_s$C$_s$A$_s$A$_s$c$_s$a$_s$g$_s$g$_s$c$_s$a$_s$c$_s$c$_s$ T$_s$G$_s$C$_s$c | | |
| | | | 430 | T$_o$C$_o$A$_o$A$_o$c$_s$a$_s$g$_s$g$_s$c$_s$a$_s$c$_s$c$_s$ T$_o$G$_o$C$_o$C | | |
| | | | 431 | t$_s$c$_s$a$_s$a$_s$c$_s$a$_s$g$_s$g$_s$c$_s$a$_s$c$_s$c$_s$t$_s$g$_s$c$_s$c | | |
| 913 | 73 | AACCTGCAGCTCAGAT | 432 | A$_s$A$_s$C$_s$C$_s$t$_s$g$_s$c$_s$a$_s$g$_s$c$_s$t$_s$c$_s$ A$_s$G$_s$A$_s$T | | |
| | | | 433 | A$_s$A$_s$C$_s$C$_s$t$_s$g$_s$c$_s$a$_s$g$_s$c$_s$t$_s$c$_s$ A$_s$G$_s$A$_s$t | | |
| | | | 434 | A$_o$A$_o$C$_o$C$_o$t$_s$g$_s$c$_s$a$_s$g$_s$c$_s$t$_s$c$_s$ A$_o$G$_o$A$_o$T | | |
| | | | 435 | a$_s$a$_s$c$_s$c$_s$t$_s$g$_s$c$_s$a$_s$g$_s$c$_s$t$_s$c$_s$a$_s$g$_s$a$_s$t | | |
| 929 | 74 | GGTGTGACAGATAAGG | 436 | G$_s$G$_s$T$_s$G$_s$t$_s$g$_s$a$_s$c$_s$a$_s$g$_s$a$_s$t$_s$ A$_s$A$_s$G$_s$G | | |
| | | | 437 | G$_s$G$_s$T$_s$G$_s$t$_s$g$_s$a$_s$c$_s$a$_s$g$_s$a$_s$t$_s$ A$_s$A$_s$G$_s$g | | |
| | | | 438 | G$_o$G$_o$T$_o$G$_o$t$_s$g$_s$a$_s$c$_s$a$_s$g$_s$a$_s$t$_s$ A$_o$A$_o$G$_o$G | | |
| | | | 439 | g$_s$g$_s$t$_s$g$_s$t$_s$g$_s$a$_s$c$_s$a$_s$g$_s$a$_s$t$_s$a$_s$a$_s$g$_s$g | | |
| 945 | 75 | CCTCTGAGGAGGCACA | 440 | C$_s$C$_s$T$_s$C$_s$t$_s$g$_s$a$_s$g$_s$g$_s$a$_s$g$_s$g$_s$ C$_s$A$_s$C$_s$A | | |
| | | | 441 | C$_s$C$_s$T$_s$C$_s$t$_s$g$_s$a$_s$g$_s$g$_s$a$_s$g$_s$g$_s$ C$_s$A$_s$C$_s$a | | |
| | | | 442 | C$_o$C$_o$T$_o$C$_o$t$_s$g$_s$a$_s$g$_s$g$_s$a$_s$g$_s$g$_s$ C$_o$A$_o$C$_o$A | | |
| | | | 443 | c$_s$c$_s$t$_s$c$_s$t$_s$g$_s$a$_s$g$_s$g$_s$a$_s$g$_s$g$_s$c$_s$a$_s$c$_s$a | | |
| 961 | 76 | ACAACAAAAAAACTGT | 444 | A$_s$C$_s$A$_s$A$_s$c$_s$a$_s$a$_s$a$_s$a$_s$a$_s$a$_s$a$_s$ C$_s$T$_s$G$_s$T | | |
| | | | 445 | A$_s$C$_s$A$_s$A$_s$c$_s$a$_s$a$_s$a$_s$a$_s$a$_s$a$_s$a$_s$ C$_s$T$_s$G$_s$t | | |
| | | | 446 | A$_o$C$_o$A$_o$A$_o$c$_s$a$_s$a$_s$a$_s$a$_s$a$_s$a$_s$a$_s$ C$_o$T$_o$G$_o$T | | |
| | | | 447 | a$_s$c$_s$a$_s$a$_s$c$_s$a$_s$a$_s$a$_s$a$_s$a$_s$a$_s$a$_s$c$_s$t$_s$g$_s$t | | |
| 977 | 77 | AAAACAAAAAAACACA | 448 | A$_s$A$_s$A$_s$A$_s$c$_s$a$_s$a$_s$a$_s$a$_s$a$_s$a$_s$a$_s$ C$_s$A$_s$C$_s$A | | |
| | | | 449 | A$_s$A$_s$A$_s$A$_s$c$_s$a$_s$a$_s$a$_s$a$_s$a$_s$a$_s$a$_s$ C$_s$A$_s$C$_s$a | | |
| | | | 450 | A$_o$A$_o$A$_o$A$_o$c$_s$a$_s$a$_s$a$_s$a$_s$a$_s$a$_s$a$_s$ C$_o$A$_o$C$_o$A | | |
| | | | 451 | a$_s$a$_s$a$_s$a$_s$c$_s$a$_s$a$_s$a$_s$a$_s$a$_s$a$_s$a$_s$c$_s$a$_s$c$_s$a | | |
| 993 | 78 | CATCTACCAAAAAAAA | 452 | C$_s$A$_s$T$_s$C$_s$t$_s$a$_s$c$_s$c$_s$a$_s$a$_s$a$_s$a$_s$ A$_s$A$_s$A$_s$A | | |
| | | | 453 | C$_s$A$_s$T$_s$C$_s$t$_s$a$_s$c$_s$c$_s$a$_s$a$_s$a$_s$a$_s$ A$_s$A$_s$A$_s$a | | |
| | | | 454 | C$_o$A$_o$T$_o$C$_o$t$_s$a$_s$c$_s$c$_s$a$_s$a$_s$a$_s$a$_s$ A$_o$A$_o$A$_o$A | | |
| | | | 455 | c$_s$a$_s$t$_s$c$_s$t$_s$a$_s$c$_s$c$_s$a$_s$a$_s$a$_s$a$_s$a$_s$a$_s$a$_s$a | | |
| 1009 | 79 | TCACACACAAGTCATG | 456 | T$_s$C$_s$A$_s$C$_s$a$_s$c$_s$a$_s$c$_s$a$_s$a$_s$g$_s$t$_s$ C$_s$A$_s$T$_s$G | | |
| | | | 457 | T$_s$C$_s$A$_s$C$_s$a$_s$c$_s$a$_s$c$_s$a$_s$a$_s$g$_s$t$_s$ C$_s$A$_s$T$_s$g | | |
| | | | 458 | T$_o$C$_o$A$_o$C$_o$a$_s$c$_s$a$_s$c$_s$a$_s$a$_s$g$_s$t$_s$ C$_o$A$_o$T$_o$G | | |
| | | | 459 | t$_s$c$_s$a$_s$c$_s$a$_s$c$_s$a$_s$c$_s$a$_s$a$_s$g$_s$t$_s$c$_s$a$_s$t$_s$g | | |

TABLE 1-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 1025 | 80 | TGTCTCCATTCTCTCA | 460 | T$_s$G$_s$T$_s$C$_s$t$_s$c$_s$c$_s$a$_s$t$_s$t$_s$c$_s$t$_s$C$_s$T$_s$C$_s$A | | |
| | | | 461 | T$_s$G$_s$T$_s$C$_s$t$_s$c$_s$c$_s$a$_s$t$_s$t$_s$c$_s$t$_s$C$_s$T$_s$C$_s$a | | |
| | | | 462 | T$_o$G$_o$T$_o$C$_o$t$_s$c$_s$c$_s$a$_s$t$_s$t$_s$c$_s$t$_s$C$_o$T$_o$C$_o$A | | |
| | | | 463 | t$_s$g$_s$t$_s$c$_s$t$_s$c$_s$c$_s$a$_s$t$_s$t$_s$c$_s$t$_s$c$_s$t$_s$c$_s$a | | |
| 1041 | 81 | GAGGAGCCAGGGACTC | 464 | G$_s$A$_s$G$_s$G$_s$a$_s$g$_s$c$_s$c$_s$a$_s$g$_s$g$_s$g$_s$A$_s$C$_s$T$_s$C | | |
| | | | 465 | G$_s$A$_s$G$_s$G$_s$a$_s$g$_s$c$_s$c$_s$a$_s$g$_s$g$_s$g$_s$A$_s$C$_s$T$_s$c | | |
| | | | 466 | G$_o$A$_o$G$_o$G$_o$a$_s$g$_s$c$_s$c$_s$a$_s$g$_s$g$_s$g$_s$A$_o$C$_o$T$_o$C | | |
| | | | 467 | g$_s$a$_s$g$_s$g$_s$a$_s$g$_s$c$_s$c$_s$a$_s$g$_s$g$_s$g$_s$a$_s$c$_s$t$_s$c | | |
| 1057 | 82 | ATGTTGTTAAACAGTA | 468 | A$_s$T$_s$G$_s$T$_s$t$_s$g$_s$t$_s$t$_s$a$_s$a$_s$a$_s$c$_s$A$_s$G$_s$T$_s$A | | |
| | | | 469 | A$_s$T$_s$G$_s$T$_s$t$_s$g$_s$t$_s$t$_s$a$_s$a$_s$a$_s$c$_s$A$_s$G$_s$T$_s$a | | |
| | | | 470 | A$_o$T$_o$G$_o$T$_o$t$_s$g$_s$t$_s$t$_s$a$_s$a$_s$a$_s$c$_s$A$_o$G$_o$T$_o$A | | |
| | | | 471 | a$_s$t$_s$g$_s$t$_s$t$_s$g$_s$t$_s$t$_s$a$_s$a$_s$a$_s$c$_s$a$_s$g$_s$t$_s$a | | |
| 1073 | 83 | ACAAAATAAGAAAGCC | 472 | A$_s$C$_s$A$_s$A$_s$a$_s$a$_s$t$_s$a$_s$a$_s$g$_s$a$_s$a$_s$A$_s$G$_s$C$_s$C | | |
| | | | 473 | A$_s$C$_s$A$_s$A$_s$a$_s$a$_s$t$_s$a$_s$a$_s$g$_s$a$_s$a$_s$A$_s$G$_s$C$_s$c | | |
| | | | 474 | A$_o$C$_o$A$_o$A$_o$a$_s$a$_s$t$_s$a$_s$a$_s$g$_s$a$_s$a$_s$A$_o$G$_o$C$_o$C | | |
| | | | 475 | a$_s$c$_s$a$_s$a$_s$a$_s$a$_s$t$_s$a$_s$a$_s$g$_s$a$_s$a$_s$a$_s$g$_s$c$_s$c | | |
| 1089 | 84 | TGAATTAACAATTCAA | 476 | T$_s$G$_s$A$_s$A$_s$t$_s$t$_s$a$_s$a$_s$c$_s$a$_s$a$_s$t$_s$T$_s$C$_s$A$_s$A | | |
| | | | 477 | T$_s$G$_s$A$_s$A$_s$t$_s$t$_s$a$_s$a$_s$c$_s$a$_s$a$_s$t$_s$T$_s$C$_s$A$_s$a | | |
| | | | 478 | T$_o$G$_o$A$_o$A$_o$t$_s$t$_s$a$_s$a$_s$c$_s$a$_s$a$_s$t$_s$T$_o$C$_o$A$_o$A | | |
| | | | 479 | t$_s$g$_s$a$_s$a$_s$t$_s$t$_s$a$_s$a$_s$c$_s$a$_s$a$_s$t$_s$t$_s$c$_s$a$_s$a | | |
| 1105 | 85 | AGTTTGTGCTATTCTG | 480 | A$_s$G$_s$T$_s$T$_s$t$_s$g$_s$t$_s$g$_s$c$_s$t$_s$a$_s$t$_s$T$_s$C$_s$T$_s$G | | |
| | | | 481 | A$_s$G$_s$T$_s$T$_s$t$_s$g$_s$t$_s$g$_s$c$_s$t$_s$a$_s$t$_s$T$_s$C$_s$T$_s$g | | |
| | | | 482 | A$_o$G$_o$T$_o$T$_o$t$_s$g$_s$t$_s$g$_s$c$_s$t$_s$a$_s$t$_s$T$_o$C$_o$T$_o$G | | |
| | | | 483 | a$_s$g$_s$t$_s$t$_s$t$_s$g$_s$t$_s$g$_s$c$_s$t$_s$a$_s$t$_s$t$_s$c$_s$t$_s$g | | |
| 1121 | 86 | GCTTAGTTTTAATTGT | 484 | G$_s$C$_s$T$_s$T$_s$a$_s$g$_s$t$_s$t$_s$t$_s$t$_s$a$_s$a$_s$T$_s$T$_s$G$_s$T | | |
| | | | 485 | G$_s$C$_s$T$_s$T$_s$a$_s$g$_s$t$_s$t$_s$t$_s$t$_s$a$_s$a$_s$T$_s$T$_s$G$_s$t | | |
| | | | 486 | G$_o$C$_o$T$_o$T$_o$a$_s$g$_s$t$_s$t$_s$t$_s$t$_s$a$_s$a$_s$T$_o$T$_o$G$_o$T | | |
| | | | 487 | g$_s$c$_s$t$_s$t$_s$a$_s$g$_s$t$_s$t$_s$t$_s$t$_s$a$_s$a$_s$t$_s$t$_s$g$_s$t | | |
| 1137 | 87 | CTTAGAATGGCTTTGT | 488 | C$_s$T$_s$T$_s$A$_s$g$_s$a$_s$a$_s$t$_s$g$_s$g$_s$c$_s$t$_s$T$_s$T$_s$G$_s$T | | |
| | | | 489 | C$_s$T$_s$T$_s$A$_s$g$_s$a$_s$a$_s$t$_s$g$_s$g$_s$c$_s$t$_s$T$_s$T$_s$G$_s$t | | |
| | | | 490 | C$_o$T$_o$T$_o$A$_o$g$_s$a$_s$a$_s$t$_s$g$_s$g$_s$c$_s$t$_s$T$_o$T$_o$G$_o$T | | |
| | | | 491 | c$_s$t$_s$t$_s$a$_s$g$_s$a$_s$a$_s$t$_s$g$_s$g$_s$c$_s$t$_s$t$_s$t$_s$g$_s$t | | |
| 1153 | 88 | CCCGTTTCCCCAATGA | 492 | C$_s$C$_s$C$_s$G$_s$t$_s$t$_s$t$_s$c$_s$c$_s$c$_s$c$_s$a$_s$A$_s$T$_s$G$_s$A | | |
| | | | 493 | C$_s$C$_s$C$_s$G$_s$t$_s$t$_s$t$_s$c$_s$c$_s$c$_s$c$_s$a$_s$A$_s$T$_s$G$_s$a | | |
| | | | 494 | C$_o$C$_o$C$_o$G$_o$t$_s$t$_s$t$_s$c$_s$c$_s$c$_s$c$_s$a$_s$A$_o$T$_o$G$_o$A | | |
| | | | 495 | c$_s$c$_s$c$_s$g$_s$t$_s$t$_s$t$_s$c$_s$c$_s$c$_s$c$_s$a$_s$a$_s$t$_s$g$_s$a | | |
| 1169 | 89 | TCCACCTGAAGTTCAC | 496 | T$_s$C$_s$C$_s$A$_s$c$_s$c$_s$t$_s$g$_s$a$_s$a$_s$g$_s$t$_s$T$_s$C$_s$A$_s$C | | |
| | | | 497 | T$_s$C$_s$C$_s$A$_s$c$_s$c$_s$t$_s$g$_s$a$_s$a$_s$g$_s$t$_s$T$_s$C$_s$A$_s$c | | |
| | | | 498 | T$_o$C$_o$C$_o$A$_o$c$_s$c$_s$t$_s$g$_s$a$_s$a$_s$g$_s$t$_s$T$_o$C$_o$A$_o$C | | |
| | | | 499 | t$_s$c$_s$c$_s$a$_s$c$_s$c$_s$t$_s$g$_s$a$_s$a$_s$g$_s$t$_s$t$_s$c$_s$a$_s$c | | |
| 1185 | 90 | CTATTCTGTCTCCTCA | 500 | C$_s$T$_s$A$_s$T$_s$t$_s$c$_s$t$_s$g$_s$t$_s$c$_s$t$_s$c$_s$C$_s$T$_s$C$_s$A | | |
| | | | 501 | C$_s$T$_s$A$_s$T$_s$t$_s$c$_s$t$_s$g$_s$t$_s$c$_s$t$_s$c$_s$C$_s$T$_s$C$_s$a | | |
| | | | 502 | C$_o$T$_o$A$_o$T$_o$t$_s$c$_s$t$_s$g$_s$t$_s$c$_s$t$_s$c$_s$C$_o$T$_o$C$_o$A | | |
| | | | 503 | c$_s$t$_s$a$_s$t$_s$t$_s$c$_s$t$_s$g$_s$t$_s$c$_s$t$_s$c$_s$c$_s$t$_s$c$_s$a | | |
| 1201 | 91 | GACGCTTCCTATCACT | 504 | G$_s$A$_s$C$_s$G$_s$c$_s$t$_s$t$_s$c$_s$c$_s$t$_s$a$_s$t$_s$C$_s$A$_s$C$_s$T | | |
| | | | 505 | G$_s$A$_s$C$_s$G$_s$c$_s$t$_s$t$_s$c$_s$c$_s$t$_s$a$_s$t$_s$C$_s$A$_s$C$_s$t | | |
| | | | 506 | G$_o$A$_o$C$_o$G$_o$c$_s$t$_s$t$_s$c$_s$c$_s$t$_s$a$_s$t$_s$C$_o$A$_o$C$_o$T | | |
| | | | 507 | g$_s$a$_s$c$_s$g$_s$c$_s$t$_s$t$_s$c$_s$c$_s$t$_s$a$_s$t$_s$c$_s$a$_s$c$_s$t | | |
| 1217 | 92 | AAAGGAGTATCTGCCA | 508 | A$_s$A$_s$A$_s$G$_s$g$_s$a$_s$g$_s$t$_s$a$_s$t$_s$c$_s$t$_s$G$_s$C$_s$C$_s$A | | |
| | | | 509 | A$_s$A$_s$A$_s$G$_s$g$_s$a$_s$g$_s$t$_s$a$_s$t$_s$c$_s$t$_s$G$_s$C$_s$C$_s$a | | |
| | | | 510 | A$_o$A$_o$A$_o$G$_o$g$_s$a$_s$g$_s$t$_s$a$_s$t$_s$c$_s$t$_s$G$_o$C$_o$C$_o$A | | |
| | | | 511 | a$_s$a$_s$a$_s$g$_s$g$_s$a$_s$g$_s$t$_s$a$_s$t$_s$c$_s$t$_s$g$_s$c$_s$c$_s$a | | |

TABLE 1-continued

Oligomeric compounds of the invention
Oligomeric compounds were evaluated for their potential to knockdown Survivin
mRNA in 15PC3 cells. The data are presented as percentage downregulation relative
to mock transfected cells. Transcript steady state was monitored by Real-time PCR
and normalised to the GAPDH transcript steady state. Note that all LNA C are 5'-
Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 1233 | 93 | TCACACAGCAGTGGCA | 512 | T$_s$C$_s$A$_s$C$_s$a$_s$c$_s$a$_s$g$_s$c$_s$a$_s$g$_s$t$_s$G$_s$G$_s$C$_s$A | | |
| | | | 513 | T$_s$C$_s$A$_s$C$_s$a$_s$c$_s$a$_s$g$_s$c$_s$a$_s$g$_s$t$_s$G$_s$G$_s$C$_s$a | | |
| | | | 514 | T$_o$C$_o$A$_o$C$_o$a$_s$c$_s$a$_s$g$_s$c$_s$a$_s$g$_s$t$_s$G$_o$G$_o$C$_o$A | | |
| | | | 515 | t$_s$c$_s$a$_s$c$_s$a$_s$c$_s$a$_s$g$_s$c$_s$a$_s$g$_s$t$_s$g$_s$g$_s$c$_s$a | | |
| 1249 | 94 | CACTGGGCCTGTCTAA | 516 | C$_s$A$_s$C$_s$T$_s$g$_s$g$_s$g$_s$c$_s$c$_s$t$_s$g$_s$t$_s$C$_s$T$_s$A$_s$A | | |
| | | | 517 | C$_s$A$_s$C$_s$T$_s$g$_s$g$_s$g$_s$c$_s$c$_s$t$_s$g$_s$t$_s$C$_s$T$_s$A$_s$a | | |
| | | | 518 | C$_o$A$_o$C$_o$T$_o$g$_s$g$_s$g$_s$c$_s$c$_s$t$_s$g$_s$t$_s$C$_o$T$_o$A$_o$A | | |
| | | | 519 | c$_s$a$_s$c$_s$t$_s$g$_s$g$_s$g$_s$c$_s$c$_s$t$_s$g$_s$t$_s$c$_s$t$_s$a$_s$a | | |
| 1265 | 95 | CATGTGCCCCGCGGCT | 520 | C$_s$A$_s$T$_s$G$_s$t$_s$g$_s$c$_s$c$_s$c$_s$c$_s$g$_s$c$_s$G$_s$G$_s$C$_s$T | | |
| | | | 521 | C$_s$A$_s$T$_s$G$_s$t$_s$g$_s$c$_s$c$_s$c$_s$c$_s$g$_s$c$_s$G$_s$G$_s$C$_s$t | | |
| | | | 522 | C$_o$A$_o$T$_o$G$_o$t$_s$g$_s$c$_s$c$_s$c$_s$c$_s$g$_s$c$_s$G$_o$G$_o$C$_o$T | | |
| | | | 523 | c$_s$a$_s$t$_s$g$_s$t$_s$g$_s$c$_s$c$_s$c$_s$c$_s$g$_s$c$_s$g$_s$g$_s$c$_s$t | | |
| 1281 | 96 | AGGGAGGAGCGGCCAG | 524 | A$_s$G$_s$G$_s$G$_s$a$_s$g$_s$g$_s$a$_s$g$_s$c$_s$g$_s$g$_s$C$_s$C$_s$A$_s$G | | |
| | | | 525 | A$_s$G$_s$G$_s$G$_s$a$_s$g$_s$g$_s$a$_s$g$_s$c$_s$g$_s$g$_s$C$_s$C$_s$A$_s$g | | |
| | | | 526 | A$_o$G$_o$G$_o$G$_o$a$_s$g$_s$g$_s$a$_s$g$_s$c$_s$g$_s$g$_s$C$_o$C$_o$A$_o$G | | |
| | | | 527 | a$_s$g$_s$g$_s$g$_s$a$_s$g$_s$g$_s$a$_s$g$_s$c$_s$g$_s$g$_s$c$_s$c$_s$a$_s$g | | |
| 1297 | 97 | CCACTGCCTTTTTCTG | 528 | C$_s$C$_s$A$_s$C$_s$t$_s$g$_s$c$_s$c$_s$t$_s$t$_s$t$_s$t$_s$T$_s$C$_s$T$_s$G | | |
| | | | 529 | C$_s$C$_s$A$_s$C$_s$t$_s$g$_s$c$_s$c$_s$t$_s$t$_s$t$_s$t$_s$T$_s$C$_s$T$_s$g | | |
| | | | 530 | C$_o$C$_o$A$_o$C$_o$t$_s$g$_s$c$_s$c$_s$t$_s$t$_s$t$_s$t$_s$T$_o$C$_o$T$_o$G | | |
| | | | 531 | c$_s$c$_s$a$_s$c$_s$t$_s$g$_s$c$_s$c$_s$t$_s$t$_s$t$_s$t$_s$t$_s$c$_s$t$_s$g | | |
| 1313 | 98 | TTAAAAGGATTTAGG | 532 | T$_s$T$_s$A$_s$A$_s$a$_s$a$_s$a$_s$g$_s$g$_s$a$_s$t$_s$t$_s$T$_s$A$_s$G$_s$G | | |
| | | | 533 | T$_s$T$_s$A$_s$A$_s$a$_s$a$_s$a$_s$g$_s$g$_s$a$_s$t$_s$t$_s$T$_s$A$_s$G$_s$g | | |
| | | | 534 | T$_o$T$_o$A$_o$A$_o$a$_s$a$_s$a$_s$g$_s$g$_s$a$_s$t$_s$t$_s$T$_o$A$_o$G$_o$G | | |
| | | | 535 | t$_s$t$_s$a$_s$a$_s$a$_s$a$_s$a$_s$g$_s$g$_s$a$_s$t$_s$t$_s$t$_s$a$_s$g$_s$g | | |
| 1329 | 99 | CATCGAGCCAAGTCAT | 536 | C$_s$A$_s$T$_s$C$_s$g$_s$a$_s$g$_s$c$_s$c$_s$a$_s$a$_s$g$_s$T$_s$C$_s$A$_s$T | | |
| | | | 537 | C$_s$A$_s$T$_s$C$_s$g$_s$a$_s$g$_s$c$_s$c$_s$a$_s$a$_s$g$_s$T$_s$C$_s$A$_s$t | | |
| | | | 538 | C$_o$A$_o$T$_o$C$_o$g$_s$a$_s$g$_s$c$_s$c$_s$a$_s$a$_s$g$_s$T$_o$C$_o$A$_o$T | | |
| | | | 539 | c$_s$a$_s$t$_s$c$_s$g$_s$a$_s$g$_s$c$_s$c$_s$a$_s$a$_s$g$_s$t$_s$c$_s$a$_s$t | | |
| 1345 | 100 | AGCCAGTCCCCCACAG | 540 | A$_s$G$_s$C$_s$C$_s$a$_s$g$_s$t$_s$c$_s$c$_s$c$_s$c$_s$c$_s$A$_s$C$_s$A$_s$G | | |
| | | | 541 | A$_s$G$_s$C$_s$C$_s$a$_s$g$_s$t$_s$c$_s$c$_s$c$_s$c$_s$c$_s$A$_s$C$_s$A$_s$g | | |
| | | | 542 | A$_o$G$_o$C$_o$C$_o$a$_s$g$_s$t$_s$c$_s$c$_s$c$_s$c$_s$c$_s$A$_o$C$_o$A$_o$G | | |
| | | | 543 | a$_s$g$_s$c$_s$c$_s$a$_s$g$_s$t$_s$c$_s$c$_s$c$_s$c$_s$c$_s$a$_s$c$_s$a$_s$g | | |
| 1361 | 101 | CGGCCTGCAGCAGCCC | 544 | C$_s$G$_s$G$_s$C$_s$c$_s$t$_s$g$_s$c$_s$a$_s$g$_s$c$_s$a$_s$G$_s$C$_s$C$_s$C | | |
| | | | 545 | C$_s$G$_s$G$_s$C$_s$c$_s$t$_s$g$_s$c$_s$a$_s$g$_s$c$_s$a$_s$G$_s$C$_s$C$_s$c | | |
| | | | 546 | C$_o$G$_o$G$_o$C$_o$c$_s$t$_s$g$_s$c$_s$a$_s$g$_s$c$_s$a$_s$G$_o$C$_o$C$_o$C | | |
| | | | 547 | c$_s$g$_s$g$_s$c$_s$c$_s$t$_s$g$_s$c$_s$a$_s$g$_s$c$_s$a$_s$g$_s$c$_s$c$_s$c | | |
| 1377 | 102 | TGGGCTGACAGACACA | 548 | T$_s$G$_s$G$_s$G$_s$c$_s$t$_s$g$_s$a$_s$c$_s$a$_s$g$_s$a$_s$C$_s$A$_s$C$_s$A | | |
| | | | 549 | T$_s$G$_s$G$_s$G$_s$c$_s$t$_s$g$_s$a$_s$c$_s$a$_s$g$_s$a$_s$C$_s$A$_s$C$_s$a | | |
| | | | 550 | T$_o$G$_o$G$_o$G$_o$c$_s$t$_s$g$_s$a$_s$c$_s$a$_s$g$_s$a$_s$C$_o$A$_o$C$_o$A | | |
| | | | 551 | t$_s$g$_s$g$_s$g$_s$c$_s$t$_s$g$_s$a$_s$c$_s$a$_s$g$_s$a$_s$c$_s$a$_s$c$_s$a | | |
| 1393 | 103 | TGACAGATGTGAAGGT | 552 | T$_s$G$_s$A$_s$C$_s$a$_s$g$_s$a$_s$t$_s$g$_s$t$_s$g$_s$a$_s$A$_s$G$_s$G$_s$T | | |
| | | | 553 | T$_s$G$_s$A$_s$C$_s$a$_s$g$_s$a$_s$t$_s$g$_s$t$_s$g$_s$a$_s$A$_s$G$_s$G$_s$t | | |
| | | | 554 | T$_o$G$_o$A$_o$C$_o$a$_s$g$_s$a$_s$t$_s$g$_s$t$_s$g$_s$a$_s$A$_o$G$_o$G$_o$T | | |
| | | | 555 | t$_s$g$_s$a$_s$c$_s$a$_s$g$_s$a$_s$t$_s$g$_s$t$_s$g$_s$a$_s$a$_s$g$_s$g$_s$t | | |
| 1409 | 104 | CCCCGTGTGGAGAACG | 556 | C$_s$C$_s$C$_s$C$_s$g$_s$t$_s$g$_s$t$_s$g$_s$g$_s$a$_s$g$_s$A$_s$A$_s$C$_s$G | | |
| | | | 557 | C$_s$C$_s$C$_s$C$_s$g$_s$t$_s$g$_s$t$_s$g$_s$g$_s$a$_s$g$_s$A$_s$A$_s$C$_s$g | | |
| | | | 558 | C$_o$C$_o$C$_o$C$_o$g$_s$t$_s$g$_s$t$_s$g$_s$g$_s$a$_s$g$_s$A$_o$A$_o$C$_o$G | | |
| | | | 559 | c$_s$c$_s$c$_s$c$_s$g$_s$t$_s$g$_s$t$_s$g$_s$g$_s$a$_s$g$_s$a$_s$a$_s$c$_s$g | | |
| 1425 | 105 | GCGGACTGCGTCTCTC | 560 | G$_s$C$_s$G$_s$G$_s$a$_s$c$_s$t$_s$g$_s$c$_s$g$_s$t$_s$c$_s$T$_s$C$_s$T$_s$C | | |
| | | | 561 | G$_s$C$_s$G$_s$G$_s$a$_s$c$_s$t$_s$g$_s$c$_s$g$_s$t$_s$c$_s$T$_s$C$_s$T$_s$c | | |
| | | | 562 | G$_o$C$_o$G$_o$G$_o$a$_s$c$_s$t$_s$g$_s$c$_s$g$_s$t$_s$c$_s$T$_o$C$_o$T$_o$C | | |
| | | | 563 | g$_s$c$_s$g$_s$g$_s$a$_s$c$_s$t$_s$g$_s$c$_s$g$_s$t$_s$c$_s$t$_s$c$_s$t$_s$c | | |

TABLE 1-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl Cytosine

| Target site | SEQ ID NO | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 1441 | 106 | GAAAGCGGGGACCTGG | 564 | G$_s$A$_s$A$_s$A$_s$g$_s$c$_s$g$_s$g$_s$g$_s$g$_s$a$_s$c$_s$C$_s$T$_s$G$_s$G | | |
| | | | 565 | G$_s$A$_s$A$_s$A$_s$g$_s$c$_s$g$_s$g$_s$g$_s$g$_s$a$_s$c$_s$C$_s$T$_s$G$_s$g | | |
| | | | 566 | G$_o$A$_o$A$_o$A$_o$g$_s$c$_s$g$_s$g$_s$g$_s$g$_s$a$_s$c$_s$C$_o$T$_o$G$_o$G | | |
| | | | 567 | g$_s$a$_s$a$_s$a$_s$g$_s$c$_s$g$_s$g$_s$g$_s$g$_s$a$_s$c$_s$c$_s$t$_s$g$_s$g | | |
| 1457 | 107 | AGGTGCTGCCTCCAAA | 568 | A$_s$G$_s$C$_s$T$_s$g$_s$c$_s$t$_s$g$_s$c$_s$c$_s$t$_s$c$_s$C$_s$A$_s$A$_s$A | | |
| | | | 569 | A$_s$G$_s$C$_s$T$_s$g$_s$c$_s$t$_s$g$_s$c$_s$c$_s$t$_s$c$_s$C$_s$A$_s$A$_s$a | | |
| | | | 570 | A$_o$G$_o$C$_o$T$_o$g$_s$c$_s$t$_s$g$_s$c$_s$c$_s$t$_s$c$_s$C$_o$A$_o$A$_o$A | | |
| | | | 571 | a$_s$g$_s$c$_s$t$_s$g$_s$c$_s$t$_s$g$_s$c$_s$c$_s$t$_s$c$_s$c$_s$a$_s$a$_s$a | | |
| 1473 | 108 | ACTTCAGCCCTGCGGG | 572 | A$_s$C$_s$T$_s$T$_s$c$_s$a$_s$g$_s$c$_s$c$_s$c$_s$t$_s$g$_s$C$_s$G$_s$G$_s$G | | |
| | | | 573 | A$_s$C$_s$T$_s$T$_s$c$_s$a$_s$g$_s$c$_s$c$_s$c$_s$t$_s$g$_s$C$_s$G$_s$G$_s$g | | |
| | | | 574 | A$_o$C$_o$T$_o$T$_o$c$_s$a$_s$g$_s$c$_s$c$_s$c$_s$t$_s$g$_s$C$_o$G$_o$G$_o$G | | |
| | | | 575 | a$_s$c$_s$t$_s$t$_s$c$_s$a$_s$g$_s$c$_s$c$_s$c$_s$t$_s$g$_s$c$_s$g$_s$g$_s$g | | |
| 1489 | 109 | CATCATCTTACGCCAG | 576 | C$_s$A$_s$T$_s$C$_s$a$_s$t$_s$c$_s$t$_s$t$_s$a$_s$c$_s$g$_s$C$_s$C$_s$A$_s$G | | |
| | | | 577 | C$_s$A$_s$T$_s$C$_s$a$_s$t$_s$c$_s$t$_s$t$_s$a$_s$c$_s$g$_s$C$_s$C$_s$A$_s$g | | |
| | | | 578 | C$_o$A$_o$T$_o$C$_o$a$_s$t$_s$c$_s$t$_s$t$_s$a$_s$c$_s$g$_s$C$_o$C$_o$A$_o$G | | |
| | | | 579 | c$_s$a$_s$t$_s$c$_s$a$_s$t$_s$c$_s$t$_s$t$_s$a$_s$c$_s$g$_s$c$_s$c$_s$a$_s$g | | |
| 1505 | 110 | GAGGGCGAATCAAATC | 580 | G$_s$A$_s$G$_s$G$_s$g$_s$c$_s$g$_s$a$_s$a$_s$t$_s$c$_s$a$_s$A$_s$A$_s$T$_s$C | | |
| | | | 581 | G$_s$A$_s$G$_s$G$_s$g$_s$c$_s$g$_s$a$_s$a$_s$t$_s$c$_s$a$_s$A$_s$A$_s$T$_s$c | | |
| | | | 582 | G$_o$A$_o$G$_o$G$_o$g$_s$c$_s$g$_s$a$_s$a$_s$t$_s$c$_s$a$_s$A$_o$A$_o$T$_o$C | | |
| | | | 583 | g$_s$a$_s$g$_s$g$_s$g$_s$c$_s$g$_s$a$_s$a$_s$t$_s$c$_s$a$_s$a$_s$a$_s$t$_s$c | | |
| 1521 | 111 | GCTCTATGACAGGGAG | 584 | G$_s$C$_s$T$_s$C$_s$t$_s$a$_s$t$_s$g$_s$a$_s$c$_s$a$_s$g$_s$G$_s$G$_s$A$_s$G | | |
| | | | 585 | G$_s$C$_s$T$_s$C$_s$t$_s$a$_s$t$_s$g$_s$a$_s$c$_s$a$_s$g$_s$G$_s$G$_s$A$_s$g | | |
| | | | 586 | G$_o$C$_o$T$_o$C$_o$t$_s$a$_s$t$_s$g$_s$a$_s$c$_s$a$_s$g$_s$G$_o$G$_o$A$_o$G | | |
| | | | 587 | g$_s$c$_s$t$_s$c$_s$t$_s$a$_s$t$_s$g$_s$a$_s$c$_s$a$_s$g$_s$g$_s$g$_s$a$_s$g | | |
| 1537 | 112 | AACAATCCACCCTGCA | 588 | A$_s$A$_s$C$_s$A$_s$a$_s$t$_s$c$_s$c$_s$a$_s$c$_s$c$_s$c$_s$T$_s$G$_s$C$_s$A | | |
| | | | 589 | A$_s$A$_s$C$_s$A$_s$a$_s$t$_s$c$_s$c$_s$a$_s$c$_s$c$_s$c$_s$T$_s$G$_s$C$_s$a | | |
| | | | 590 | A$_o$A$_o$C$_o$A$_o$a$_s$t$_s$c$_s$c$_s$a$_s$c$_s$c$_s$c$_s$T$_o$G$_o$C$_o$A | | |
| | | | 591 | a$_s$a$_s$c$_s$a$_s$a$_s$t$_s$c$_s$c$_s$a$_s$c$_s$c$_s$c$_s$t$_s$g$_s$c$_s$a | | |
| 1553 | 113 | TTTCCAGGGAAGCTGT | 592 | T$_s$T$_s$T$_s$C$_s$c$_s$a$_s$g$_s$c$_s$g$_s$a$_s$a$_s$g$_s$C$_s$T$_s$G$_s$T | | |
| | | | 593 | T$_s$T$_s$T$_s$C$_s$c$_s$a$_s$g$_s$c$_s$g$_s$a$_s$a$_s$g$_s$C$_s$T$_s$G$_s$t | | |
| | | | 594 | T$_o$T$_o$T$_o$C$_o$c$_s$a$_s$g$_s$c$_s$g$_s$a$_s$a$_s$g$_s$C$_o$T$_o$G$_o$T | | |
| | | | 595 | t$_s$t$_s$t$_s$c$_s$c$_s$a$_s$g$_s$c$_s$g$_s$a$_s$a$_s$g$_s$c$_s$t$_s$g$_s$t | | |
| 1569 | 114 | AGATGACCTCCAGAGG | 596 | A$_s$G$_s$A$_s$T$_s$g$_s$a$_s$c$_s$c$_s$t$_s$c$_s$c$_s$a$_s$G$_s$A$_s$G$_s$G | | |
| | | | 597 | A$_s$G$_s$A$_s$T$_s$g$_s$a$_s$c$_s$c$_s$t$_s$c$_s$c$_s$a$_s$G$_s$A$_s$G$_s$g | | |
| | | | 598 | A$_o$G$_o$A$_o$T$_o$g$_s$a$_s$c$_s$c$_s$t$_s$c$_s$c$_s$a$_s$G$_o$A$_o$G$_o$G | | |
| | | | 599 | a$_s$g$_s$a$_s$t$_s$g$_s$a$_s$c$_s$c$_s$t$_s$c$_s$c$_s$a$_s$g$_s$a$_s$g$_s$g | | |
| 1585 | 115 | TTCTCAGGAACAGCCG | 600 | T$_s$T$_s$C$_s$T$_s$c$_s$a$_s$g$_s$g$_s$a$_s$a$_s$c$_s$a$_s$G$_s$C$_s$C$_s$G | | |
| | | | 601 | T$_s$T$_s$C$_s$T$_s$c$_s$a$_s$g$_s$g$_s$a$_s$a$_s$c$_s$a$_s$G$_s$C$_s$C$_s$g | | |
| | | | 602 | T$_o$T$_o$C$_o$T$_o$c$_s$a$_s$g$_s$g$_s$a$_s$a$_s$c$_s$a$_s$G$_o$C$_o$C$_o$G | | |
| | | | 603 | t$_s$t$_s$c$_s$t$_s$c$_s$a$_s$g$_s$g$_s$a$_s$a$_s$c$_s$a$_s$g$_s$c$_s$c$_s$g | | |
| 1601 | 116 | ATGACAGGCTTTTTAT | 604 | A$_s$T$_s$G$_s$A$_s$c$_s$a$_s$g$_s$g$_s$c$_s$t$_s$t$_s$t$_s$T$_s$T$_s$A$_s$T | | |
| | | | 605 | A$_s$T$_s$G$_s$A$_s$c$_s$a$_s$g$_s$g$_s$c$_s$t$_s$t$_s$t$_s$T$_s$T$_s$A$_s$t | | |
| | | | 606 | A$_o$T$_o$G$_o$A$_o$c$_s$a$_s$g$_s$g$_s$c$_s$t$_s$t$_s$t$_s$T$_o$T$_o$A$_o$T | | |
| | | | 607 | a$_s$t$_s$g$_s$a$_s$c$_s$a$_s$g$_s$g$_s$c$_s$t$_s$t$_s$t$_s$t$_s$t$_s$a$_s$t | | |

TABLE 2

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl-Cytosine.

| Target site | Seq ID NO: | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 62(c) | 117 | AGGCAGGGGGCAACGT | 608 | A$_s$G$_s$C$_s$a$_s$g$_s$g$_s$g$_s$g$_s$g$_s$c$_s$a$_s$A$_s$C$_s$G$_s$T | <20 | <20 |
|  |  |  | 609 | A$_s$G$_s$C$_s$a$_s$g$_s$g$_s$g$_s$g$_s$g$_s$c$_s$a$_s$A$_s$C$_s$G$_s$t |  |  |
|  |  |  | 610 | A$_o$G$_o$C$_o$a$_s$g$_s$g$_s$g$_s$g$_s$g$_s$c$_s$a$_s$A$_o$C$_o$G$_o$T |  |  |
|  |  |  | 611 | a$_s$g$_s$g$_s$c$_s$a$_s$g$_s$g$_s$g$_s$g$_s$g$_s$c$_s$a$_s$a$_s$c$_s$g$_s$t |  |  |
| 119(c) | 118 | CCAAGAAGGGCCAGTT | 612 | C$_s$C$_s$A$_s$A$_s$g$_s$a$_s$a$_s$g$_s$g$_s$g$_s$c$_s$c$_s$A$_s$G$_s$T$_s$T | 87 | 33 |
|  |  |  | 613 | C$_s$C$_s$A$_s$A$_s$g$_s$a$_s$a$_s$g$_s$g$_s$g$_s$c$_s$c$_s$A$_s$G$_s$T$_s$t |  |  |
|  |  |  | 614 | C$_o$C$_o$A$_o$A$_s$g$_s$a$_s$a$_s$g$_s$g$_s$g$_s$c$_s$c$_s$A$_o$G$_o$T$_o$T |  |  |
|  |  |  | 615 | c$_s$c$_s$a$_s$a$_s$g$_s$a$_s$a$_s$g$_s$g$_s$g$_s$c$_s$c$_s$a$_s$g$_s$t$_s$t |  |  |
| 190(c) | 119 | TGGCTCGTTCTCACTG | 616 | T$_s$G$_s$G$_s$C$_s$t$_s$c$_s$g$_s$t$_s$t$_s$c$_s$t$_s$c$_s$A$_s$G$_s$T$_s$G | 79 | 27 |
|  |  |  | 617 | T$_s$G$_s$G$_s$C$_s$t$_s$c$_s$g$_s$t$_s$t$_s$c$_s$t$_s$c$_s$A$_s$G$_s$T$_s$g |  |  |
|  |  |  | 618 | T$_o$G$_o$G$_o$C$_o$t$_s$c$_s$g$_s$t$_s$t$_s$c$_s$t$_s$c$_s$A$_o$G$_o$T$_o$G |  |  |
|  |  |  | 619 | t$_s$g$_s$g$_s$c$_s$t$_s$c$_s$g$_s$t$_s$t$_s$c$_s$t$_s$c$_s$a$_s$g$_s$t$_s$g |  |  |
| 193(c) | 120 | GTCTGGCTCGTTCTCA | 620 | G$_s$T$_s$C$_s$T$_s$g$_s$g$_s$c$_s$t$_s$c$_s$g$_s$t$_s$t$_s$C$_s$T$_s$C$_s$A | 84 | 47 |
|  |  |  | 621 | G$_s$T$_s$C$_s$T$_s$g$_s$g$_s$c$_s$t$_s$c$_s$g$_s$t$_s$t$_s$C$_s$T$_s$C$_s$a |  |  |
|  |  |  | 622 | G$_o$T$_o$C$_o$T$_o$g$_s$g$_s$c$_s$t$_s$c$_s$g$_s$t$_s$t$_s$C$_o$T$_o$C$_o$A |  |  |
|  |  |  | 623 | g$_s$t$_s$c$_s$t$_s$g$_s$g$_s$c$_s$t$_s$c$_s$g$_s$t$_s$t$_s$c$_s$t$_s$c$_s$a |  |  |
| 194(c) | 121 | AGTCTGGCTCGTTCTC | 624 | A$_s$G$_s$T$_s$C$_s$t$_s$g$_s$g$_s$c$_s$t$_s$c$_s$g$_s$t$_s$T$_s$C$_s$T$_s$C | 75 | 49 |
|  |  |  | 625 | A$_s$G$_s$T$_s$C$_s$t$_s$g$_s$g$_s$c$_s$t$_s$c$_s$g$_s$t$_s$T$_s$C$_s$T$_s$C |  |  |
|  |  |  | 626 | A$_o$G$_o$T$_o$C$_o$t$_s$g$_s$g$_s$c$_s$t$_s$c$_s$g$_s$t$_s$T$_o$C$_o$T$_o$C |  |  |
|  |  |  | 627 | a$_s$g$_s$t$_s$c$_s$t$_s$g$_s$g$_s$c$_s$t$_s$c$_s$g$_s$t$_s$t$_s$c$_s$t$_s$c |  |  |
| 168(c) | 122 | TGGATGAAGCCAGCCT | 628 | T$_s$G$_s$G$_s$A$_s$t$_s$g$_s$a$_s$a$_s$g$_s$c$_s$c$_s$a$_s$G$_s$C$_s$C$_s$T | 67 | 41 |
|  |  |  | 629 | T$_s$G$_s$G$_s$A$_s$t$_s$g$_s$a$_s$a$_s$g$_s$c$_s$c$_s$a$_s$G$_s$C$_s$C$_s$t |  |  |
|  |  |  | 630 | T$_o$G$_o$G$_o$A$_o$t$_s$g$_s$a$_s$a$_s$g$_s$c$_s$c$_s$a$_s$G$_o$C$_o$C$_o$T |  |  |
|  |  |  | 631 | t$_s$g$_s$g$_s$a$_s$t$_s$g$_s$a$_s$a$_s$g$_s$c$_s$c$_s$a$_s$g$_s$c$_s$c$_s$t |  |  |
| 215(c) | 123 | AGCAGAAGAAACACTG | 632 | A$_s$G$_s$C$_s$A$_s$g$_s$a$_s$a$_s$g$_s$a$_s$a$_s$a$_s$c$_s$A$_s$C$_s$T$_s$G | 85 | 26 |
|  |  |  | 633 | A$_s$G$_s$C$_s$A$_s$g$_s$a$_s$a$_s$g$_s$a$_s$a$_s$a$_s$c$_s$A$_s$C$_s$T$_s$g |  |  |
|  |  |  | 634 | A$_o$G$_o$C$_o$A$_o$g$_s$a$_s$a$_s$g$_s$a$_s$a$_s$a$_s$c$_s$A$_o$C$_o$T$_o$G |  |  |
|  |  |  | 635 | a$_s$g$_s$c$_s$a$_s$g$_s$a$_s$a$_s$g$_s$a$_s$a$_s$a$_s$c$_s$a$_s$c$_s$t$_s$g |  |  |
| 261(c) | 124 | TCCTCTATGGGTCGT | 636 | T$_s$C$_s$C$_s$T$_s$c$_s$t$_s$a$_s$t$_s$g$_s$g$_s$g$_s$g$_s$T$_s$C$_s$G$_s$T | 23 | <20 |
|  |  |  | 637 | T$_s$C$_s$C$_s$T$_s$c$_s$t$_s$a$_s$t$_s$g$_s$g$_s$g$_s$g$_s$T$_s$C$_s$G$_s$t |  |  |
|  |  |  | 638 | T$_o$C$_o$C$_o$T$_o$c$_s$t$_s$a$_s$t$_s$g$_s$g$_s$g$_s$g$_s$T$_o$C$_o$G$_o$T |  |  |
|  |  |  | 639 | t$_s$c$_s$c$_s$t$_s$c$_s$t$_s$a$_s$t$_s$g$_s$g$_s$g$_s$g$_s$t$_s$c$_s$g$_s$t |  |  |
| 286(c) | 125 | GCAACCGGACGAATGC | 640 | G$_s$C$_s$A$_s$A$_s$c$_s$c$_s$g$_s$g$_s$a$_s$c$_s$g$_s$a$_s$A$_s$T$_s$G$_s$C | 64 | <20 |
|  |  |  | 641 | G$_s$C$_s$A$_s$A$_s$c$_s$c$_s$g$_s$g$_s$a$_s$c$_s$g$_s$a$_s$A$_s$T$_s$G$_s$c |  |  |
|  |  |  | 642 | G$_o$C$_o$A$_o$A$_s$c$_s$c$_s$g$_s$g$_s$a$_s$c$_s$g$_s$a$_s$A$_o$T$_o$G$_o$C |  |  |
|  |  |  | 643 | g$_s$c$_s$a$_s$a$_s$c$_s$c$_s$g$_s$g$_s$a$_s$c$_s$g$_s$a$_s$a$_s$t$_s$g$_s$c |  |  |
| 267(c) | 126 | TTATGTTCCTCTATGG | 644 | T$_s$T$_s$A$_s$T$_s$g$_s$t$_s$t$_s$c$_s$c$_s$t$_s$c$_s$t$_s$A$_s$T$_s$G$_s$G | 53 | <20 |
|  |  |  | 645 | T$_s$T$_s$A$_s$T$_s$g$_s$t$_s$t$_s$c$_s$c$_s$t$_s$c$_s$t$_s$A$_s$T$_s$G$_s$g |  |  |
|  |  |  | 646 | T$_o$T$_o$A$_o$T$_o$g$_s$t$_s$t$_s$c$_s$c$_s$t$_s$c$_s$t$_s$A$_o$T$_o$G$_o$G |  |  |
|  |  |  | 647 | t$_s$t$_s$a$_s$t$_s$g$_s$t$_s$t$_s$c$_s$c$_s$t$_s$c$_s$t$_s$a$_s$t$_s$g$_s$g |  |  |
| 325(c) | 127 | GGTTAATTCTTCAAAC | 648 | G$_s$G$_s$T$_s$T$_s$a$_s$a$_s$t$_s$t$_s$c$_s$t$_s$t$_s$c$_s$A$_s$A$_s$A$_s$C | 17 | <20 |
|  |  |  | 649 | G$_s$G$_s$T$_s$T$_s$a$_s$a$_s$t$_s$t$_s$c$_s$t$_s$t$_s$c$_s$A$_s$A$_s$A$_s$c |  |  |
|  |  |  | 650 | G$_o$G$_o$T$_o$T$_o$a$_s$a$_s$t$_s$t$_s$c$_s$t$_s$t$_s$c$_s$A$_o$A$_o$A$_o$A |  |  |
|  |  |  | 651 | g$_s$g$_s$t$_s$t$_s$a$_s$a$_s$t$_s$t$_s$c$_s$t$_s$t$_s$c$_s$a$_s$a$_s$a$_s$c |  |  |
| 353(c) | 128 | GTCTGTCCAGTTTCAA | 652 | C$_s$T$_s$C$_s$T$_s$g$_s$t$_s$c$_s$c$_s$a$_s$g$_s$t$_s$t$_s$T$_s$C$_s$A$_s$A | 76 | 60 |
|  |  |  | 653 | C$_s$T$_s$C$_s$T$_s$g$_s$t$_s$c$_s$c$_s$a$_s$g$_s$t$_s$t$_s$T$_s$C$_s$A$_s$a | 77 |  |
|  |  |  | 654 | C$_o$T$_o$C$_o$T$_o$g$_s$t$_s$c$_s$c$_s$a$_s$g$_s$t$_s$t$_s$T$_o$C$_o$A$_o$A |  |  |
|  |  |  | 655 | c$_s$t$_s$c$_s$t$_s$g$_s$t$_s$c$_s$c$_s$a$_s$g$_s$t$_s$t$_s$t$_s$c$_s$a$_s$a |  |  |
| 375(c) | 129 | GCAATTTGTTCTTGG | 656 | G$_s$C$_s$A$_s$A$_s$t$_s$t$_s$t$_s$g$_s$t$_s$t$_s$c$_s$T$_s$T$_s$G$_s$G | 73 | 49 |
|  |  |  | 657 | G$_s$C$_s$A$_s$A$_s$t$_s$t$_s$t$_s$g$_s$t$_s$t$_s$c$_s$T$_s$T$_s$G$_s$g |  |  |
|  |  |  | 658 | G$_o$C$_o$A$_o$A$_o$t$_s$t$_s$t$_s$g$_s$t$_s$t$_s$c$_s$T$_o$T$_o$G$_o$G |  |  |
|  |  |  | 659 | g$_s$c$_s$a$_s$a$_s$t$_s$t$_s$t$_s$g$_s$t$_s$t$_s$c$_s$t$_s$t$_s$g$_s$g |  |  |

TABLE 2-continued

Oligomeric compounds of the invention
Oligomeric compounds were evaluated for their potential to knockdown Survivin mRNA in 15PC3 cells. The data are presented as percentage downregulation relative to mock transfected cells. Transcript steady state was monitored by Real-time PCR and normalised to the GAPDH transcript steady state. Note that all LNA C are 5'-Methyl-Cytosine.

| Target site | Seq ID NO: | Oligomeric compound Sequence 5'-3' | Seq ID | Specific design of Oligomeric compound Capital letters β-D-oxy-LNA S = phosphorthioate O = —O—P(O)₂—O— Small letters DNA sugar | % Inhibition at 25 nM | % Inhibition at 5 nM oligo |
|---|---|---|---|---|---|---|
| 464(c) | 130 | CTCAATCCATGGCAGC | 660 | CₛTₛCₛAₛaₛtₛcₛcₛaₛtₛgₛgₛCₛAₛGₛC | 77 | 40 |
|  |  |  | 661 | CₛTₛCₛAₛaₛtₛcₛcₛaₛtₛgₛgₛCₛAₛGₛc |  |  |
|  |  |  | 662 | CₒTₒCₒAₒaₛtₛcₛcₛaₛtₛgₛgₛCₒAₒGₒC |  |  |
|  |  |  | 663 | cₛtₛcₛaₛaₛtₛcₛcₛaₛtₛgₛgₛcₛaₛgₛc |  |  |
| 159(c) | 131 | CCAGCCTCGGCCATCC | 664 | CₛCₛAₛGₛcₛcₛtₛcₛgₛgₛcₛcₛAₛTₛCₛC | 80 | 29 |
|  |  |  | 665 | CₛCₛAₛGₛcₛcₛtₛcₛgₛgₛcₛcₛAₛTₛCₛC | 94 |  |
|  |  |  | 666 | CₒCₒAₒGₒcₛcₛtₛcₛgₛgₛcₛcₛAₒTₒCₒC |  |  |
|  |  |  | 667 | cₛcₛaₛgₛcₛcₛtₛcₛgₛgₛcₛcₛaₛtₛcₛc |  |  |
| 350(c) | 132 | TGTCCAGTTTCAAAAA | 668 | TₛGₛTₛCₛcₛaₛgₛtₛtₛtₛcₛaₛAₛAₛAₛA | <20 | <20 |
|  |  |  | 669 | TₛGₛTₛCₛcₛaₛgₛtₛtₛtₛcₛaₛAₛAₛAₛa |  |  |
|  |  |  | 670 | TₒGₒTₒCₒcₛaₛgₛtₛtₛtₛcₛaₛAₒAₒAₒA |  |  |
|  |  |  | 671 | tₛgₛtₛcₛcₛaₛgₛtₛtₛtₛcₛaₛaₛaₛaₛa |  |  |
| 351(c) | 133 | CTGTCCAGTTTCAAAA | 672 | CₛTₛGₛTₛcₛcₛaₛgₛtₛtₛtₛcₛAₛAₛAₛA | <20 | <20 |
|  |  |  | 673 | CₛTₛGₛTₛcₛcₛaₛgₛtₛtₛtₛcₛAₛAₛAₛa |  |  |
|  |  |  | 674 | CₒTₒGₒTₒcₛcₛaₛgₛtₛtₛtₛcₛAₒAₒAₒA |  |  |
|  |  |  | 675 | cₛtₛgₛtₛcₛcₛaₛgₛtₛtₛtₛcₛaₛaₛaₛa |  |  |
| 47(c) | 134 | TCGGGGCACCCATGCC | 676 | TₛCₛGₛGₛgₛgₛcₛaₛcₛcₛcₛaₛTₛGₛCₛC |  |  |
|  |  |  | 677 | TₛCₛGₛGₛgₛgₛcₛaₛcₛcₛcₛaₛTₛGₛCₛC |  |  |
|  |  |  | 678 | TₒCₒGₒGₒgₛgₛcₛaₛcₛcₛcₛaₛTₒGₒCₒC |  |  |
|  |  |  | 679 | tₛcₛgₛgₛgₛgₛcₛaₛcₛcₛcₛaₛtₛgₛcₛc |  |  |
| 456(c) | 135 | ATGGCAGCCAGCTGCT | 680 | AₛTₛGₛGₛcₛaₛgₛcₛcₛaₛgₛcₛTₛGₛCₛT |  |  |
|  |  |  | 681 | AₛTₛGₛGₛcₛaₛgₛcₛcₛaₛgₛcₛTₛGₛCₛt |  |  |
|  |  |  | 682 | AₒTₒGₒGₒcₛaₛgₛcₛcₛaₛgₛcₛTₒGₒCₒT |  |  |
|  |  |  | 683 | aₛtₛgₛgₛcₛaₛgₛcₛcₛaₛgₛcₛtₛgₛcₛt |  |  |
| 470(c) | 136 | AGAGGCCTCAATCCAT | 684 | AₛGₛAₛGₛgₛcₛcₛtₛcₛaₛaₛtₛCₛCₛAₛT |  |  |
|  |  |  | 685 | AₛGₛAₛGₛgₛcₛcₛtₛcₛaₛaₛtₛCₛCₛAₛt |  |  |
|  |  |  | 686 | AₒGₒAₒGₒgₛcₛcₛtₛcₛaₛaₛtₛCₒCₒAₒT |  |  |
|  |  |  | 687 | aₛgₛaₛgₛgₛcₛcₛtₛcₛaₛaₛtₛcₛcₛaₛt |  |  |
| 55(c) | 137 | GGGCAACGTCGGGGCA | 688 | GₛGₛGₛCₛaₛaₛcₛgₛtₛcₛgₛgₛGₛGₛCₛA |  |  |
|  |  |  | 689 | GₛGₛGₛCₛaₛaₛcₛgₛtₛcₛgₛgₛGₛGₛCₛa |  |  |
|  |  |  | 690 | GₒGₒGₒCₒaₛaₛcₛgₛtₛcₛgₛgₛGₒGₒCₒA |  |  |
|  |  |  | 691 | gₛgₛgₛcₛaₛaₛcₛgₛtₛcₛgₛgₛgₛgₛcₛa |  |  |
| 66(c) | 138 | TGCCAGGCAGGGGCA | 692 | TₛGₛCₛCₛaₛgₛgₛcₛaₛgₛgₛgₛGₛCₛAₛ |  |  |
|  |  |  | 693 |  |  |  |
|  |  |  | 694 | TₛGₛCₛCₛaₛaₛcₛgₛtₛcₛgₛgₛGₛGₛCₛA |  |  |
|  |  |  | 695 | tₛgₛcₛcₛaₛgₛgₛcₛaₛgₛgₛgₛgₛcₛa |  |  |
| 140(c) | 139 | CCGGGGTGCAGGCGCA | 696 | CₛCₛGₛGₛgₛgₛtₛgₛcₛaₛgₛgₛCₛGₛCₛA |  |  |
|  |  |  | 697 | CₛCₛGₛGₛgₛgₛtₛgₛcₛaₛgₛgₛCₛGₛCₛa |  |  |
|  |  |  | 698 | CₒCₒGₒGₒgₛgₛtₛgₛcₛaₛgₛgₛCₒGₒCₒA |  |  |
|  |  |  | 699 | cₛcₛgₛgₛgₛgₛtₛgₛcₛaₛgₛgₛcₛgₛcₛa |  |  |
| 148(c) | 140 | CATCCGCTCCGGGGTG | 700 | CₛAₛTₛCₛcₛgₛcₛtₛcₛcₛgₛgₛGₛGₛTₛG |  |  |
|  |  |  | 701 | CₛAₛTₛCₛcₛgₛcₛtₛcₛcₛgₛgₛGₛGₛTₛg |  |  |
|  |  |  | 702 | CₒAₒTₒCₒcₛgₛcₛtₛcₛcₛgₛgₛGₒGₒTₒG |  |  |
|  |  |  | 703 | CₛAₛTₛCₛCₛGₛCₛTₛCₛCₛGₛGₛGₛGₛTₛG |  |  |
| 177(c) | 141 | GTGGGCAGTGGATGA | 704 | GₛTₛGₛGₛgₛgₛcₛaₛgₛtₛgₛgₛAₛTₛGₛA |  |  |
|  |  |  | 705 | GₛTₛGₛGₛgₛgₛcₛaₛgₛtₛgₛgₛAₛTₛGₛa |  |  |
|  |  |  | 706 | GₒTₒGₒGₒgₛgₛcₛaₛgₛtₛgₛgₛAₒTₒGₒA |  |  |
|  |  |  | 707 | gₛtₛgₛgₛgₛgₛcₛaₛgₛtₛgₛgₛaₛtₛgₛa |  |  |
| 260(c) | 142 | CCTCTATGGGTCGTC | 708 | CₛCₛTₛCₛtₛaₛtₛgₛgₛgₛgₛtₛCₛGₛTₛC |  |  |
|  |  |  | 709 | CₛCₛTₛCₛtₛaₛtₛgₛgₛgₛgₛtₛCₛGₛTₛt |  |  |
|  |  |  | 710 | CₒCₒTₒCₒcₛtₛaₛtₛgₛgₛgₛgₛtₛCₒGₒTₒC |  |  |
|  |  |  | 711 | cₛcₛtₛcₛtₛaₛtₛgₛgₛgₛgₛtₛcₛgₛtₛc |  |  |

TABLE 2-continued

Oligomeric compounds of the invention
Oligomeric compounds were evaluated for their potential to knockdown Survivin
mRNA in 15PC3 cells. The data are presented as percentage downregulation relative
to mock transfected cells. Transcript steady state was monitored by Real-time PCR
and normalised to the GAPDH transcript steady state. Note that all LNA C are 5'-
Methyl-Cytosine.

| Target site | Seq ID NO: | Oligomeric compound Sequence 5'-3' | Seq ID | Specific design of Oligomeric compound Capital letters β-D-oxy-LNA S = phosphorthioate O = —O—P(O)$_2$—O— Small letters DNA sugar | % Inhibition at 25 nM | % Inhibition at 5 nM oligo |
|---|---|---|---|---|---|---|
| 274(c) | 143 | ATGCTTTTTATGTTCC | 712 | A$_s$T$_s$G$_s$C$_s$t$_s$t$_s$t$_s$t$_s$a$_s$t$_s$g$_s$T$_s$T$_s$C$_s$C | | |
| | | | 713 | A$_s$T$_s$G$_s$C$_s$t$_s$t$_s$t$_s$t$_s$a$_s$t$_s$g$_s$T$_s$T$_s$C$_s$t | | |
| | | | 714 | A$_o$T$_o$G$_o$C$_o$t$_s$t$_s$t$_s$t$_s$a$_s$t$_s$g$_s$T$_o$T$_o$C$_o$C | | |
| | | | 715 | a$_s$t$_s$g$_s$c$_s$t$_s$t$_s$t$_s$t$_s$a$_s$t$_s$g$_s$t$_s$t$_s$c$_s$c | | |
| 384(c) | 144 | GTTTGCTTTGCAATTT | 716 | G$_s$T$_s$T$_s$T$_s$c$_s$C$_s$t$_s$t$_s$t$_s$g$_s$c$_s$a$_s$A$_s$T$_s$T$_s$T | | |
| | | | 717 | G$_s$T$_s$T$_s$T$_s$c$_s$C$_s$t$_s$t$_s$t$_s$g$_s$c$_s$a$_s$A$_s$T$_s$T$_s$t | | |
| | | | 718 | G$_o$T$_o$T$_o$T$_o$c$_s$C$_s$t$_s$t$_s$t$_s$g$_s$c$_s$a$_s$A$_o$T$_o$T$_o$T | | |
| | | | 719 | g$_s$t$_s$t$_s$t$_s$c$_s$c$_s$t$_s$t$_s$t$_s$g$_s$c$_s$a$_s$a$_s$t$_s$t$_s$t | | |
| ISIS 23722 | 145 | TGTGCTATTCTGTGAATT (18-mer) | 720 | T$_s$G$_s$T$_s$G$_s$c$_s$t$_s$a$_s$t$_s$t$_s$c$_s$t$_s$g$_s$t$_s$g$_s$A$_s$A$_s$T$_s$T | | |
| | | | 721 | T$_o$G$_o$T$_o$G$_s$c$_s$t$_s$a$_s$t$_s$t$_s$c$_s$t$_s$g$_s$t$_s$g$_s$A$_o$A$_o$T$_o$T | | |
| | | | 722 | t$_s$g$_s$t$_s$g$_s$c$_s$t$_s$a$_s$t$_s$t$_s$c$_s$t$_s$g$_s$t$_s$g$_s$a$_s$a$_s$t$_s$t | | |
| | | | 723 | *T$_s$G$_s$T$_s$G$_s$c$_s$t$_s$a$_s$t$_s$t$_s$c$_s$t$_s$g$_s$t$_s$g$_s$A$_s$A$_s$T$_s$T* | | |
| | 146 | | 724 | T$_s$A̲$_s$A̲$_s$G$_s$c$_s$t$_s$g̲$_s$t$_s$t$_s$c$_s$t$_s$a̲$_s$t$_s$g$_s$T̲$_s$G̲$_s$T$_s$T* | | |
| | | | 725 | T$_s$A̲$_s$A̲$_s$G$_s$c$_s$t$_s$g̲$_s$t$_s$t$_s$c$_s$t$_s$a̲$_s$t$_s$g$_s$T̲$_s$G̲$_s$T$_s$T* | | |
| | | | 726 | *T$_s$A̲$_s$A̲$_s$G$_s$c$_s$t$_s$g̲$_s$t$_s$t$_s$c$_s$t$_s$a̲$_s$t$_s$g$_s$T̲$_s$G̲$_s$T$_s$T** | | |

*relates to compound Underlined indicates mismatch compared to above compound. Compound 145F and 146F contains the MOE chemistry in capital letters italic which is the compound ISIS23722.

TABLE 3

IC$_{50}$ (nM) of LNA (β-D-oxy-LNA) containing
oligomeric in two cell lines of different
origin
Oligomeric compounds were evaluated for their
potential to knockdown Survivin mRNA in 15PC3
and MCF7 cells. Transcript steady state was
monitored by Real-time PCR and normalised to
the GAPDH transcript steady state.

| Seq ID/NO | MCF7 | 15PC3 |
|---|---|---|
| 147 | 28 | 5 |
| 148 | | <5 |
| 155 | | <5 |
| 156 | | 5 |
| 163 | 8 | 3 |
| 164 | | <5 |
| 175 | 11 | 3 |
| 199 | 1 | <1 |
| 200 | | <1 |
| 203 | | 1 |
| 612 | | <5 |
| 620 | | <25 |
| 623 | | <5 |
| 652 | | <5 |

TABLE 3-continued

IC$_{50}$ (nM) of LNA (β-D-oxy-LNA) containing
oligomeric in two cell lines of different
origin
Oligomeric compounds were evaluated for their
potential to knockdown Survivin mRNA in 15PC3
and MCF7 cells. Transcript steady state was
monitored by Real-time PCR and normalised to
the GAPDH transcript steady state.

| Seq ID/NO | MCF7 | 15PC3 |
|---|---|---|
| 653 | | <25 |
| 656 | | <25 |
| 664 | | <25 |
| 665 | | <5 |

As showed In table 1 and 2, SEQ ID NO 2, 3, 4, 5, 6, 8, 9, 10, 11, 12, 13, 14, 15, 118, 119, 120, 121, 122, 123, 125, 126, 128, 129, 130 and 131 demonstrated at least 30% inhibition of survivin expression at 25 nM in these experiments and are therefore preferred.

Compounds of particular interest are 147, 148, 155, 156, 163, 164, 199, 200, 203, 616, 617, 624, 625, 652, 653, 660, 661, 664 and 665.

Example 11

Improved Inhibition In Vitro of Survivin Expression Using LNA Antisense Oligomeric Compounds Compared to Phosphorothioates and MOE Comparison of mRNA inhibition by using phosphorothioates and MOE (Calbiochem) versus LNA containing antisense oligomeric compound in 15PC3 cells was performed. A LNA version of ISIS23722 was compared to the MOE containing compound, which is an 18-mer 4MOE/PS+10PS+ 4MOE/PS and compared to an iso-sequential phosphorthioate. Transfection was performed of 15PC3 with oligonucleotides or media (mock) (see example 5). Survivin mRNA was monitored with realtime PCR and normalised to GAPDH. Survivin mRNA presented relative to mock expression (see Table 4).

TABLE 4

Percentage down regulation of mRNA

|  | 0.2 nM | 1 nM | 5 nM | 25 nM | 100 nM |
|---|---|---|---|---|---|
| LNA version of ISIS23722 (4LNA/PS + 10PS + 4LNA/PS): 145A | <20% | 48% | 79% | 84% | 76% |
| MOE compound ISIS23722 (4MOE/PS + 10PS + 4MOE/PS): 145F | <20% | <20% | <20% | <20% | 46% |
| Phosphorthioate version of ISIS23722 (18PS) 145D | 22% | <20% | <20% | <20% | <20% |
| LNA version of ISIS23722 with 6 mismatches: 146C | — | — | — | <20% | <20% |
| MOE compound ISIS23722 with 6 mismatches: 146F | — | — | — | <20% | <20% |

In another experiment, the supernatants from each culture well were also included in the analysis in order to allow late apoptotic cells to be analyzed. The 18-mer LNA, PS and MOE compounds above were compared to LNA 16-mers of the invention. 15PC3 cells were transfected with the indicated oligos at the given concentrations (see Example 5). Total RNA was extracted at 24 hours. Cells in the media supernatant were included in the analysis. Survivin mRNA was monitored with realtime PCR and normalised to GAPDH. Survivin mRNA presented relative to mock expression. (see Table 5)

TABLE 5

Down regulation of mRNA (percentage of mock expression)

| Description: Seq ID | 100 nM | 25 nM | 5 nM |
|---|---|---|---|
| LNA version of ISIS23722 (4LNA/PS + 10PS + 4LNA/PS): 145A | 91% | 94% | 89% |
| LNA version of ISIS23722 (4LNA/PO + 10PS + 4LNA/PO): 145C | 89% | 88% | 79% |
| MOE compound ISIS23722 (4MOE/PS + 10PS + 4MOE/PS): 145F | 68% | 36% | <20% |
| Phosphorthioate version of ISIS23722 (18PS): 145D | 35% | <20% | <20% |
| LNA compound 2A (16-mer) | 99% | 90% | 66% |
| LNA compound 6A (16-mer) | — | 98% | 90% |
| LNA compound 15B (16-mer) | 97% | 97% | 99% |

Example 12

Apoptosis Induction by LNA Antisense Oligomeric Compounds

Cells were seeded to a density of 12000 cells per well in white 96 well plate (Nunc 136101) in DMEM the day prior to transfection. The next day cells were washed once in pre-warmed OptiMEM followed by addition of 72 μl OptiMEM containing 5 μg/ml Lipofectamine 2000 (In vitrogen). Cells were incubated for 7 min before adding 18 μl oligonucleotides diluted in OptiMEM. The final oligonucleotide concentration ranged from 5 nM to 25 nM. After 4 h of treatment, cells were washed in OptiMEM and 100 μl DMEM containing serum was added. Following oligo treatment cells were allowed to recover for the period indicated before they were removed from the CO2 incubated and equilibrated to room temperature for 15 min. The highly sensitive Caspase 3/7-Glo™ Reagent (Promega) was added directly to the cells in 96well and plates were incubated for 20 min before recording luminescence (luciferase activity) in Luminoskan Ascent instrument from Thermo Labsystems after further 1 min lag period. The luciferase activity is measured as Relative Light Units per seconds (RLU/s). The data was processed in the Ascent software 2.4.2, and graphs were drawn in excel. (see FIG. 8)

Example 13

Figure 10:
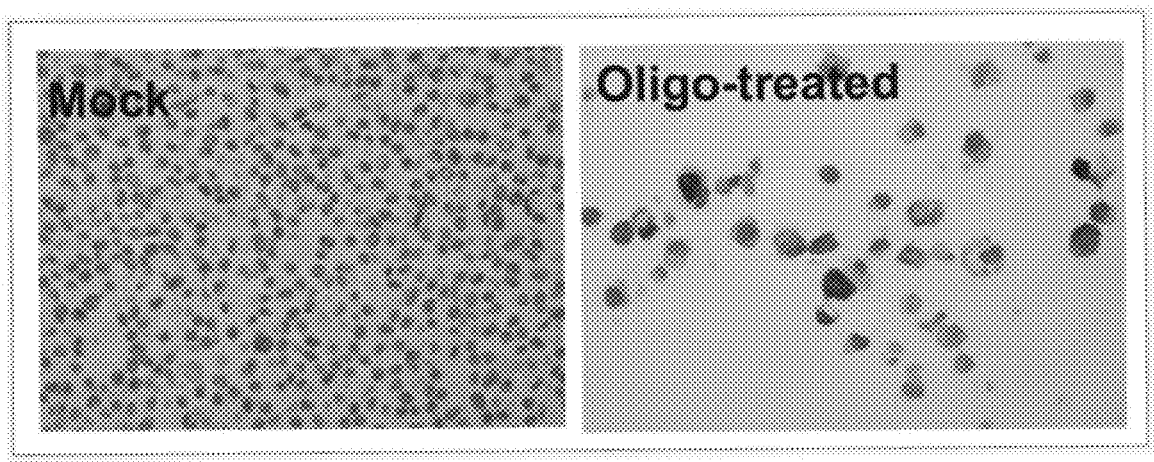
FIG. 10 Using immunohistochemistry detection of active Caspase 3 was detected in 15PC3 cells treated with LNA antisense oligonucleotides 15A targeting Survivin.

Improved Induction of Apoptosis In Vitro Using LNA Antisense Oligomeric Compounds Compared to Phosphorothioates and MOE Measurement of apoptosis using BD™ cytometric bead array (CBA) (cat. 557816). Cells were transfected using lipofectamine 2000 as described (see Example 5). 24 h following transfection, the cells from the supernatant was spun down and the adherent cells were trypsionised and spun down. The cell pellet was resuspended/washed in PBS and counted to bring cell concentration to $2 \times 10^6$ cells/ml lysis buffer containing protease inhibitors. The procedure was proceeded as described by manufacturer with the following modifications. When cells were lysed, they were lysed for 40 min and vortexed with a 10 min interval. $1 \times 10^5$ cells were incubated with Caspase 3, Bcl-2 and PARP beads, mixed briefly and incubated for 1 h at room temperature. Caspase 3 activity, Bcl2 expression and induction of PARP in oligo treated cells were analysed using the using the BD™ CBA software. Data were transferred to excel and graphs were drawn. All data were-related to mock (which is set to one). FIG. 9 shows that the LNA containing compounds (145A and 145C) improves induction of apoptosis compared to the iso-sequential MOE compound ISIS27322 (here 145F) and the iso-sequential phosphorthioate compound (145D). Mismatch controls of a LNA compound (146C) and the MOE compound (146F) as well as the LNA compound 15A was also included in the study. Furthermore, Caspase 3 activation of compound 15A was detected by immunohistochemical analysis of LNA oligomeric compound treated cells (FIG. 10).

Example 14

Antisense Oligonucleotide Inhibition of Survivin in Proliferating Cancer Cells

Figure 11:
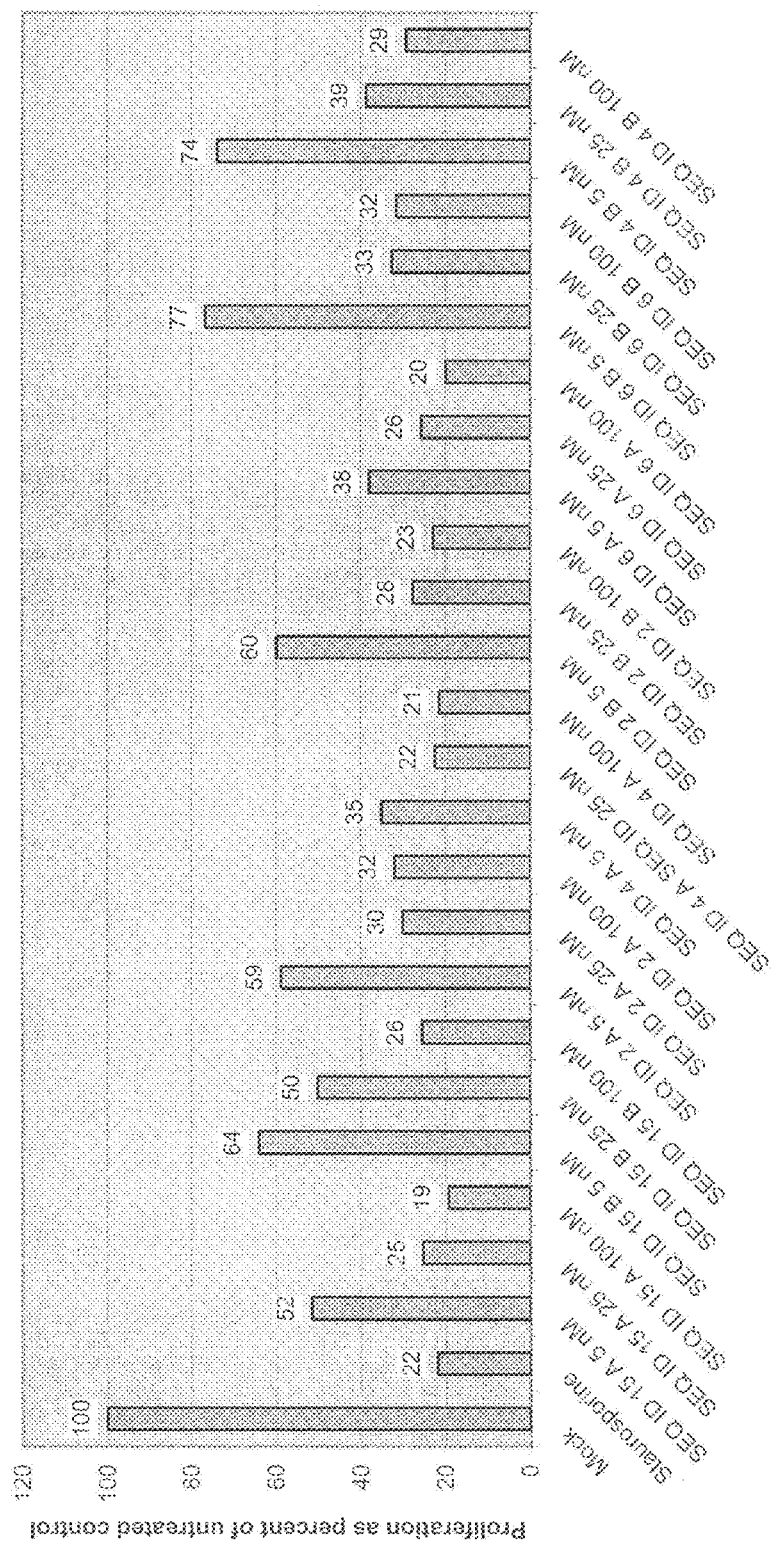
FIG. 11 LNA antisense inhibition of Survivin in proliferating cancer cells. For example, compound 6A is particularly potent.
Figure 12:
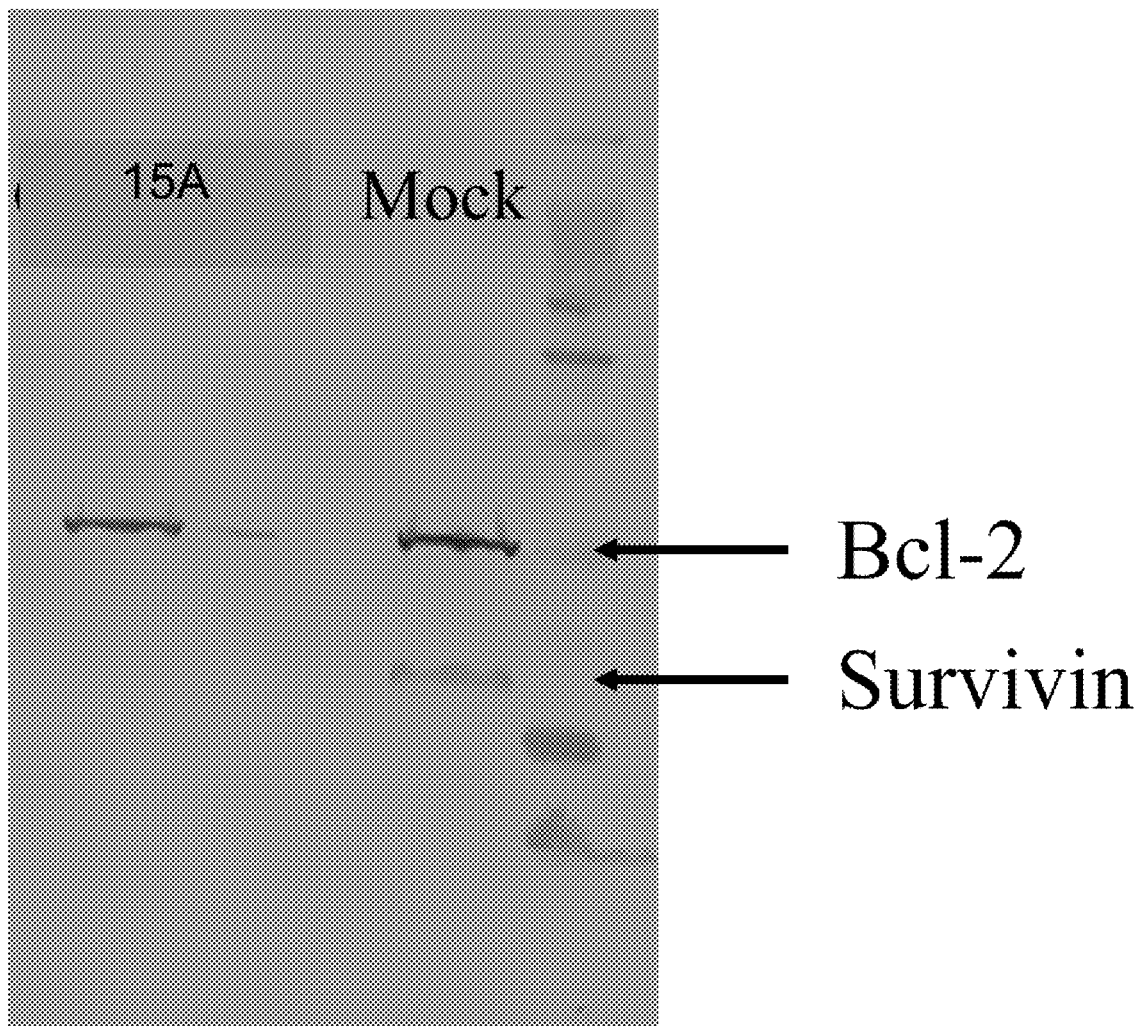
FIG. 12 Down regulation of Survivin in 15PC3 cells transfected with compound 15A analyzed by western blotting at 100 nM.

Cells were seeded to a density of 12000 cells per well in white 96 well plate (Nunc 136101) in DMEM the day prior to transfection. The next day cells were washed once in pre-warmed OptiMEM followed by addition of 72 μl OptiMEM containing 5 μg/ml Lipofectamine2000 (In vitrogen). Cells were incubated for 7 min before adding 18 μl oligonucleotides diluted in OptiMEM. The final oligonucleotide concentration ranged from 5 nM to 100 nM. After 4 h of treatment, cells were washed in OptiMEM and 100 μl serum containing DMEM was added. Following oligo treatment cells were allowed to recover for the period indicated, viable cells were measured by adding 20 μl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (Cell-Titer 96® AQ$_{ueous}$ One Solution Cell Proliferation Assay, Promega). Viable cells were measured at 490 nm in a Powerwave (Biotek Instruments). Growth rate (ΔOD/h) were plotted against oligo concentration. (see FIG. 11).

Example 15

Measurement of Ploidy (Cell Cycle) and DNA Degradation (Apoptosis) of Cells Following Treatment with Oligomeric Compounds Targeting Survivin The late stage in the apoptotic cascade leads to large numbers of small fragments of DNA which can be analysed by propidium iodide staining of the cells, furthermore, propidium iodide staining can be used to asses ploidy in treated cells. To assess ploidy/apoptosis of cells treated with oligomeric compound directed against Survivin, cells were washed in PBA and fixed for 1 h in 70% EtOH at 4° C. After treatment with 50 μg/ml RNAse (Sigma) for 20 min at room temperature cells were washed with PBS and incubated with 40 μg/ml propidium iodide (Sigma or BD) for 30 min. All samples were analysed using fluorescence activated cell sorter (FACSCalibur, Becton Dickinson) and Cell Quest software. In the DNA histogram the hypodiploid or the sub-G1 peak represented the apoptotic cells.

Example 16

Measurement of Changes in the Mitochondrial Membrane Potential of Cells Following Treatment with Oligomeric Compounds Targeting Survivin To measure changes in the mitochondrial membrane potential the MitoSensor™ reagent method (Becton Dickinson, Cat # K2017-1) was used. MitoSensor™ reagent is taken up by healthy cells, in which it forms aggregates that emit red fluorescence. Upon apoptosis the mitochondrial membrane potential changes and does not allow the reagent to aggregate within the mitochondria and therefore it remains in the cytoplasm in its monomeric form where it emits green fluorescence. Cells treated with oligomeric compounds directed against Survivin were washed and incubated in MitoSensor Reagent diluted in Incubation buffer as described by manufacturer. Changes in membrane potential following oligo treatment was detected by fluorescence activated cell sorter (FACSCalibur, Becton Dickinson) and by the use of Cell Quest software.

Example 17

Inhibition of Capillary Formation of Endothelial Cells Following Antisense Oligo Treatment Endothelial monolayer cells (e.g. HUVEC) were incubated with antisense oligos directed against survivin. Tube formation was analysed by either of the two following methods. The first method was the BD BioCoat angiogenesis tube formation system. Cells were transfected with oligos as described (example 5). Transfected cells were seeded at $2 \times 10^4$ cells/96 well onto matrigel polymerized BD Biocoat angiogeneis plates. The plates were incubated for the hours/days indicated with or without PMA (5-50 nM), VEGF (20-200 ng/ml), Suramin or vehicle. The plates were stained with Cacein AM as stated by the manufacturer and images were taken. Total tube length was measured using MetaMorph. Althernatively, cells were seeded in rat tail type I collagen (3 mg/ml, Becton Dickinson) in 0.1 volume of 10×DMEM, neutralised with sterile 1 M NaOH and kept on ice or in matrigel. Cells were added to the collagen suspension at a final concentration of $1 \times 10^6$ cells/ml collagen. The cell-collagen mixture was added to 6-well or 35 mm plates and placed in a humidified incubator at 37° C. When gelled 3 ml of culture medium plus an extra 10% FBS were added and cells were allow to form capillary-like vascular tubes over the period indicated in the presence or absence of PMA (16 nM), VEGF (50 ng/ml). Tube formation was quantified following cryostat sectioning of the gels and examination of sections by phase-contrast microscopy.

Example 18

Measurement of In Vitro Cytotoxicity Following Treatment with Oligomeric Compounds Targeting Survivin Cells were seeded ($0.3-1.2 \times 10^4$) and treated with antisense oligos as described (example for MTS assay Example 12). At the times indicated, 20-50 μl medium from the antisense treated cells were transferred to 96-well plates in order to measure the release of LDH to the medium. An equal volume of LHD substrate was added as described by the manufacturer. Released LDH was measured using a 30-minute coupled enzymatic assay, which results in the conversion of a tetrazolium salt (INT) into a red formazan product. The amount of colour formed is proportional to the number of lysed cells. Visible wavelength absorbance data (measured at 490 nm) were collected using a standard 96-well plate reader (Powerwave, Bio-Tek Instruments). As positive control cells were treated for about 45 minutes with 0.9% Triton X-100 (=100% lysis). Cytotoxicity was plotted relative to mock and Triton-x 100 treated cells (100% lysis=100% cytotoxicity).

Example 19

In Vivo Model: Tumour Growth Inhibition of Human Tumour Cells Grown In Vivo by Systemic Treatment with Antisense Oligonucleotides Female NMRI athymic nude mice of 6 weeks old were purchased from M&B, Denmark and allowed to acclimatize for at least one week before entering experiments. Human cancer cells typically $10^6$ cells suspended in 300 μl matrigel (BD Bioscience), were subcutaneously injected into the flanks of 7-8 week old NMRI athymic female nude mice. When the tumour growth was established, typically 7-12 days post tumour cell injection; different antisense oligonucleotides were administrated at 5 mg/kg/day for up to 28 days using ALZET osmotic pumps implanted subcutaneously. Prior to dorsal implantation the pumps were incubated overnight at room temperature in sterile PBS to start the pumps.

Control animals received saline alone for the same period. Each experimental group included at least 5 mice. Anti-tumour activities were estimated by the inhibition of tumour volume. Tumour growth was followed regularly by measuring 2 perpendicular diameters. Tumour volumes were calculated according to the formula $(\pi \times L \times D^2/6)$, where L represents the largest diameter and D the tumour diameter perpendicular to L. At the end of treatment the animals were sacrificed and tumour weights were measured. Mean tumour volume and weights of groups were compared using Mann-Whitney's test. All analysis was made in SPSS version 11.0 for windows. Optimally a Western blot analysis may also be performed to measure if the antisense oligonucleotides have an inhibitory effect on protein levels. At the end of treatment period mice were therefore anaesthetised and the tumours were excised and immediately frozen in liquid nitrogen. The tumours were homogenized in lysis buffer (i.e. 20 mM Tris-Cl [pH 7.5]; 2% Triton X-100; 1/100 vol. Protease Inhibitor Cocktail Set III (Calbiochem); 1/100 vol. Protease Inhibitor Cocktail Set II (Calbiochem)) at 4° C. with the use of a motor-driven homogeniser. 500 μl lysis buffer was applied per 100 mg tumour tissue. Tumour lysates from each group of mice were pooled and centrifuged at 13.000 g for 5 min at 4° C. to remove tissue debris. Protein concentrations of the tumour extracts were determined using the BCA Protein Assay Reagent Kit (Pierce, Rockford). The protein extracts (50-100 μg) were fractionated on a gradient SDS-PAGE gel spanning from 4-20% and transferred to PVDF membranes and visualized by aminoblack staining. The expression of survivin was detected with anti-human survivin antibody followed by horseradish peroxidase-conjugated anti-goat IgG (DAKO). Immunoreactivity was detected by the ECL Plus (Amersham biotech) and quantitated by a Versadoc 5000 lite system (Bio-Rad).

Example 20

In Vivo Model: Tumor Growth Inhibition of Human Tumour Fragments Transplanted in Nude Mice After Intraperetoneal Treatment with LNA Antisense Oligos Tumour growth inhibiting activity of LNA antisense oligonucleotides was tested in xenotransplanted athymic nude mice, NMRI nu/nu, from Oncotest's (Freiburg, Germany) breeding colony. Human tumour fragments from breast (MDA MB 231), prostate (PC3) or lung tumours (LXFE 397, Oncotest) were obtained from xenografts in serial passage in nude mice. After removal of tumors from donor mice, they were cut into fragments (1-2 mm diameter) and placed in RPMI 1640 culture medium until subcutaneous implantation. Recipient mice were anaesthetized by inhalation of isoflurane. A small incision was made in the skin of the back. The tumor fragments (2 fragments per mouse) were transplanted with tweezers. MDA MB 231 and LXFE 397 tumors were transplanted in female mice, PC3 tumors were transplanted in male mice. When a mean tumour diameter 4-6 mm was reached, animals were randomized and treated with oligonucleotides at 20 mg/kg intraperetoneally once a day for three weeks excluding weekends. A vehicle (saline) and positive control group (Taxol, 20 mg/kg/day) were included in all experiments. All groups consisted of 6 mice. The tumour volume was determined by two-dimensional measurement with a caliper on the day of randomization (Day 0) and then twice weekly. Tumor volumes were calculated according to the formula: $(a \times b^2) \times 0.5$ where a represents the largest and b the perpendicular tumor diameter. Mice were observed daily for 28 days after randomization until tumour volume was doubled. Mice were sacrificed when the tumour diameters exceeded 1.6 cm. For the evaluation of the statistical significance of tumour inhibition, the U-test by Mann-Whitney-Wilcoxon was performed. By convention, p-values <0.05 indicate significance of tumor inhibition.

Example 21

Biodistribution of Oligonucleotides in Mice

Female NMRI athymic nude mice of 6 weeks old were purchased from M&B, Denmark and allowed to acclimatize for at least one week before entering experiments. Human cancer cells typically $10^6$ cells suspended in 300 μl matrigel (BD Bioscience) were subcutaneously injected into the flanks of 7-8 week old NMRI athymic female nude mice. When tumour growth was evident, tritium labelled oligonucleotides were administrated at 5 mg/kg/day for 14 days using ALZET osmotic pumps implanted subcutaneously. The oligonucleotides were tritium labeled as described by Graham M J et al. (J Pharmacol Exp Ther 1998; 286(1): 447-458). Oligonucleotides were quantitated by scintillation counting of tissue extracts from all major organs (liver, kidney, spleen, heart, stomach, lungs, small intestine, large intestine, lymph nodes, skin, muscle, fat, bone, bone marrow) and subcutaneous transplanted human tumour tissue.

Example 22

Uptake of LNA Oligomeric Compound in Human Tumour Xenografts

Human 15PC3 xenografted tumors according to Example 13 were homogenized in 10 volumes of 0.5% Igepal CA-630, 25 mM Tris pH 8.0, 25 mM EDTA, 100 mM NaCl, 1 mg/ml Proteinase K1 and incubated overnight at 37 degrees celsius followed by phenol-chloroform extraction. The concentration of antisense oligonucleotide 2650 in the combined aqueous phase was determined using a sequence specific ELISA assay. Two probes, one labelled with biotin and one labelled with digoxigenin (DIG) with complementary sequences to the antisense oligonucleotide are hybridised to the antisense oligo. The complex is captured by immobilized streptavidin and quantified using a horse radish peroxidase-conjugated anti-digoxigenin antibody and standard ELISA procedures. Briefly, 10 nM DNA capture probe (5'-aactgtgc-Biotin-3') and 10 nM LNA detection probe (5'-DIG-GATGTTTCgat-gtttc-3')(SEQ ID NO: 738) were mixed with sample or standards in 1% blocking reagent (Roche cat. 1 096 176) in PBS. The probes were annealed to the oligo by heating the mixture to 70 degrees celsius and gradual cooling to 20 degrees Celsius. The mixture was transferred to streptavidin-coated wells. The amount of captured DIG-probe is quantified using an HRP-conjugated Anti-DIG antibody fragment (Roche) and standard ELISA procedures. At least 1.3 μg/g tumours tissue of the oligomeric compound 15A was detected (data not adjusted for recovery).

The present invention has been described with specificity in accordance with certain of its preferred embodiments. Therefore, the following examples serve only to illustrate the invention and are not intended to limit the same.

The invention claimed is:

1. A method for treating prostatic, breast or lung carcinoma, said method comprising administering an effective amount of an oligonucleotide compound having the sequence as defined in SEQ ID NO: 130 to a patient in need thereof.

2. The method according to claim 1, wherein said carcinoma is.

3. The method according to claim 1, wherein said carcinoma is breast carcinoma.

4. The method according to claim 1, wherein said carcinoma is lung carcinoma.

5. The method according to claim 1, wherein the oligonucleotide compound has the sequence as defined in SEQ ID NO: 660.

6. The method according to claim 1, wherein the oligonucleotide compound has the sequence as defined in SEQ ID NO: 661.

7. The method according to claim 1, wherein the oligonucleotide compound has the sequence as defined in SEQ ID NO: 662.

8. The method according to claim 1, wherein the oligonucleotide compound has the sequence as defined in SEQ ID NO: 663.

9. The method according to claim 1, wherein the oligonucleotide compound is administered parenterally.

10. The method according to claim 1, wherein the oligonucleotide compound is administered intravenously.

11. The method according to claim 1, wherein the oligonucleotide compound is administered by bolus injection into a target organ.

12. The method according to claim 1, wherein the oligonucleotide compound is administered intraperitoneally.

* * * * *

UNITED STATES PATENT AND TRADEMARK OFFICE
CERTIFICATE OF CORRECTION

| | |
|---|---|
| PATENT NO. | : 7,741,309 B2 |
| APPLICATION NO. | : 12/493625 |
| DATED | : June 22, 2010 |
| INVENTOR(S) | : Hansen et al. |

It is certified that error appears in the above-identified patent and that said Letters Patent is hereby corrected as shown below:

In column 455, claim 2, lines 34-35, "The method according to claim 1, wherein said carcinoma is." should read --The method according to claim 1, wherein said carcinoma is prostatic carcinoma.--.

Signed and Sealed this
Fifteenth Day of March, 2011

David J. Kappos
*Director of the United States Patent and Trademark Office*

SEQUENCE LISTING

<160> NUMBER OF SEQ ID NOS: 741

<210> SEQ ID NO 1
<211> LENGTH: 1619
<212> TYPE: DNA
<213> ORGANISM: Homo sapiens

<400> SEQUENCE: 1

| | | | | | | |
|---|---|---|---|---|---|---|
| ccgccagatt | tgaatcgcgg | gacccgttgg | cagaggtggc | ggcggcggca | tgggtgcccc | 60 |
| gacgttgccc | cctgcctggc | agccctttct | caaggaccac | cgcatctcta | cattcaagaa | 120 |
| ctggcccttc | ttggagggct | gcgcctgcac | cccggagcgg | atggccgagg | ctggcttcat | 180 |
| ccactgcccc | actgagaacg | agccagactt | ggcccagtgt | ttcttctgct | tcaaggagct | 240 |
| ggaaggctgg | gagccagatg | acgaccccat | agaggaacat | aaaaagcatt | cgtccggttg | 300 |
| cgctttcctt | tctgtcaaga | agcagtttga | agaattaacc | cttggtgaat | ttttgaaact | 360 |
| ggacagagaa | agagccaaga | acaaaattgc | aaaggaaacc | aacaataaga | agaaagaatt | 420 |
| tgaggaaact | gcgaagaaag | tgcgccgtgc | catcgagcag | ctggctgcca | tggattgagg | 480 |
| cctctggccg | gagctgcctg | tcccagagt | ggctgcacca | cttccagggt | ttattccctg | 540 |
| gtgccaccag | ccttcctgtg | ggccccttag | caatgtctta | ggaaaggaga | tcaacatttt | 600 |
| caaattagat | gtttcaactg | tgctcctgtt | ttgtcttgaa | agtggcacca | gaggtgcttc | 660 |
| tgcctgtgca | gcgggtgctg | ctggtaacag | tggctgcttc | tctctctctc | tctctttttt | 720 |
| gggggctcat | ttttgctgtt | ttgattcccg | ggcttaccag | gtgagaagtg | agggaggaag | 780 |
| aaggcagtgt | ccctttttgct | agagctgaca | gctttgttcg | cgtgggcaga | gccttccaca | 840 |
| gtgaatgtgt | ctggacctca | tgttgttgag | gctgtcacag | tcctgagtgt | ggacttggca | 900 |
| ggtgcctgtt | gaatctgagc | tgcaggttcc | ttatctgtca | cacctgtgcc | tcctcagagg | 960 |
| acagttttt | tgttgttgtg | ttttttttgtt | ttttttttt | ggtagatgca | tgacttgtgt | 1020 |
| gtgatgagag | aatggagaca | gagtccctgg | ctcctctact | gtttaacaac | atggctttct | 1080 |
| tattttgttt | gaattgttaa | ttcacagaat | agcacaaact | acaattaaaa | ctaagcacaa | 1140 |
| agccattcta | agtcattggg | gaaacggggt | gaacttcagg | tggatgagga | gacagaatag | 1200 |
| agtgatagga | agcgtctggc | agatactcct | tttgccactg | ctgtgtgatt | agacaggccc | 1260 |
| agtgagccgc | ggggcacatg | ctggccgctc | ctccctcaga | aaaggcagt | ggcctaaatc | 1320 |
| cttttttaaat | gacttggctc | gatgctgtgg | gggactggct | gggctgctgc | aggccgtgtg | 1380 |
| tctgtcagcc | caaccttcac | atctgtcacg | ttctccacac | gggggagaga | cgcagtccgc | 1440 |
| ccaggtcccc | gctttctttg | gaggcagcag | ctcccgcagg | gctgaagtct | ggcgtaagat | 1500 |
| gatggatttg | attcgccctc | ctccctgtca | tagagctgca | gggtggattg | ttacagcttc | 1560 |
| gctgaaaacc | tctggaggtc | atctcggctg | ttcctgagaa | ataaaaagcc | tgtcatttc | 1619 |

<210> SEQ ID NO 2
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 2
gcagtggatg aagcca        16

```
<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
gccaagtctg gctcgt                                                    16

<210> SEQ ID NO 4
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 4
aacactgggc caagtc                                                    16

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
gcagaagaaa cactgg                                                    16

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
aagcagaaga aacact                                                    16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
ctcccagcct tccagc                                                    16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
ttctttcttc ttattg                                                    16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide
```

-continued

```
<400> SEQUENCE: 9
tgggaccagg cagctc                                                     16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
tggtgcagcc actctg                                                     16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
gaataaaccc tggaag                                                     16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
tggcaccagg gaataa                                                     16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ctaagacatt gctaag                                                     16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
ttgatctcct ttccta                                                     16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
gcacagttga aacatc                                                     16

<210> SEQ ID NO 16
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 16
gattcaaatc tggcgg                                                     16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
tgccaacggg tcccgc                                                     16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
ccgccgccgc cacctc                                                     16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
cgtcggggca cccatg                                                     16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
gccaggcagg gggcaa                                                     16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
tccttgagaa agggct                                                     16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
```

-continued tgtagagatg cggtgg					16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
agggccagtt cttgaa					16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
gcgcagccct ccaaga					16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
ccgctccggg gtgcag					16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
agccagcctc ggccat					16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
gtggggcagt ggatga					16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
gtctggctcg ttctca					16

<210> SEQ ID NO 29
<211> LENGTH: 16
<212> TYPE: DNA
<213> ORGANISM: Artificial sequence -continued

```
<220> FEATURE:
<223> OTHER INFORMATION: Synthetic oligonucleotide

<400> SEQUENCE: 29
agaaacactg ggccaa                                                       16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 30
agctccttga agcaga                                                       16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
tggctcccag ccttcc                                                       16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
ctatggggtc gtcatc                                                       16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33 tgcttttat gttcct                                                        16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
agcgcaaccg gacgaa                                                       16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
tcttgacaga aaggaa                                                       16
```

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
aattcttcaa actgct                                              16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
aaattcacca agggtt                                              16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
ctctgtccag tttcaa                                              16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
ttgttcttgg ctcttt                                              16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
ggtttccttt gcaatt                                              16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
ctttcttctt attgtt                                              16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 42
gcagtttcct caaatt                                                   16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
acggcgcact ttcttc                                                   16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
ccagctgctc gatggc                                                   16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
cctcaatcca tggcag                                                   16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
cagctccggc cagagg                                                   16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
ccactctggg accagg                                                   16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
cctggaagtg gtgcag                                                   16

<210> SEQ ID NO 49
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
gcaccaggga ataaac                                                        16

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
cacaggaagg ctggtg                                                        16

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
acattgctaa ggggcc                                                        16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
gatctccttt cctaag                                                        16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
ctaatttgaa aatgtt                                                        16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
agcacagttg aaacat                                                        16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
```

```
ttcaagacaa aacagg                                                    16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
cacctctggt gccact                                                    16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
gctgcacagg cagaag                                                    16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
gttaccagca gcaccc                                                    16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
gagagaagca gccact                                                    16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
aaaaaagaga gagaga                                                    16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
gcaaaaatga gccccc                                                    16

<210> SEQ ID NO 62
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 62
cccgggaatc aaaaca                                                    16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 63
cttctcacct ggtaag                                                    16

<210> SEQ ID NO 64
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 64
ccttcttcct ccctca                                                    16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
agcaaaaggg acactg                                                    16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
caaagctgtc agctct                                                    16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
gctctgccca cgcgaa                                                    16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
acattcactg tggaag                                                    16
```

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
aacatgaggt ccagac                                                        16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
ctgtgacagc ctcaac                                                        16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
aagtccacac tcagga                                                        16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
tcaacaggca cctgcc                                                        16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
aacctgcagc tcagat                                                        16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
ggtgtgacag ataagg                                                        16

<210> SEQ ID NO 75
<211> LENGTH: 16
<212> TYPE: DNA
<213> ORGANISM: Artificial sequence
<220> FEATURE:

-continued

<223> OTHER INFORMATION: Synthetic oligonucleotide

<400> SEQUENCE: 75
cctctgagga ggcaca                                                    16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
acaacaaaaa aactgt                                                    16

<210> SEQ ID NO 77
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 77
aaaacaaaaa aacaca                                                    16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
catctaccaa aaaaaa                                                    16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
tcacacacaa gtcatg                                                    16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
tgtctccatt ctctca                                                    16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gaggagccag ggactc                                                    16

```
<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
atgttgttaa acagta                                                     16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
acaaaataag aaagcc                                                     16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
tgaattaaca attcaa                                                     16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
agtttgtgct attctg                                                     16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
gcttagtttt aattgt                                                     16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
cttagaatgg ctttgt                                                     16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 88
cccgtttccc caatga                                                    16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
tccacctgaa gttcac                                                    16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ctattctgtc tcctca                                                    16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
gacgcttcct atcact                                                    16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
aaaggagtat ctgcca                                                    16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tcacacagca gtggca                                                    16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
cactgggcct gtctaa                                                    16

<210> SEQ ID NO 95
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 95
catgtgcccc gcggct                                                    16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
agggaggagc ggccag                                                    16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
ccactgcctt tttctg                                                    16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
ttaaaaagga tttagg                                                    16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
catcgagcca agtcat                                                    16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
agccagtccc ccacag                                                    16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
```

-continued cggcctgcag cagccc                                            16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
tgggctgaca gacaca                                            16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
tgacagatgt gaaggt                                            16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
ccccgtgtgg agaacg                                            16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
gcggactgcg tctctc                                            16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gaaagcgggg acctgg                                            16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
agctgctgcc tccaaa                                            16

<210> SEQ ID NO 108
<211> LENGTH: 16
<212> TYPE: DNA
<213> ORGANISM: Artificial sequence

```
<220> FEATURE:
<223> OTHER INFORMATION: Synthetic oligonucleotide

<400> SEQUENCE: 108
acttcagccc tgcggg                                                    16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
catcatctta cgccag                                                    16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
gagggcgaat caaatc                                                    16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
gctctatgac agggag                                                    16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
aacaatccac cctgca                                                    16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
tttccagcga agctgt                                                    16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
agatgacctc cagagg                                                    16
```

```
<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
ttctcaggaa cagccg                                               16

<210> SEQ ID NO 116
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 116
atgacaggct ttttat                                               16

<210> SEQ ID NO 117
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 117
aggcaggggg caacgt                                               16

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ccaagaaggg ccagtt                                               16

<210> SEQ ID NO 119
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 119
tggctcgttc tcagtg                                               16

<210> SEQ ID NO 120
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 120
gtctggctcg ttctca                                               16

<210> SEQ ID NO 121
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 121
agtctggctc gttctc    16

<210> SEQ ID NO 122
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 122
tggatgaagc cagcct    16

<210> SEQ ID NO 123
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 123
agcagaagaa acactg    16

<210> SEQ ID NO 124
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 124
tcctctatgg ggtcgt    16

<210> SEQ ID NO 125
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 125
gcaaccggac gaatgc    16

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 126
ttatgttcct ctatgg    16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 127
ggttaattct tcaaac    16

<210> SEQ ID NO 128

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 128
ctctgtccag tttcaa                                                       16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 129
gcaattttgt tcttgg                                                       16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 130
ctcaatccat ggcagc                                                       16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 131
ccagcctcgg ccatcc                                                       16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 132
tgtccagttt caaaaa                                                       16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 133
ctgtccagtt tcaaaa                                                       16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 134
```
tcggggcacc catgcc                                    16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 135
atggcagcca gctgct                                    16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 136
agaggcctca atccat                                    16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 137
gggcaacgtc ggggca                                    16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 138
tgccaggcag ggggca                                    16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 139
ccggggtgca ggcgca                                    16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 140
catccgctcc ggggtg                                    16

<210> SEQ ID NO 141
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 141
gtggggcagt ggatga                                                    16

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
cctctatggg gtcgtc                                                    16

<210> SEQ ID NO 143
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 143
atgcttttta tgttcc                                                    16

<210> SEQ ID NO 144
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 144
gtttcctttg caattt                                                    16

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 145
tgtgctattc tgtgaatt                                                  18

<210> SEQ ID NO 146

<400> SEQUENCE: 146

000

<210> SEQ ID NO 147
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
```

<221> NAME/KEY: misc_feature
<222> LOCATION: (1)..(16)
<223> OTHER INFORMATION: phosphorthioate linkage

<400> SEQUENCE: 147
gcagtggatg aagcca                                                         16

<210> SEQ ID NO 148
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 148
gcagtggatg aagcca                                                         16

<210> SEQ ID NO 149
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 149
gcagtggatg aagcca                                                         16

<210> SEQ ID NO 150
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 150
gcagtggatg aagcca                                                         16

<210> SEQ ID NO 151
<211> LENGTH: 16
<212> TYPE: DNA
<213> ORGANISM: Artificial sequence
<220> FEATURE:
<223> OTHER INFORMATION: Synthetic oligonucleotide

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 151
gccaagtctg gctcgt                                              16

<210> SEQ ID NO 152
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 152
gccaagtctg gctcgt                                              16

<210> SEQ ID NO 153
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 153
gccaagtctg gctcgt                                              16

<210> SEQ ID NO 154
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 154
```
gccaagtctg gctcgt                                                          16

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 155
aacactgggc caagtc                                                          16

<210> SEQ ID NO 156
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 156
aacactgggc caagtc                                                          16

<210> SEQ ID NO 157
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 157
aacactgggc caagtc                                                          16

<210> SEQ ID NO 158
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 158
aacactgggc caagtc                                                     16

<210> SEQ ID NO 159
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 159
gcagaagaaa cactgg                                                     16

<210> SEQ ID NO 160
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 160
gcagaagaaa cactgg                                                     16

<210> SEQ ID NO 161
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage
```

-continued

<400> SEQUENCE: 161
gcagaagaaa cactgg                                              16

<210> SEQ ID NO 162
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 162
gcagaagaaa cactgg                                              16

<210> SEQ ID NO 163
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 163
aagcagaaga aacact                                              16

<210> SEQ ID NO 164
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 164
aagcagaaga aacact                                              16

<210> SEQ ID NO 165
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base

```
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 165
aagcagaaga aacact                                                        16

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 166
aagcagaaga aacact                                                        16

<210> SEQ ID NO 167
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 167
ctcccagcct tccagc                                                        16

<210> SEQ ID NO 168
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 168
ctcccagcct tccagc                                                        16

<210> SEQ ID NO 169
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 169
ctcccagcct tccagc                                                   16

<210> SEQ ID NO 170
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 170
ctcccagcct tccagc                                                   16

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 171
ttctttcttc ttattg                                                   16

<210> SEQ ID NO 172
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
```

```
<222> LOCATION: (1)..(16)
<223> OTHER INFORMATION: phosphorthioate linkage

<400> SEQUENCE: 172
ttctttcttc ttattg                                                   16

<210> SEQ ID NO 173
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 173
ttctttcttc ttattg                                                   16

<210> SEQ ID NO 174
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 174
ttctttcttc ttattg                                                   16

<210> SEQ ID NO 175
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 175
tgggaccagg cagctc                                                   16

<210> SEQ ID NO 176
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 176
tgggaccagg cagctc                                                     16

<210> SEQ ID NO 177
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 177
tgggaccagg cagctc                                                     16

<210> SEQ ID NO 178
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 178
ttctttcttc ttattg                                                     16

<210> SEQ ID NO 179
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 179
tggtgcagcc actctg                                                     16
```

<210> SEQ ID NO 180
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 180
tggtgcagcc actctg                                                     16

<210> SEQ ID NO 181
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 181
tggtgcagcc actctg                                                     16

<210> SEQ ID NO 182
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 182
tggtgcagcc actctg                                                     16

<210> SEQ ID NO 183
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)

<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 183
gaataaaccc tggaag                                              16

<210> SEQ ID NO 184
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 184
gaataaaccc tggaag                                              16

<210> SEQ ID NO 185
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 185
gaataaaccc tggaag                                              16

<210> SEQ ID NO 186
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 186
gaataaaccc tggaag                                              16

<210> SEQ ID NO 187
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 187
tggcaccagg gaataa                                                       16

<210> SEQ ID NO 188
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 188
tggcaccagg gaataa                                                       16

<210> SEQ ID NO 189
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 189
tggcaccagg gaataa                                                       16

<210> SEQ ID NO 190
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage
```

<400> SEQUENCE: 190
tggcaccagg gaataa                                                   16

<210> SEQ ID NO 191
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 191
ctaagacatt gctaag                                                   16

<210> SEQ ID NO 192
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 192
ctaagacatt gctaag                                                   16

<210> SEQ ID NO 193
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 193
ctaagacatt gctaag                                                   16

<210> SEQ ID NO 194
<211> LENGTH: 16

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 194
ctaagacatt gctaag                                                    16

<210> SEQ ID NO 195
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 195
ttgatctcct ttccta                                                    16

<210> SEQ ID NO 196
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 196
ttgatctcct ttccta                                                    16

<210> SEQ ID NO 197
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
```

```
<223> OTHER INFORMATION: phosphorthioate linkage

<400> SEQUENCE: 197
ttgatctcct ttccta                                                      16

<210> SEQ ID NO 198
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 198
ttgatctcct ttccta                                                      16

<210> SEQ ID NO 199
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 199
gcacagttga aacatc                                                      16

<210> SEQ ID NO 200
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 200
gcacagttga aacatc                                                      16

<210> SEQ ID NO 201
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
```

```
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 201
gcacagttga aacatc                                                    16

<210> SEQ ID NO 202
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 202
gcacagttga aacatc                                                    16

<210> SEQ ID NO 203
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 203
gcacagttga aacatc                                                    16

<210> SEQ ID NO 204
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 204
gattcaaatc tggcgg                                                    16
```

```
<210> SEQ ID NO 205
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 205
gattcaaatc tggcgg                                                    16

<210> SEQ ID NO 206
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 206
gattcaaatc tggcgg                                                    16

<210> SEQ ID NO 207
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 207
gattcaaatc tggcgg                                                    16

<210> SEQ ID NO 208
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
```

```
<220> FEATURE:
<221> NAME/KEY: misc_feature
<222> LOCATION: (1)..(16)
<223> OTHER INFORMATION: phosphorthioate linkage

<400> SEQUENCE: 208
tgccaacggg tcccgc                                              16

<210> SEQ ID NO 209
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 209
tgccaacggg tcccgc                                              16

<210> SEQ ID NO 210
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 210
tgccaacggg tcccgc                                              16

<210> SEQ ID NO 211
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 211
tgccaacggg tcccgc                                              16

<210> SEQ ID NO 212
<211> LENGTH: 16
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 212
ccgccgccgc cacctc                                                     16

<210> SEQ ID NO 213
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 213
ccgccgccgc cacctc                                                     16

<210> SEQ ID NO 214
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 214
ccgccgccgc cacctc                                                     16

<210> SEQ ID NO 215
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 215
```
ccgccgccgc cacctc                                              16

<210> SEQ ID NO 216
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 216
cgtcggggca cccatg                                              16

<210> SEQ ID NO 217
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 217
cgtcggggca cccatg                                              16

<210> SEQ ID NO 218
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 218
cgtcggggca cccatg                                              16

<210> SEQ ID NO 219
<211> LENGTH: 16
<212> TYPE: DNA

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 219
cgtcggggca cccatg                                              16

<210> SEQ ID NO 220
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 220
gccaggcagg gggcaa                                              16

<210> SEQ ID NO 221
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 221
gccaggcagg gggcaa                                              16

<210> SEQ ID NO 222
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage
```

-continued

```
<400> SEQUENCE: 222
gccaggcagg gggcaa                                              16

<210> SEQ ID NO 223
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 223
gccaggcagg gggcaa                                              16

<210> SEQ ID NO 224
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 224
tccttgagaa agggct                                              16

<210> SEQ ID NO 225
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 225
tccttgagaa agggct                                              16

<210> SEQ ID NO 226
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
```

```
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 226
tccttgagaa agggct                                                        16

<210> SEQ ID NO 227
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 227
tccttgagaa agggct                                                        16

<210> SEQ ID NO 228
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 228
tgtagagatg cggtgg                                                        16

<210> SEQ ID NO 229
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 229
tgtagagatg cggtgg                                                        16
```

```
<210> SEQ ID NO 230
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 230
tgtagagatg cggtgg                                               16

<210> SEQ ID NO 231
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 231
tgtagagatg cggtgg                                               16

<210> SEQ ID NO 232
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 232
agggccagtt cttgaa                                               16

<210> SEQ ID NO 233
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
```

```
<221> NAME/KEY: misc_feature
<222> LOCATION: (1)..(16)
<223> OTHER INFORMATION: phosphorthioate linkage

<400> SEQUENCE: 233
agggccagtt cttgaa                                                      16

<210> SEQ ID NO 234
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 234
agggccagtt cttgaa                                                      16

<210> SEQ ID NO 235
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 235
agggccagtt cttgaa                                                      16

<210> SEQ ID NO 236
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 236
gcgcagccct ccaaga                                                      16

<210> SEQ ID NO 237
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 237
gcgcagccct ccaaga                                            16

<210> SEQ ID NO 238
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 238
gcgcagccct ccaaga                                            16

<210> SEQ ID NO 239
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 239
gcgcagccct ccaaga                                            16

<210> SEQ ID NO 240
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 240
```
ccgctccggg gtgcag                                                    16

<210> SEQ ID NO 241
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 241
ccgctccggg gtgcag                                                    16

<210> SEQ ID NO 242
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 242
ccgctccggg gtgcag                                                    16

<210> SEQ ID NO 243
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 243
ccgctccggg gtgcag                                                    16

<210> SEQ ID NO 244
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base

```
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 244
agccagcctc ggccat                                                   16

<210> SEQ ID NO 245
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 245
agccagcctc ggccat                                                   16

<210> SEQ ID NO 246
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 246
agccagcctc ggccat                                                   16

<210> SEQ ID NO 247
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 247
agccagcctc ggccat                                                   16

<210> SEQ ID NO 248
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 248
gtggggcagt ggatga                                              16

<210> SEQ ID NO 249
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 249
gtggggcagt ggatga                                              16

<210> SEQ ID NO 250
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 250
gtggggcagt ggatga                                              16

<210> SEQ ID NO 251
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage
```

<400> SEQUENCE: 251
gtggggcagt ggatga                                                        16

<210> SEQ ID NO 252
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 252
gtctggctcg ttctca                                                        16

<210> SEQ ID NO 253
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 253
gtctggctcg ttctca                                                        16

<210> SEQ ID NO 254
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 254
gtctggctcg ttctca                                                        16

<210> SEQ ID NO 255

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 255
gtctggctcg ttctca                                                    16

<210> SEQ ID NO 256
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 256
agaaacactg ggccaa                                                    16

<210> SEQ ID NO 257
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 257
agaaacactg ggccaa                                                    16

<210> SEQ ID NO 258
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
```

```
<222> LOCATION: (5)..(13)
<223> OTHER INFORMATION: phosphorthioate linkage

<400> SEQUENCE: 258
agaaacactg ggccaa                                                    16

<210> SEQ ID NO 259
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 259
agaaacactg ggccaa                                                    16

<210> SEQ ID NO 260
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 260
agctccttga agcaga                                                    16

<210> SEQ ID NO 261
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 261
agctccttga agcaga                                                    16

<210> SEQ ID NO 262
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 262
agctccttga agcaga                                                      16

<210> SEQ ID NO 263
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 263
agctccttga agcaga                                                      16

<210> SEQ ID NO 264
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 264
tggctcccag ccttcc                                                      16

<210> SEQ ID NO 265
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 265
tggctcccag ccttcc                                                      16
```

```
<210> SEQ ID NO 266
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 266
tggctcccag ccttcc                                               16

<210> SEQ ID NO 267
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 267
tggctcccag ccttcc                                               16

<210> SEQ ID NO 268
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 268
ctatggggtc gtcatc                                               16

<210> SEQ ID NO 269
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
```

```
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 269
ctatggggtc gtcatc                                                  16

<210> SEQ ID NO 270
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 270
ctatggggtc gtcatc                                                  16

<210> SEQ ID NO 271
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 271
ctatggggtc gtcatc                                                  16

<210> SEQ ID NO 272
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 272 tgcttttat gttcct                                                   16

<210> SEQ ID NO 273
<211> LENGTH: 16
<212> TYPE: DNA
<213> ORGANISM: Artificial sequence
```

```
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 273 tgcttttat gttcct                                                    16

<210> SEQ ID NO 274
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 274 tgcttttat gttcct                                                    16

<210> SEQ ID NO 275
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 275 tgcttttat gttcct                                                    16

<210> SEQ ID NO 276
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

-continued

```
<400> SEQUENCE: 276
agcgcaaccg gacgaa                                              16

<210> SEQ ID NO 277
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 277
agcgcaaccg gacgaa                                              16

<210> SEQ ID NO 278
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 278
agcgcaaccg gacgaa                                              16

<210> SEQ ID NO 279
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 279
agcgcaaccg gacgaa                                              16

<210> SEQ ID NO 280
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
```

```
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 280
tcttgacaga aaggaa                                                       16

<210> SEQ ID NO 281
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 281
tcttgacaga aaggaa                                                       16

<210> SEQ ID NO 282
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 282
tcttgacaga aaggaa                                                       16

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 283
tcttgacaga aaggaa                                                       16

<210> SEQ ID NO 284
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 284
aattcttcaa actgct                                                  16

<210> SEQ ID NO 285
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 285
aattcttcaa actgct                                                  16

<210> SEQ ID NO 286
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 286
aattcttcaa actgct                                                  16

<210> SEQ ID NO 287
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (1)..(16)
<223> OTHER INFORMATION: phosphorthioate linkage

<400> SEQUENCE: 287
aattcttcaa actgct                                                   16

<210> SEQ ID NO 288
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 288
aaattcacca agggtt                                                   16

<210> SEQ ID NO 289
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 289
aaattcacca agggtt                                                   16

<210> SEQ ID NO 290
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 290
aaattcacca agggtt                                                   16
```

<210> SEQ ID NO 291
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 291
aaattcacca agggtt                                                   16

<210> SEQ ID NO 292
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 292
ctctgtccag tttcaa                                                   16

<210> SEQ ID NO 293
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 293
ctctgtccag tttcaa                                                   16

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base

```
<220> FEATURE:
<221> NAME/KEY: misc_feature
<222> LOCATION: (5)..(13)
<223> OTHER INFORMATION: phosphorthioate linkage

<400> SEQUENCE: 294
ctctgtccag tttcaa                                                           16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 295
ctctgtccag tttcaa                                                           16

<210> SEQ ID NO 296
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 296
ttgttcttgg ctcttt                                                           16

<210> SEQ ID NO 297
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 297
ttgttcttgg ctcttt                                                           16

<210> SEQ ID NO 298
<211> LENGTH: 16
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 298
ttgttcttgg ctcttt                                                  16

<210> SEQ ID NO 299
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 299
ttgttcttgg ctcttt                                                  16

<210> SEQ ID NO 300
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 300
ggtttccttt gcaatt                                                  16

<210> SEQ ID NO 301
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 301
``` ggtttcctttt gcaatt                                                    16

<210> SEQ ID NO 302
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 302
ggtttccttt gcaatt                                                     16

<210> SEQ ID NO 303
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 303
ggtttccttt gcaatt                                                     16

<210> SEQ ID NO 304
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 304
ctttcttctt attgtt                                                     16

<210> SEQ ID NO 305
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:

```
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 305
ctttcttctt attgtt                                                    16

<210> SEQ ID NO 306
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 306
ctttcttctt attgtt                                                    16

<210> SEQ ID NO 307
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 307
ctttcttctt attgtt                                                    16

<210> SEQ ID NO 308
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 308
gcagtttcct caaatt                                                    16

<210> SEQ ID NO 309
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 309
gcagtttcct caaatt                                                   16

<210> SEQ ID NO 310
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 310
gcagtttcct caaatt                                                   16

<210> SEQ ID NO 311
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 311
gcagtttcct caaatt                                                   16

<210> SEQ ID NO 312
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
```

<223> OTHER INFORMATION: phosphorthioate linkage

<400> SEQUENCE: 312
acggcgcact ttcttc                                                        16

<210> SEQ ID NO 313
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 313
acggcgcact ttcttt                                                        16

<210> SEQ ID NO 314
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 314
acggcgcact ttcttc                                                        16

<210> SEQ ID NO 315
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 315
acggcgcact ttcttc                                                        16

<210> SEQ ID NO 316
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base

```
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 316
ccagctgctc gatggc                                                       16

<210> SEQ ID NO 317
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 317
ccagctgctc gatggt                                                       16

<210> SEQ ID NO 318
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 318
ccagctgctc gatggc                                                       16

<210> SEQ ID NO 319
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 319
ccagctgctc gatggc                                                       16
```

```
<210> SEQ ID NO 320
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 320
cctcaatcca tggcag                                                 16

<210> SEQ ID NO 321
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 321
cctcaatcca tggcag                                                 16

<210> SEQ ID NO 322
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 322
cctcaatcca tggcag                                                 16

<210> SEQ ID NO 323
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: misc_feature
<222> LOCATION: (1)..(16)
<223> OTHER INFORMATION: phosphorthioate linkage

<400> SEQUENCE: 323
cctcaatcca tggcag                                                   16

<210> SEQ ID NO 324
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 324
cagctccggc cagagg                                                   16

<210> SEQ ID NO 325
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 325
cagctccggc cagagg                                                   16

<210> SEQ ID NO 326
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 326
```

```
cagctccggc cagagg                                              16

<210> SEQ ID NO 327
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 327
cagctccggc cagagg                                              16

<210> SEQ ID NO 328
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 328
ccactctggg accagg                                              16

<210> SEQ ID NO 329
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 329
ccactctggg accagg                                              16

<210> SEQ ID NO 330
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
```

```
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 330
ccactctggg accagg                                                       16

<210> SEQ ID NO 331
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 331
ccactctggg accagg                                                       16

<210> SEQ ID NO 332
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 332
cctggaagtg gtgcag                                                       16

<210> SEQ ID NO 333
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 333
cctggaagtg gtgcag                                                       16

<210> SEQ ID NO 334
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 334
cctggaagtg gtgcag                                                         16

<210> SEQ ID NO 335
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 335
cctggaagtg gtgcag                                                         16

<210> SEQ ID NO 336
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 336
gcaccaggga ataaac                                                         16

<210> SEQ ID NO 337
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

```
<400> SEQUENCE: 337
gcaccaggga ataaac                                              16

<210> SEQ ID NO 338
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 338
gcaccaggga ataaac                                              16

<210> SEQ ID NO 339
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 339
gcaccaggga ataaac                                              16

<210> SEQ ID NO 340
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 340
cacaggaagg ctggtg                                              16

<210> SEQ ID NO 341
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
```

```
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 341
cacaggaagg ctggtg                                              16

<210> SEQ ID NO 342
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 342
cacaggaagg ctggtg                                              16

<210> SEQ ID NO 343
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 343
cacaggaagg ctggtg                                              16

<210> SEQ ID NO 344
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 344
acattgctaa ggggcc                                              16
```

```
<210> SEQ ID NO 345
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 345
acattgctaa ggggcc                                                  16

<210> SEQ ID NO 346
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 346
acattgctaa ggggcc                                                  16

<210> SEQ ID NO 347
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 347
acattgctaa ggggcc                                                  16

<210> SEQ ID NO 348
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
```

```
<221> NAME/KEY: misc_feature
<222> LOCATION: (1)..(16)
<223> OTHER INFORMATION: phosphorthioate linkage

<400> SEQUENCE: 348
gatctccttt cctaag                                                    16

<210> SEQ ID NO 349
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 349
gatctccttt cctaag                                                    16

<210> SEQ ID NO 350
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 350
gatctccttt cctaag                                                    16

<210> SEQ ID NO 351
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 351
gatctccttt cctaag                                                    16

<210> SEQ ID NO 352
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 352
ctaatttgaa aatgtt                                                            16

<210> SEQ ID NO 353
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 353
ctaatttgaa aatgtt                                                            16

<210> SEQ ID NO 354
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 354
ctaatttgaa aatgtt                                                            16

<210> SEQ ID NO 355
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 355
```
ctaatttgaa aatgtt                                                    16

<210> SEQ ID NO 356
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 356
agcacagttg aaacat                                                    16

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 357
agcacagttg aaacat                                                    16

<210> SEQ ID NO 358
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 358
agcacagttg aaacat                                                    16

<210> SEQ ID NO 359
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 359
agcacagttg aaacat                                                     16

<210> SEQ ID NO 360
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 360
ttcaagacaa aacagg                                                     16

<210> SEQ ID NO 361
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 361
ttcaagacaa aacagg                                                     16

<210> SEQ ID NO 362
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage
```

```
<400> SEQUENCE: 362
ttcaagacaa aacagg                                                       16

<210> SEQ ID NO 363
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 363
ttcaagacaa aacagg                                                       16

<210> SEQ ID NO 364
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 364
cacctctggt gccact                                                       16

<210> SEQ ID NO 365
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 365
cacctctggt gccact                                                       16

<210> SEQ ID NO 366
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
```

```
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 366
cacctctggt gccact                                               16

<210> SEQ ID NO 367
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 367
cacctctggt gccact                                               16

<210> SEQ ID NO 368
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 368
gctgcacagg cagaag                                               16

<210> SEQ ID NO 369
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 369
gctgcacagg cagaag                                               16

<210> SEQ ID NO 370
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 370
gctgcacagg cagaag                                                 16

<210> SEQ ID NO 371
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 371
gctgcacagg cagaag                                                 16

<210> SEQ ID NO 372
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 372
gttaccagca gcaccc                                                 16

<210> SEQ ID NO 373
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
```

```
<222> LOCATION: (1)..(16)
<223> OTHER INFORMATION: phosphorthioate linkage

<400> SEQUENCE: 373
gttaccagca gcaccc                                                           16

<210> SEQ ID NO 374
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 374
gttaccagca gcaccc                                                           16

<210> SEQ ID NO 375
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 375
gttaccagca gcaccc                                                           16

<210> SEQ ID NO 376
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 376
gagagaagca gccact                                                           16

<210> SEQ ID NO 377
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 377
gagagaagca gccact                                                   16

<210> SEQ ID NO 378
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 378
gagagaagca gccact                                                   16

<210> SEQ ID NO 379
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 379
gagagaagca gccact                                                   16

<210> SEQ ID NO 380
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 380
aaaaaagaga gagaga                                                   16
```

<210> SEQ ID NO 381
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 381
aaaaaagaga gagaga                                                      16

<210> SEQ ID NO 382
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 382
aaaaaagaga gagaga                                                      16

<210> SEQ ID NO 383
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 383
aaaaaagaga gagaga                                                      16

<210> SEQ ID NO 384
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)

-continued

<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 384
gcaaaaatga gccccc                                                 16

<210> SEQ ID NO 385
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 385
gcaaaaatga gccccc                                                 16

<210> SEQ ID NO 386
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 386
gcaaaaatga gccccc                                                 16

<210> SEQ ID NO 387
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 387
gcaaaaatga gccccc                                                 16

<210> SEQ ID NO 388
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 388
cccgggaatc aaaaca                                                    16

<210> SEQ ID NO 389
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 389
cccgggaatc aaaaca                                                    16

<210> SEQ ID NO 390
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 390
cccgggaatc aaaaca                                                    16

<210> SEQ ID NO 391
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage
```

```
<400> SEQUENCE: 391
cccgggaatc aaaaca                                                    16

<210> SEQ ID NO 392
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 392
cttctcacct ggtaag                                                    16

<210> SEQ ID NO 393
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 393
cttctcacct ggtaag                                                    16

<210> SEQ ID NO 394
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 394
cttctcacct ggtaag                                                    16

<210> SEQ ID NO 395
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 395
cttctcacct ggtaag                                                    16

<210> SEQ ID NO 396
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 396
ccttcttcct ccctca                                                    16

<210> SEQ ID NO 397
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 397
ccttcttcct ccctca                                                    16

<210> SEQ ID NO 398
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
```

<223> OTHER INFORMATION: phosphorthioate linkage

<400> SEQUENCE: 398
ccttcttcct ccctca					16

<210> SEQ ID NO 399
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 399
ccttcttcct ccctca					16

<210> SEQ ID NO 400
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 400
agcaaaaggg acactg					16

<210> SEQ ID NO 401
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 401
agcaaaaggg acactg					16

<210> SEQ ID NO 402
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base

```
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 402
agcaaaaggg acactg                                                      16

<210> SEQ ID NO 403
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 403
agcaaaaggg acactg                                                      16

<210> SEQ ID NO 404
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 404
caaagctgtc agctct                                                      16

<210> SEQ ID NO 405
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 405
caaagctgtc agctct                                                      16
```

```
<210> SEQ ID NO 406
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 406
caaagctgtc agctct                                                      16

<210> SEQ ID NO 407
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 407
caaagctgtc agctct                                                      16

<210> SEQ ID NO 408
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 408
gctctgccca cgcgaa                                                      16

<210> SEQ ID NO 409
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
```

```
<220> FEATURE:
<221> NAME/KEY: misc_feature
<222> LOCATION: (1)..(16)
<223> OTHER INFORMATION: phosphorthioate linkage

<400> SEQUENCE: 409
gctctgccca cgcgaa                                                       16

<210> SEQ ID NO 410
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 410
gctctgccca cgcgaa                                                       16

<210> SEQ ID NO 411
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 411
gctctgccca cgcgaa                                                       16

<210> SEQ ID NO 412
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 412
acattcactg tggaag                                                       16

<210> SEQ ID NO 413
<211> LENGTH: 16
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 413
acattcactg tggaag                                                    16

<210> SEQ ID NO 414
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 414
acattcactg tggaag                                                    16

<210> SEQ ID NO 415
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 415
acattcactg tggaag                                                    16

<210> SEQ ID NO 416
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 416
aacatgaggt ccagac                                                          16

<210> SEQ ID NO 417
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 417
aacatgaggt ccagac                                                          16

<210> SEQ ID NO 418
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 418
aacatgaggt ccagac                                                          16

<210> SEQ ID NO 419
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 419
aacatgaggt ccagac                                                          16

<210> SEQ ID NO 420
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:

```
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 420
ctgtgacagc ctcaac                                              16

<210> SEQ ID NO 421
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 421
ctgtgacagc ctcaac                                              16

<210> SEQ ID NO 422
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 422
ctgtgacagc ctcaac                                              16

<210> SEQ ID NO 423
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 423
ctgtgacagc ctcaac                                              16

<210> SEQ ID NO 424
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 424
aagtccacac tcagga                                                       16

<210> SEQ ID NO 425
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 425
aagtccacac tcagga                                                       16

<210> SEQ ID NO 426
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 426
aagtccacac tcagga                                                       16

<210> SEQ ID NO 427
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
```

<223> OTHER INFORMATION: phosphorthioate linkage

<400> SEQUENCE: 427
aagtccacac tcagga						16

<210> SEQ ID NO 428
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 428
tcaacaggca cctgcc						16

<210> SEQ ID NO 429
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 429
tcaacaggca cctgcc						16

<210> SEQ ID NO 430
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 430
tcaacaggca cctgcc						16

```
<210> SEQ ID NO 431
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 431
tcaacaggca cctgcc                                                      16

<210> SEQ ID NO 432
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 432
aacctgcagc tcagat                                                      16

<210> SEQ ID NO 433
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 433
aacctgcagc tcagat                                                      16

<210> SEQ ID NO 434
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
```

-continued

```
<221> NAME/KEY: misc_feature
<222> LOCATION: (5)..(13)
<223> OTHER INFORMATION: phosphorthioate linkage

<400> SEQUENCE: 434
aacctgcagc tcagat                                                            16

<210> SEQ ID NO 435
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 435
aacctgcagc tcagat                                                            16

<210> SEQ ID NO 436
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 436
ggtgtgacag ataagg                                                            16

<210> SEQ ID NO 437
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 437
ggtgtgacag ataagg                                                            16

<210> SEQ ID NO 438
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 438
ggtgtgacag ataagg                                                   16

<210> SEQ ID NO 439
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 439
ggtgtgacag ataagg                                                   16

<210> SEQ ID NO 440
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 440
cctctgagga ggcaca                                                   16

<210> SEQ ID NO 441
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 441
```
cctctgagga ggcaca                                                                 16

<210> SEQ ID NO 442
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 442
cctctgagga ggcaca                                                                 16

<210> SEQ ID NO 443
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 443
cctctgagga ggcaca                                                                 16

<210> SEQ ID NO 444
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 444
acaacaaaaa aactgt                                                                 16

<210> SEQ ID NO 445
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base

```
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 445
acaacaaaaa aactgt                                                          16

<210> SEQ ID NO 446
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 446
acaacaaaaa aactgt                                                          16

<210> SEQ ID NO 447
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 447
acaacaaaaa aactgt                                                          16

<210> SEQ ID NO 448
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 448
aaaacaaaaa aacaca                                                          16

<210> SEQ ID NO 449
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 449
aaaacaaaaa aacaca                                                    16

<210> SEQ ID NO 450
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 450
aaaacaaaaa aacaca                                                    16

<210> SEQ ID NO 451
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 451
aaaacaaaaa aacaca                                                    16

<210> SEQ ID NO 452
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

```
<400> SEQUENCE: 452
catctaccaa aaaaaa                                                  16

<210> SEQ ID NO 453
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 453
catctaccaa aaaaaa                                                  16

<210> SEQ ID NO 454
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 454
catctaccaa aaaaaa                                                  16

<210> SEQ ID NO 455
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 455
catctaccaa aaaaaa                                                  16

<210> SEQ ID NO 456
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
```

```
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 456
tcacacacaa gtcatg                                                    16

<210> SEQ ID NO 457
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 457
tcacacacaa gtcatg                                                    16

<210> SEQ ID NO 458
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 458
tcacacacaa gtcatg                                                    16

<210> SEQ ID NO 459
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 459
tcacacacaa gtcatg                                                    16
```

```
<210> SEQ ID NO 460
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 460
tgtctccatt ctctca                                                     16

<210> SEQ ID NO 461
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 461
tgtctccatt ctctca                                                     16

<210> SEQ ID NO 462
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 462
tgtctccatt ctctca                                                     16

<210> SEQ ID NO 463
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (1)..(16)
<223> OTHER INFORMATION: phosphorthioate linkage

<400> SEQUENCE: 463
tgtctccatt ctctca                                                       16

<210> SEQ ID NO 464
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 464
gaggagccag ggactc                                                       16

<210> SEQ ID NO 465
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 465
gaggagccag ggactc                                                       16

<210> SEQ ID NO 466
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 466
gaggagccag ggactc                                                       16
```

```
<210> SEQ ID NO 467
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 467
gaggagccag ggactc                                                      16

<210> SEQ ID NO 468
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 468
atgttgttaa acagta                                                      16

<210> SEQ ID NO 469
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 469
atgttgttaa acagta                                                      16

<210> SEQ ID NO 470
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
```

<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 470
atgttgttaa acagta                                                 16

<210> SEQ ID NO 471
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 471
atgttgttaa acagta                                                 16

<210> SEQ ID NO 472
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 472
acaaaataag aaagcc                                                 16

<210> SEQ ID NO 473
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 473
acaaaataag aaagcc                                                 16

<210> SEQ ID NO 474
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 474
acaaaataag aaagcc                                                16

<210> SEQ ID NO 475
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 475
acaaaataag aaagcc                                                16

<210> SEQ ID NO 476
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 476
tgaattaaca attcaa                                                16

<210> SEQ ID NO 477
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

-continued

```
<400> SEQUENCE: 477
tgaattaaca attcaa                                                    16

<210> SEQ ID NO 478
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 478
tgaattaaca attcaa                                                    16

<210> SEQ ID NO 479
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 479
tgaattaaca attcaa                                                    16

<210> SEQ ID NO 480
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 480
agtttgtgct attctg                                                    16

<210> SEQ ID NO 481
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
```

```
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 481
agtttgtgct attctg                                                   16

<210> SEQ ID NO 482
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 482
agtttgtgct attctg                                                   16

<210> SEQ ID NO 483
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 483
agtttgtgct attctg                                                   16

<210> SEQ ID NO 484
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 484
gcttagtttt aattgt                                                   16

<210> SEQ ID NO 485
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 485
gcttagtttt aattgt                                                    16

<210> SEQ ID NO 486
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 486
gcttagtttt aattgt                                                    16

<210> SEQ ID NO 487
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 487
gcttagtttt aattgt                                                    16

<210> SEQ ID NO 488
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
```

```
<222> LOCATION: (1)..(16)
<223> OTHER INFORMATION: phosphorthioate linkage

<400> SEQUENCE: 488
cttagaatgg ctttgt                                                    16

<210> SEQ ID NO 489
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 489
cttagaatgg ctttgt                                                    16

<210> SEQ ID NO 490
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 490
cttagaatgg ctttgt                                                    16

<210> SEQ ID NO 491
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 491
cttagaatgg ctttgt                                                    16

<210> SEQ ID NO 492
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 492
cccgtttccc caatga                                                        16

<210> SEQ ID NO 493
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 493
cccgtttccc caatga                                                        16

<210> SEQ ID NO 494
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 494
cccgtttccc caatga                                                        16

<210> SEQ ID NO 495
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 495
cccgtttccc caatga                                                        16
```

```
<210> SEQ ID NO 496
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 496
tccacctgaa gttcac                                                   16

<210> SEQ ID NO 497
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 497
tccacctgaa gttcac                                                   16

<210> SEQ ID NO 498
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 498
tccacctgaa gttcac                                                   16

<210> SEQ ID NO 499
<211> LENGTH: 16
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 499
tccacctgaa gttcac                                                  16

<210> SEQ ID NO 500
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 500
ctattctgtc tcctca                                                  16

<210> SEQ ID NO 501
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 501
ctattctgtc tcctca                                                  16

<210> SEQ ID NO 502
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 502
```

```
ctattctgtc tcctca                                                    16

<210> SEQ ID NO 503
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 503
ctattctgtc tcctca                                                    16

<210> SEQ ID NO 504
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 504
gacgcttcct atcact                                                    16

<210> SEQ ID NO 505
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 505
gacgcttcct atcact                                                    16

<210> SEQ ID NO 506
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
```

```
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 506
gacgcttcct atcact                                                    16

<210> SEQ ID NO 507
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 507
gacgcttcct atcact                                                    16

<210> SEQ ID NO 508
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 508
aaaggagtat ctgcca                                                    16

<210> SEQ ID NO 509
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 509
aaaggagtat ctgcca                                                    16

<210> SEQ ID NO 510
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 510
aaaggagtat ctgcca                                              16

<210> SEQ ID NO 511
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 511
aaaggagtat ctgcca                                              16

<210> SEQ ID NO 512
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 512
tcacacagca gtggca                                              16

<210> SEQ ID NO 513
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
```

<223> OTHER INFORMATION: phosphorthioate linkage

<400> SEQUENCE: 513
tcacacagca gtggca                                                          16

<210> SEQ ID NO 514
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 514
tcacacagca gtggca                                                          16

<210> SEQ ID NO 515
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 515
tcacacagca gtggca                                                          16

<210> SEQ ID NO 516
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 516
cactgggcct gtctaa                                                          16

<210> SEQ ID NO 517
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base

```
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 517
cactgggcct gtctaa                                                    16

<210> SEQ ID NO 518
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 518
cactgggcct gtctaa                                                    16

<210> SEQ ID NO 519
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 519
cactgggcct gtctaa                                                    16

<210> SEQ ID NO 520
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 520
catgtgcccc gcggct                                                    16
```

```
<210> SEQ ID NO 521
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 521
catgtgcccc gcggct                                                   16

<210> SEQ ID NO 522
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 522
catgtgcccc gcggct                                                   16

<210> SEQ ID NO 523
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 523
catgtgcccc gcggct                                                   16

<210> SEQ ID NO 524
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
```

```
<220> FEATURE:
<221> NAME/KEY: misc_feature
<222> LOCATION: (1)..(16)
<223> OTHER INFORMATION: phosphorthioate linkage

<400> SEQUENCE: 524
agggaggagc ggccag                                                    16

<210> SEQ ID NO 525
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 525
agggaggagc ggccag                                                    16

<210> SEQ ID NO 526
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 526
agggaggagc ggccag                                                    16

<210> SEQ ID NO 527
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 527
agggaggagc ggccag                                                    16

<210> SEQ ID NO 528
<211> LENGTH: 16
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 528
ccactgcctt tttctg                                               16

<210> SEQ ID NO 529
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 529
ccactgcctt tttctg                                               16

<210> SEQ ID NO 530
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 530
ccactgcctt tttctg                                               16

<210> SEQ ID NO 531
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 531
```
ccactgcctt tttctg                                          16

<210> SEQ ID NO 532
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 532
ttaaaaagga tttagg                                          16

<210> SEQ ID NO 533
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 533
ttaaaaagga tttagg                                          16

<210> SEQ ID NO 534
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 534
ttaaaaagga tttagg                                          16

<210> SEQ ID NO 535
<211> LENGTH: 16
<212> TYPE: DNA

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 535
ttaaaaagga tttagg                                                         16

<210> SEQ ID NO 536
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 536
catcgagcca agtcat                                                         16

<210> SEQ ID NO 537
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 537
catcgagcca agtcat                                                         16

<210> SEQ ID NO 538
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage
```

```
<400> SEQUENCE: 538
catcgagcca agtcat                                                           16

<210> SEQ ID NO 539
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 539
catcgagcca agtcat                                                           16

<210> SEQ ID NO 540
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 540
agccagtccc ccacag                                                           16

<210> SEQ ID NO 541
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 541
agccagtccc ccacag                                                           16

<210> SEQ ID NO 542
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
```

```
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 542
agccagtccc ccacag                                              16

<210> SEQ ID NO 543
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 543
agccagtccc ccacag                                              16

<210> SEQ ID NO 544
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 544
cggcctgcag cagccc                                              16

<210> SEQ ID NO 545
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 545
cggcctgcag cagccc                                              16
```

```
<210> SEQ ID NO 546
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 546
cggcctgcag cagccc                                                     16

<210> SEQ ID NO 547
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 547
cggcctgcag cagccc                                                     16

<210> SEQ ID NO 548
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 548
tgggctgaca gacaca                                                     16

<210> SEQ ID NO 549
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
```

```
<221> NAME/KEY: misc_feature
<222> LOCATION: (1)..(16)
<223> OTHER INFORMATION: phosphorthioate linkage

<400> SEQUENCE: 549
tgggctgaca gacaca                                                      16

<210> SEQ ID NO 550
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 550
tgggctgaca gacaca                                                      16

<210> SEQ ID NO 551
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 551
tgggctgaca gacaca                                                      16

<210> SEQ ID NO 552
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 552
tgacagatgt gaaggt                                                      16

<210> SEQ ID NO 553
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 553
tgacagatgt gaaggt                                                    16

<210> SEQ ID NO 554
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 554
tgacagatgt gaaggt                                                    16

<210> SEQ ID NO 555
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 555
tgacagatgt gaaggt                                                    16

<210> SEQ ID NO 556
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 556
```
ccccgtgtgg agaacg    16

<210> SEQ ID NO 557
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 557
ccccgtgtgg agaacg    16

<210> SEQ ID NO 558
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 558
ccccgtgtgg agaacg    16

<210> SEQ ID NO 559
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 559
ccccgtgtgg agaacg    16

<210> SEQ ID NO 560
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base

```
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 560
gcggactgcg tctctc                                                   16

<210> SEQ ID NO 561
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 561
gcggactgcg tctctc                                                   16

<210> SEQ ID NO 562
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 562
gcggactgcg tctctc                                                   16

<210> SEQ ID NO 563
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 563
gcggactgcg tctctc                                                   16

<210> SEQ ID NO 564
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 564
gaaagcgggg acctgg                                                       16

<210> SEQ ID NO 565
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 565
gaaagcgggg acctgg                                                       16

<210> SEQ ID NO 566
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 566
gaaagcgggg acctgg                                                       16

<210> SEQ ID NO 567
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage
```

<400> SEQUENCE: 567
gaaagcgggg acctgg                                                                 16

<210> SEQ ID NO 568
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 568
agctgctgcc tccaaa                                                                 16

<210> SEQ ID NO 569
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 569
agctgctgcc tccaaa                                                                 16

<210> SEQ ID NO 570
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 570
agctgctgcc tccaaa                                                                 16

<210> SEQ ID NO 571

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 571
agctgctgcc tccaaa                                                        16

<210> SEQ ID NO 572
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 572
acttcagccc tgcggg                                                        16

<210> SEQ ID NO 573
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 573
acttcagccc tgcggg                                                        16

<210> SEQ ID NO 574
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
```

```
<222> LOCATION: (5)..(13)
<223> OTHER INFORMATION: phosphorthioate linkage

<400> SEQUENCE: 574
acttcagccc tgcggg                                                  16

<210> SEQ ID NO 575
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 575
acttcagccc tgcggg                                                  16

<210> SEQ ID NO 576
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 576
catcatctta cgccag                                                  16

<210> SEQ ID NO 577
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 577
catcatctta cgccag                                                  16

<210> SEQ ID NO 578
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 578
catcatctta cgccag                                              16

<210> SEQ ID NO 579
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 579
catcatctta cgccag                                              16

<210> SEQ ID NO 580
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 580
gagggcgaat caaatc                                              16

<210> SEQ ID NO 581
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 581
gagggcgaat caaatc                                              16
```

<210> SEQ ID NO 582
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 582
gagggcgaat caaatc                                                 16

<210> SEQ ID NO 583
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 583
gagggcgaat caaatc                                                 16

<210> SEQ ID NO 584
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 584
gctctatgac agggag                                                 16

<210> SEQ ID NO 585
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)

```
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 585
gctctatgac agggag                                                      16

<210> SEQ ID NO 586
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 586
gctctatgac agggag                                                      16

<210> SEQ ID NO 587
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 587
gctctatgac agggag                                                      16

<210> SEQ ID NO 588
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 588
aacaatccac cctgca                                                      16

<210> SEQ ID NO 589
<211> LENGTH: 16
<212> TYPE: DNA
<213> ORGANISM: Artificial sequence
```

```
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 589
aacaatccac cctgca                                                      16

<210> SEQ ID NO 590
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 590
aacaatccac cctgca                                                      16

<210> SEQ ID NO 591
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 591
aacaatccac cctgca                                                      16

<210> SEQ ID NO 592
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

-continued

```
<400> SEQUENCE: 592
tttccagcga agctgt                                                        16

<210> SEQ ID NO 593
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 593
tttccagcga agctgt                                                        16

<210> SEQ ID NO 594
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 594
tttccagcga agctgt                                                        16

<210> SEQ ID NO 595
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 595
tttccagcga agctgt                                                        16

<210> SEQ ID NO 596
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
```

```
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 596
agatgacctc cagagg                                                    16

<210> SEQ ID NO 597
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 597
agatgacctc cagagg                                                    16

<210> SEQ ID NO 598
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 598
agatgacctc cagagg                                                    16

<210> SEQ ID NO 599
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 599
agatgacctc cagagg                                                    16

<210> SEQ ID NO 600
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 600
ttctcaggaa cagccg                                                  16

<210> SEQ ID NO 601
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 601
ttctcaggaa cagccg                                                  16

<210> SEQ ID NO 602
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 602
ttctcaggaa cagccg                                                  16

<210> SEQ ID NO 603
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (1)..(16)
<223> OTHER INFORMATION: phosphorthioate linkage

<400> SEQUENCE: 603
ttctcaggaa cagccg                                               16

<210> SEQ ID NO 604
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 604
atgacaggct ttttat                                               16

<210> SEQ ID NO 605
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 605
atgacaggct ttttat                                               16

<210> SEQ ID NO 606
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 606
atgacaggct ttttat                                               16
```

```
<210> SEQ ID NO 607
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 607
atgacaggct ttttat                                                        16

<210> SEQ ID NO 608
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 608
aggcaggggg caacgt                                                        16

<210> SEQ ID NO 609
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 609
aggcaggggg caacgt                                                        16

<210> SEQ ID NO 610
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
```

```
<220> FEATURE:
<221> NAME/KEY: misc_feature
<222> LOCATION: (5)..(13)
<223> OTHER INFORMATION: phosphorthioate linkage

<400> SEQUENCE: 610
aggcaggggg caacgt                                                    16

<210> SEQ ID NO 611
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 611
aggcaggggg caacgt                                                    16

<210> SEQ ID NO 612
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 612
ccaagaaggg ccagtt                                                    16

<210> SEQ ID NO 613
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 613
ccaagaaggg ccagtt                                                    16

<210> SEQ ID NO 614
<211> LENGTH: 16
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 614
ccaagaaggg ccagtt                                                     16

<210> SEQ ID NO 615
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 615
ccaagaaggg ccagtt                                                     16

<210> SEQ ID NO 616
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 616
tggctcgttc tcagtg                                                     16

<210> SEQ ID NO 617
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 617
```

```
tggctcgttc tcagtg                                              16

<210> SEQ ID NO 618
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 618
tggctcgttc tcagtg                                              16

<210> SEQ ID NO 619
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 619
tggctcgttc tcagtg                                              16

<210> SEQ ID NO 620
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 620
gtctggctcg ttctca                                              16

<210> SEQ ID NO 621
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
```

```
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 621
gtctggctcg ttctca                                                     16

<210> SEQ ID NO 622
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 622
gtctggctcg ttctca                                                     16

<210> SEQ ID NO 623
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 623
gtctggctcg ttctca                                                     16

<210> SEQ ID NO 624
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 624
agtctggctc gttctc                                                     16

<210> SEQ ID NO 625
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 625
agtctggctc gttctc                                                     16

<210> SEQ ID NO 626
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 626
agtctggctc gttctc                                                     16

<210> SEQ ID NO 627
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 627
agtctggctc gttctc                                                     16

<210> SEQ ID NO 628
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
```

```
<223> OTHER INFORMATION: phosphorthioate linkage

<400> SEQUENCE: 628
tggatgaagc cagcct                                                   16

<210> SEQ ID NO 629
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 629
tggatgaagc cagcct                                                   16

<210> SEQ ID NO 630
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 630
tggatgaagc cagcct                                                   16

<210> SEQ ID NO 631
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 631
tggatgaagc cagcct                                                   16

<210> SEQ ID NO 632
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
```

```
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 632
agcagaagaa acactg                                              16

<210> SEQ ID NO 633
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 633
agcagaagaa acactg                                              16

<210> SEQ ID NO 634
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 634
agcagaagaa acactg                                              16

<210> SEQ ID NO 635
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 635
agcagaagaa acactg                                              16
```

<210> SEQ ID NO 636
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 636
tcctctatgg ggtcgt                                           16

<210> SEQ ID NO 637
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 637
tcctctatgg ggtcgt                                           16

<210> SEQ ID NO 638
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 638
tcctctatgg ggtcgt                                           16

<210> SEQ ID NO 639
<211> LENGTH: 16
<212> TYPE: DNA
<213> ORGANISM: Artificial sequence
<220> FEATURE:
<223> OTHER INFORMATION: Synthetic oligonucleotide

```
<220> FEATURE:
<221> NAME/KEY: misc_feature
<222> LOCATION: (1)..(16)
<223> OTHER INFORMATION: phosphorthioate linkage

<400> SEQUENCE: 639
tcctctatgg ggtcgt                                              16

<210> SEQ ID NO 640
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 640
gcaaccggac gaatgc                                              16

<210> SEQ ID NO 641
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 641
gcaaccggac gaatgc                                              16

<210> SEQ ID NO 642
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 642
```

```
gcaaccggac gaatgc                                                       16
```

<210> SEQ ID NO 643
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 643

```
gcaaccggac gaatgc                                                       16
```

<210> SEQ ID NO 644
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 644

```
ttatgttcct ctatgg                                                       16
```

<210> SEQ ID NO 645
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 645

```
ttatgttcct ctatgg                                                       16
```

<210> SEQ ID NO 646
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base

```
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 646
ttatgttcct ctatgg                                                   16

<210> SEQ ID NO 647
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 647
ttatgttcct ctatgg                                                   16

<210> SEQ ID NO 648
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 648
ggttaattct tcaaac                                                   16

<210> SEQ ID NO 649
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 649
ggttaattct tcaaac                                                   16

<210> SEQ ID NO 650
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 650
ggttaattct tcaaac                                              16

<210> SEQ ID NO 651
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 651
ggttaattct tcaaac                                              16

<210> SEQ ID NO 652
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 652
ctctgtccag tttcaa                                              16

<210> SEQ ID NO 653
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage
```

```
<400> SEQUENCE: 653
ctctgtccag tttcaa                                                      16

<210> SEQ ID NO 654
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 654
ctctgtccag tttcaa                                                      16

<210> SEQ ID NO 655
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 655
ctctgtccag tttcaa                                                      16

<210> SEQ ID NO 656
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 656
gcaattttgt tcttgg                                                      16

<210> SEQ ID NO 657
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
```

<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 657
gcaattttgt tcttgg                                               16

<210> SEQ ID NO 658
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 658
gcaattttgt tcttgg                                               16

<210> SEQ ID NO 659
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 659
gcaattttgt tcttgg                                               16

<210> SEQ ID NO 660
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 660
ctcaatccat ggcagc                                               16

```
<210> SEQ ID NO 661
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 661
ctcaatccat ggcagc                                               16

<210> SEQ ID NO 662
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 662
ctcaatccat ggcagc                                               16

<210> SEQ ID NO 663
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 663
ctcaatccat ggcagc                                               16

<210> SEQ ID NO 664
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
```

-continued

```
<221> NAME/KEY: misc_feature
<222> LOCATION: (1)..(16)
<223> OTHER INFORMATION: phosphorthioate linkage

<400> SEQUENCE: 664
ccagcctcgg ccatcc                                                          16

<210> SEQ ID NO 665
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 665
ccagcctcgg ccatcc                                                          16

<210> SEQ ID NO 666
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 666
ccagcctcgg ccatcc                                                          16

<210> SEQ ID NO 667
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 667
ccagcctcgg ccatcc                                                          16

<210> SEQ ID NO 668
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 668
tgtccagttt caaaaa                                               16

<210> SEQ ID NO 669
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 669
tgtccagttt caaaaa                                               16

<210> SEQ ID NO 670
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 670
tgtccagttt caaaaa                                               16

<210> SEQ ID NO 671
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 671
```
tgtccagttt caaaaa                                           16

<210> SEQ ID NO 672
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 672
ctgtccagtt tcaaaa                                           16

<210> SEQ ID NO 673
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 673
ctgtccagtt tcaaaa                                           16

<210> SEQ ID NO 674
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 674
ctgtccagtt tcaaaa                                           16

<210> SEQ ID NO 675
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 675
ctgtccagtt tcaaaa                                                    16

<210> SEQ ID NO 676
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 676
tcggggcacc catgcc                                                    16

<210> SEQ ID NO 677
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 677
tcggggcacc catgcc                                                    16

<210> SEQ ID NO 678
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage
```

-continued

<400> SEQUENCE: 678
tcggggcacc catgcc                                                         16

<210> SEQ ID NO 679
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 679
tcggggcacc catgcc                                                         16

<210> SEQ ID NO 680
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 680
atggcagcca gctgct                                                         16

<210> SEQ ID NO 681
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 681
atggcagcca gctgct                                                         16

<210> SEQ ID NO 682
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base

```
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 682
atggcagcca gctgct                                                        16

<210> SEQ ID NO 683
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 683
atggcagcca gctgct                                                        16

<210> SEQ ID NO 684
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 684
agaggcctca atccat                                                        16

<210> SEQ ID NO 685
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 685
agaggcctca atccat                                                        16

<210> SEQ ID NO 686
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 686
agaggcctca atccat                                                   16

<210> SEQ ID NO 687
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 687
agaggcctca atccat                                                   16

<210> SEQ ID NO 688
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 688
gggcaacgtc ggggca                                                   16

<210> SEQ ID NO 689
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
```

```
<222> LOCATION: (1)..(16)
<223> OTHER INFORMATION: phosphorthioate linkage

<400> SEQUENCE: 689
gggcaacgtc ggggca                                                       16

<210> SEQ ID NO 690
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 690
gggcaacgtc ggggca                                                       16

<210> SEQ ID NO 691
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 691
gggcaacgtc ggggca                                                       16

<210> SEQ ID NO 692
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 692
tgccaggcag ggggca                                                       16

<210> SEQ ID NO 693

<400> SEQUENCE: 693

000
```

```
<210> SEQ ID NO 694
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 694
tgccaggcag ggggca                                                   16

<210> SEQ ID NO 695
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 695
tgccaggcag ggggca                                                   16

<210> SEQ ID NO 696
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 696
ccggggtgca ggcgca                                                   16

<210> SEQ ID NO 697
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
```

```
<221> NAME/KEY: misc_feature
<222> LOCATION: (1)..(16)
<223> OTHER INFORMATION: phosphorthioate linkage

<400> SEQUENCE: 697
ccggggtgca ggcgca                                                          16

<210> SEQ ID NO 698
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 698
ccggggtgca ggcgca                                                          16

<210> SEQ ID NO 699
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 699
ccggggtgca ggcgca                                                          16

<210> SEQ ID NO 700
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 700
catccgctcc ggggtg                                                          16

<210> SEQ ID NO 701
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 701
catccgctcc ggggtg                                              16

<210> SEQ ID NO 702
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 702
catccgctcc ggggtg                                              16

<210> SEQ ID NO 703
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 703
catccgctcc ggggtg                                              16

<210> SEQ ID NO 704
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified 3ba16e
<220> FEATURE:
<221> NAME/KEY: misc_feature
<222> LOCATION: (1)..(16)
<223> OTHER INFORMATION: phosphorthioate linkage

<400> SEQUENCE: 704
```
gtggggcagt ggatga                                                       16

<210> SEQ ID NO 705
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 705
gtggggcagt ggatga                                                       16

<210> SEQ ID NO 706
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 706
gtggggcagt ggatga                                                       16

<210> SEQ ID NO 707
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 707
gtggggcagt ggatga                                                       16

<210> SEQ ID NO 708
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base

```
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 708
cctctatggg gtcgtc                                                          16

<210> SEQ ID NO 709
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 709
cctctatggg gtcgtt                                                          16

<210> SEQ ID NO 710
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 710
cctctatggg gtcgtc                                                          16

<210> SEQ ID NO 711
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 711
cctctatggg gtcgtc                                                          16

<210> SEQ ID NO 712
<211> LENGTH: 16
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 712
atgcttttta tgttcc                                               16

<210> SEQ ID NO 713
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 713
atgcttttta tgttct                                               16

<210> SEQ ID NO 714
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 714
atgcttttta tgttcc                                               16

<210> SEQ ID NO 715
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage
```

```
<400> SEQUENCE: 715
atgcttttta tgttcc                                               16

<210> SEQ ID NO 716
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 716
gtttcctttg caattt                                               16

<210> SEQ ID NO 717
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(15)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 717
gtttcctttg caattt                                               16

<210> SEQ ID NO 718
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 718
gtttcctttg caattt                                               16

<210> SEQ ID NO 719
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: phosphorthioate linkage

<400> SEQUENCE: 719
gtttcctttg caattt                                                        16

<210> SEQ ID NO 720
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 720
tgtgctattc tgtgaatt                                                      18

<210> SEQ ID NO 721
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 721
tgtgctattc tgtgaatt                                                      18

<210> SEQ ID NO 722
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(13)
<223> OTHER INFORMATION: phosphorthioate linkage

<400> SEQUENCE: 722
tgtgctattc tgtgaatt                                                      18
```

```
<210> SEQ ID NO 723
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 723
tgtgctattc tgtgaatt                                               18

<210> SEQ ID NO 724
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 724
taagctgttc tatgtgtt                                               18

<210> SEQ ID NO 725
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (5)..(13)
<223> OTHER INFORMATION: phosphorthioate linkage

<400> SEQUENCE: 725
taagctgttc tatgtgtt                                               18

<210> SEQ ID NO 726
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: modified_base
<222> LOCATION: (1)..(4)
<223> OTHER INFORMATION: beta-D-oxy-LNA modified base
<220> FEATURE:
<221> NAME/KEY: modified_base
<222> LOCATION: (13)..(16)
<223> OTHER INFORMATION: beta-D-oxy-LNA modified base
<220> FEATURE:
<221> NAME/KEY: misc_feature
<222> LOCATION: (1)..(16)
<223> OTHER INFORMATION: phosphorthioate linkage

<400> SEQUENCE: 726
taagctgttc tatgtgtt                                                 18

<210> SEQ ID NO 727
<211> LENGTH: 19
<212> TYPE: DNA
<213> ORGANISM: Artificial sequence
<220> FEATURE:
<223> OTHER INFORMATION: Primer

<400> SEQUENCE: 727
caggtccccg ctttctttg                                                19

<210> SEQ ID NO 728
<211> LENGTH: 18
<212> TYPE: DNA
<213> ORGANISM: Artificial sequence
<220> FEATURE:
<223> OTHER INFORMATION: Primer

<400> SEQUENCE: 728
ggaggagggc gaatcaaa                                                 18

<210> SEQ ID NO 729
<211> LENGTH: 26
<212> TYPE: DNA
<213> ORGANISM: Artificial sequence
<220> FEATURE:
<223> OTHER INFORMATION: Probe

<400> SEQUENCE: 729
ccatcatctt acgccagact tcagcc                                        26

<210> SEQ ID NO 730
<211> LENGTH: 21
<212> TYPE: DNA
<213> ORGANISM: Artificial sequence
<220> FEATURE:
<223> OTHER INFORMATION: Primer

<400> SEQUENCE: 730
aaggaccacc gcatctctac a                                             21

<210> SEQ ID NO 731
<211> LENGTH: 22
<212> TYPE: DNA
<213> ORGANISM: Artificial sequence
<220> FEATURE:
<223> OTHER INFORMATION: Primer

<400> SEQUENCE: 731
ccaagtctgg ctcgttctca gt                                            22

<210> SEQ ID NO 732
<211> LENGTH: 23
```

```
<212> TYPE: DNA
<213> ORGANISM: Artificial sequence
<220> FEATURE:
<223> OTHER INFORMATION: Probe

<400> SEQUENCE: 732
cgaggctggc ttcatccact gcc                                          23

<210> SEQ ID NO 733
<211> LENGTH: 21
<212> TYPE: DNA
<213> ORGANISM: Artificial sequence
<220> FEATURE:
<223> OTHER INFORMATION: Primer

<400> SEQUENCE: 733
aaggctgtgg gcaaggtcat c                                            21

<210> SEQ ID NO 734
<211> LENGTH: 23
<212> TYPE: DNA
<213> ORGANISM: Artificial sequence
<220> FEATURE:
<223> OTHER INFORMATION: Primer

<400> SEQUENCE: 734
gtcagatcca cgacggacac att                                          23

<210> SEQ ID NO 735
<211> LENGTH: 34
<212> TYPE: DNA
<213> ORGANISM: Artificial sequence
<220> FEATURE:
<223> OTHER INFORMATION: Probe

<400> SEQUENCE: 735
gaagctcact ggcatggcat ggccttccgt gttc                              34

<210> SEQ ID NO 736
<211> LENGTH: 25
<212> TYPE: DNA
<213> ORGANISM: Artificial sequence
<220> FEATURE:
<223> OTHER INFORMATION: Primer

<400> SEQUENCE: 736
agcacaaagc cattctaagt cattg                                        25

<210> SEQ ID NO 737
<211> LENGTH: 23
<212> TYPE: DNA
<213> ORGANISM: Artificial sequence
<220> FEATURE:
<223> OTHER INFORMATION: Primer

<400> SEQUENCE: 737
tccatcatct tacgccagac ttc                                          23

<210> SEQ ID NO 738
<211> LENGTH: 16
<212> TYPE: DNA
<213> ORGANISM: Artificial sequence
<220> FEATURE:
<223> OTHER INFORMATION: Probe

<400> SEQUENCE: 738
```

```
gatgtttcga tgtttc                                                     16

<210> SEQ ID NO 739
<211> LENGTH: 18
<212> TYPE: DNA
<213> ORGANISM: Artificial sequence
<220> FEATURE:
<223> OTHER INFORMATION: Primer

<400> SEQUENCE: 739
aacggatttg gtcgtatt                                                   18

<210> SEQ ID NO 740
<211> LENGTH: 18
<212> TYPE: DNA
<213> ORGANISM: Artificial sequence
<220> FEATURE:
<223> OTHER INFORMATION: Primer

<400> SEQUENCE: 740
taagcagttg gtggtgca                                                   18

<210> SEQ ID NO 741
<211> LENGTH: 18
<212> TYPE: DNA
<213> ORGANISM: Artificial sequence
<220> FEATURE:
<223> OTHER INFORMATION: poly-T oligonucleotide
<220> FEATURE:
<223> OTHER INFORMATION: this sequence may encompass 12-18 nucleotides
      according to the specification as filed

<400> SEQUENCE: 741
tttttttttt tttttttt                                                   18
```